United States Patent
Edwards et al.

(10) Patent No.: US 7,951,818 B2
(45) Date of Patent: May 31, 2011

(54) IMIDAZOLOPYRIDINE COMPOUNDS USEFUL FOR THE TREATMENT OF DEGENERATIVE AND INFLAMMATORY DISEASES

(75) Inventors: Paul John Edwards, Laval (CA); Sébastien Laurent Xavier Martina, Mechelen (BE); Martin James Inglis Andrews, Mechelen (BE); Grégory Louis Joseph Bar, Mechelen (BE); Brigitte Allart, Mechelen (BE); Andrew Burritt, San Diego, CA (US); Xueliang Tao, San Diego, CA (US); Friedrich Erich Karl Kroll, Mechelen (BE)

(73) Assignee: Galapagos NV, Mechelen (BE)

( * ) Notice: Subject to any disclaimer, the term of this patent is extended or adjusted under 35 U.S.C. 154(b) by 174 days.

(21) Appl. No.: 11/998,818

(22) Filed: Nov. 30, 2007

(65) Prior Publication Data

US 2009/0048245 A1     Feb. 19, 2009

Related U.S. Application Data

(60) Provisional application No. 60/868,149, filed on Dec. 1, 2006, provisional application No. 60/994,740, filed on Sep. 21, 2007.

(51) Int. Cl.
  *A61K 31/44* (2006.01)
(52) U.S. Cl. ........ 514/303; 544/333; 546/121; 546/167; 546/268.1; 548/373.1; 548/469; 549/59
(58) Field of Classification Search .................. 514/303; 544/333; 546/121, 167, 268.1; 548/373.1, 548/469; 549/59
See application file for complete search history.

(56) References Cited

FOREIGN PATENT DOCUMENTS

| WO | WO00/11000 | 3/2000 |
|---|---|---|
| WO | WO2004/014908 | 2/2004 |
| WO | WO2004/026867 | 4/2004 |
| WO | WO2006/004702 | 1/2006 |
| WO | WO2007/131991 | 11/2007 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, New York: John Wiley & Sons, 1996, vol. 1, 975-976.*
Huang H. et al. (2006). Cell Death Differ. 13:1879-1891. "Osteoclast differentiation requires TAK1 and MKK6 for NFATc1 induction and NF-κB transactivation by RANKL"
Irie T et al. (2000) FEBS Lett. 467:160-164. "TAK1 mediates an activation signal from toll-like receptor(s) to nuclear factor-κB in lipopolysaccharide-stimulated macrophages."
Klatt AR et al. (2006) Biomedicine&Pharmacotherapy 60:55-61. "TAK1 downregulation reduces IL-1β induced expression of MMP13, MMP1 and TNF-alpha."
Kremer JM. et al. (2003) N Engl J Med. 349:1907-1915. "Treatment of RA by selective inhibition of T-cell activation with fusion protein CTLA4Ig."
Lee DM, Weinblatt ME (2001). Lancet. 358: 903-11. "Rheumatoid arthritis."
Muzikami J. et al. (2002) Mol. Cell Biol. 22: 992-1000. "Receptor Activator of NF-B Ligand (RANKL) Activates TAK1 Mitogen-Activated Protein Kinase . . . ".
New L. et al. (2003) Mol Biol Cell. 14(6):2603-16. "Regulation of PRAK subcellular location by p38 MAP kinases.."
Ninomiya-Tsuji J. et al. (1999). Nature 398: 252-256. The kinase TAK1 can activate the NIK-IκB as well as the MAP kinase cascade in the IL-1 signalling pathway.
O'Dell JR et al. (2002). Arthritis Rheum. 46:1164-70. "Treatment of RA with methotrexate and hydroxychloroquine, methotrexate and sulfasalazine, . . . ".
O'Dell JR. et al.(2004) N Engl J Med. 350(25):2591-602. "Therapeutic strategies for rheumatoid arthritis."
Reif S. et al. (2005) Digestion. 71:124-130. "Matrix metalloproteinases 2 and 9 are markers of inflammation but not of the degree of fibrosis in chornic hepatitis C".
Rosenberg GA. (2002). Glia. 39:279-91. "Matrix metalloproteinases in neuroinflammation."
Sakurai H. et al. (1999). J. Biol. Chem. 274: 10641-10648. "Functional Interactions of Transforming Growth Factor -activated Kinase 1 with IB Kinases to Stimulate NF-B . . . ".
Sato S. et al. (2005) Nat. Immunol. 6: 1087-1095. "Essential function for the kinase TAK1 in innate and adaptive immune responses".
Schanstra JP. et al. (2002) J Clin Invest. 110:371-9. "In vivo bradykinin B2 receptor activation reduces renal fibrosis."
Shi Y et al. (2003). Mol Cell Biol. 23:7732-41. "Elimination of protein kinase MK5/PRAK activity by targeted homologous recombination."
Shibuya H. et al. (1998). EMBO J. 17: 1019-1028. "Role of TAK1 and TAB1 in BMP signaling in early Xenopus development."

(Continued)

*Primary Examiner* — James O Wilson
*Assistant Examiner* — Douglas M Willis
(74) *Attorney, Agent, or Firm* — Klauber & Jackson LLC

(57) ABSTRACT

Novel imidazolopyridine compounds are disclosed that have a formula represented by the following:

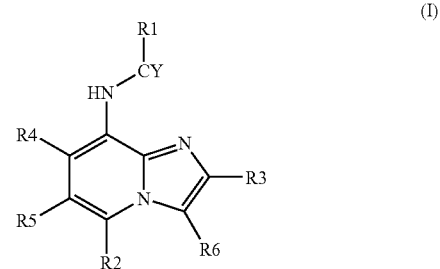

The compounds may be prepared as pharmaceutical compositions, and may be used for the prevention and treatment of a variety of conditions in mammals including humans, including by way of non-limiting example, ECM degradation, joint degradation and/or inflammation, and others.

33 Claims, 3 Drawing Sheets

OTHER PUBLICATIONS

Shim JH. et al. (2005) Genes Dev. 19:2668-2681. "TAK1, but not TAB1 or TAB2, plays an essential role in multiple signaling pathways in vivo."

Andreakos E, et al. (2003). Arthritis Rheum. 48: 1901-12. "Heterogeneous requirement of IkB kinase 2 for inflammatory cytokine and matrix metalloproteinase production in RA".

Blonska M. et al. (2005) J. Biol. Chem. 280: 43056-43063. "TAK1 Is Recruited to the Tumor Necrosis Factor- (TNF-) Receptor 1 Complex in a Receptor-interacting Protein (RIP).."

Boutros M. at al. (2002) Dev. Cell 3(5): 711-722. "Sequential activation of signaling pathways during innate immune responses in *Drosophila*."

Choy EH, Panayi GS. (2001). N Engl J Med. 344: 907-16. "Cytokine pathways and joint inflammation in rheumatoid arthritis."

Coussens LM, et al. (2002). Science 295: 2387-92. "Matrix metalloproteinase inhibitors and cancer: trials and tribulations."

Creemers EE, et al. (2001). Circ Res. 2001 89:201-10. "Matrix metalloproteinase inhibition after myocardial infarction."

Cunnane G, et al. (2001). Arthritis Rheum 44: 2263-74. "Early joint erosions and serum levels of matrix metalloproteinase 1, matrix metalloproteinase 3, . . . ".

Dong W. et al. (2006). J. Biol. Chem. 281: 26029-26040. "The IRAK-1-BCL10-MALT1-TRAF6-TAK1 Cascade Mediates Signaling to NF-B from Toll-like receptor 4".

Edwards J. C.W. et al. (2004) N Engl J Med. 350:2572-2581. "Efficacy of B-cell-targeted therapy with rituximab in patients with RA."

Firestein GS. (2003). Nature. 423:356-61. "Evolving concepts of rheumatoid arthritis."

Gapski R, et al. (2004). J Periodontol. 75:441-52. "Effect of Systemic Matrix Metalloproteinase Inhibition on Periodontal Wound Repair: A Proof of Concept Trial."

Gomez-Reino JJ et al. (2003). Arthritis Rheum. 48: 2122-7. "Treatment of rheumatoid arthritis with tumor necrosis factor inhibitors . . . ".

Smolen JS, Steiner G. (2003). Nat Rev Drug Discov. 2: 473-88. "Therapeutic strategies for rheumatoid arthritis."

St. Clair E.W. et al. (2004). Arthritis Rheum. 50 :3432-43.Combination of infliximab and methotrexate therapy for early rheumatoid arthritis: a randomized, controlled trial.

Suzuki et al. (2004). Treat Respir Med. 3:17-27. "Matrix metalloproteinases in the pathogenesis of asthma and COPD."

Vidal S. et al. (2001). Genes & Dev. 15: 1900-1912. "Mutations in the *Drosophila* dTAK1 gene reveal a conserved function for MAPKKKs . . . "

Wan YY. et al. (2006). Nat. Immunol. 7: 851-858. "The kinase TAK1 integrates antigen and cytokine receptor signaling for T cell development, survival and function."

Yamagushi K et al. (1995). Science 270: 2008-2011. "Identification of a Member of the MAPKKK Family as a Potential Mediator of TGF- Signal Transduction."

Yang YH et al. (2004). Arthritis Rheum. 50:976-84."Modulation of inflammation and response to dexamethasone by Annexin 1 in antigen-induced arthritis."

* cited by examiner

Schematic view of a normal joint and its changes in rheumatoid arthritis (From Smolen and Steiner, 2003).

Increased expression of MMP1 by SFs triggered with cytokines involved in rheumatoid arthritis pathology.

Dose-dependent inhibition of the "TNF-α -based trigger"-induced expression of MMP1 by SFs by a known anti-inflammatory compound.

IMIDAZOLOPYRIDINE COMPOUNDS USEFUL FOR THE TREATMENT OF DEGENERATIVE AND INFLAMMATORY DISEASES

RELATED APPLICATIONS

The present application claims the benefit under 35 U.S.C. §119 of U.S. Provisional Application No. 60/868,149, filed Dec. 1, 2006, and U.S. Provisional Application No. 60/994,740, filed Sep. 21, 2007, the contents of each of which are hereby incorporated by reference in their entireties.

BACKGROUND OF THE INVENTION

1. Field of the Invention

The present invention relates to a class of imidazolopyridines compounds capable of binding to the active site of a serine/threonine kinase, and which can be used to treat conditions involving the degradation of extra-cellular matrix (ECM), such as joint degeneration and diseases involving such degradation and/or inflammation.

2. Description of the Related Art

Diseases involving the degradation of extra-cellular matrix include, but are not limited to, psoriatic arthritis, juvenile arthritis, early arthritis, reactive arthritis, osteoarthritis, ankylosing spondylitis, osteoporosis, musculoskeletal diseases like tendonitis and periodontal disease, cancer metastasis, airway diseases (COPD, asthma), renal and liver fibrosis, cardio-vascular diseases like atherosclerosis and heart failure, and neurological diseases like neuroinflammation and multiple sclerosis. Diseases involving primarily joint degeneration include, but are not limited to, psoriatic arthritis, juvenile arthritis, early arthritis, reactive arthritis, osteoarthritis, and ankylosing spondylitis.

Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not to slow down the disease but to attain remission in order to stop the joint destruction. Besides the severity of the disease outcome, the high prevalence of RA (~0.8% of adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

It is widely accepted that RA is an auto-immune disease, the initial trigger(s) does mediate, in a predisposed host, a cascade of events that leads to the activation of various cell types (B-cells, T-cells, macrophages, fibroblasts, endothelial cells, dendritic cells and others). Concomitantly, an increased production of various cytokines is observed in the joints and tissues surrounding the joint (e.g. TNF-α, IL-6, IL-1, IL-15, IL-18 and others). As the disease progresses, the cellular activation and cytokine production cascade becomes self-perpetuating. At this early stage, the destruction of joint structures is already very clear. Thirty percent of the patients have radiographic evidence of bone erosions at the time of diagnosis and this proportion increases to 60 percent after two years.

Histological analysis of the joints of RA patients clearly evidences the mechanisms involved in the RA-associated degradative processes (FIG. 1). This analysis shows that the main effector responsible for RA-associated joint degradation is the pannus; whereas the synovial fibroblast (SF), by producing diverse proteolytic enzymes, is the prime driver of cartilage and bone erosion. A joint classically contains two adjacent bones that articulate on a cartilage layer, surrounded by the synovial membrane and joint capsule. In the advanced RA patient, the synovium of the joint increases in size to form the pannus, due to the proliferation of the synovial fibroblasts and the infiltration of mononuclear cells such as T-cells, B-cells, monocytes, macrophages and neutrophils. The pannus mediates the degradation of the adjacent cartilage, leading to the narrowing of the joint space, and has the potential to invade adjacent bone and cartilage. As bone and cartilage tissues are composed mainly of collagen type I or II, respectively, the pannus destructive and invasive properties are mediated by the secretion of collagenolytic proteases, principally the matrix metalloproteinases (MMPs). The erosion of the bone under and adjacent to the cartilage is also part of the RA process, and results principally from the presence of osteoclasts at the interface of bone and pannus. Osteoclasts are multinucleated cells that, upon adhesion to the bone tissue, form a closed compartment, within which the osteoclasts secrete proteases (cathepsin K, MMP9) that degrade the bone tissue. The osteoclast population in the joint is abnormally increased by osteoclast formation from precursor cells induced by the secretion of the receptor activator of NFκB ligand (RANKL) by activated SFs and T-cells.

Various collagen types have a key role in defining the stability of the extracellular matrix (ECM). Collagen type I and collagen type II, for example, are the main components of bone and cartilage, respectively. Collagen proteins typically organize into multimeric structures referred to as collagen fibrils. Native collagen fibrils are very resistant to proteolytic cleavage. Only a few types of ECM-degrading proteins have been reported to have the capacity to degrade native collagen: MMPs and cathepsins. Among the cathepsins, cathepsin K, which is active mainly in osteoclasts, is the best characterized. Among the MMPs, MMP1, MMP2, MMP8, MMP13 and MMP14 are known to have collagenolytic properties. The correlation between an increased expression of MMP1 by SFs and the progression of the arthritic disease is well-established and is predictive for joint erosive processes (Cunnane et al., 2001). In the context of RA, therefore, MMP1 represents a highly relevant collagen degrading protein. In vitro, the treatment of cultured SFs with cytokines relevant in the RA pathology (e.g. TNF-α and IL1β) will increase the expression of MMP1 by these cells (Andreakos et al., 2003). Monitoring the levels of MMP1 expressed by SFs therefore is a relevant readout in the field of RA as it is indicative for the activation of SFs towards an erosive phenotype that, in vivo, is responsible for cartilage degradation. Inhibition of the MMP1 expression by SFs represents a valuable therapeutic approach towards the treatment of RA.

The activity of the ECM-degrading proteins can also be causative or correlate with the progression of various diseases different from RA, as e.g. other diseases that involve the degradation of the joints. These diseases include, but are not limited to, psoriatic arthritis, juvenile arthritis, early arthritis, reactive arthritis, osteoarthritis, and ankylosing spondylitis. Other diseases that may be treatable with compounds identified according to the present invention and using the targets involved in the expression of MMPs as described herein are osteoporosis, musculoskeletal diseases like tendonitis and periodontal disease (Gapski et al., 2004), cancer metastasis (Coussens et al., 2002), airway diseases (COPD, asthma) (Suzuki et al., 2004), lung, renal fibrosis (Schanstra et al., 2002), liver fibrosis associated with chronic hepatitis C (Reif et al., 2005), cardio-vascular diseases like atherosclerosis and heart failure (Creemers et al., 2001), and neurological diseases like neuroinflammation and multiple sclerosis (Rosenberg, 2002). Patients suffering from such diseases may benefit from stabilizing the ECM (by protecting it from degradation).

Transforming growth factor-β activated kinase 1 (TAK1), is a member of the mitogen-activated protein kinase kinase kinase (MAP3K) family, originally identified as a key regulator of MAP kinase activation in TGFβ/BMP signaling (Yamaguchi et al. 1995; Shibuya et al. 1998). Later studies have reported that Drosophila TAK1 is required for both c-jun N-terminal kinase and NFκB activation in response to immune challenge by gram-negative bacteria infection (Vidal et al., 2001; Boutros et al., 2002). By now, TAK1 has also been shown to function as a critical upstream molecule of NFκB and MAPK signaling in various mammalian cell types after stimulation with IL1, TNF and lipopolysaccharide, which activates Toll-like receptor (TLR) signaling (Ninomiya-Tsuji et al., 1999; Sakurai et al., 1999; Irie et al., 2000; Blonska et al., 2005; Shim et al., 2005; Dong et al., 2006). In addition, TAK1 was shown to be required for RANKL induced osteoclast differentiation (Mizukami et al., 2002; Huang et al., 2006). In these signaling cascades, TAK1 is recruited to TRAF6 complexes in response to IL1R, TLR and RANKL signaling or to TRAF2 complexes in response to TNFR stimulation. Activated TAK1 phosphorylates MAPK kinases (MAP2K) MKK4 and MKK3/6, which in turn can activate JNK and p38 mitogen-activated protein kinase, leading to the activation of the activator protein 1 (AP1) transcription factor. Furthermore, TAK1 activates IκB kinase (IKK) signaling pathway, leading to the nuclear translocation of NFκB. Furthermore, studies with mice having B-cell specific or T-cell specific TAK1 deficiencies revealed that TAK1 was indispensable for cellular responses to B cell receptor cross-linking and T cell development, survival and function (Sato et al., 2005; Wan et al., 2006). It has also recently been shown that siRNA-mediated knock-down of TAK1 in the human SW1353 chondrosarcoma cell line significantly reduced IL1 triggered expression of MMP1 and MMP13, enzymes involved in ECM degradation in arthritis (Klatt et al. 2006). Taken together, these findings suggest critical roles for TAK1 in inflammatory and immunological responses.

Since TAK1 is a key molecule in pro-inflammatory signaling pathways, TAK1 inhibition can be expected to be effective in diseases associated with inflammation and tissue destruction such as rheumatoid arthritis. With respect to the latter, it has recently been shown that siRNA-mediated knock-down of TAK1 in the human SW1353 chondrosarcoma cell line significantly reduced IL1 triggered expression of MMP1 and MMP13, enzymes involved in ECM degradation in arthritis (Klatt et al. 2006).

The current therapies for RA are not satisfactory due to a limited efficacy (no adequate therapy exists for 30% of the patients). This calls for additional strategies to achieve remission. Remission is required since residual disease bears the risk of progressive joint damage and thus progressive disability. Inhibiting the immuno-inflammatory component of the RA disease, which represents the main target of drugs currently used for RA treatment, does not result in a blockade of joint degradation, the major hallmark of the disease.

Accordingly, a need exists for the identification of new agents that can more effectively and reliably treat conditions such as RA, and it is in response to this need and toward its satisfaction, that the present invention is directed.

SUMMARY OF THE INVENTION

The present invention relates to a class of imidazolopyridines compounds that inhibit pro-inflammatory cytokine-driven MMP1 expression in RA synovial fibroblasts and that are capable of inhibiting TAK1 kinase activity.

The present invention is based on the discovery that inhibitors of matrix metalloproteinase 1 (MMP1) expression, such as the compounds of the present invention, are useful for the treatment of diseases involving ECM degradation, joint degradation and/or inflammation, for example multiple sclerosis, rheumatoid arthritis and osteoarthritis. These compounds may also be described as inhibitors of TAK1 activity. The present invention also provides methods for the production of these compounds, pharmaceutical compositions comprising these compounds and methods for treating diseases involving ECM degradation, joint degradation and/or inflammation by administering a compound of the invention.

The present matrix metalloproteinase inhibiting compounds of the present invention are described generally as phenyl-imidazolo[1,5-a]pyridin-8-yl-amines substituted in the 5-position by an aromatic group capable of accepting electrons from, and an 8-amino substituent capable of donating electrons to, the imidazolo[1,5-a]pyridine ring.

More particularly, the present invention relates to compounds having anti-inflammatory properties in a mammalian cell, according to formula (I):

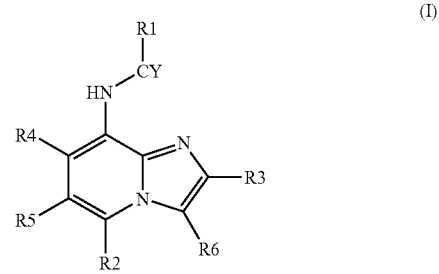

wherein:
CY represents an aryl or heteroaryl group optionally substituted with one or more groups selected from halogen, OH, $C_1$-$C_6$ alkyl, $C_1$-$C_6$ alkoxy, $NH_2$, $N(C_1$-$C_6$ alkyl)($C_1$-$C_6$-alkyl), heterocycloalkyl, cycloalkyl or $CF_3$;
$R^1$ represents H, halogen, $C_1$-$C_6$ alkyl, $C_1$-$C_6$ alkoxy, $CF_3$, CN, a heterocycloalkyl group, a cycloalkyl group, a monocyclic aryl group, a monocyclic heteroaryl group, —$CNHNR^aR^b$, —$COR^a$, —$OR^a$, —$OC(O)$—$C_1$-$C_6$ alkyl, —$(CH_2)_aCOOR^a$, —$C(O)NR^aR^b$, —$S(O)_2$ $(CH_2)_a$ $N(R^aR^b)$, —$SR^a$, $SO(CH_2)_aNR^aR^b$, —$S(O)_2$— $R^a$, —$SOR^a$, —$(CH_2)_aNR^aR^b$, —$(CH_2)_aN(R^a)S(O)_2$— $C_1$-$C_6$ alkyl, $(CH_2)_aNR^aS(O)$—$C_1$-$C_6$ alkyl, —$NR^aCO$—$R^b$, —NH—CO—CO—$OR^a$, each of which may be optionally substituted with one or more groups selected from halogen, OH, $C_1$-$C_6$ alkyl, $NH_2$, $N(C_1$-$C_6$ alkyl)($C_1$-$C_6$-alkyl), optionally substituted heterocycloalkyl, optionally substituted cycloalkyl or $CF_3$;
$R^2$ represents H, aryl or heteroaryl group optionally substituted with one or more groups selected from =O, hydroxy, halogen, CN, $C_1$-$C_6$ alkyl, $C_1$-$C_6$ alkoxy, —$CNHNR^aR^b$, —$COR^a$, —$OR^a$, —$OC(O)$—$C_1$-$C_6$ alkyl, —$(CH_2)_aCOOR^a$, —$C(O)NR^aR^b$, —$S(O)_2$ $(CH_2)_a$ $N(R^aR^b)$, —$SR^a$, —$SO(CH_2)_aNR^aR^b$, —$S(O)_2$ —$R^a$, —SOW, —$(CH_2)_aNR^aR^b$, —$(CH_2)_aN(R^a)S(O)_2$ —$R^b$, —$(CH_2)_aNR^aS(O)$—$C_1$-$C_6$ alkyl, —$NR^aCO$— $R^b$, —NH—CO—CO—$OR^a$, —NH—CO—$NR^aR^b$, each of which may be optionally substituted with one or more groups selected from halogen, —OH, $C_1$-$C_6$ alkyl, —NH$_2$, —N(C$_1$-C$_6$ alkyl)(C$_1$-C$_6$-alkyl), heterocycloalkyl, cycloalkyl or —CF$_3$;

R$^3$, R$^4$, R$^5$ and R$^6$ each independently represent H, C$_1$-C$_6$ alkyl, halogen, (CH$_2$)$_a$-aryl or (CH$_2$)$_a$ heteroaryl; optionally substituted with one or more groups selected from =O, hydroxy, halogen, CN, C$_1$-C$_6$ alkyl, C$_1$-C$_6$ alkoxy, —CNHNR$^a$R$^b$, —COR$^a$, —OR$^a$, —OC(O)—C$_1$-C$_6$ alkyl, —(CH$_2$)$_a$COOR$^a$, —C(O)NR$^a$R$^b$, —S(O)$_2$(CH$_2$)$_a$N(R$^a$R$^b$), —SR$^a$, —SO(CH$_2$)$_a$NR$^a$R$^b$, —S(O)$_2$—R$^a$, —SOR$^a$, —(CH$_2$)$_a$NR$^a$R$^b$, —(CH$_2$)$_a$N(R$^a$)S(O)$_2$—R$^b$, —(CH$_2$)$_a$NR$_a$S(O)—C$_1$-C$_6$ alkyl, —NR$^a$CO—R$^b$, —NH—CO—CO—OR$^a$, —NH—CO—NR$^a$R$^b$, each of which may be optionally substituted with one or more groups selected from halogen, —OH, C$_1$-C$_6$ alkyl, —NH$_2$, —N(C$_1$-C$_6$ alkyl)(C$_1$-C$_6$-alkyl), heterocycloalkyl, cycloalkyl or —CF$_3$;

R$^a$ and R$^b$ each independently represent H, halogen, C$_1$-C$_6$ alkyl, (CH$_2$)$_a$—N(C$_1$-C$_6$ alkyl)(C$_1$-C$_6$-alkyl)(CH$_2$)$_a$-monocyclic aryl, (CH$_2$)$_a$-monocyclic heteroaryl, (CH$_2$)$_a$-cycloalkyl or (CH$_2$)$_a$ heterocycloalkyl, each of which may be optionally substituted with one or more groups selected from halogen, —OH, C$_1$-C$_6$ alkyl, C$_1$-C$_6$ alkyl-O—C$_1$-C$_6$ alkyl, C$_1$-C$_6$ alkoxy, —NH$_2$, —NR$^c$R$^d$, NR$^c$COR$^d$, heteroaryl, heterocycloalkyl, substituted heterocycloalkyl or —CF$_3$; or R$^a$ and R$^b$ may, if joined to the same atom, represent together with the nitrogen to which they are attached a heterocycloalkyl group which may be optionally substituted with one or more groups selected from halogen, —OH, C$_1$-C$_6$ alkyl, C$_1$-C$_6$ alkoxy, —NH$_2$, —NR$^c$R$^d$, —NR$^c$COR$^d$, —C(O)NR$^c$R$^d$, optionally substituted aryl, optionally substituted aralkyl, optionally substituted heteroaryl, optionally substituted cycloalkyl or —CF$_3$;

R$^c$ and R$^d$ each independently represent H, C$_1$-C$_6$ alkyl; and

"a" is 0.1, 2 or 3;

or a pharmaceutically acceptable salt, hydrate, solvate or prodrug thereof.

The present invention also relates to compounds having anti-inflammatory properties in a mammalian cell, according to formula (II):

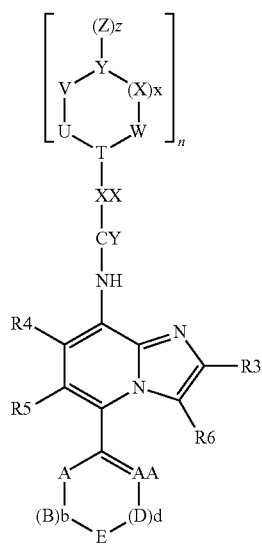

(II)

wherein:

A and B each independently represent CR$^g$R", NR", oxygen or sulphur;

AA represents CR$^g$ or N;

D represents C=O, CR$^g$R" or NR";

E represents N, CR"C(O)R$^g$ or CR"R$^g$;

T represents CR" or N;

U, V, W and X each independently represent CR"R$^h$ or NR";

R$^3$, R$^4$, R$^5$ and R$^6$ each independently represent H, C$_1$-C$_6$ alkyl, halogen, (CH$_2$)$_a$-aryl or (CH$_2$)$_a$-heteroaryl;

CY represents an aryl or heteroaryl group optionally substituted with one or more groups selected from halogen, OH, C$_1$-C$_6$ alkyl, C$_1$-C$_6$ alkoxy, NH$_2$, N(C$_1$-C$_6$ alkyl)(C$_1$-C$_6$-alkyl), heterocycloalkyl, cycloalkyl or CF$_3$;

XX represents a linker group selected from a bond, —C(O)N(CH$_2$)$_c$—, —NC(O)(CH$_2$)$_c$—, S(O)$_2$N(CH$_2$)$_c$—, —NS(O)$_2$(CH$_2$)$_c$—, or XX represents a group selected from CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$, each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl or CF$_3$;

Y represents CR", O or N; with the proviso that when Y represents O, z is 0;

Z represents H; halogen; C$_1$-C$_6$ alkyl; C$_1$-C$_6$ alkoxy; CF$_3$; CN; a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl or CF$_3$;

"b" and "d" each independently are 0 or 1; provided at least one of b or d is 1;

"c" is 0, 1, 2 or 3;

"n" is 0 or 1;

"z" is 0 or 1

R" represents H, F, or forms a double bond with an adjacent atom;

R$^e$ and R$^f$ each independently represent H, halogen, C$_1$-C$_6$ alkyl, (CH$_2$)$_c$—N(C$_1$-C$_6$ alkyl)(C$_1$-C$_6$-alkyl) (CH$_2$)$_c$-monocyclic aryl, (CH$_2$)$_c$-monocyclic heteroaryl, (CH$_2$)$_c$-cycloalkyl or (CH$_2$)$_c$-heterocycloalkyl or R$^e$ and R$^f$ may, if joined to the same atom, represent together with the nitrogen to which they are attached a heterocycloalkyl group; and R$^g$ represents H; halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$, each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl or CF$_3$;

$R^h$ independently represents H, halogen, $C_1$-$C_6$ alkyl, $C_1$-$C_6$ alkoxy, $CF_3$, CN, a heterocycloalkyl group, a cycloalkyl group, a monocyclic aryl group, a monocyclic heteroaryl group, $CNHNR^eR^f$; $COR^e$, $OR^e$, $OC(O)$—$C_1$-$C_6$ alkyl, $(CH_2)_cCOOR^e$, $C(O)NR^eR^f$, $S(O)_2(CH_2)_cN(R^eR^f)$, $SR^e$, $SO(CH_2)_cNR^eR^f$, $S(O)_2$—$R^e$, $SOR^e$, $(CH_2)_cNR^eR^f$, $(CH_2)_cN(R^e)S(O)_2$—$C_1$-$C_6$ alkyl, $(CH_2)_cNR^eS(O)$—$C_1$-$C_6$ alkyl, $NR^eCO$—$R^f$, NH—CO—CO—$OR^e$; each of which may be optionally substituted with one or more groups selected from halogen, OH, $C_1$-$C_6$ alkyl, $NH_2$, $N(C_1$-$C_6$ alkyl)($C_1$-$C_6$ alkyl), heterocycloalkyl, cycloalkyl or $CF_3$;

provided that where XX represents a linker group, then n represents 1, and where XX is not a linker group, then n represents 0; and further provided that the ring comprising A, B, AA, D and E is an aromatic system; and or a pharmaceutically acceptable salt, hydrate, solvate or prodrug thereof.

Another aspect of the present invention relates to compounds according to formula III:

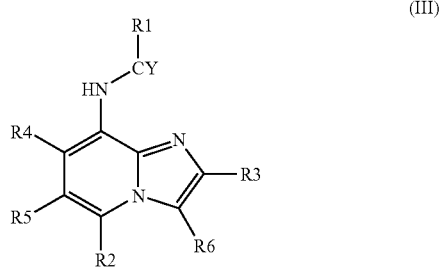

(III)

wherein $R^1$ represents H; halogen; $C_1$-$C_6$ alkyl, $C_1$-$C_6$ alkoxy, $CF_3$, CN, optionally substituted heterocycloalkyl, optionally substituted cycloalkyl, optionally substituted monocyclic aryl, optionally substituted monocyclic heteroaryl, $CNHNR^aR^b$, —$COR^a$, —$OR^a$, —$OC(O)$—$C_1$-$C_6$ alkyl, $(CH_2)_aCOOR^a$, $C(O)NR^aR^b$, $S(O)_2(CH_2)_aN(R^aR^b)$, $SR^a$, $SO(CH_2)_aNR^aR^b$, $S(O)_2$—$R^a$, $SOR^a$, $(CH_2)_aN$-$R^aR^b$; $(CH_2)_aN(R^a)S(O)_2$—$C_1$-$C_6$ alkyl, $(CH_2)_aNR^aS(O)$—$C_1$-$C_6$ alkyl, $NR^aCO$—$R^b$, NH—CO—CO—$OR^a$; each of which may be optionally substituted with one or more groups selected from halogen, OH, $C_1$-$C_6$ alkyl, $NH_2$, $N(C_1$-$C_6$ alkyl)($C_1$-$C_6$-alkyl), optionally substituted heterocycloalkyl, optionally substituted cycloalkyl or $CF_3$;

$R^2$ is selected from substituted or unsubstituted aryl, substituted or unsubstituted heteroaryl;

$R^3$, $R^4$, $R^5$ and $R^6$ are selected from H, OH, OMe, $OC_3H_5$, F, Cl, Me, Et, $SO_2Me$, $CF_3$ and $OCF_3$;

CY is selected from substituted or unsubstituted aryl, substituted or unsubstituted pyridyl, and substituted or unsubstituted pyrimidine;

$R^a$ and $R^b$ each independently represent H, halogen, $C_1$-$C_6$ alkyl, $(CH_2)_a$—$N(C_1$-$C_6$ alkyl)($C_1$-$C_6$-alkyl), $(CH_2)_a$-monocyclic aryl, $(CH_2)_a$-monocyclic heteroaryl, $(CH_2)_a$-cycloalkyl or $(CH_2)_a$ heterocycloalkyl, each of which may be optionally substituted with one or more groups selected from halogen, —OH, $C_1$-$C_6$ alkyl, $C_1$-$C_6$ alkyl-O—$C_1$-$C_6$ alkyl, $C_1$-$C_6$ alkoxy, —$NH_2$, —$NR^cR^d$, $NR^cCOR^d$, heteroaryl, heterocycloalkyl, substituted heterocycloalkyl or —$CF_3$; or $R^a$ and $R^b$ may, if joined to the same atom, represent together with the nitrogen to which they are attached a heterocycloalkyl group which may be optionally substituted with one or more groups selected from halogen, —OH, $C_1$-$C_6$ alkyl, $C_1$-$C_6$ alkoxy, —$NH_2$, —$NR^cR^d$, —$NR^cCOR^d$, —$C(O)$ $NR^cR^d$, optionally substituted aryl, optionally substituted aralkyl, optionally substituted heteroaryl, optionally substituted cycloalkyl or —$CF_3$;

$R^e$ and $R^d$ each independently represent H, $C_1$-$C_6$ alkyl; and

"a" is 0.1, 2 or 3;

or a pharmaceutically acceptable salt, solvate or prodrug thereof; or stereoisomers, isotopic variants or tautomers thereof.

Another aspect of this invention relates to the use of the present compound in a therapeutic method, a pharmaceutical composition, and the manufacture of such composition, useful for the treatment of a disease involving inflammation, and in particular, a disease characteristic of abnormal MMP expression. This invention also relates to processes for the preparation of the present compounds.

Other objects and advantages will become apparent from a consideration of the ensuing detailed description, which proceeds with reference to the following illustrative drawings.

DETAILED DESCRIPTION

Figure 1:
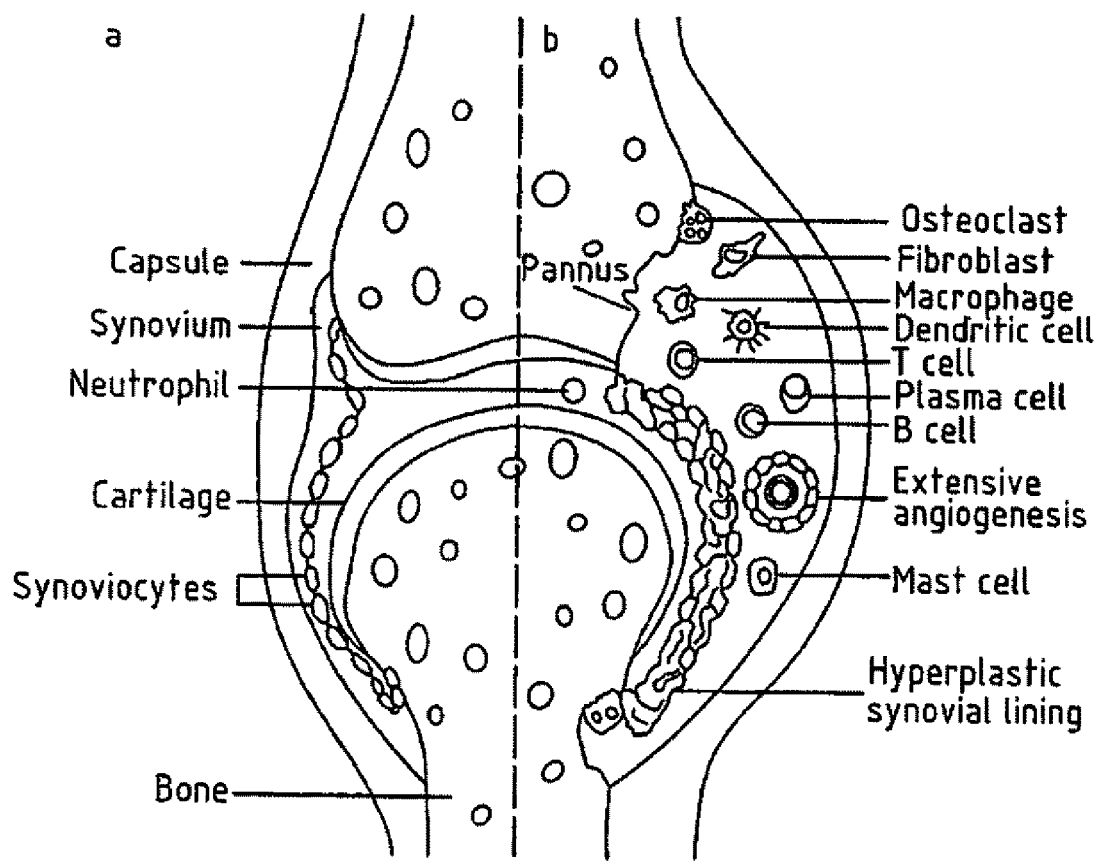
FIG. 1. This diagram shows the striking histological differences between a healthy joint and that of a RA patient.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —$CF_3$, —OH, —$OCF_3$, O—$CHF_2$, $C_1$-$C_6$ alkyl, $C_2$-$C_6$ alkenyl, $C_3$-$C_6$ alkynyl, $C_1$-$C_6$ alkoxy, aryl and di-$C_1$-$C_6$ alkylamino. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' refers to a radical —$C(O)R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

'Acylamino' refers to a radical —$NR^{21}C(O)R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

'Acyloxy' refers to the group —OC(O)R$^{23}$ where R$^{23}$ is hydrogen, alkyl, aryl or cycloalkyl.

'Alkoxy' refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like. Particular alkoxy groups are lower alkoxy, i.e. with between 1 and 6 carbon atoms.

'Substituted alkoxy' includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkoxycarbonylamino' refers to the group —NR$^{25}$C(O)OR$^{26}$, where R$^{25}$ is hydrogen, alkyl, aryl or cycloalkyl, and R$^{26}$ is alkyl or cycloalkyl.

'Alkyl' means straight or branched aliphatic hydrocarbon having 1 to about 20 carbon atoms. Preferred alkyl has 1 to about 12 carbon atoms. More preferred is lower alkyl which has 1 to 6 carbon atoms. Most preferred are groups such as methyl, ethyl and propyl. Branched means that one or more lower alkyl groups such as methyl, ethyl or propyl is attached to a linear alkyl chain. The term $C_1$-$C_6$ alkyl includes both branched and straight chain groups, exemplary straight chain groups include ethyl, propyl, butyl, exemplary branched chain groups include isopropyl, isoamyl, and the like.

'Substituted alkyl' includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

'Alkylene' refers to divalent alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

'Substituted alkylene' includes those groups recited in the definition of 'substituted' herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenyl' refers to monovalent olefinically (unsaturated) hydrocarbon groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

'Substituted alkenyl' includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenylene' refers to divalent olefinically (unsaturated) hydrocarbon groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

'Alkynyl' refers to acetylenically or alkynically (unsaturated) hydrocarbon groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

'Substituted alkynyl' includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkanoyl' or 'acyl' as used herein refers to the group R$^{27}$—C(O)—, where R$^{27}$ is hydrogen or alkyl as defined above.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 5 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly aryl groups include phenyl, naphthyl, indenyl, and tetrahydronaphthyl. The term 'aryl' includes 'bicycloaryl' as defined below.

'Bicycloaryl' refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

'Substituted Aryl' includes those groups recited in the definition of 'substituted' herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

'Fused Aryl' refers to an aryl having two of its ring carbon in common with a second aryl ring or with an aliphatic ring.

'Alkaryl' or 'arylalkyl' refers to an aryl group, as defined above, substituted with one or more alkyl groups, as defined above.

'Substituted Aralkyl' or 'substituted arylalkyl' refers to an alkyl group, as defined above, substituted with one or more aryl groups, as defined above.

'Aryloxy' refers to —O-aryl groups wherein 'aryl' is as defined above.

'Alkylamino' refers to the group alkyl-NR$^{28}$R$^{29}$, wherein each of R$^{28}$ and R$^{29}$ are independently selected from hydrogen and alkyl.

'Arylamino' refers to the group aryl-NR$^{30}$R$^{31}$, wherein each of R$^{30}$ and R$^{31}$ are independently selected from hydrogen, aryl and heteroaryl.

'Alkoxyamino' refers to a radical —N(H)OR$^{32}$ where R$^{32}$ represents an alkyl or cycloalkyl group as defined herein.

'Alkoxycarbonyl' refers to a radical —C(O)-alkoxy where alkoxy is as defined herein.

'Alkylarylamino' refers to a radical —NR$^{33}$R$^{34}$ where R$^{33}$ represents an alkyl or cycloalkyl group and R$^{34}$ is an aryl as defined herein.

'Alkylsulfonyl' refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

'Alkylsulfinyl' refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

'Alkylthio' refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

'Amino' refers to the radical —NH$_2$.

'Substituted amino' includes those groups recited in the definition of 'substituted' herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

'Aminocarbonyl' refers to the group —C(O)NR$^{37}$R$^{37}$ where each R$^{37}$ is independently hydrogen, alkyl, aryl and cycloalkyl, or where the R$^{37}$ groups are joined to form an alkylene group.

'Aminocarbonylamino' refers to the group —NR$^{38}$C(O)NR$^{38}$R$^{38}$ where each R$^{38}$ is independently hydrogen, alkyl, aryl or cycloalkyl, or where two R groups are joined to form an alkylene group.

'Aminocarbonyloxy' refers to the group —OC(O)NR$^{39}$R$^{39}$ where each R$^{39}$ is independently hydrogen, alkyl, aryl or cycloalkyl, or where the R groups are joined to form an alkylene group.

'Arylalkyloxy' refers to an —O-arylalkyl radical where arylalkyl is as defined herein.

'Arylamino' means a radical —NHR$^{40}$ where R$^{40}$ represents an aryl group as defined herein.

'Aryloxycarbonyl' refers to a radical —C(O)—O-aryl where aryl is as defined herein.

'Arylsulfonyl' refers to a radical —S(O)$_2$R$^{41}$ where R$^{41}$ is an aryl or heteroaryl group as defined herein.

'Azido' refers to the radical —N$_3$.

'Carbamoyl' refers to the radical —C(O)N(R$^{42}$)$_2$ where each R$^{42}$ group is independently hydrogen, alkyl, cycloalkyl or aryl, as defined herein, which may be optionally substituted as defined herein. A particular carbamoyl group is —C(O)NH$_2$.

'Carboxy' refers to the radical —C(O)OH.

'Carboxyamino' refers to the radical —N(H)C(O)OH.

'Cycloalkyl' refers to cyclic non-aromatic hydrocarbyl groups having from 4 to about 7 carbon atoms and having a single cyclic ring, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like.

'Substituted cycloalkyl' includes those groups recited in the definition of 'substituted' herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Cycloalkoxy' refers to the group —OR$^{43}$ where R$^{43}$ is cycloalkyl. Such cycloalkoxy groups include, by way of example, cyclopentoxy, cyclohexoxy and the like.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

'Substituted cycloalkenyl' includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Fused Cycloalkenyl' refers to a cycloalkenyl having two of its ring carbon atoms in common with a second aliphatic or aromatic ring and having its olefinic unsaturation located to impart aromaticity to the cycloalkenyl ring.

'Cyanato' refers to the radical —OCN.

'Cyano' refers to the radical —CN.

'Dialkylamino' means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

'Ethenyl' refers to substituted or unsubstituted —(C═C)—.

'Ethylene' refers to substituted or unsubstituted —(C—C)—.

'Ethynyl' refers to —(C≡C)—.

'Halo' or 'halogen' refers to fluoro (F), chloro (Cl), bromo (Br) and iodo (I). Preferred halo groups are either fluoro or chloro.

'Hydrogen' means in the context of a substituent that —H is present at the compound position and also includes its isotope, deuterium.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents include, but are not limited to —X, —R$^{46}$, —O$^-$, ═O, —OR$^{46}$, —SR$^{46}$, —S$^-$, ═S═NR$^{46}$, —CX$_3$, —CF$_3$, —CN, —OCN, —SCN, —NO, —NO$_2$, ═N$_2$, —N$_3$, —S(O)$_2$O$^-$, —S(O)$_2$OH, —S(O)$_2$R$^{46}$, —OS(O)$_2$R$^{46}$—P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

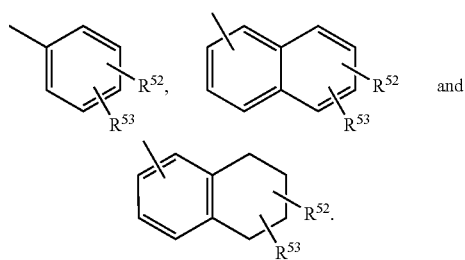

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$-alkyl, Saryl, SOaryl, SO$_2$-aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

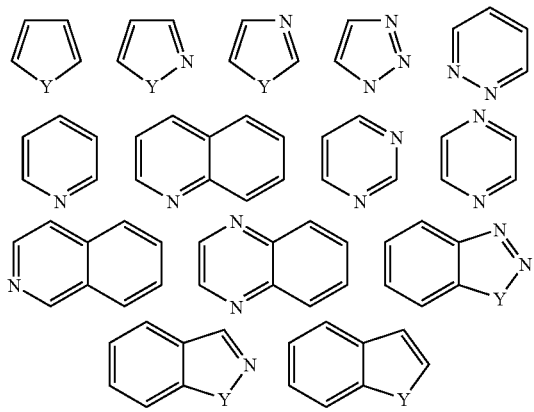

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like. The term 'heteroaryl' includes 'bicycloheteroaryl' as defined below.

'Bicycloheteroaryl' refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoindolone, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

As used herein, the term 'heterocycloalkyl' refers to a 4-7 membered, stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

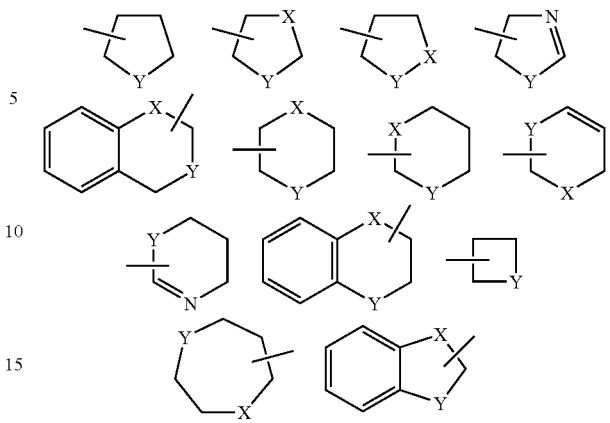

wherein each X is selected from $CR^{58}_2$, $NR^{58}$, O and S; and each Y is selected from $NR^{58}$, O and S; and $R^{58}$ is independently hydrogen, alkyl, cycloalkyl, heterocycloalkyl, aryl, heteroaryl, heteroalkyl or the like. These heterocycloalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. The term 'heterocycloalkyl' includes 'heterocycloalkenyl' as defined below.

Examples of representative heterocycloalkenyls include the following:

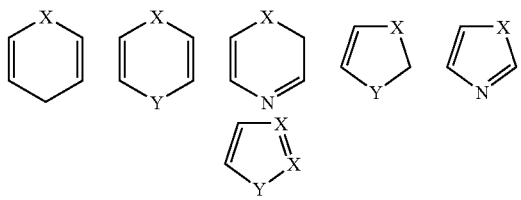

wherein each X is selected from $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

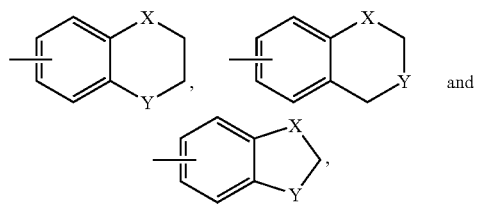

wherein each X is selected from C—$R^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

'Hetero substituent' refers to a halo, O, S or N atom-containing functionality that may be present as an $R^4$ in a $R^4C$ group present as substituents directly on a ring atom of the compounds of this invention or may be present as a substituent in the "substituted" aryl and aliphatic groups present in the compounds.

Examples of hetero substituents include:
-halo,
—$NO_2$, —$NH_2$, —$NHR^{59}$, —$N(R^{59})_2$,
—NRCOR, —$NR^{59}SOR^{59}$, —$NR^{59}SO_2R^{59}$, OH, CN,
—$CO_2H$,
—$R^{59}$—OH, —O—$R^{59}$, —$COOR^{59}$,
—$CON(R^{59})_2$, —$CONROR^{59}$,
—$SO_3H$, —$R^{59}$—S, —$SO_2N(R^{59})_2$,
—$S(O)R^{59}$, —$S(O)_2R^{59}$
wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

'Hydrogen bond donor' group refers to a group containing O—H, N—H functionality. Examples of "hydrogen bond donor" groups include —OH, —$NH_2$, and —NH—$R^{59a}$ and wherein $R^{59a}$ is alkyl, cycloalkyl, aryl, or heteroaryl.

'Dihydroxyphosphoryl' refers to the radical —$PO(OH)_2$.

'Substituted dihydroxyphosphoryl' includes those groups recited in the definition of 'substituted' herein, and particularly refers to a dihydroxyphosphoryl radical wherein one or both of the hydroxyl groups are substituted. Suitable substituents are described in detail below.

'Aminohydroxyphosphoryl' refers to the radical —PO(OH)$NH_2$.

'Substituted aminohydroxyphosphoryl' includes those groups recited in the definition of 'substituted' herein, and particularly refers to an aminohydroxyphosphoryl wherein the amino group is substituted with one or two substituents. Suitable substituents are described in detail below. In certain embodiments, the hydroxyl group can also be substituted.

'Thioalkoxy' refers to the group —$SR^{60}$ where $R^{60}$ is alkyl.

'Substituted thioalkoxy' includes those groups recited in the definition of 'substituted' herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Sulfanyl' refers to the radical HS—. 'Substituted sulfanyl' refers to a radical such as RS— wherein R is any substituent described herein.

'Sulfonyl' refers to the divalent radical —S(O$_2$)—. 'Substituted sulfonyl' refers to a radical such as $R^{61}$—(O$_2$)S— wherein $R^{61}$ is any substituent described herein. "Aminosulfonyl" or "Sulfonamide" refers to the radical $H_2N(O_2)S$—, and "substituted aminosulfonyl" or "substituted sulfonamide" refers to a radical such as $R^{62}_2N(O_2)S$— wherein each $R^{62}$ is independently any substituent described herein.

'Sulfone' refers to the group —$SO_2R^{63}$. In particular embodiments, $R^{63}$ is selected from H, lower alkyl, alkyl, aryl and heteroaryl.

'Sulphonamide' refers to a group of compounds containing the chemical group —$SO_2NH_2$.

'Thioaryloxy' refers to the group —$SR^{64}$ where $R^{64}$ is aryl.
'Thioketo' refers to the group =S.
'Thiol' refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Preventing' or 'prevention' refers to a reduction in risk of acquiring a disease or disorder (i.e., causing at least one of the clinical symptoms of the disease not to develop in a subject that may be exposed to or predisposed to the disease but does not yet experience or display symptoms of the disease). This term encompasses the term 'prophylaxis', which means a measure taken for the prevention of a disease.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated. In particular, with regard to treating an disease involving cartilage or joint degradation and/or inflammation, the terms "therapeutically effective amount" or "effective TAK1-inhibiting amount" is intended to mean that effective amount of an compound of the present invention that will bring about a biologically meaningful decrease in the production of TAK1 in the subject's disease affected tissues, such that cartilage or joint degradation and/or inflammation is meaningfully reduced. A compound having MMP1-inhibiting properties or a "MMP1-inhibiting compound" means a compound of the present invention that provided to a cell in effective amounts is able to cause a biologically meaningful decrease in the production of MMP1 in such cells.

'Treating' or 'treatment' of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

'Compounds of the present invention', and equivalent expressions, are meant to embrace compounds of Formula (I or II) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radio-isotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention relates to a class of imidazolopyridines compounds capable of binding to the active site of a serine/threonine kinase, the expression of which is involved in the pathway resulting in the degradation of extra-cellular matrix (ECM), and which is a causative factor in joint degeneration and diseases involving such degradation and/or inflammation.

In a general aspect, the invention relates to compounds of Formula I:

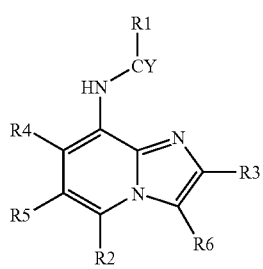

(I)

wherein:
CY represents an aryl or heteroaryl group optionally substituted with one or more groups selected from halogen, OH, $C_1$-$C_6$ alkyl, $C_1$-$C_6$ alkoxy, $NH_2$, $N(C_1$-$C_6$ alkyl)($C_1$-$C_6$-alkyl), heterocycloalkyl, cycloalkyl or $CF_3$;

$R^1$ represents H, halogen, $C_1$-$C_6$ alkyl, $C_1$-$C_6$ alkoxy, $CF_3$, CN, a heterocycloalkyl group, a cycloalkyl group, a monocyclic aryl group, a monocyclic heteroaryl group, —CNHNR$^a$R$^b$, —COR$^a$, —OR$^a$, —OC(O)—$C_1$-$C_6$ alkyl, —(CH$_2$)$_a$COOR$^a$, —C(O)NR$^a$R$^b$, —S(O)$_2$(CH$_2$)$_a$ N(R$^a$R$^b$), —SR$^a$, SO(CH$_2$)$_a$NR$^a$R$^b$, —S(O)$_2$—R$^a$, —SOR$^a$, —(CH$_2$)$_a$NR$^a$R$^b$, —(CH$_2$)$_a$N(R$^a$)S(O)$_2$—$C_1$-$C_6$ alkyl, (CH$_2$)$_a$NR$^a$S(O)—$C_1$-$C_6$ alkyl, —NR$^a$CO—R$^b$, —NH—CO—CO—OR$^a$, each of which may be optionally substituted with one or more groups selected from halogen, OH, $C_1$-$C_6$ alkyl, $NH_2$, $N(C_1$-$C_6$ alkyl)($C_1$-$C_6$-alkyl), optionally substituted heterocycloalkyl, optionally substituted cycloalkyl or $CF_3$;

$R^2$ represents H, aryl or heteroaryl group optionally substituted with one or more groups selected from =O, hydroxy, halogen, CN, $C_1$-$C_6$ alkyl, $C_1$-$C_6$ alkoxy, —CNHNR$^a$R$^b$, —COR$^a$, —OR$^a$, —OC(O)—$C_1$-$C_6$ alkyl, —(CH$_2$)$_a$COOR$^a$, —C(O)NR$^a$R$^b$, —S(O)$_2$(CH$_2$)$_a$ N(R$^a$R$^b$), —SR$^a$, —SO(CH$_2$)$_a$NR$^a$R$^b$, —S(O)$_2$—R$^a$, —SOR$^a$, —(CH$_2$)$_a$NR$^a$R$^b$, —(CH$_2$)$_a$N(R$^a$)S(O)$_2$—R$^b$, —(CH$_2$)$_a$NR$^a$S(O)—$C_1$-$C_6$ alkyl, —NR$^a$CO—R$^b$, —NH—CO—CO—OR$^a$, —NH—CO—NR$^a$R$^b$, each of which may be optionally substituted with one or more groups selected from halogen, —OH, $C_1$-$C_6$ alkyl, —NH$_2$, —N($C_1$-$C_6$ alkyl)($C_1$-$C_6$-alkyl), heterocycloalkyl, cycloalkyl or —CF$_3$;

$R^3$, $R^4$, $R^5$ and $R^6$ each independently represent H, $C_1$-$C_6$ alkyl, halogen, (CH$_2$)$_a$-aryl or (CH$_2$)$_a$ heteroaryl; optionally substituted with one or more groups selected from =O, hydroxy, halogen, CN, $C_1$-$C_6$ alkyl, $C_1$-$C_6$ alkoxy, —CNHNR$^a$R$^b$, —COR$^a$, —OR$^a$, —OC(O)—$C_1$-$C_6$ alkyl, —(CH$_2$)$_a$COOR$^a$, —C(O)NR$^a$R$^b$, —S(O)$_2$(CH$_2$)$_a$N(R$^a$R$^b$), —SR$^a$—SO(CH$_2$)$_a$NR$^a$R$^b$, —S(O)$_2$—R$^a$, —SOR$^a$, —(CH$_2$)$_a$NR$^a$R$^b$, —(CH$_2$)$_a$N(R$^a$)S(O)$_2$—R$^b$, —(CH$_2$)$_a$NR$^a$S(O)—$C_1$-$C_6$ alkyl, —NR$^a$CO—R$^b$, —NH—CO—CO—OR$^a$, —NH—CO—NR$^a$R$^b$; each of which may be optionally substituted with one or more groups selected from halogen, —OH, $C_1$-$C_6$ alkyl, —NH$_2$, —N($C_1$-$C_6$ alkyl)($C_1$-$C_6$-alkyl), heterocycloalkyl, cycloalkyl or —CF$_3$;

$R^a$ and $R^b$ each independently represent H, halogen, $C_1$-$C_6$ alkyl, (CH$_2$)$_a$—N($C_1$-$C_6$ alkyl)($C_1$-$C_6$-alkyl) (CH$_2$)$_a$-monocyclic aryl, (CH$_2$)$_a$-monocyclic heteroaryl, (CH$_2$)$_a$-cycloalkyl or (CH$_2$)$_a$-heterocycloalkyl; each of which may be optionally substituted with one or more groups selected from halogen, —OH, $C_1$-$C_6$ alkyl, $C_1$-$C_6$ alkyl-O—$C_1$-$C_6$ alkyl, $C_1$-$C_6$ alkoxy, —NH$_2$, —NR$^c$R$^d$, NR$^c$COR$^d$, heteroaryl, heterocycloalkyl, substituted heterocycloalkyl or —CF$_3$; or R$^a$ and R$^b$ may, if joined to the same atom, represent together with the nitrogen to which they are attached a heterocycloalkyl group which may be optionally substituted with one or more groups selected from halogen, —OH, $C_1$-$C_6$ alkyl, $C_1$-$C_6$ alkoxy, —NH$_2$, —NR$^c$R$^d$, —NR$^c$COR$^d$, —C(O) NR$^c$R$^d$, optionally substituted aryl, optionally substituted aralkyl, optionally substituted heteroaryl, optionally substituted cycloalkyl or —CF$_3$;

$R^c$ and $R^d$ each independently represent H, $C_1$-$C_6$ alkyl; and

"a" is 0.1, 2 or 3;

or a pharmaceutically acceptable salt, hydrate, solvate or prodrug thereof.

The present invention also relates to compounds having anti-inflammatory properties in a mammalian cell, according to formula (II):

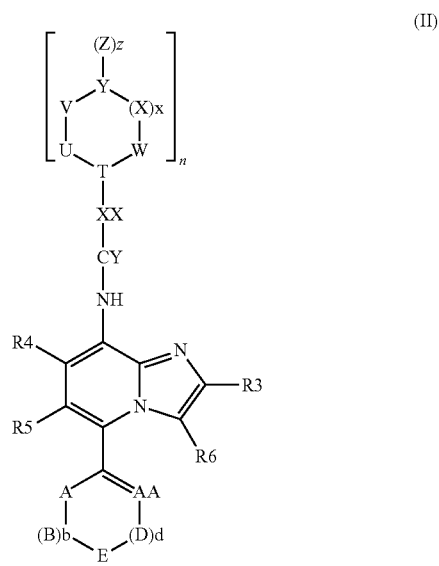

(II)

wherein:
A and B each independently represent CR$^g$R", NR", oxygen or sulphur;

AA represents CR$^g$ or N;

D represents C=O, CR$^g$R" or NR";

E represents N, CR"C(O)R$^g$ or CR"R$^g$;

T represents CR" or N;

U, V, W and X each independently represent CR"R$^h$ or NR";

R$^3$, R$^4$, R$^5$ and R$^6$ each independently represent H, C$_1$-C$_6$ alkyl, halogen, (CH$_2$)$_a$-aryl or (CH$_2$)$_a$-heteroaryl;

CY represents an aryl or heteroaryl group optionally substituted with one or more groups selected from halogen, OH, C$_1$-C$_6$ alkyl, C$_1$-C$_6$ alkoxy, NH$_2$, N(C$_1$-C$_6$ alkyl)(C$_1$-C$_6$-alkyl), heterocycloalkyl, cycloalkyl or CF$_3$;

XX represents a linker group selected from a bond, —C(O)N(CH$_2$)$_c$—, —NC(O)(CH$_2$)$_c$—, S(O)$_2$N(CH$_2$)$_c$—, —NS(O)$_2$(CH$_2$)$_c$—, or XX represents a group selected from CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$, each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl or CF$_3$;

Y represents CR", O or N; with the proviso that when Y represents O, z is 0;

Z represents H, halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl or CF$_3$;

"b" and "d" each independently are 0 or 1; provided at least one of b or d is 1;

"c" is 0, 1, 2 or 3;

"n" is 0 or 1;

"z" is 0 or 1

R" represents H, F, or forms a double bond with an adjacent atom;

R$^e$ and R$^f$ each independently represent H, halogen, C$_1$-C$_6$ alkyl, (CH$_2$)$_c$—N(C$_1$-C$_6$ alkyl)(C$_1$-C$_6$-alkyl) (CH$_2$)$_c$-monocyclic aryl, (CH$_2$)$_c$-monocyclic heteroaryl, (CH$_2$)$_c$- cycloalkyl or (CH$_2$)$_c$-heterocycloalkyl or R$^e$ and R$^f$ may, if joined to the same atom, represent together with the nitrogen to which they are attached a heterocycloalkyl group; and R$^g$ represents H, halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$; NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl or CF$_3$;

R$^h$ independently represents H, halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$; C(O)NR$^e$R$^f$; S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl or CF$_3$;

provided that where XX represents a linker group, then n represents 1, and where XX is not a linker group, then n represents 0; and further provided that the ring comprising A, B, AA, D and E is an aromatic system; and or a pharmaceutically acceptable salt, hydrate, solvate or prodrug thereof.

Another aspect of the present invention relates to compounds according to formula III:

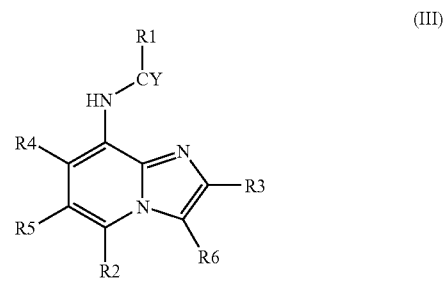

(III)

wherein

R$^1$ represents H, halogen, C$_1$-C$_6$ alkyl, C$_1$-C$_6$ alkoxy, CF$_3$, CN, optionally substituted heterocycloalkyl, optionally substituted cycloalkyl, optionally substituted monocyclic aryl, optionally substituted monocyclic heteroaryl, CNHNR$^a$R$^b$; —COR$^a$; —OR$^a$; —OC(O)—C$_1$-C$_6$ alkyl; (CH$_2$)$_a$COOR$^a$; C(O)NR$^a$R$^b$; S(O)$_2$(CH$_2$)$_a$N(R$^a$R$^b$), SR$^a$, SO(CH$_2$)$_a$NR$^a$R$^b$, S(O)$_2$—R$^a$, SOR$^a$, (CH$_2$)$_a$NR$^a$R$^b$, (CH$_2$)$_a$N(R$^a$)S(O)$_2$—C$_1$-C$_6$ alkyl, (CH$_2$)$_a$NR$^a$S(O)—C$_1$-C$_6$ alkyl, NR$^a$CO—R$^b$; NH—CO—CO—OR$^a$; each of which may be optionally substituted with one or more groups selected from H, halogen, OH, C1-C6 alkyl, NH$_2$, N(C$_1$-C$_6$ alkyl)(C$_1$-C$_6$-alkyl) optionally substituted heterocycloalkyl, optionally substituted cycloalkyl or CF$_3$ R$^2$ is selected from substituted or unsubstituted aryl, substituted or unsubstituted heteroaryl;

R$^3$, R$^4$, R$^5$ and R$^6$ are selected from H, OH, OMe, OC$_3$H$_5$, F, Cl, Me, Et, SO$_2$Me, CF$_3$ and OCF$_3$;

CY is selected from substituted or unsubstituted aryl, substituted or unsubstituted pyridyl, and substituted or unsubstituted pyrimidine;

R$^a$ and R$^b$ each independently represent H, halogen, C$_1$-C$_6$ alkyl, (CH$_2$)$_a$—N(C$_1$-C$_6$ alkyl)(C$_1$-C$_6$-alkyl), (CH$_2$)$_a$-monocyclic aryl, (CH$_2$)$_a$-monocyclic heteroaryl, (CH$_2$)$_a$-cycloalkyl or (CH$_2$)$_a$ heterocycloalkyl, each of which may be optionally substituted with one or more groups selected from halogen, —OH, C$_1$-C$_6$ alkyl, C$_1$-C$_6$ alkyl-O—C$_1$-C$_6$ alkyl, C$_1$-C$_6$ alkoxy, —NH$_2$, —NR$^c$R$^d$, NR$^c$COR$^d$, heteroaryl, heterocycloalkyl, substituted heterocycloalkyl or —CF$_3$; or R$^a$ and R$^b$ may, if joined to the same atom, represent together with the nitrogen to which they are attached a heterocycloalkyl group which may be optionally substituted with one or more groups selected from halogen, —OH, C$_1$-C$_6$ alkyl, $C_1$-$C_6$ alkoxy, —$NH_2$, —$NR^cR^d$, —$NR^cCOR^d$, —$C(O)NR^cR^d$, optionally substituted aryl, optionally substituted aralkyl, optionally substituted heteroaryl, optionally substituted cycloalkyl or —$CF_3$;

$R^c$ and $R^d$ each independently represent H, $C_1$-$C_6$ alkyl; and

"a" is 0.1, 2 or 3;

or a pharmaceutically acceptable salt, solvate or prodrug thereof; or stereoisomers, isotopic variants or tautomers thereof.

In one embodiment, with respect to compounds of formula III, CY is selected from substituted phenyl, substituted pyridyl, and substituted pyrimidine.

In one embodiment, with respect to compounds of formula III, CY is:

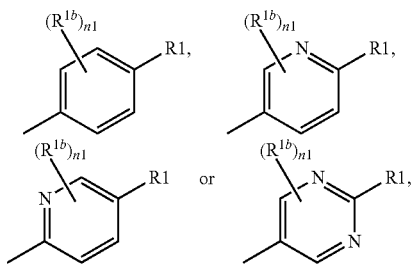

and wherein $R^1$ is as described for formula III; the subscript n1 is selected from 1-4; and each $R^{1b}$ is independently selected from hydrogen, substituted or unsubstituted $C_1$-$C_6$ alkyl, $C_1$-$C_6$ alkoxy, $C_1$-$C_6$ haloalkyl, cyano, and halo.

In one embodiment, the subscript n1 is selected from 1-2; and each $R^{1b}$ is independently selected from hydrogen, alkyl, haloalkyl and halo.

In another embodiment, the subscript n1 is selected from 1-2; and each $R^{1b}$ is independently selected from hydrogen, Me, $CF_3$, Cl and F.

In one embodiment, with respect to compounds of formula III, CY is:

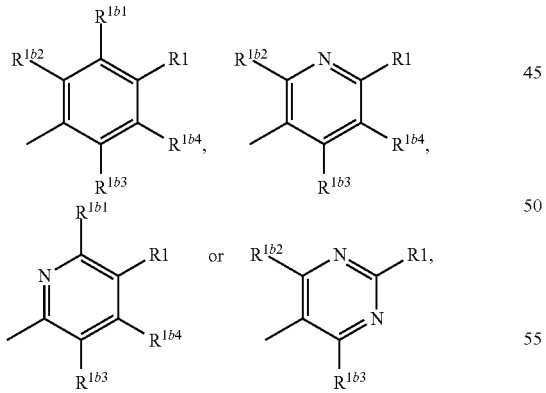

and wherein $R^1$ is as described for formula III; and each $R^{1b1}$, $R^{1b2}$, $R^{1b3}$, and $R^{1b4}$ is independently selected from hydrogen, substituted or unsubstituted $C_1$-$C_6$ alkyl, $C_1$-$C_6$ alkoxy, $C_1$-$C_6$ haloalkyl, cyano, and halo.

In one embodiment, each $R^{1b1}$, $R^{1b2}$, $R^{1b3}$, and $R^{1b4}$ is H.

In another embodiment, one of $R^{1b1}$, $R^{1b2}$, $R^{1b3}$, and $R^{1b4}$ is Me, Cl, F or $CF_3$; and the rest are H.

In another embodiment, two of $R^{1b1}$, $R^{1b2}$, $R^{1b3}$, and $R^{1b4}$ are Cl, or F; and the rest are H.

In one embodiment, with respect to compounds of formula III, $R^3$, $R^4$, $R^5$ and $R^6$ are all H.

In another embodiment, with respect to compounds of formula III, CY is selected from substituted phenyl, substituted pyridyl, and substituted pyrimidine; and $R^i$ is -L-$R^{1a}$; and wherein L is selected from a bond, alkylene, —CO—, and —$SO_2$—; and $R^{1a}$ is selected from substituted or unsubstituted alkyl, substituted or unsubstituted cycloalkyl, substituted or unsubstituted aryl, substituted or unsubstituted heterocycloalkyl, substituted or unsubstituted heteroaryl, substituted or unsubstituted amino, substituted or unsubstituted aralkyl, substituted or unsubstituted heteroarylalkyl and substituted or unsubstituted aminoalkyl.

In one embodiment, with respect to compounds of formula III, the compound is according to formula IIIa, IIIb, IIIc or IIId:

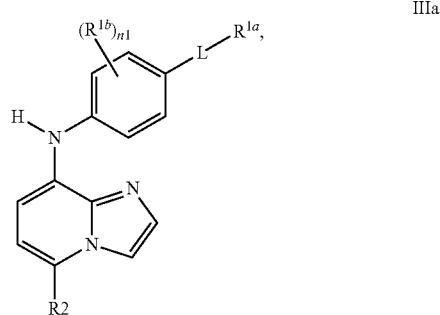

IIIa

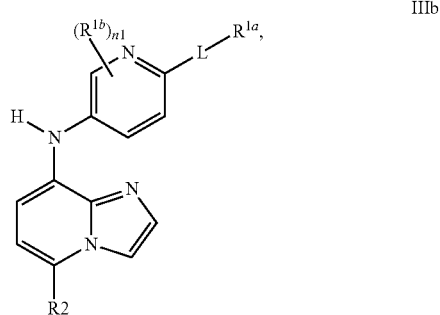

IIIb

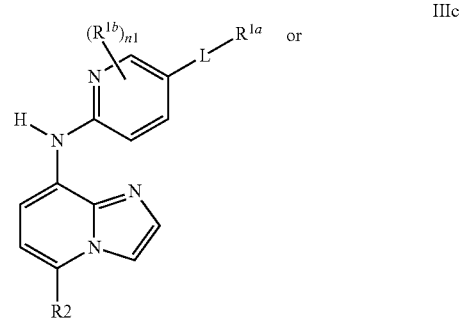

IIIc or

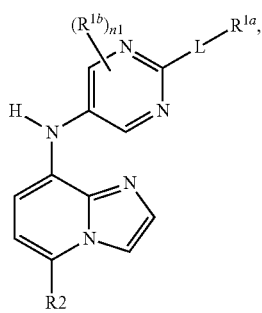

IIId wherein L and $R^{1a}$ are as described above; the subscript n1 is selected from 1-4; and each $R^{1b}$ is independently selected from hydrogen, substituted or unsubstituted $C_1$-$C_6$ alkyl, $C_1$-$C_6$ alkoxy, $C_1$-$C_6$ haloalkyl, cyano, and halo.

In one embodiment, each $R^{1b}$ is independently selected from Me, Et, Pr, iso-Pr, Cl, F, CN, OMe, OEt, $CF_3$, $CF_2CF_3$ and $OCF_3$.

In one embodiment, with respect to compounds of formulae IIIa-IIId, L is —CO— or $SO_2$—; and $R^{1a}$ is selected from substituted or unsubstituted $C_1$-$C_6$ alkyl, substituted or unsubstituted cycloalkyl, substituted or unsubstituted aryl, substituted or unsubstituted heterocycloalkyl, substituted or unsubstituted heteroaryl, substituted or unsubstituted aralkyl, and substituted or unsubstituted heteroarylalkyl.

In one embodiment, with respect to compounds of formulae IIIa-IIId, L is —CO— or $SO_2$—; and $R^{1a}$ is substituted or unsubstituted amino.

In one embodiment, with respect to compounds of formulae IIIa-IIId, L is —CO— or $SO_2$—; and $R^{1a}$ is substituted or unsubstituted alkylamino, substituted or unsubstituted dialkylamino, substituted or unsubstituted cycloalkylamino, substituted or unsubstituted arylamino, substituted or unsubstituted aralkylamino, substituted or unsubstituted heteroarylamino, and substituted or unsubstituted heteroarylalkylamino.

In one embodiment, with respect to compounds of formulae IIIa-IIId, L is a bond, —CO—, $SO_2$, and —$(CH_2)_{m1}$—; the subscript m1 is selected from 1-4; and $R^{1a}$ is

and wherein the ring P is substituted or unsubstituted heterocycloalkyl.

In one embodiment the ring P is substituted or unsubstituted:

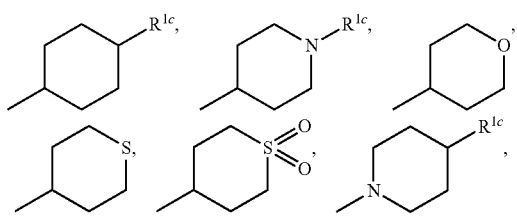

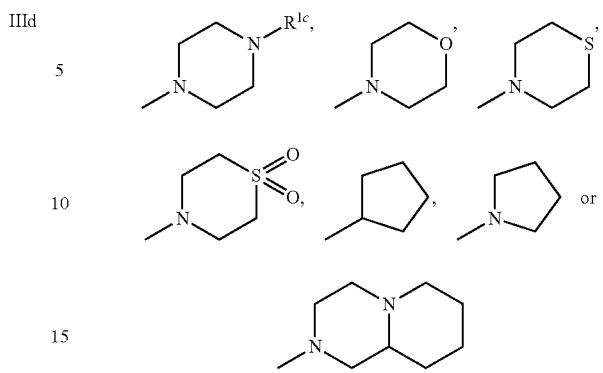

and wherein $R^{1c}$ is selected from hydrogen, halo, hydroxyl, substituted or unsubstituted alkyl, substituted or unsubstituted cycloalkyl or substituted or unsubstituted heterocycloalkyl; provided that $R^{1c}$ is other than halo or hydroxyl when it is attached to N.

In one embodiment, $R^{1c}$ is alkyl or haloalkyl. In another embodiment, $R^{1c}$ is Me, Et, i-Pr, n-Pr, 3-pentyl, 3-methylbutyl, $CF_3$, $CH_2CHF_2$, $CH_2CH_2F$, 1-methylpropyl, cyclopropyl, cyclobutyl, or cyclohexyl.

In one embodiment, $R^{1c}$ is substituted or unsubstituted heterocycloalkyl.

In one embodiment, $R^{1c}$ is substituted or unsubstituted piperidine, piperazine, or pyrrolidine.

In one embodiment, $R^{1c}$ is substituted piperidine, piperazine, or pyrrolidine; and the substitution is selected from $C_1$-$C_6$ alkyl, hydroxyl or halo. In another embodiment, the substitution is selected from Me, OH, Cl and F.

In one embodiment, $R^{1c}$ is

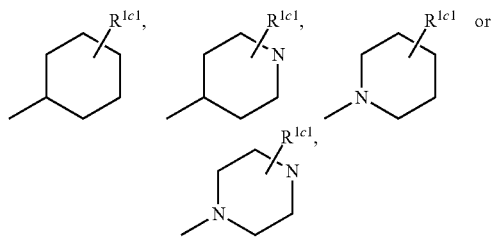

and wherein $R^{1c1}$ is selected from hydrogen, halo, hydroxyl, substituted or unsubstituted $C_1$-$C_6$ alkyl, provided that $R^{1c1}$ is other than halo or hydroxyl when it is attached to N.

In another embodiment, $R^{1c}$ is

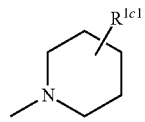

and wherein $R^{1c1}$ is selected from hydrogen, halo, hydroxyl, substituted or unsubstituted alkyl.

In another embodiment, $R^{1c}$ is

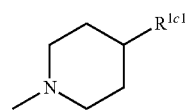

and wherein $R^{1c1}$ is selected from hydrogen, halo, hydroxyl, substituted or unsubstituted alkyl.

In one embodiment, $R^{1c1}$ is H, Me, Cl or F.

In one embodiment, with respect to compounds of formulae IIIa-IIId, $R^{1a}$ is ring P substituted with $(R^{1d})_{n2}$; and wherein each $R^{1d}$ is H, $C_1$-$C_6$ alkyl, halo, $C_1$-$C_6$ haloalkyl, CN, $C_1$-$C_6$ alkoxy or $C_1$-$C_6$ haloalkoxy and n2 is 0, 1, or 2.

In one embodiment, each $R^{1d}$ is independently selected from H, Me, Et, Pr, iso-Pr, Cl, F, CN, OMe, OEt, $CF_3$, $CF_2CF_3$ or $OCF_3$.

In one embodiment, with respect to compounds of formulae IIIa-IIId, $R^{1a}$ is

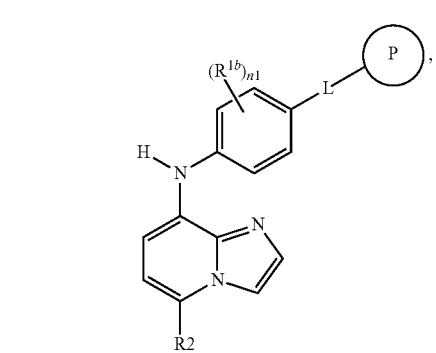

and wherein $R^{1c1}$ is H, OH or Me.

In one embodiment, with respect to compounds of formulae IIIa-IIId, the compound is according to formula IVa, IVb, IVc, or IVd:

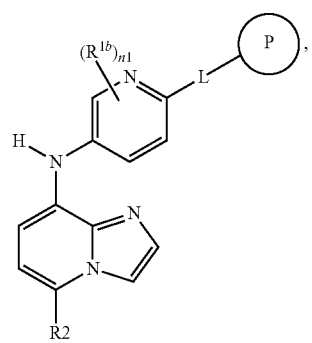

IVa

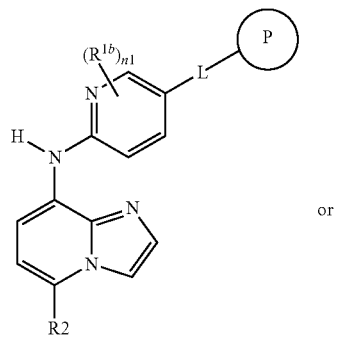

IVb

IVc

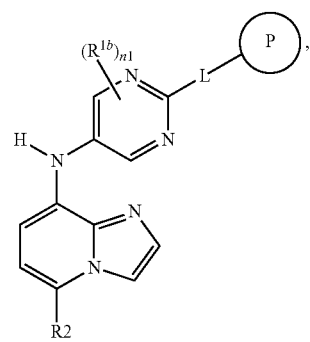

or

IVd and wherein L is bond, —CO—, $SO_2$, and —$(CH_2)_{m1}$—; the subscript m1 is selected from 1-4; the ring P is as described in the preceding paragraph; each $R^{1b}$ is independently selected from hydrogen, substituted or unsubstituted $C_1$-$C_6$ alkyl, $C_1$-$C_6$ alkoxy, cyano, and halo; the subscript n1, is selected from 1-4; and $R^2$ is independently selected from substituted or unsubstituted aryl and heteroaryl; or a pharmaceutically acceptable salt, solvate or prodrug thereof; and stereoisomers, isotopic variants and tautomers thereof.

In one embodiment, the compound is according to formula IVa.

In one embodiment, with respect to compounds of formulae IVa-IVd, L is a bond.

In another embodiment, with respect to compounds of formulae IVa-IVd, L is —CO—.

In another embodiment, with respect to compounds of formulae IVa-IVd, L is —$SO_2$—.

In another embodiment, with respect to compounds of formulae IVa-IVd, L is —$CH_2$—.

In one embodiment, with respect to compounds of formulae IVa-IVd, the ring P is substituted or unsubstituted pyrrolidine, thiomorpholine, piperidine, morpholine or piperazine.

In one embodiment, with respect to compounds of formulae IVa-IVd, the ring P is substituted or unsubstituted piperidine, morpholine or piperazine.

In one embodiment, with respect to compounds of formulae IVa-IVd, each $R^{1b}$ is H.

In another embodiment, with respect to compounds of formulae IVa-IVd, the subscript n1 is 1 and $R^{1b}$ is selected from Me, Et, Pr, iso-Pr, Cl, F, CN, OMe, or $CF_3$.

In another embodiment, with respect to compounds of formulae IVa-IVd, the compound is according to formula Va, Vb, Vc, Vd, Ve, Vf, Vg, Vh or Vi:

Va 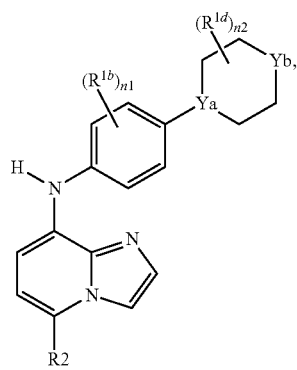
Vb 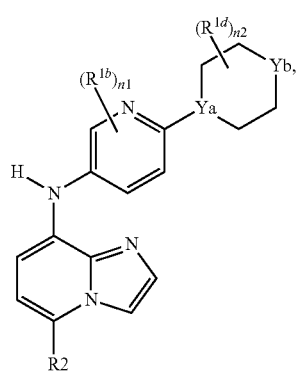
Vc 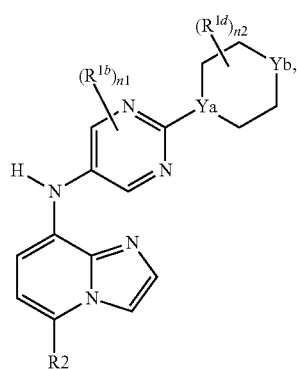
Vd 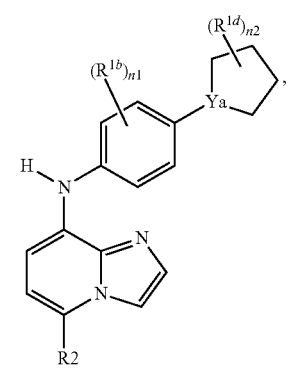
-continued
Ve 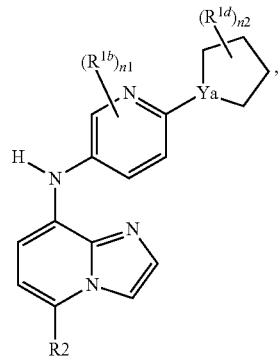
Vf 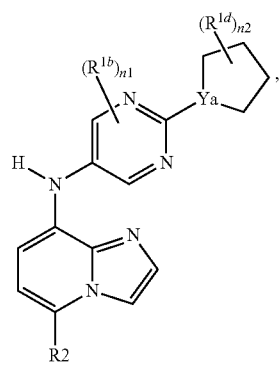
Vg 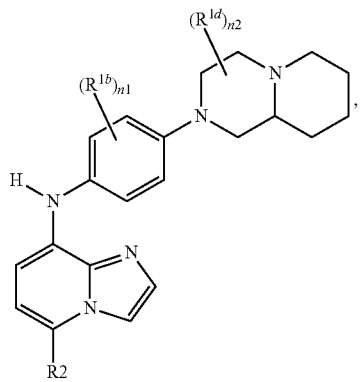
Vh 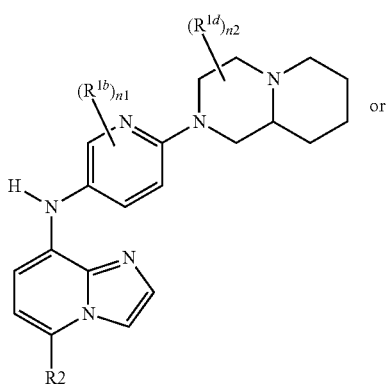
or

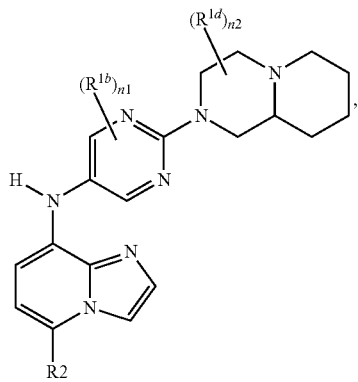

Vi

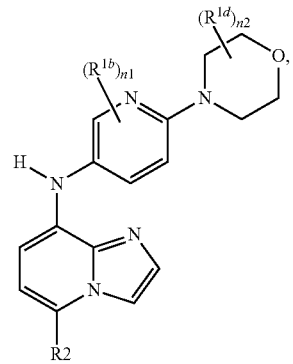

VIb

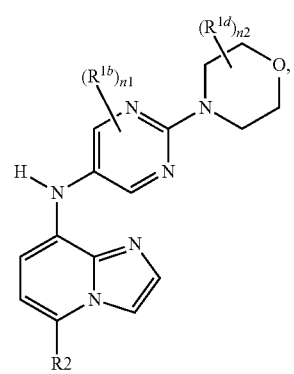

VIc and wherein R² is as described for formula III; Ya is C or N, Yb is C—R$^{1c}$, O, S, SO$_2$ or N—R$^{1c}$, each R$^{1b}$ is independently selected from Me, Et, Pr, iso-Pr, Cl, F, CN, OMe, OEt, CF$_3$, CF$_2$CF$_3$ or OCF$_3$ and R$^{1c}$ is selected from hydrogen, substituted or unsubstituted C$_1$-C$_6$ alkyl, substituted or unsubstituted cycloalkyl or substituted or unsubstituted heterocycloalkyl; each R$^{1d}$ is independently selected from H, Me, Et, Pr, iso-Pr, Cl, F, CN, OMe, OEt, CF$_3$, CF$_2$CF$_3$ or OCF$_3$, each n1 is independently an integer between 0 and 2 and each n2 is independently an integer between 0 and 2.

In one embodiment, with respect to compounds of formulae Va-Vi, Ya is N.

In one embodiment, with respect to compounds of formulae Va-Vi, Yb is O.

In one embodiment, with respect to compounds of formulae Va-Vc, Yb is N—R$^{1c}$.

In one embodiment, with respect to compounds of formulae Va-Vc, Yb is CR$^{1c}$ and Ya is N.

In one embodiment, with respect to compounds of formulae Va-Vc, Ya is N, Yb is CR$^{1c}$ and R$^{1c}$ is substituted or unsubstituted piperidine.

In another embodiment, with respect to compounds of formulae Va-Ve, the compound is according to formula VIa, VIb, VIc, VId, Ve, VIf, VIg, VIh, VIi, VIj, VIk or VII:

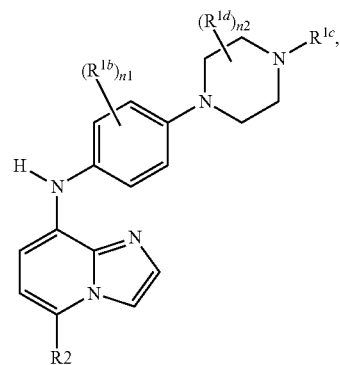

VId

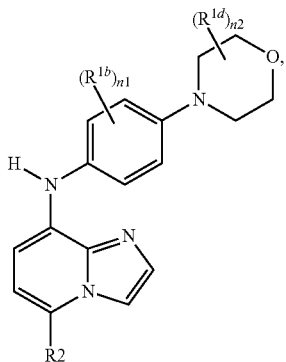

VIa

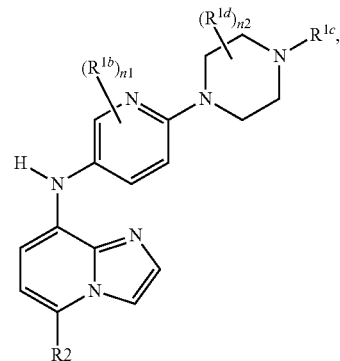

VIe

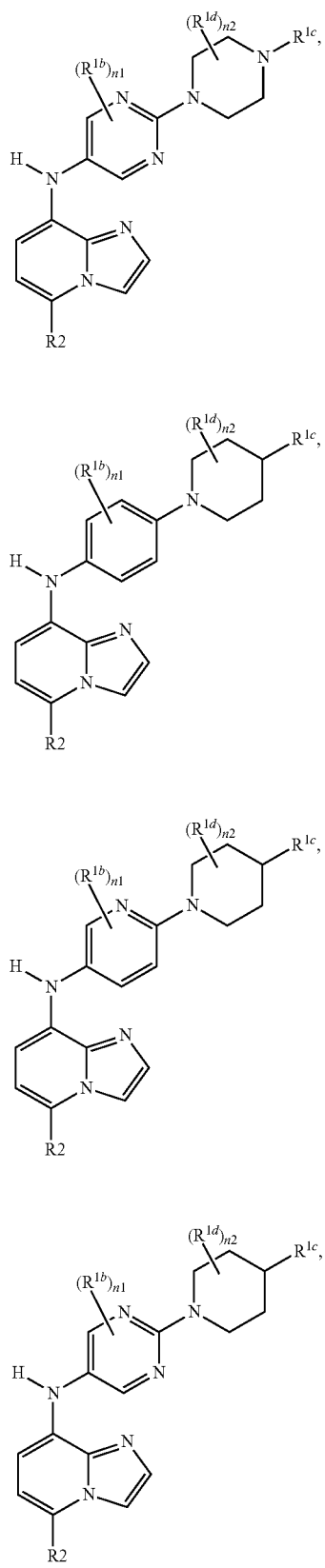
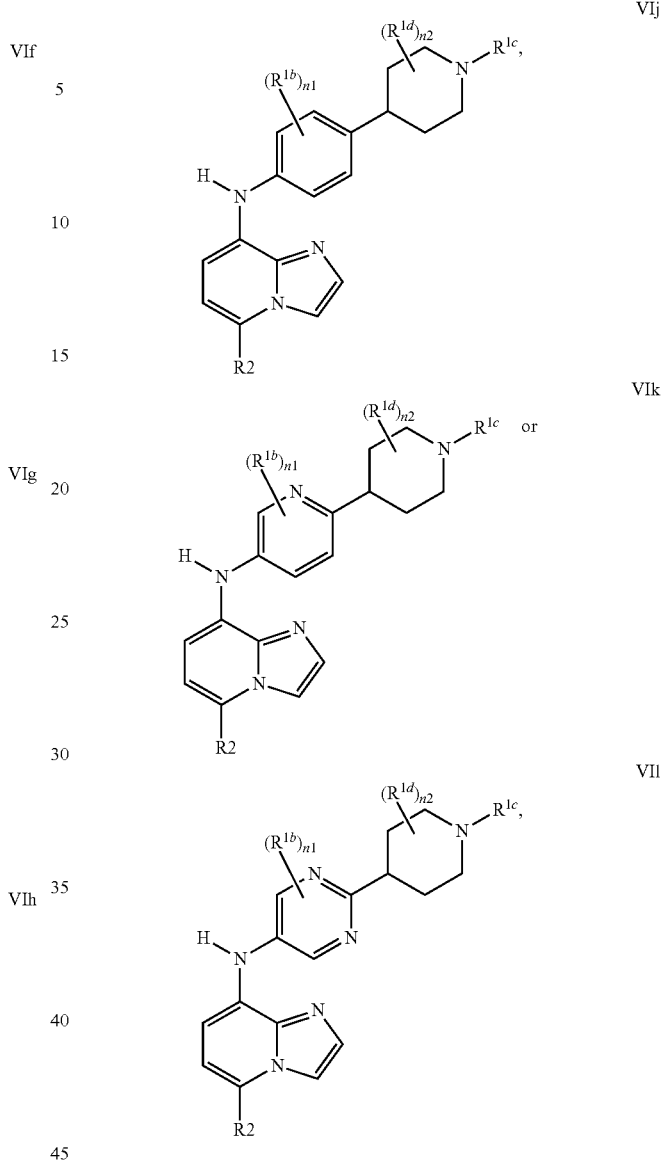

and wherein $R^2$ is as described for formula III; each $R^{1b}$ is independently selected from Me, Et, Pr, iso-Pr, Cl, F, CN, OMe, OEt, $CF_3$, $CF_2CF_3$ or $OCF_3$ and $R^{1c}$ is selected from hydrogen, substituted or unsubstituted alkyl or substituted or unsubstituted cycloalkyl or substituted or unsubstituted heterocycloalkyl; each $R^{1d}$ is independently selected from H, Me, Et, Pr, iso-Pr, Cl, F, CN, OMe, OEt, $CF_3$, $CF_2CF_3$ or $OCF_3$, each n1 is independently an integer between 0 and 2 and each n2 is independently an integer between 0 and 2.

In one embodiment the compounds are according formulae VIa, VId, VIg or VIh.

In one embodiment, with respect to compounds of formulae VIa-VIl, $R^{1c}$ is H.

In another embodiment, with respect to compounds of formulae VId-VIl, $R^{1c}$ is substituted or unsubstituted alkyl, substituted or unsubstituted cycloalkyl, or substituted or unsubstituted heterocycloalkyl.

In another embodiment, with respect to compounds of formulae VId-VIl, $R^{1c}$ is Me, Et, Pr, i-Pr, t-Bu, i-Bu, i-pentyl, cyclopropyl, cyclobutyl, cyclopentyl, cyclohexyl, cyclopropylmethyl, or piperidine.

In another embodiment, with respect to compounds of formulae VId-VIl, $R^{1c}$ is piperidine substituted by one or more OH, Me or F.

In another embodiment, with respect to compounds of formulae VIg-VIl, $R^{1c}$ is piperidine substituted by one or more OH, Me or F.

In another embodiment, with respect to compounds of formulae Va-Ve, the compound is according to formula VIm, VIn, or VIo:

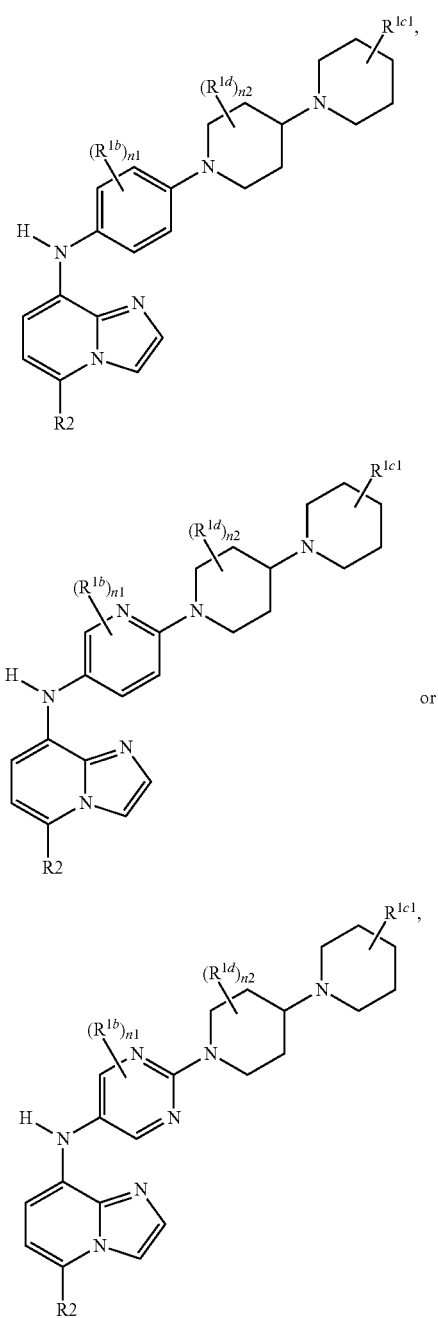

and wherein $R^2$ is as described for formula III; $R^{1b}$, $R^{1d}$, n1 and n2 are as described for formulae Va-Vi; and $R^{1c1}$ is H, Me, F, Cl, or OH.

In another embodiment, with respect to compounds of formulae IVa-IVd, the compound is according to formula VIIa, VIIb, VIIc, VIId, VIIe, or VIIf:

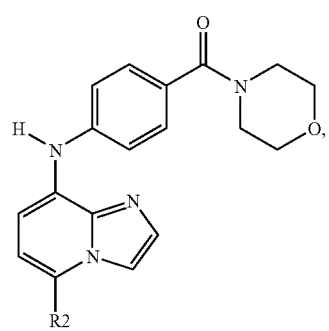

VIIa

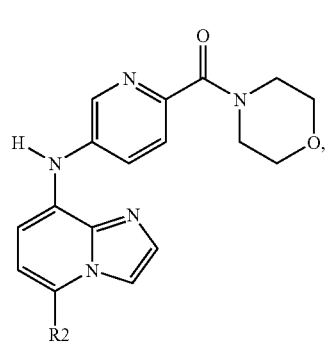

VIIb

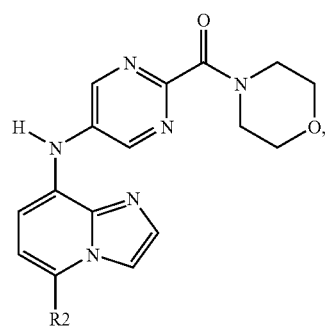

VIIc

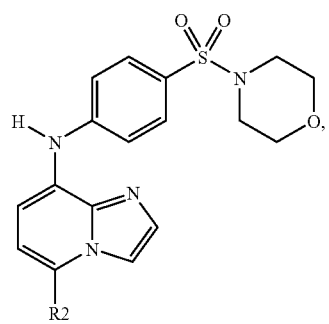

VIId

VIIe
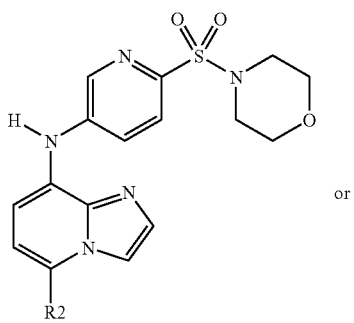
or
VIIf
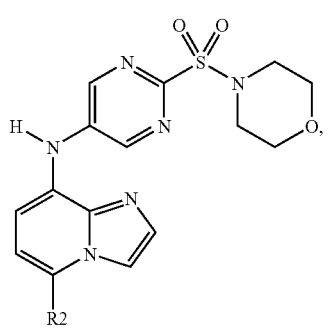
and wherein R² is as described for formula III.
In one embodiment, the compound is according to Formula VIa or VId.
In another embodiment, with respect to compounds of formulae IVa-IVd, the compound is according to formula VIIIa, VIIIb, VIIIc, VIIId, VIIIe, VIIIf, VIIIg, VIIIh, VIIIi:
VIIIa
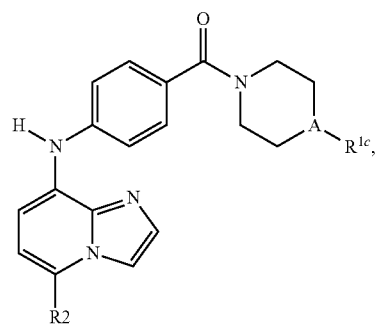
VIIIb

VIIIc
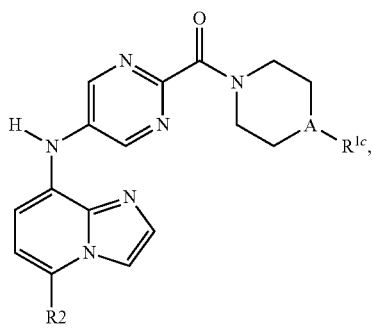
VIIId
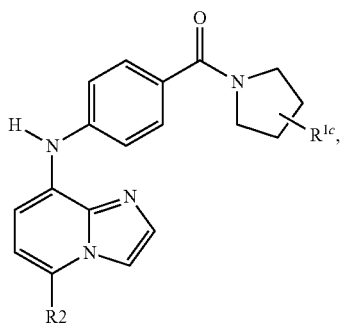
VIIIe
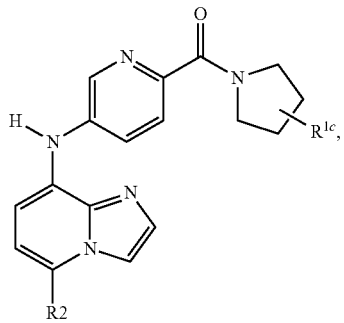
VIIIf
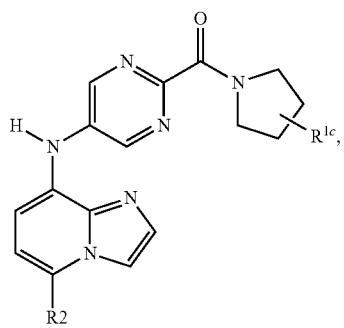
VIIIg
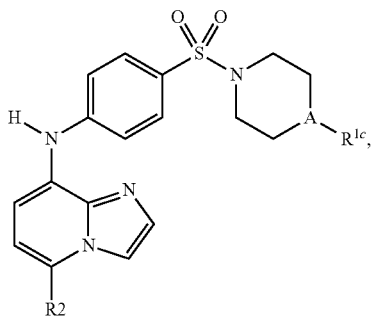

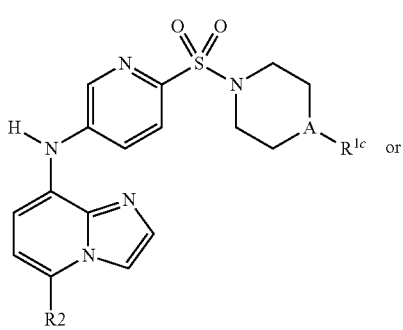

VIIIh

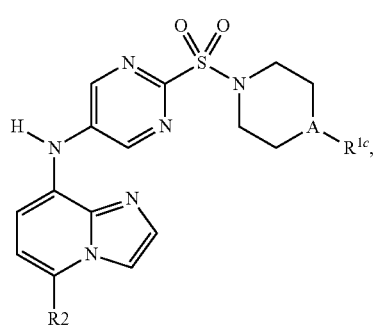

VIIIi and wherein $R^2$ is as described for formula III; A is CH or N; and $R^{1c}$ is hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, the compounds are according to Formulae VIIIa, VIIId or VIIIg In one embodiment, with respect to compounds of formulae VIIIa-VIIIi, $R^{1c}$ is H.

In another embodiment, with respect to compounds of formulae VIIIa-VIIIi, $R^{1c}$ is substituted or unsubstituted alkyl or substituted or unsubstituted cycloalkyl.

In another embodiment, with respect to compounds of formulae VIIIa-VIIIi, $R^{1c}$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae VIIIa-VIIIi, $R^{1c}$ is substituted or unsubstituted aryl, aralkyl or heteroaryl.

In another embodiment, with respect to compounds of formulae VIIIa-VIIIi, $R^{1c}$ is substituted or unsubstituted phenyl, benzyl or pyridyl.

In another embodiment, with respect to compounds of formula III, the compound is according to formula IXa, or IXb:

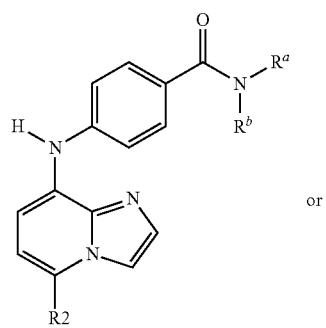

IXa

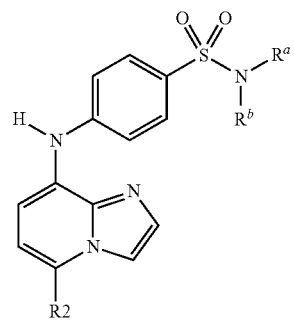

IXb and wherein $R^2$ is as described for formula III; each $R^a$ and $R^b$ is independently hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, with respect to compounds of formulae IXa-IXb, $R^a$ is H.

In another embodiment, with respect to compounds of formulae IXa-IXb, $R^a$ is Me, Et or n-Pr.

In another embodiment, with respect to compounds of formulae IXa-IXb, $R^b$ is substituted or unsubstituted alkyl or substituted or unsubstituted cycloalkyl.

In another embodiment, with respect to compounds of formulae IXa-IXb, $R^b$ is Me, Et, Pr, i-Pr, t-Bu, i-Bu, i-pentyl, cyclopropyl, cyclobutyl, cyclopentyl, cyclohexyl, or cyclopropylmethyl.

In another embodiment with respect to compounds of formulae IXa-IXb, $R^b$ is substituted or unsubstituted heterocycloalkyl.

In another embodiment with respect to compounds of formulae IXa-IXb, $R^b$ is substituted pyrrolidine.

In another embodiment with respect to compounds for formulae IXa, $R^b$ is pyrrolidine substituted by benzyl.

In another embodiment, with respect to compounds of formulae IXa-IXb, $R^b$ is substituted or unsubstituted aryl, aralkyl or heteroaryl.

In another embodiment, with respect to compounds of formulae IXa-IXb, $R^b$ is substituted or unsubstituted phenyl, benzyl or pyridyl.

In one embodiment, with respect to compounds of formulae III-IXb, $R^2$ is selected from substituted or unsubstituted aryl.

In another embodiment, with respect to compounds of formulae III-IXb, $R^2$ is selected from substituted or unsubstituted phenyl.

In another embodiment, with respect to compounds of formulae III-IXb, $R^2$ is selected from substituted or unsubstituted heteroaryl.

In another embodiment, with respect to compounds of formulae III-IXb, $R^2$ is selected from substituted or unsubstituted phenyl, pyridyl, indolyl, isoindolyl, pyrrolyl, furanyl, thienyl, pyrazolyl, oxazolyl, and thiazolyl.

In another embodiment, with respect to compounds of formulae III-IXb, $R^2$ is

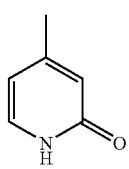

In another embodiment, with respect to compounds of formulae III-IXb, $R^2$ is

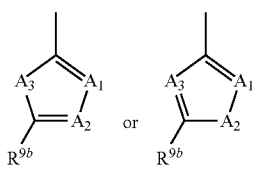

and each of $A^1$, $A^2$ and $A^3$ is independently selected from S, O, N, $NR^{9a}$, and $CR^{9a}$; each of $R^{9a}$ is independently H or substituted or unsubstituted $C_1$-$C_6$ alkyl; and $R^{9b}$ is $CONH_2$, CONHMe, or CN.

In another embodiment, with respect to compounds of formulae III-IXb, $R^2$ is

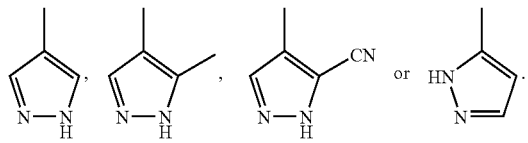

In another embodiment, with respect to compounds of formulae III-IXb, $R^2$ is

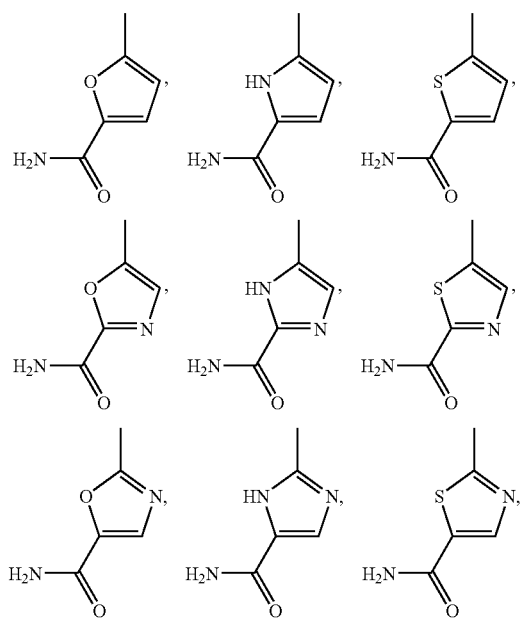

In another embodiment, with respect to compounds of formulae III-IXb, $R^2$ is

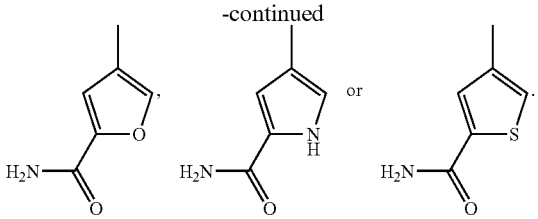

In another embodiment, with respect to compounds of formulae III-IXb, $R^2$ is

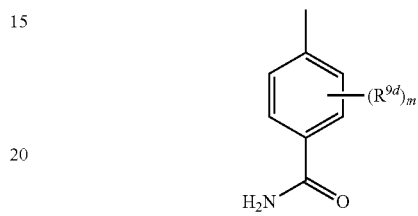

and wherein the subscript m is selected from 1-4 and each $R^{9d}$ is independently H, substituted or unsubstituted $C_1$-$C_6$ alkyl or halo. In another embodiment, with respect to compounds of formulae III-IXb, $R^2$ is

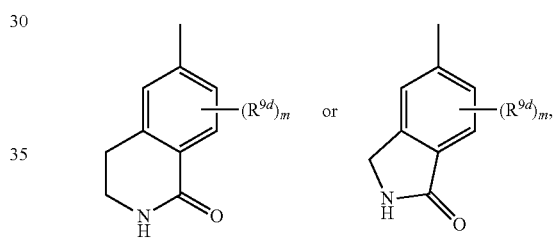

and wherein the subscript m is selected from 1-4 and each $R^{9d}$ is independently H, substituted or unsubstituted $C_1$-$C_6$ alkyl or halo.

In another embodiment, with respect to compounds of formulae III-IXb, $R^2$ is

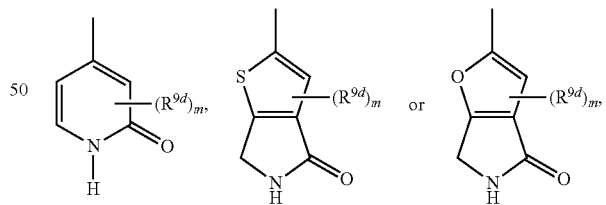

and wherein the subscript m is selected from 1-3 and each $R^{9d}$ is independently H, substituted or unsubstituted $C_1$-$C_6$ alkyl or halo.

In one embodiment, with respect to compounds of formulae III-IXb, $R^2$ is as described above and each $R^{9d}$ is H.

In another embodiment, with respect to compounds of formulae III-IXb, $R^2$ is as described above; and m is 1 or 2; and each $R^{9d}$ is Me, Cl or F.

In another embodiment, with respect to compounds of formula III, the compound is according to Formulae Xa, Xb or Xc:

Xa

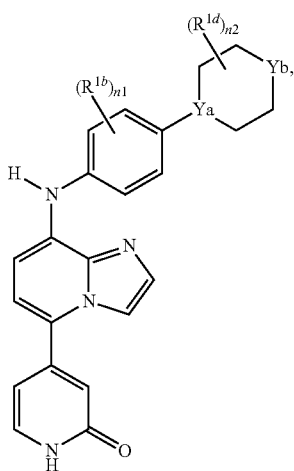

Xb

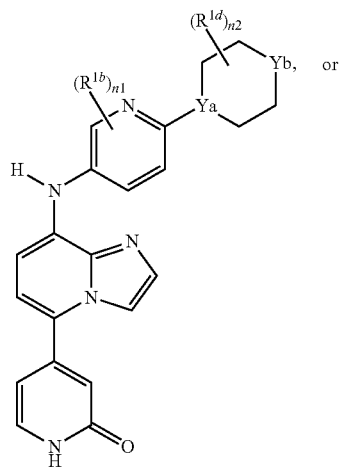

or

Xc

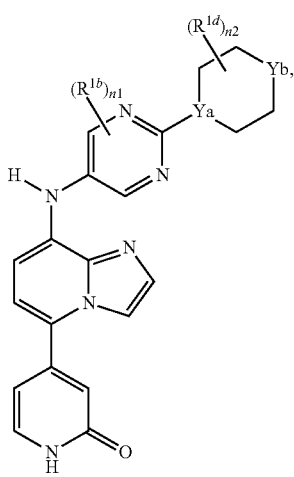

wherein Ya is C or N, Yb is C—R$^b$, O, S, SO$_2$ or N—R$^b$, each R$^{1b}$ is independently selected from Me, Et, Pr, iso-Pr, Cl, F, CN, OMe, OEt, CF$_3$, CF$_2$CF$_3$ or OCF$_3$ and R$^{1c}$ is selected from hydrogen, substituted or unsubstituted alkyl, substituted or unsubstituted cycloalkyl or substituted or unsubstituted heterocycloalkyl; each R$^{1d}$ is independently selected from H, Me, Et, Pr, iso-Pr, Cl, F, CN, OMe, OEt, CF$_3$, CF$_2$CF$_3$ or OCF$_3$, each n1 is independently an integer between 0 and 2 and each n2 is independently an integer between 0 and 2.

In another embodiment, with respect to compounds of Formula Xa-Xc, Ya is N.

In another embodiment, with respect to compounds of Formula Xa-Xc, Ya is C.

In one embodiment, with respect to compounds of formulae Xa-Xc, Yb is O.

In one embodiment, with respect to compounds of formulae Xa-Xc, Yb is N—R$^{1c}$.

In one embodiment, with respect to compounds of formulae Xa-Xc, Yb is CR$^{1c}$ and Ya is N.

In one embodiment, with respect to compounds of formulae Xa-Xc, Ya is N, Yb is CR$^{1c}$ and R$^{1c}$ is substituted or unsubstituted piperidine.

In another embodiment, with respect to compounds of formula III, the compound is according to formula XIa, XIb, XIc, XId, XIe, XIf, XIg, XIh, XIi, XIj, XIk or XIl:

XIa

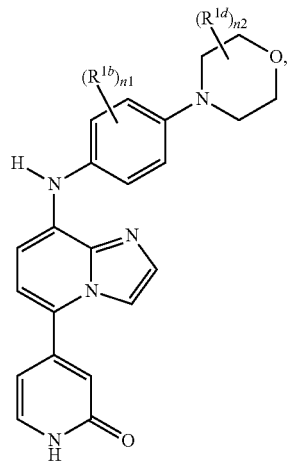

XIb

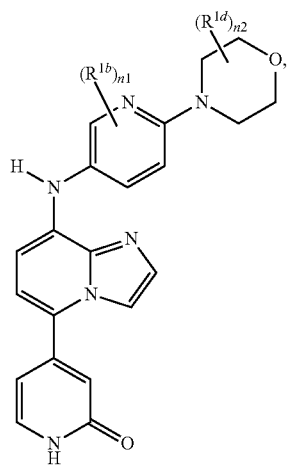

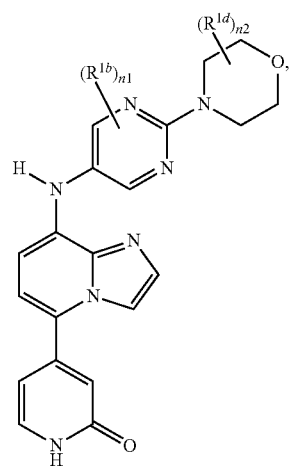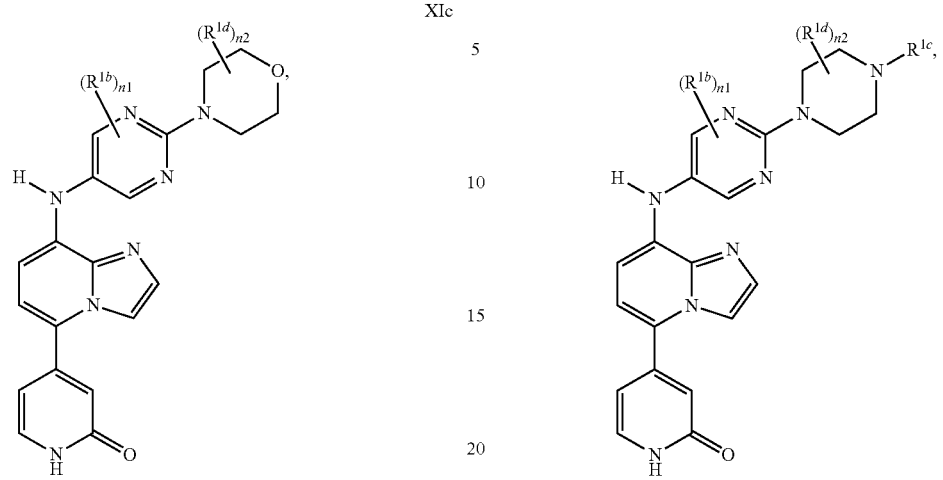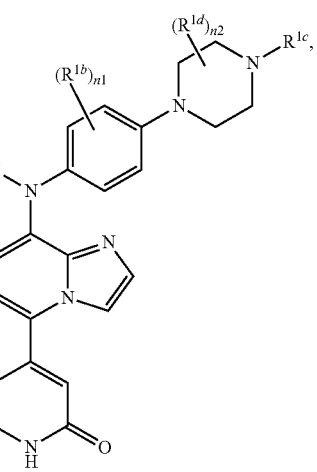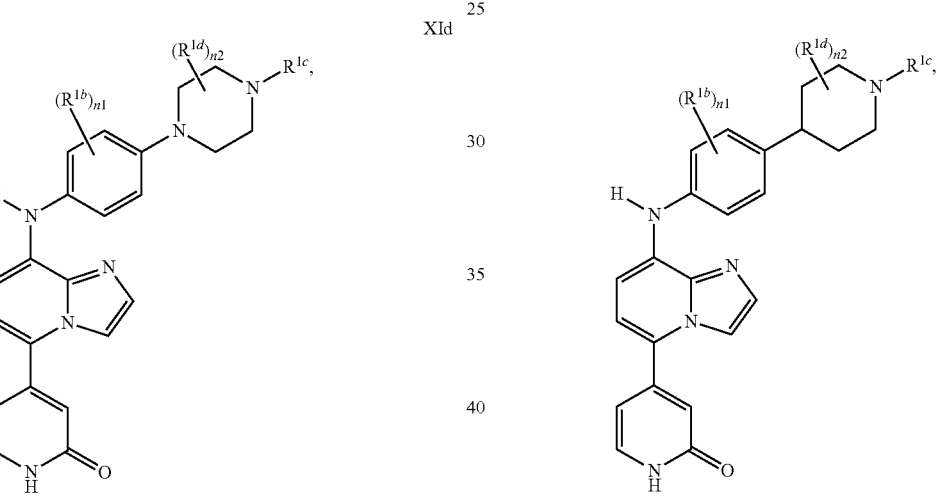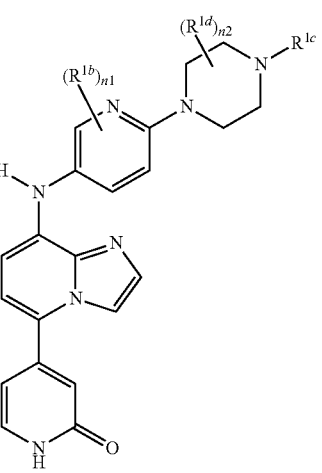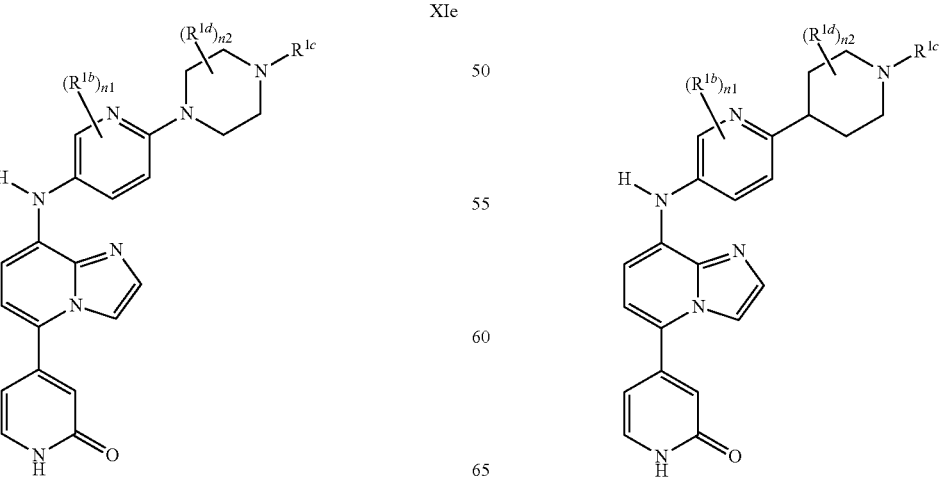

XIi 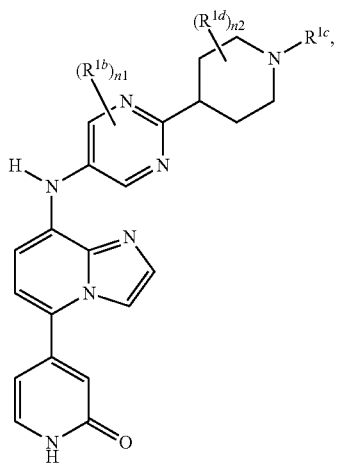

XIj 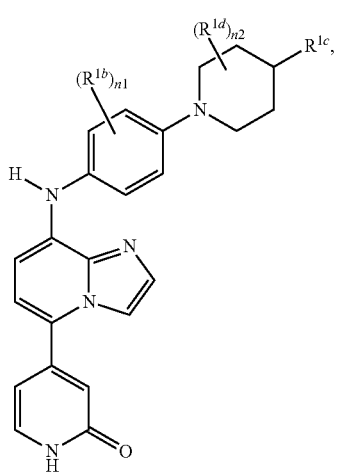

XIk 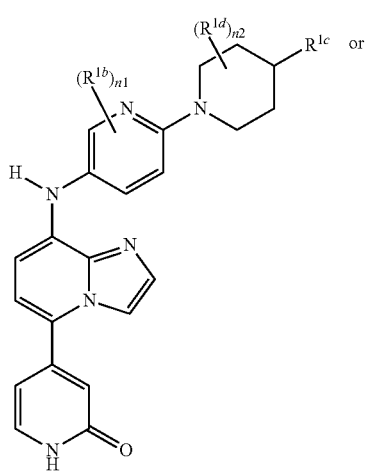

XIl 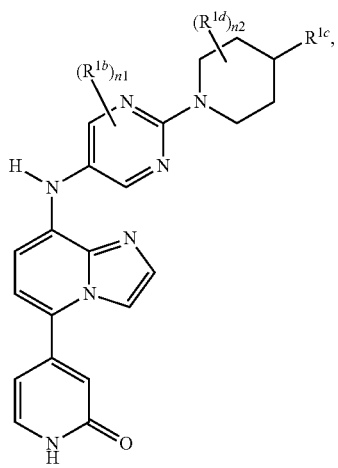

each $R^{1b}$ is independently selected from Me, Et, Pr, iso-Pr, Cl, F, CN, OMe, OEt, $CF_3$, $CF_2CF_3$ or $OCF_3$ and $R^{1c}$ is selected from hydrogen, substituted or unsubstituted alkyl or substituted or unsubstituted cycloalkyl or substituted or unsubstituted heterocycloalkyl; each $R^{1d}$ is independently selected from H, Me, Et, Pr, iso-Pr, Cl, F, CN, OMe, OEt, $CF_3$, $CF_2CF_3$ or $OCF_3$, each n1 is independently an integer between 0 and 2 and each n2 is independently an integer between 0 and 2.

In one embodiment, the compounds are according to formulae XIa, XId, XIg or XIj.

In one embodiment, with respect to compounds of formulae XIc-XIl, $R^{1c}$ is H.

In another embodiment, with respect to compounds of formulae XIc-XIl, $R^{1c}$ is substituted or unsubstituted $C_1$-$C_6$ alkyl, substituted or unsubstituted cycloalkyl or substituted or unsubstituted heterocycloalkyl.

In another embodiment, with respect to compounds of formulae IXa-IXf, $R^{1c}$ is Me, Et, Pr, i-Pr, t-Bu, i-Bu, i-pentyl, cyclopropyl, cyclobutyl, cyclopentyl, cyclohexyl, cyclopropylmethyl or piperidine.

In another embodiment, with respect to compounds of formulae XId-XIl, $R^{1c}$ is piperidine substituted by one or more OH, Me or F.

In another embodiment, with respect to compounds of formulae XIg-XIl, $R^{1c}$ is piperidine substituted by one or more OH, Me or F.

In another embodiment, with respect to compounds of formula III, the compound is according to formula XIm, XIn, or XIo,

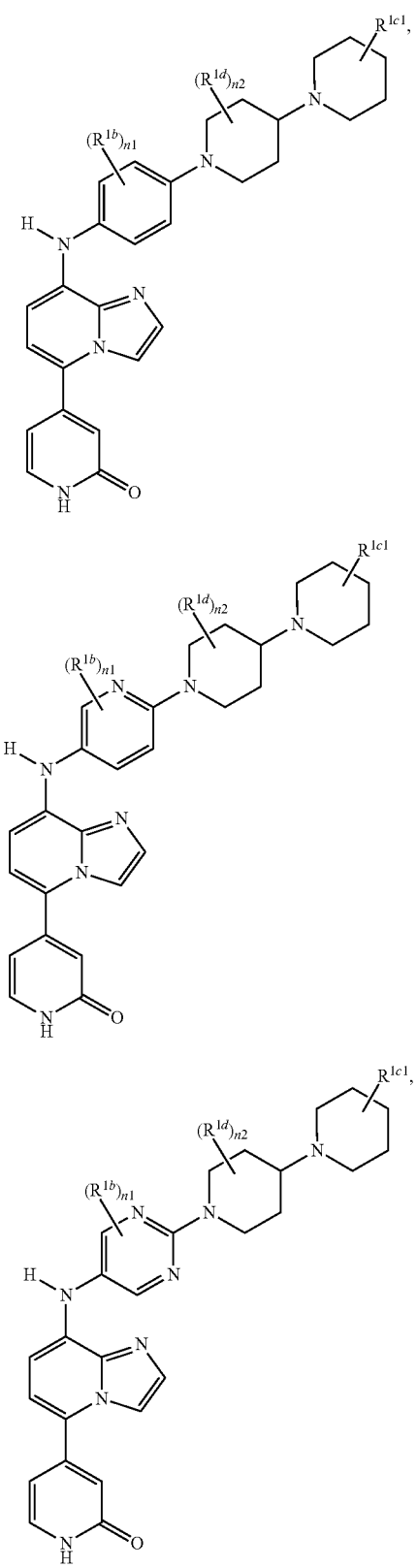
In another embodiment, with respect to compounds of formula III, the compound is according to formula XIIa, XIIb, XIIc, XIId, XIIe, or XIIf:
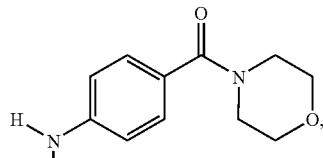
XIIa
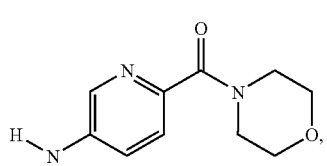
XIIb
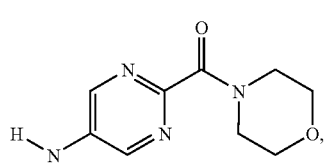
XIIc
and wherein $R^2$ is as described for formula III; $R^{1b}$, $R^{1d}$, n1 and n2 are as described for formulae Va-Vi; and $R^{1c1}$ is H, Me, F, Cl, or OH.

-continued
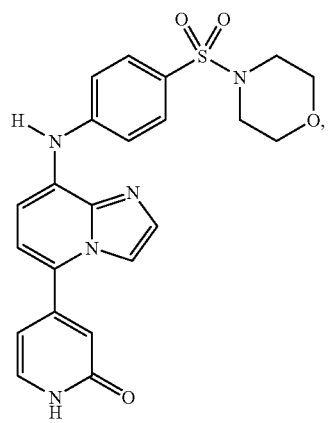
XIId
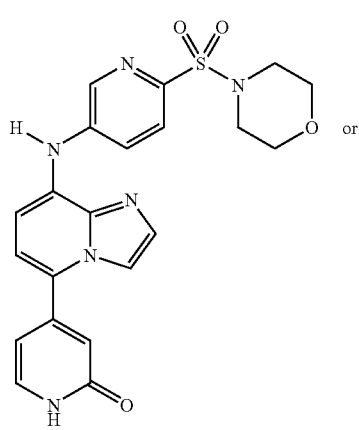
XIIe
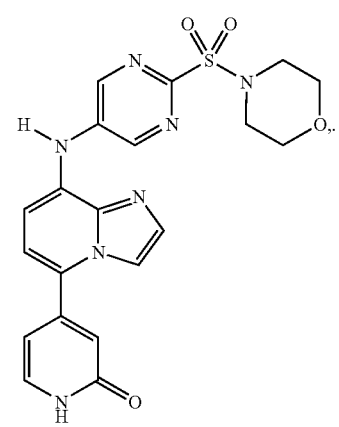
XIIf
In one embodiment, the compounds are according to Formulae Xa or Xd.
In another embodiment, with respect to compounds of formula III, the compound is according to formula XIIIa, XIIIb, XIIIc, XIIId, XIIIe, or XIIIf:
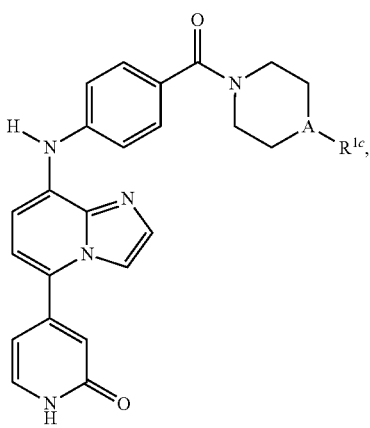
XIIIa
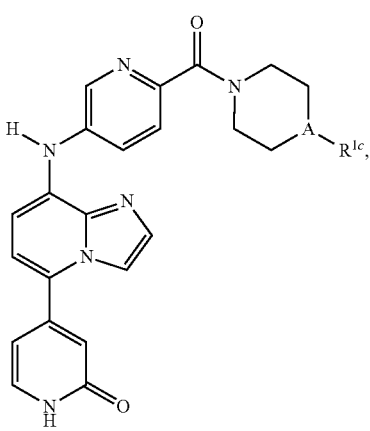
XIIIb
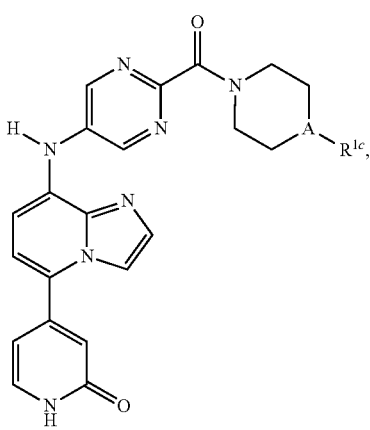
XIIIc XIIId

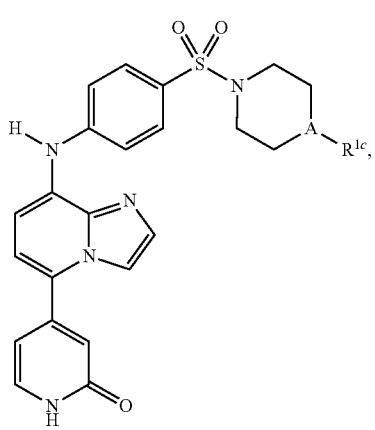

XIIIe

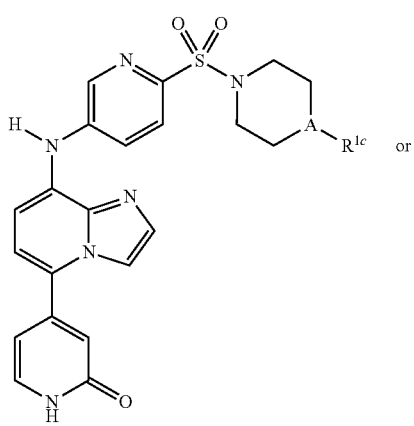
or

XIIIf

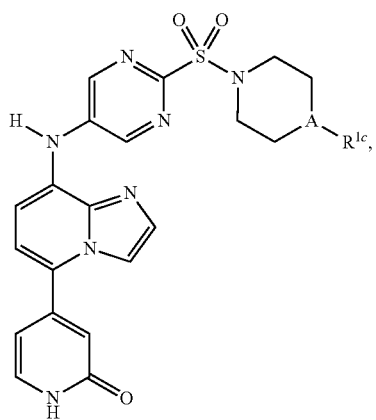

wherein A is CH or N; and $R^{1c}$ is hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, the compounds are according to formulae XIIa or XIId.

In one embodiment the compounds are according to formulae XIIIa or XIIId.

In one embodiment, with respect to compounds of formulae XIIa-XIIIf, $R^{1c}$ is H.

In another embodiment, with respect to compounds of formulae XIIa-XIIIf, $R^{1c}$ is substituted or unsubstituted alkyl or substituted or unsubstituted cycloalkyl.

In another embodiment, with respect to compounds of formulae XIIa-XIIIf, $R^{1c}$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae XIIa-XIIIf, $R^{1c}$ is substituted or unsubstituted aryl, aralkyl or heteroaryl.

In another embodiment, with respect to compounds of formulae XIIa-XIIIf, $R^{1c}$ is substituted or unsubstituted phenyl, benzyl or pyridyl.

In another embodiment, with respect to compounds of formula III, the compound is according to formula XIVa, or XIVb:

XIVa

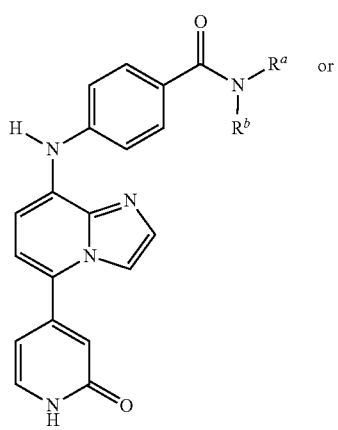
or

XIVb

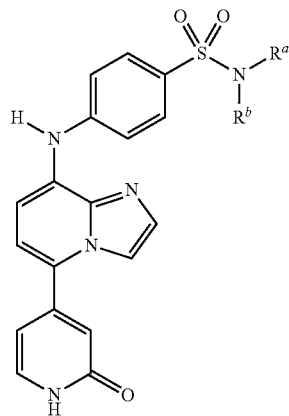

and wherein each $R^a$ and $R^b$ is independently hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, with respect to compounds of formulae XIVa-XIVb, $R^a$ is H.

In another embodiment, with respect to compounds of formulae XIVa-XIVb, $R^a$ is Me, Et or n-Pr.

In another embodiment, with respect to compounds of formulae XIVa-XIVb, $R^b$ is substituted or unsubstituted alkyl or substituted or unsubstituted cycloalkyl.

In another embodiment, with respect to compounds of formulae XIVa-XIVb, $R^b$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae XIVa-XIVb, $R^b$ is substituted or unsubstituted aryl, aralkyl or heteroaryl.

In another embodiment, with respect to compounds of formulae XIVa-XIVb, $R^b$ is substituted or unsubstituted phenyl, benzyl or pyridyl.

In another embodiment with respect to compounds of formulae XIVa-XIVb, $R^b$ is substituted or unsubstituted heterocycloalkyl.

In another embodiment with respect to compounds of formulae XIVa-XIVb, $R^b$ is substituted pyrrolidine.

In another embodiment with respect to compounds for formulae XIVa, $R^b$ is pyrrolidine substituted by benzyl.

In another embodiment, with respect to compounds of formula III, the compound is according to formula XVa, XVb, XVc, XVd, XVe, XVf, XVg, XVh, XVi, XVj, XVk, or XVl:

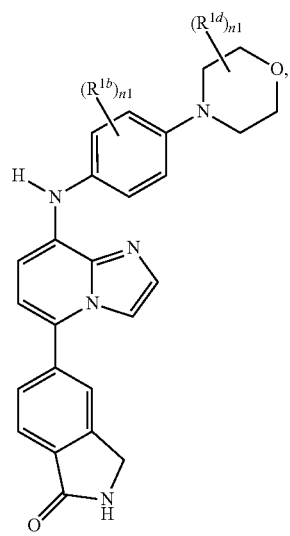

XVa

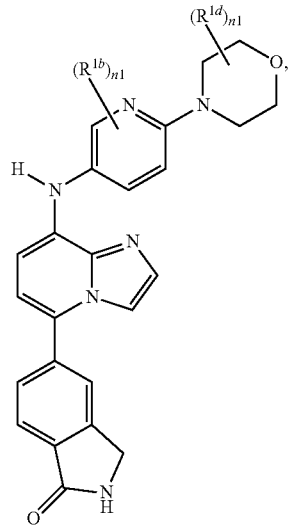

XVb

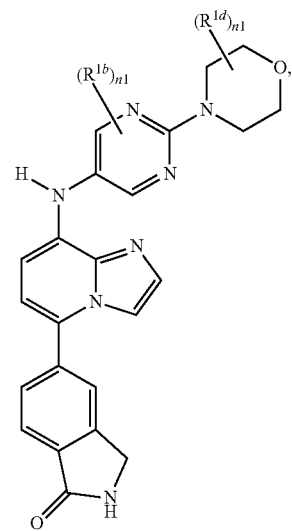

XVc

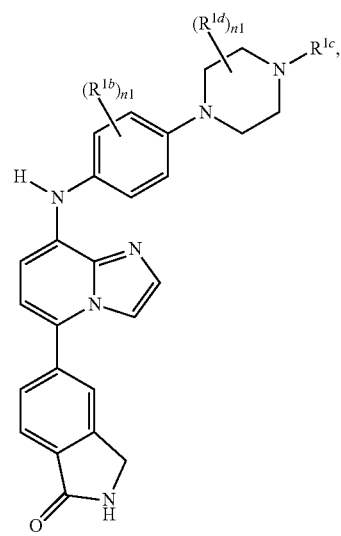

XVd

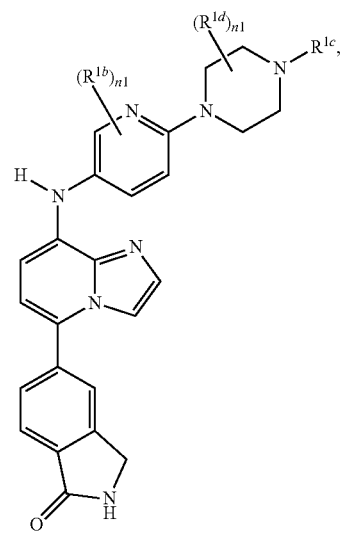

XVe

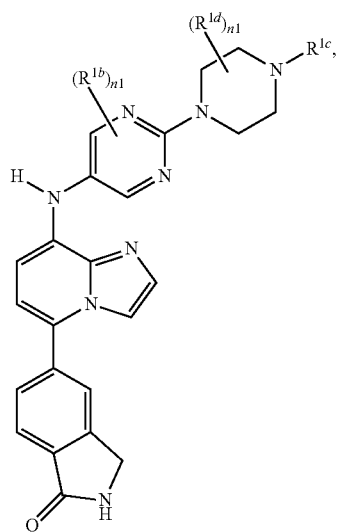 XVf
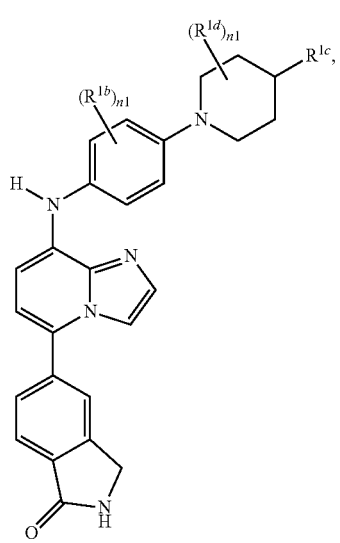 XVg
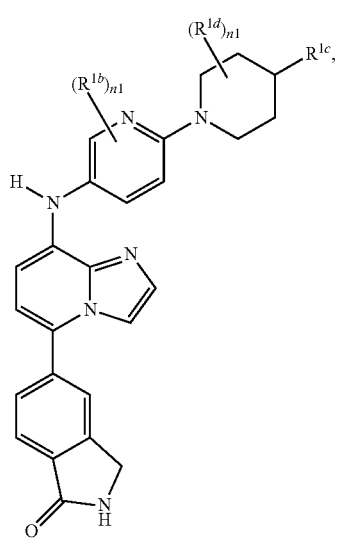 XVh
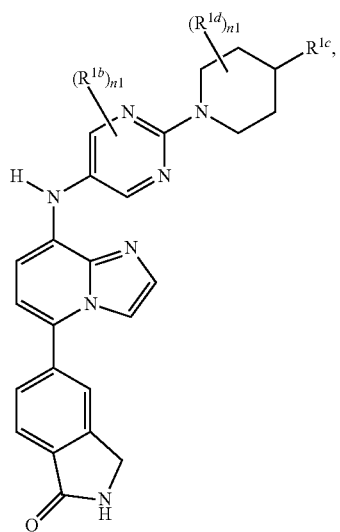 XVi
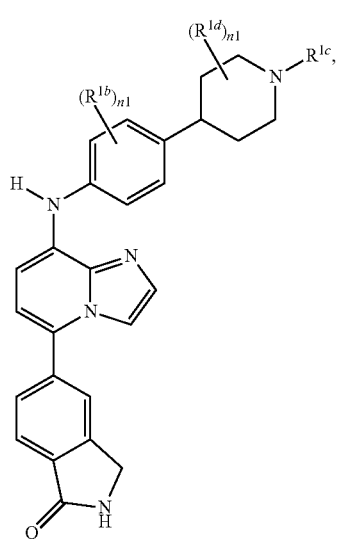 XVj
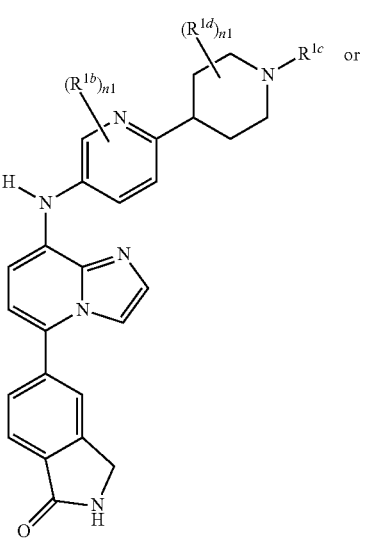 XVk or -continued

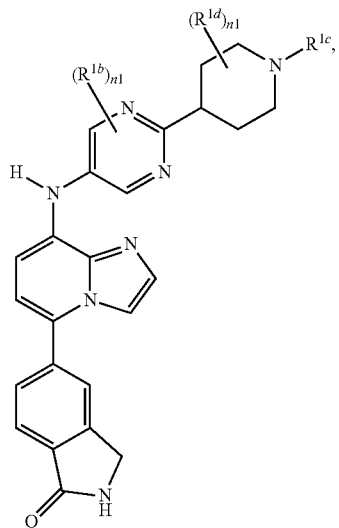

XVl and wherein $R^{1c}$ is hydrogen, substituted or unsubstituted alkyl, substituted or unsubstituted cycloalkyl, or substituted or unsubstituted heterocycloalkyl and wherein each $R^{1b}$ is independently selected from Me, Et, Pr, iso-Pr, Cl, F, CN, OMe, OEt, $CF_3$, $CF_2CF_3$ or $OCF_3$ each $R^{1d}$ is independently selected from H, Me, Et, Pr, iso-Pr, Cl, F, CN, OMe, OEt, $CF_3$, $CF_2CF_3$ or $OCF_3$, each n1 is independently an integer between 0 and 2 and each n2 is independently an integer between 0 and 2.

In one embodiment, the compounds are according to formulae XVa, XVd, XVg or XVj.

In one embodiment, with respect to compounds of formulae XVa-XVf, $R^{1c}$ is H.

In another embodiment, with respect to compounds of formulae XVa-XVf, $R^{1c}$ is substituted or unsubstituted alkyl, substituted or unsubstituted cycloalkyl or substituted or unsubstituted heterocycloalkyl.

In another embodiment, with respect to compounds of formulae XVa-XVf, $R^{1c}$ is Me, Et, Pr, i-Pr, t-Bu, i-Bu, i-pentyl, cyclopropyl, cyclobutyl, cyclopentyl, cyclohexyl, cyclopropylmethyl or piperidine.

In another embodiment, with respect to compounds of formulae XVd-XVl, $R^{1c}$ is piperidine substituted by one or more OH, Me or F.

In another embodiment, with respect to compounds of formulae XVg-XVl, $R^{1c}$ is piperidine substituted by one or more OH, Me or F.

In another embodiment, with respect to compounds of formula III, the compound is according to formula XVm, XVn, or XVo,

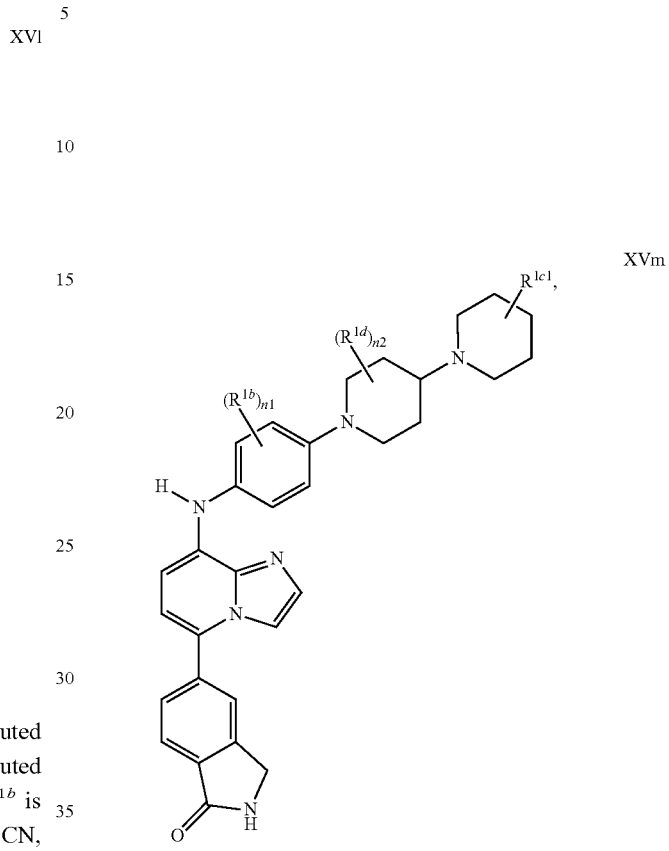

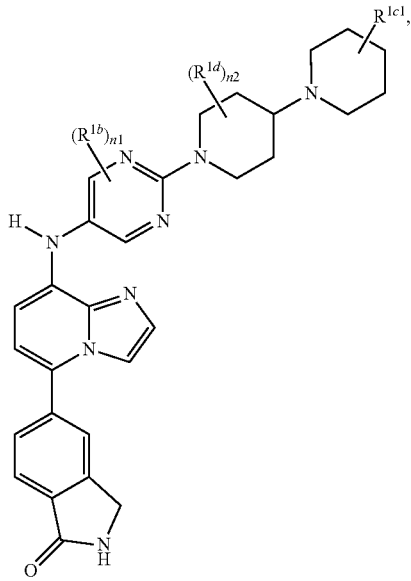
XVo
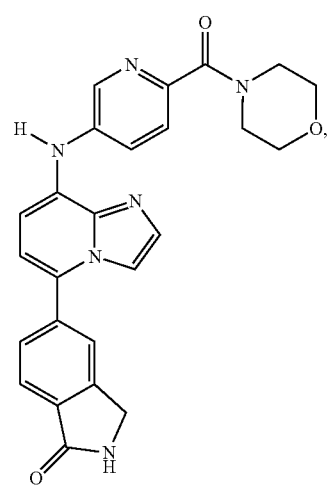
XVIb
and wherein R² is as described for formula III; $R^{1b}$, $R^{1d}$, n1 and n2 are as described for formulae Va-Vi; and $R^{1c1}$ is H, Me, F, Cl, or OH.
In another embodiment, with respect to compounds of formula III, the compound is according to formula XVIa, XVIb, XVIc, XVId, XVIe, or XVIf:
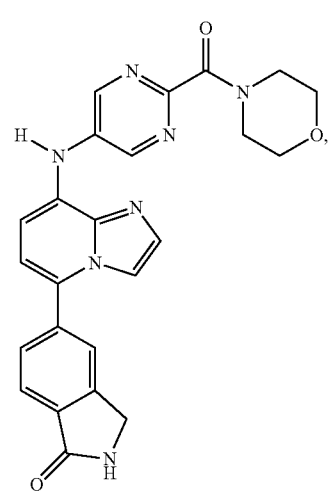
XVIc
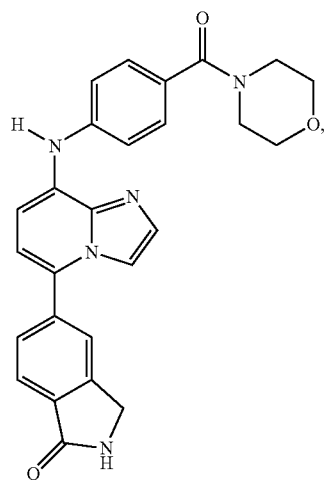
XVIa
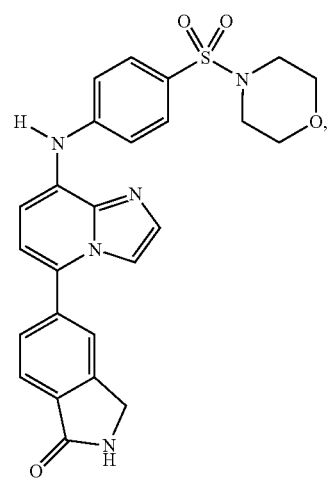
XVId XVIe
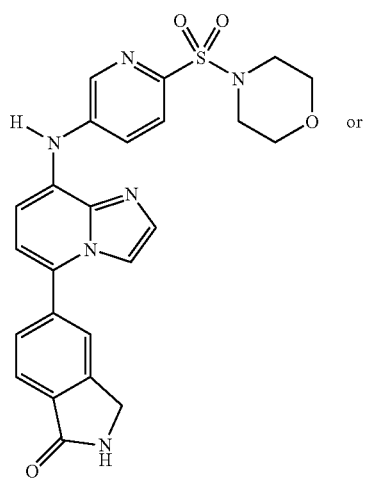
or
XVIf
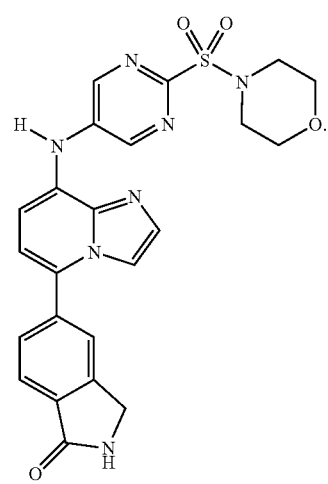
XVIIb
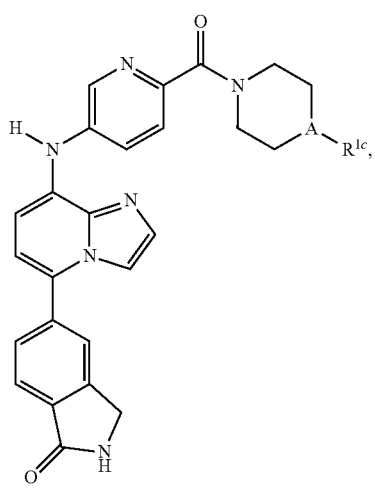
XVIIc
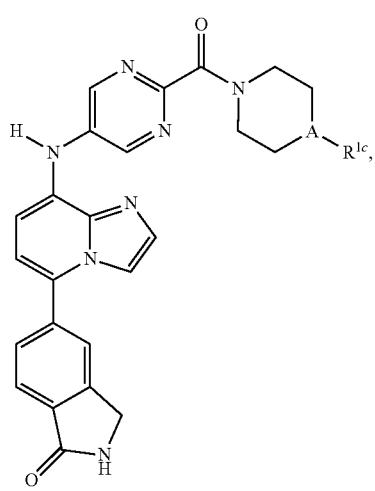
In another embodiment, with respect to compounds of formula III, the compound is according to formula XVIIa, XVIIb, XVIIc, XVIId, XVIIe, or XVIIf:
XVIIa
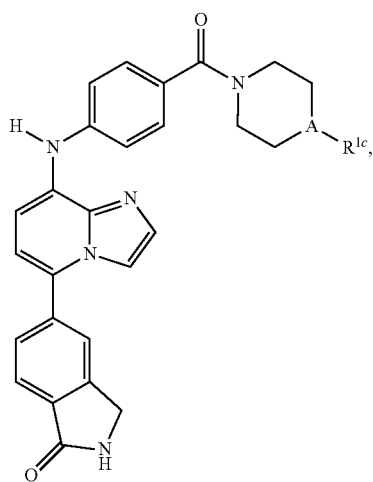
XVIId
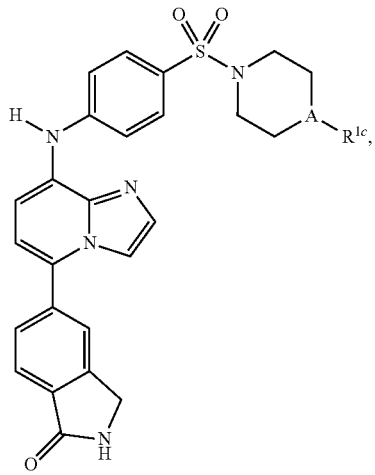

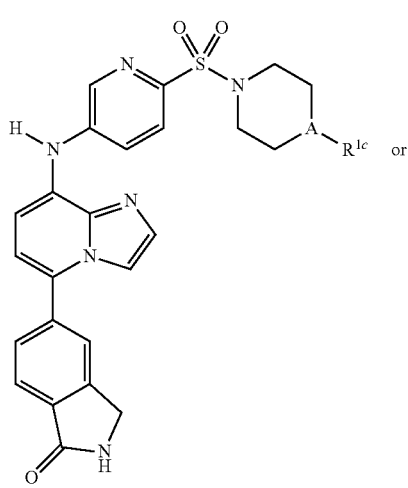

XVIIe

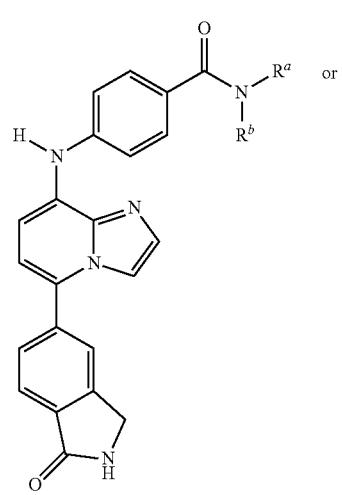

XVIIIa

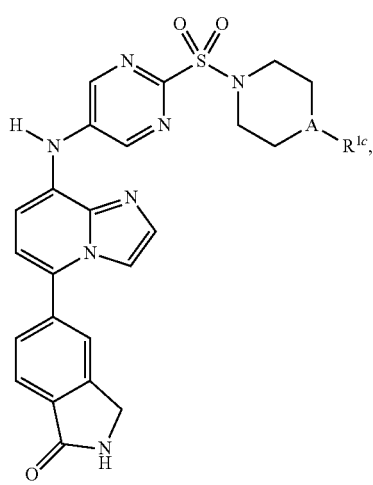

XVIIf

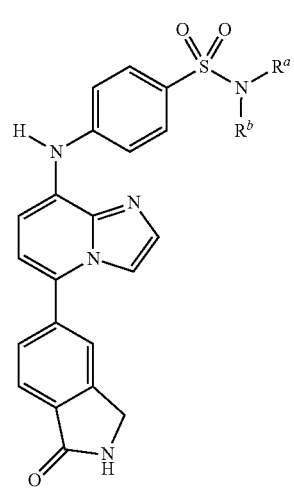

XVIIIb wherein A is CH or N; and $R^{1c}$ is hydrogen, substituted or unsubstituted $C_1$-$C_6$ alkyl, substituted or unsubstituted aryl, substituted or unsubstituted aralkyl, substituted or unsubstituted heteroaryl or substituted or unsubstituted cycloalkyl.

In one embodiment, the compounds are according to formulae XVIa or XVId.

In one embodiment, the compounds are according to formulae XVIIa or XVIId.

In one embodiment, with respect to compounds of formulae XVIa-XVIIf, $R^{1c}$ is H.

In another embodiment, with respect to compounds of formulae XVIa-XVIIf, $R^{1c}$ is substituted or unsubstituted alkyl or substituted or unsubstituted cycloalkyl.

In another embodiment, with respect to compounds of formulae XVIa-XVIIf, $R^{1c}$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae XVIa-XVIIf, $R^{1c}$ is substituted or unsubstituted aryl, aralkyl or heteroaryl.

In another embodiment, with respect to compounds of formulae XVIa-XVIIf, $R^{1c}$ is substituted or unsubstituted phenyl, benzyl or pyridyl.

In another embodiment, with respect to compounds of formula III, the compound is according to formula XVIIIa, or XVIIIb:

and wherein each $R^a$ and $R^b$ is independently hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, with respect to compounds of formulae XVIIIa-XVIIIb, $R^a$ is H.

In another embodiment, with respect to compounds of formulae XVIIIa-XVIIIb, $R^a$ is Me, Et or n-Pr.

In another embodiment, with respect to compounds of formulae XVIIIa-XVIIIb, $R^b$ is substituted or unsubstituted $C_1$-$C_6$ alkyl or substituted or unsubstituted cycloalkyl.

In another embodiment, with respect to compounds of formulae XVIIIa-XVIIIb, $R^b$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae XVIIIa-XVIIIb, $R^b$ is substituted or unsubstituted aryl, aralkyl or heteroaryl.

In another embodiment, with respect to compounds of formulae XVIIIa-XVIIIb, $R^b$ is substituted or unsubstituted phenyl, benzyl or pyridyl.

In another embodiment with respect to compounds of formulae XIVa-XIVb, $R^b$ is substituted or unsubstituted heterocycloalkyl.

In another embodiment with respect to compounds of formulae XIVa-XIVb, $R^b$ is substituted pyrrolidine.

In another embodiment with respect to compounds for formulae XIVa, R$^b$ is pyrrolidine substituted by benzyl.
In another embodiment, with respect to compounds of formula III, the compound is according to formula XIXa, XIXb, XIXc, XIXd, XIXe, XIXf, XIXg or XIXh:
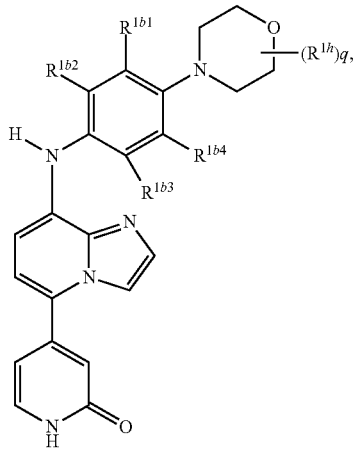
XIXa
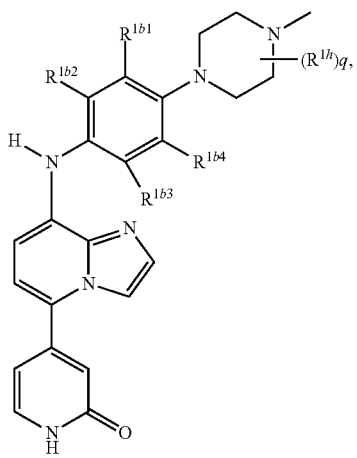
XIXb
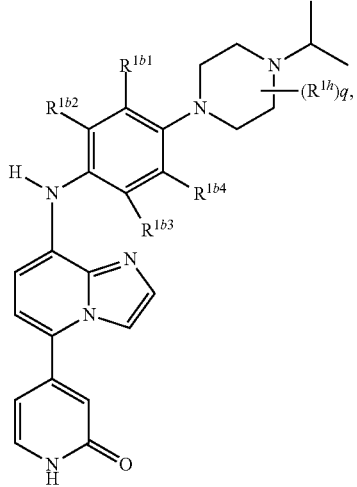
XIXc
-continued
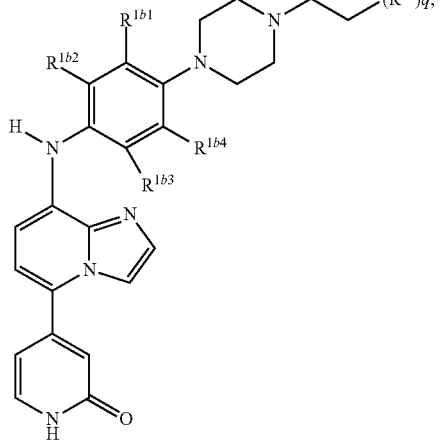
XIXd
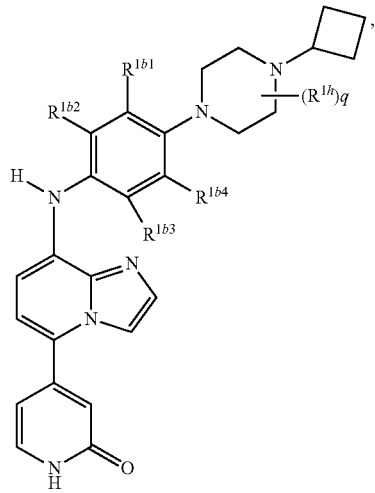
XIXe
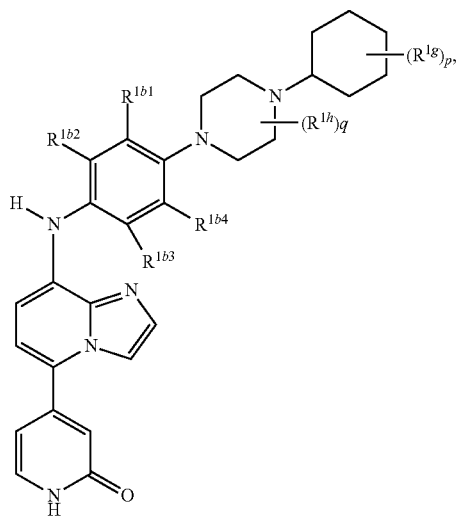
XIXf -continued

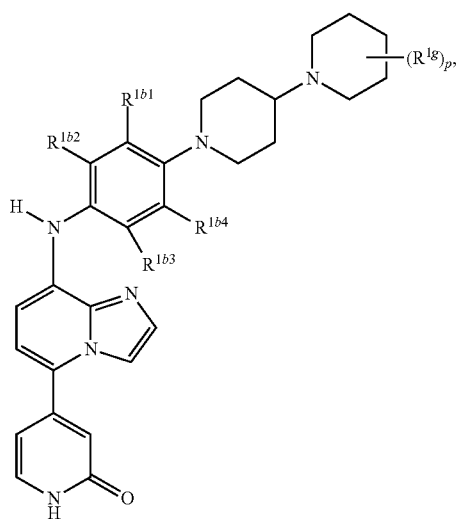

XIXg

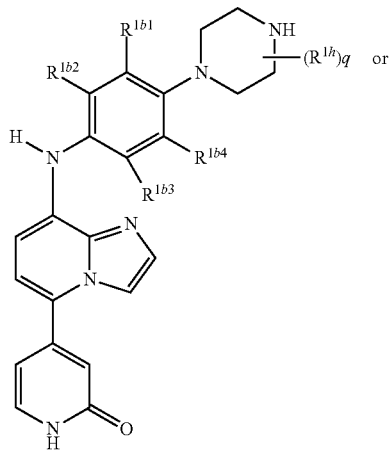

XIXh

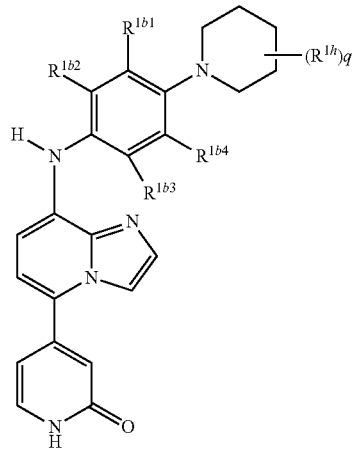

XIXi and wherein each $R^{1b1}$, $R^{1b2}$, $R^{1b3}$ and $R^{1b4}$ is independently hydrogen, F or $CF_3$, each $R^{1g}$ is indepdendently H, OH or Me, each $R^{1h}$ is independently H, Me or F, p is 0, 1 or 2 and q is 0, 1 or 2.

In one embodiment, with respect to compounds of formulae XIXa-XIXi, at least two of $R^{1b1}$, $R^{1b2}$, $R^{1b3}$ and $R^{1b4}$ are H.

In one embodiment, with respect to compounds of formulae XIXa-XIXi, at least three of $R^{1b1}$, $R^{1b2}$, $R^{1b3}$ and $R^{1b4}$ are H.

In one embodiment, with respect to compounds of formulae XIXa-XIXi, all of $R^{1b1}$, $R^{1b2}$, $R^{1b3}$ and $R^{1b4}$ are H.

In one embodiment with respect to compounds of formula XIXa or XIXh, $R^{1h}$ is Me and q is 2.

In one embodiment with respect to compounds of formula XIXa or XIXh, q is 0.

In one embodiment with respect to compounds of formula XIXg, p is 1 and $R^{1g}$ is OH or Me.

In one embodiment with respect to compounds of formula XIXi, q is 1 or 2 and $R^{1g}$ is Me or F.

In another embodiment, with respect to compounds of formula III, the compound is according to formula XXa, XXb, XXc, XXd, or XXe:

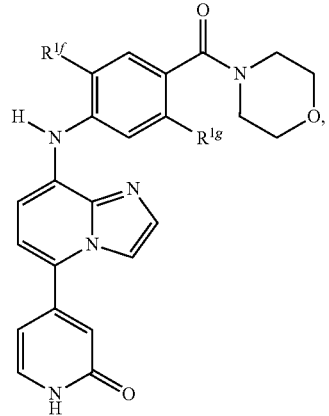

XXa

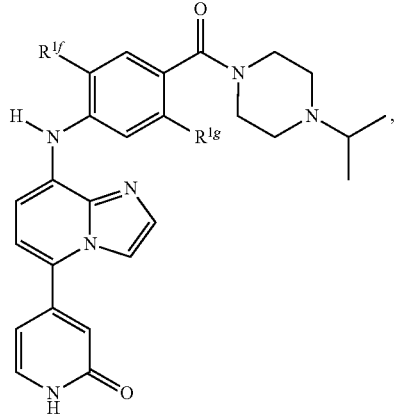

XXb

73
-continued
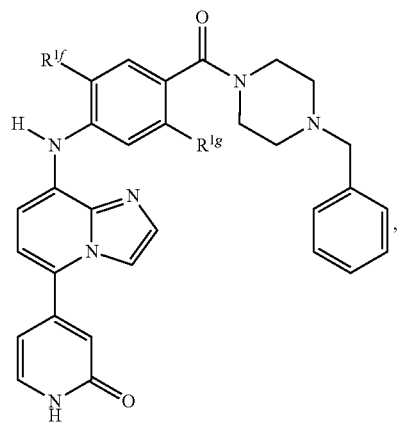
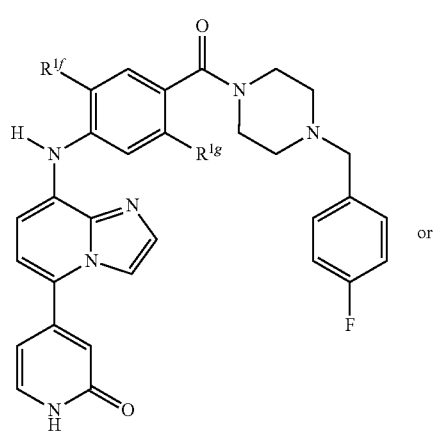
or
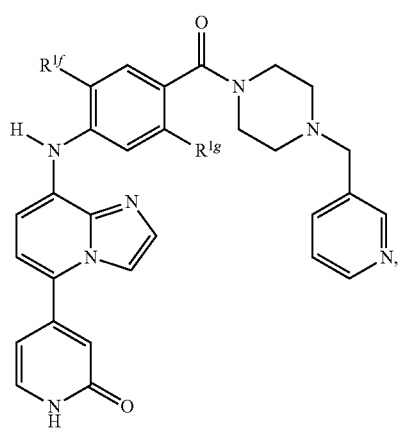
and wherein each $R^{1f}$ and $R^{1g}$ is hydrogen or F.
74
In another embodiment, with respect to compounds of formula III, the compound is according to formula XXIa, XXIb, XXIc, XXId, XXIe, or XXIf:
XXIa
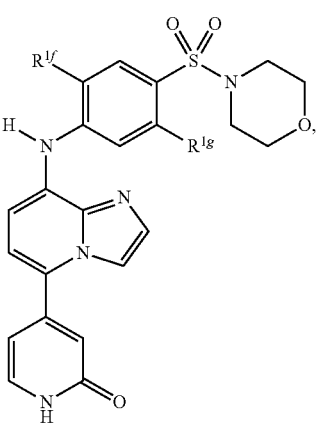
XXIb
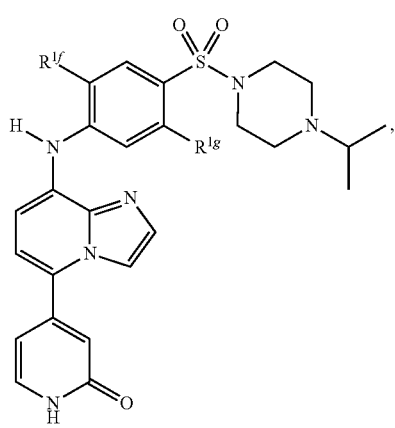
XXIc
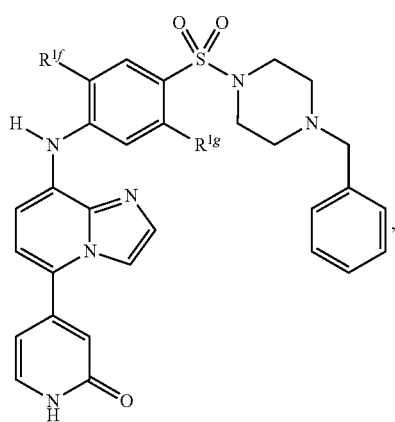

-continued
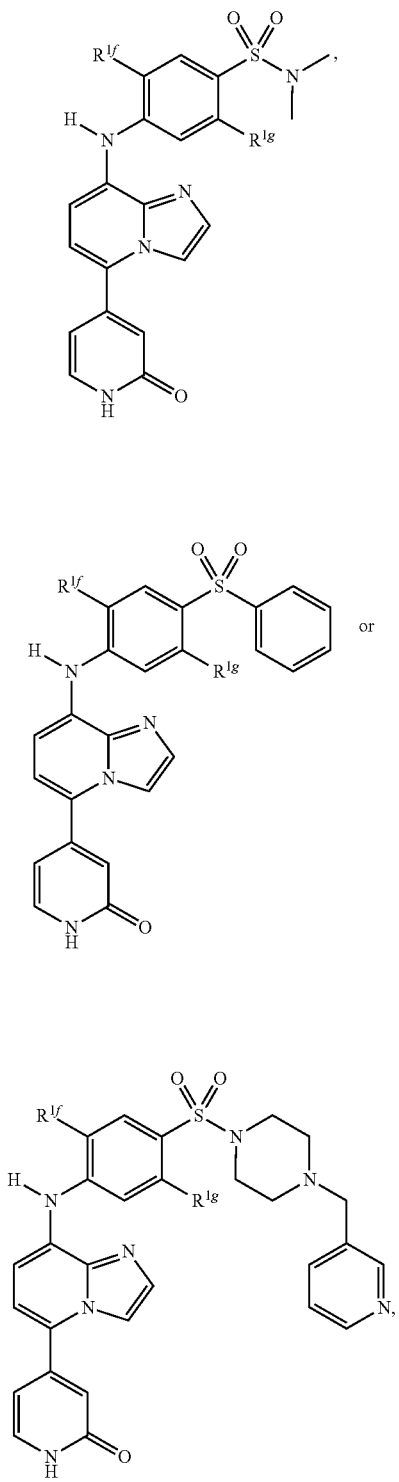
and wherein each $R^{1f}$ and $R^{1g}$ is hydrogen or F.
In another embodiment, with respect to compounds of formula III, the compound is according to formula XXIIa, XXIIb, XXIIc, XXIId, XXIIe, or XXIIf:
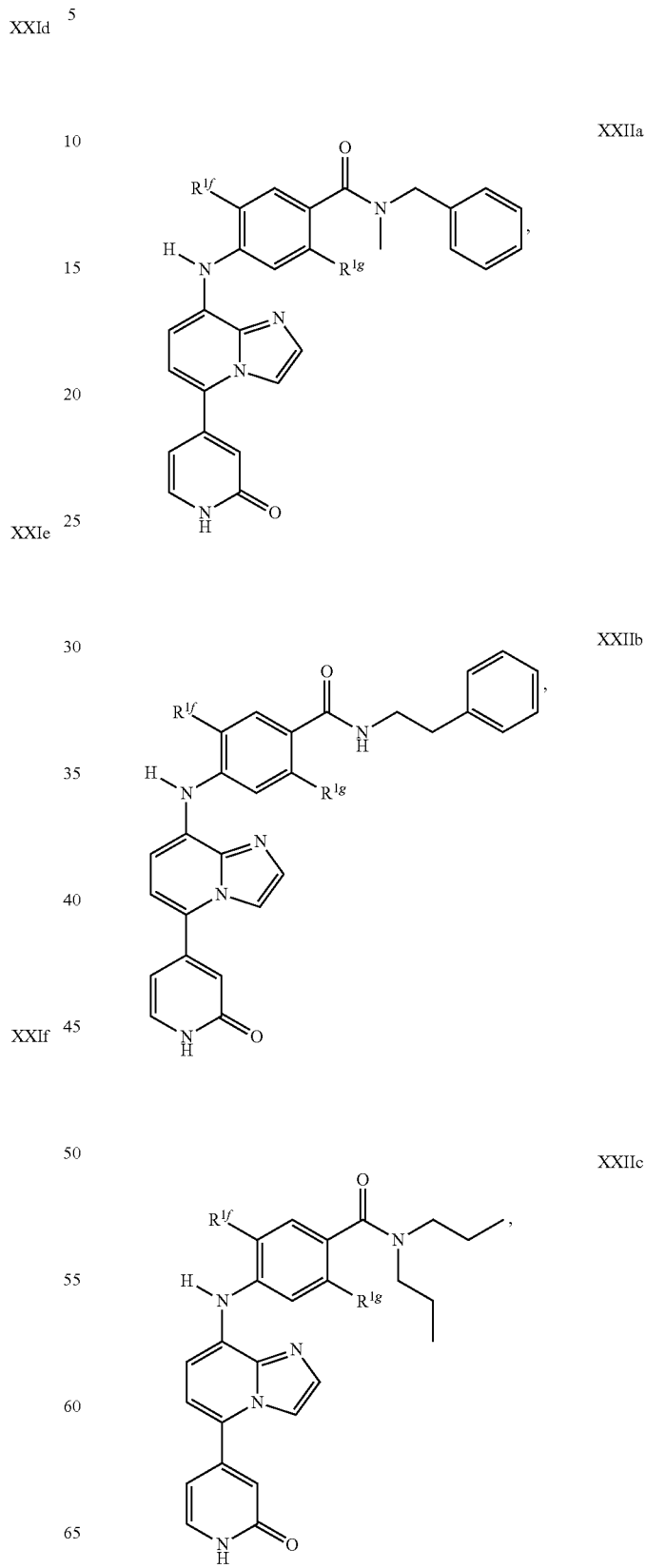

-continued

XXIId

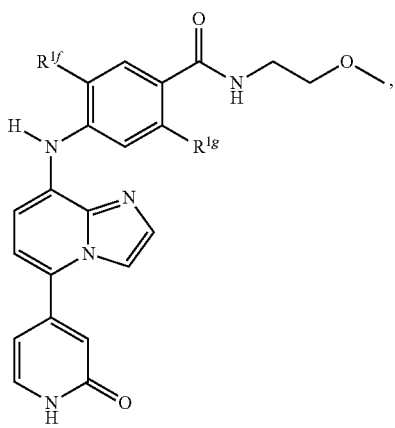

XXIIe

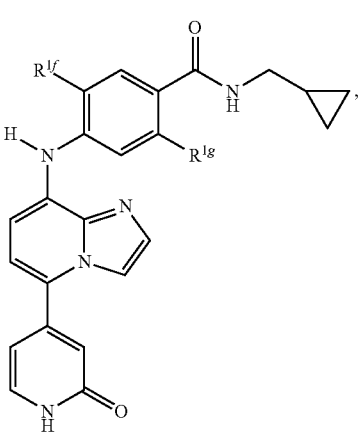

or

XXIIf and wherein each $R^{1f}$ and $R^{1g}$ is hydrogen or F.

In one embodiment, with respect to compounds of formulae XXa-XXIIf, each $R^{1f}$ and $R^{1g}$ is H.

In another embodiment, with respect to compounds of formulae XXa-XXIIf, $R^{1f}$ is F and $R^{1g}$ is H.

In another embodiment, with respect to compounds of formulae XXa-XXIIf, $R^{1f}$ is H and $R^{1g}$ is F.

In preferred embodiments of the invention include the following compounds of Formula III and pharmaceutically acceptable salts, solvates or prodrugs thereof:

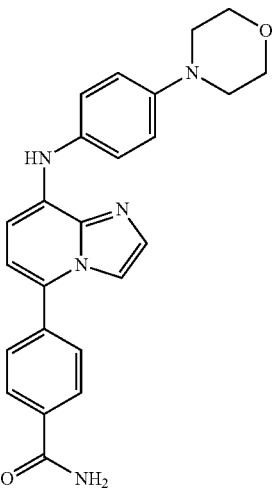

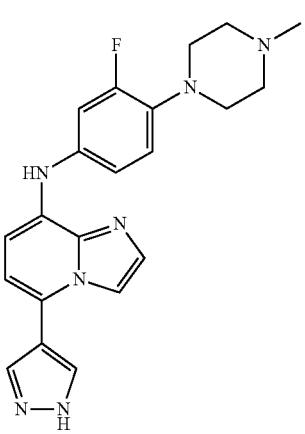

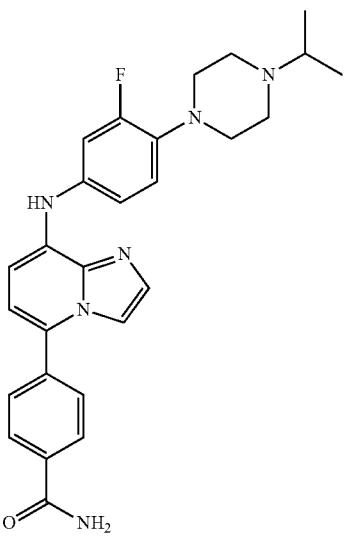

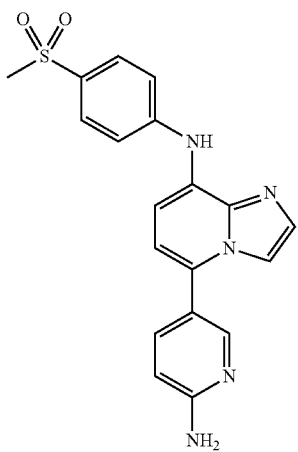
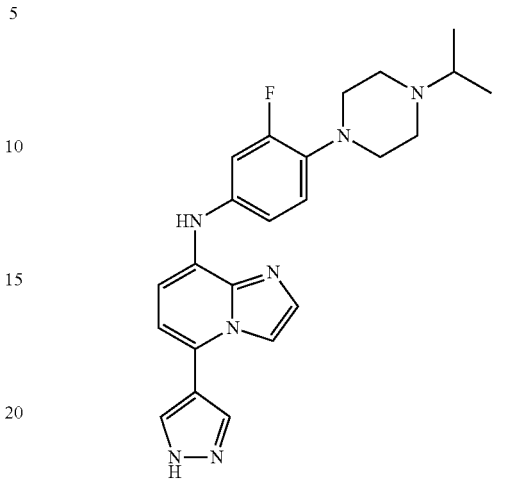
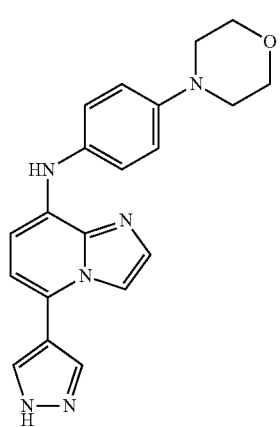
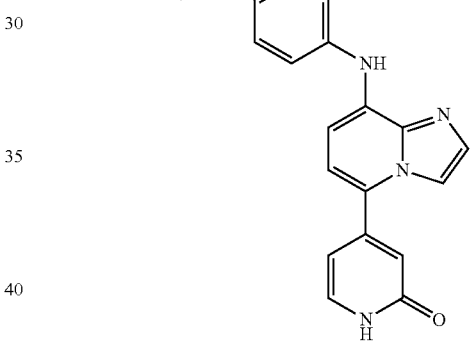
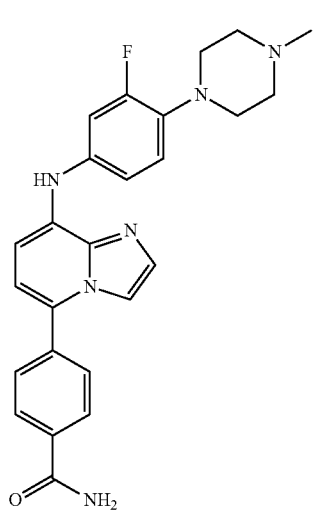
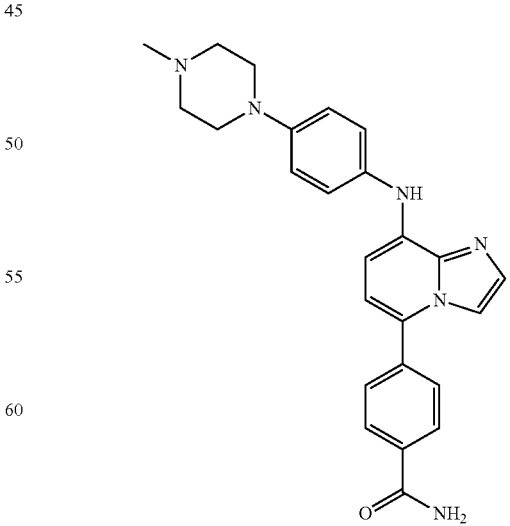

81
-continued
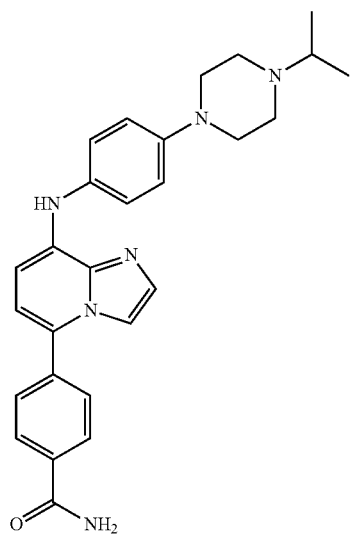
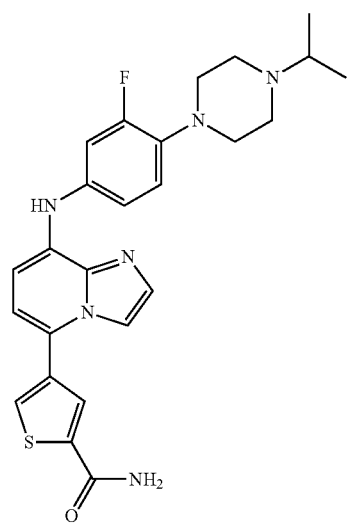
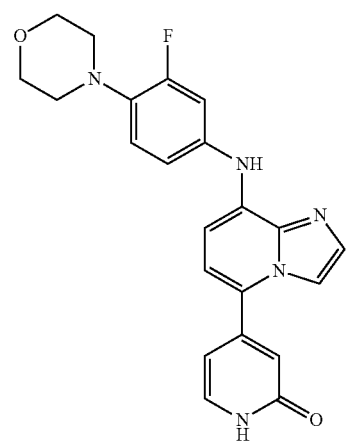
82
-continued
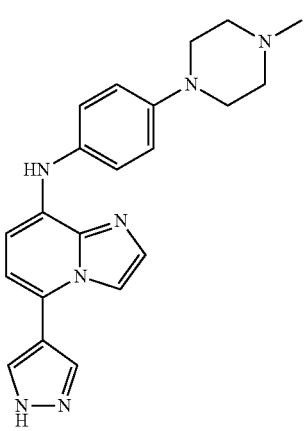
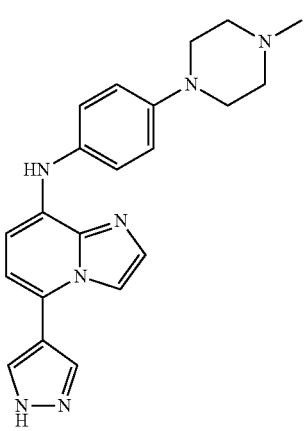
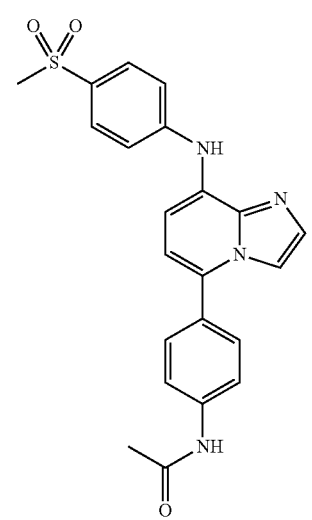

-continued
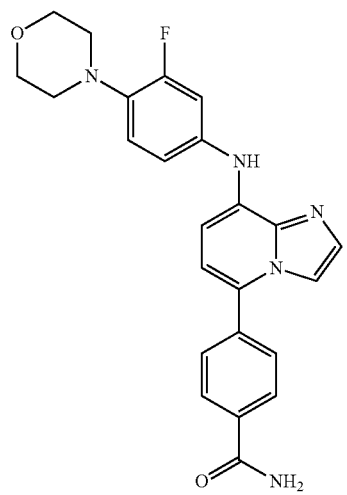
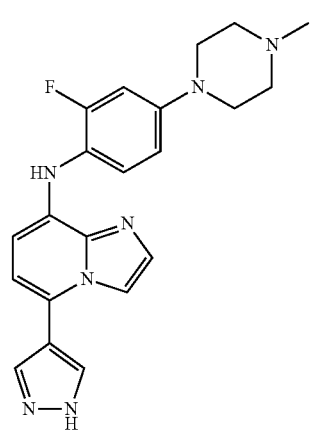
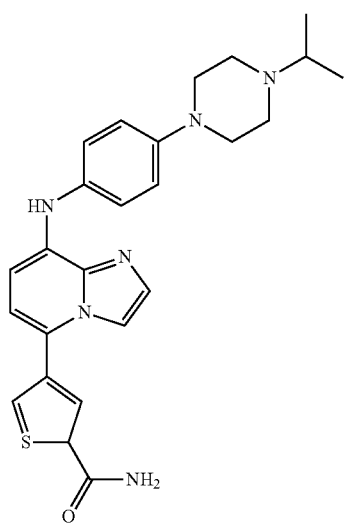
-continued
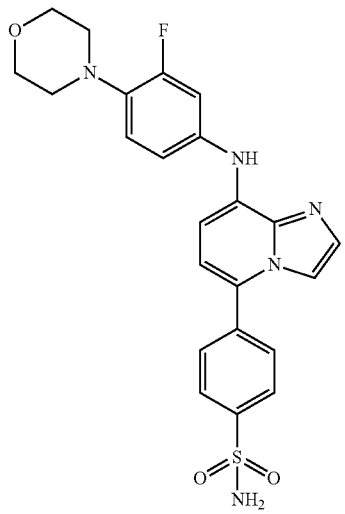
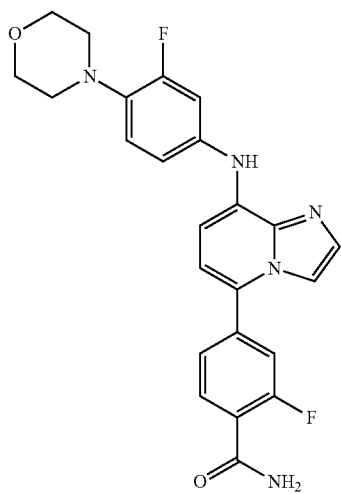
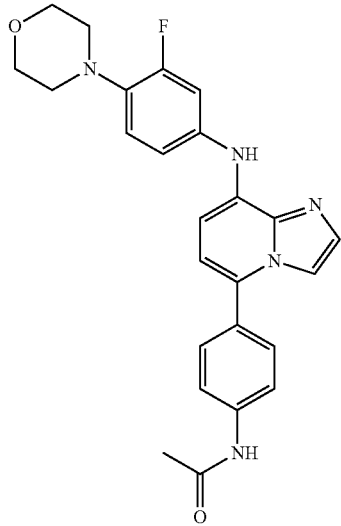

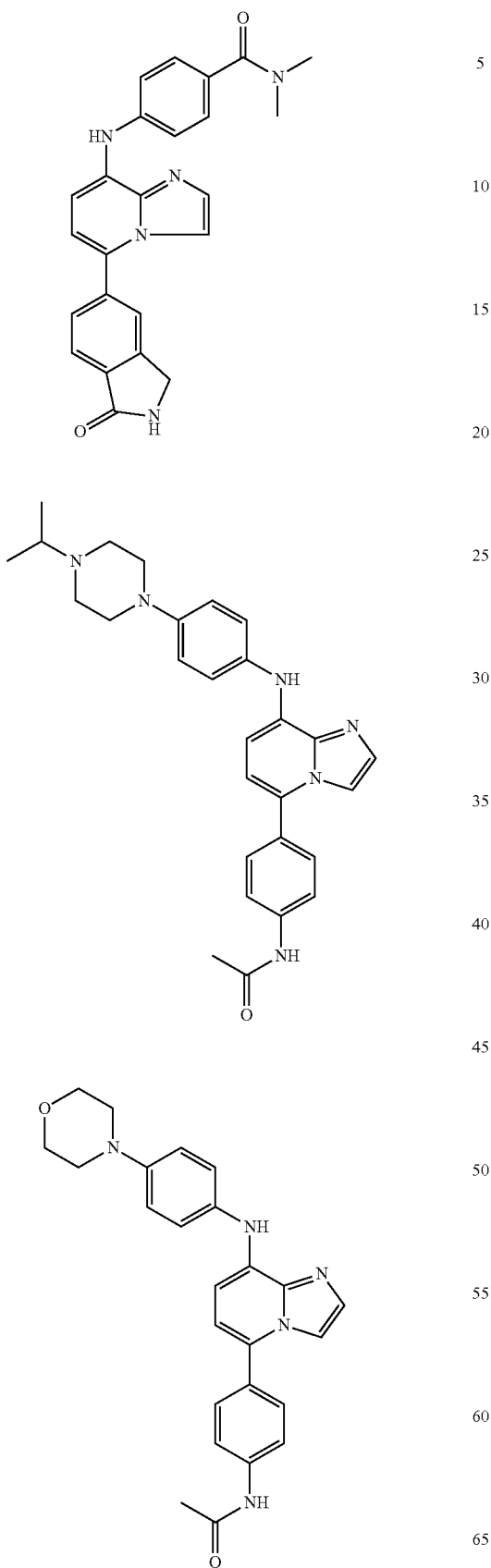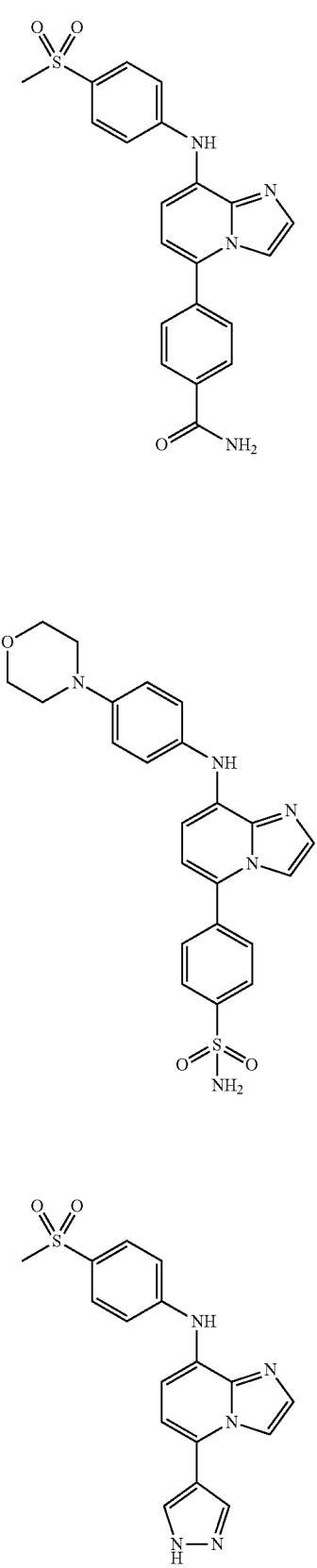

87
-continued
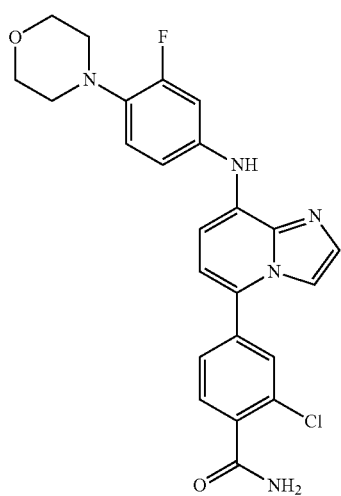
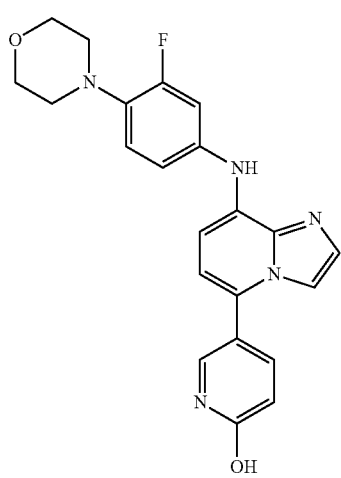
88
-continued
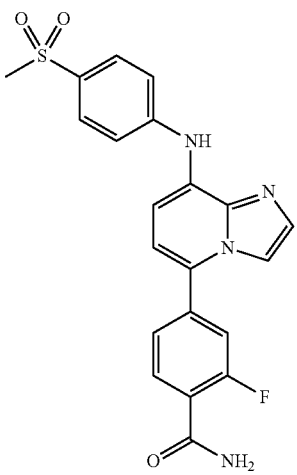
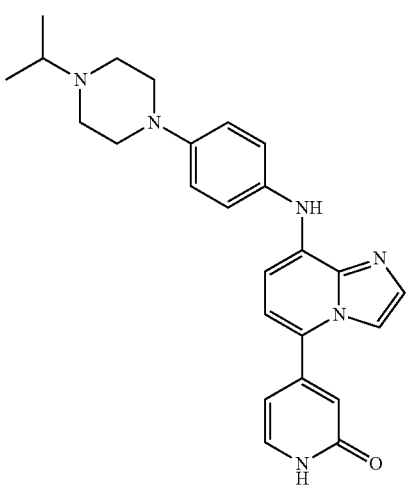

-continued
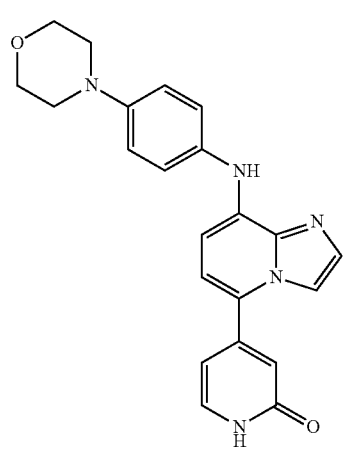
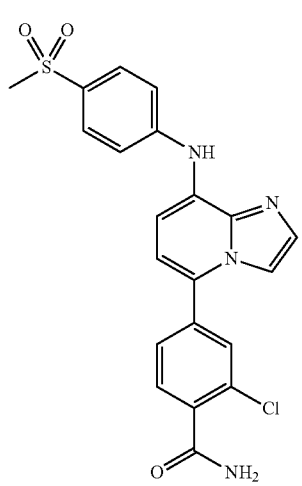
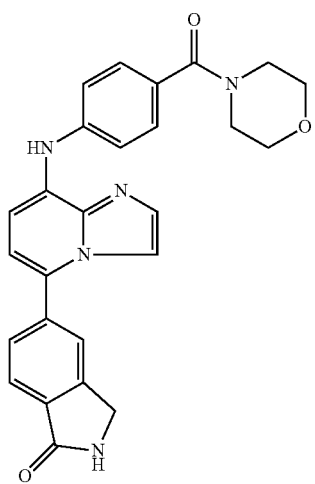
-continued
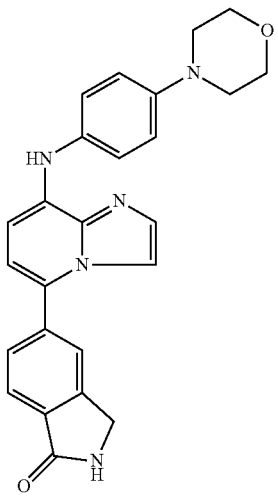
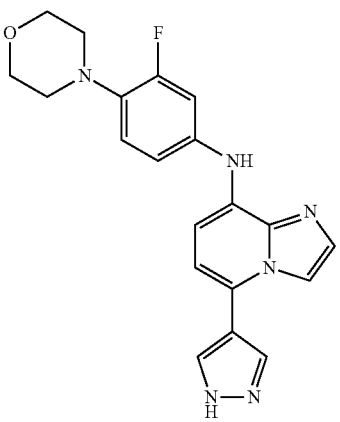
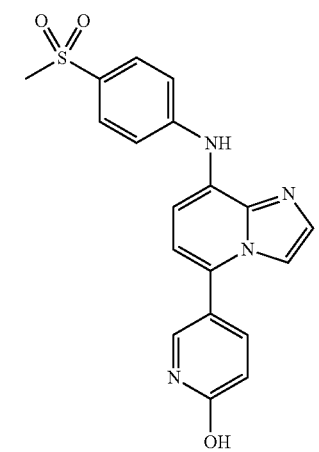

91
-continued
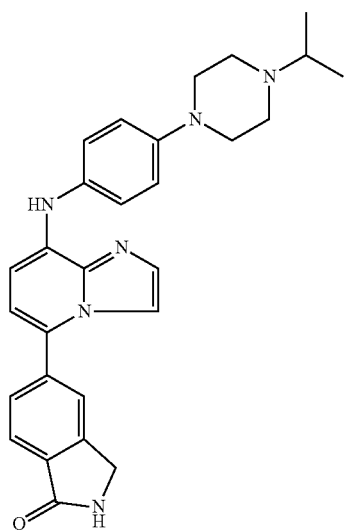
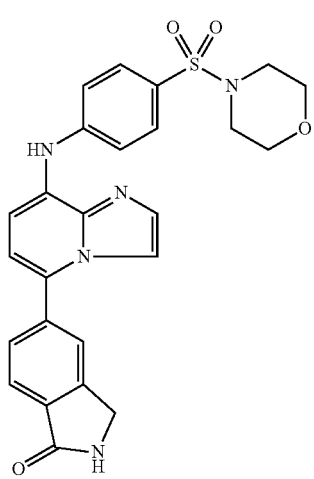
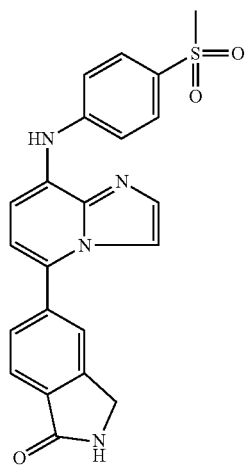
92
-continued
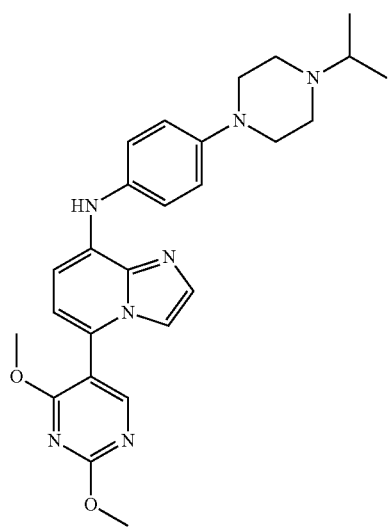
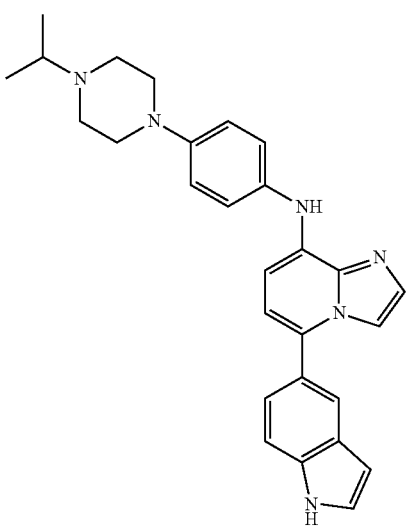
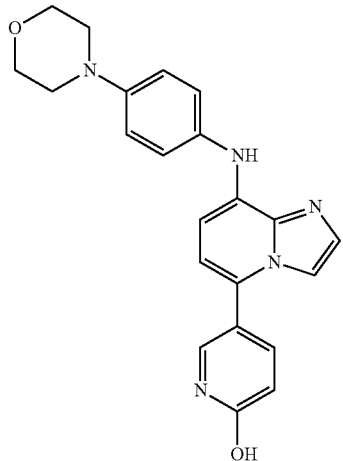

93
-continued
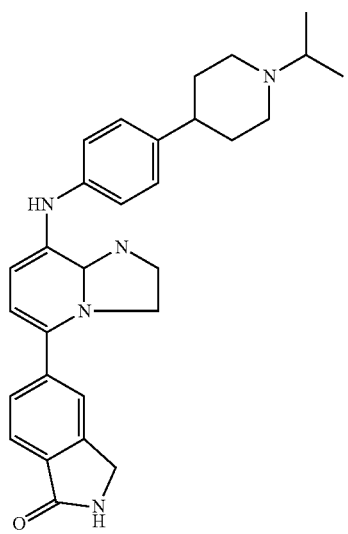
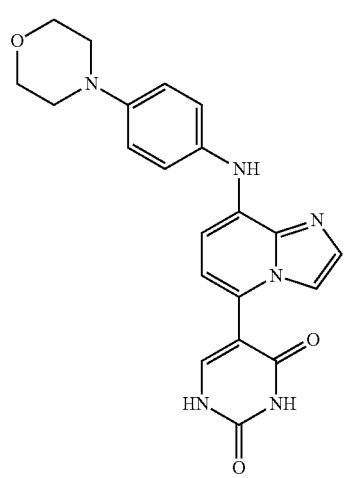
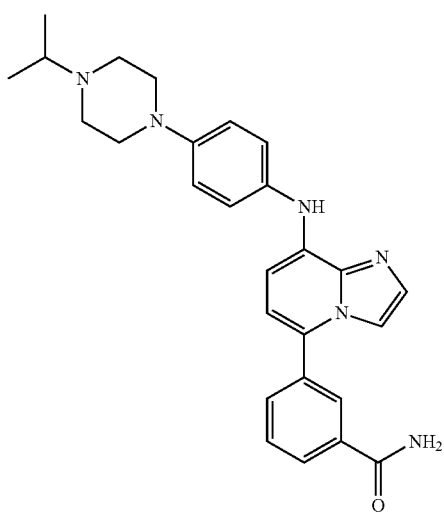
94
-continued
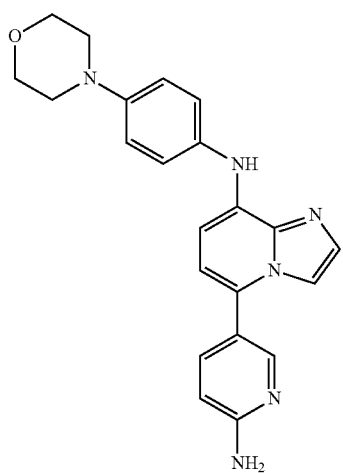
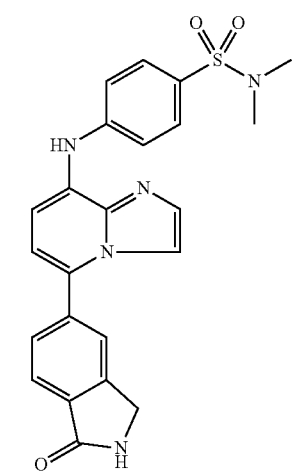
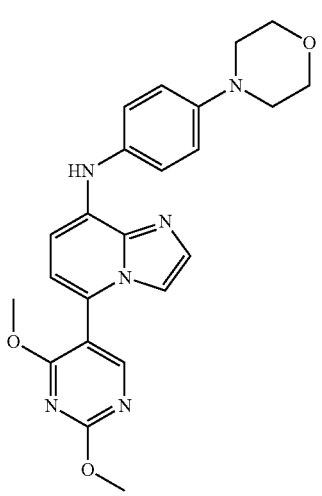

95
-continued
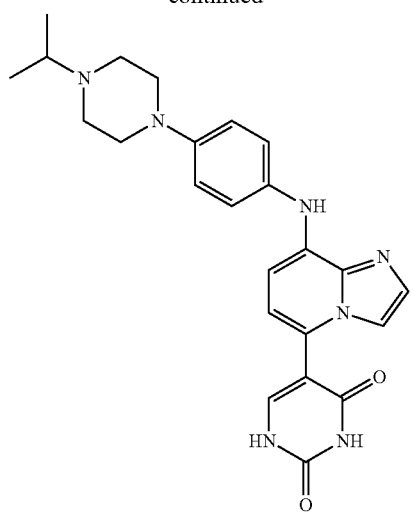
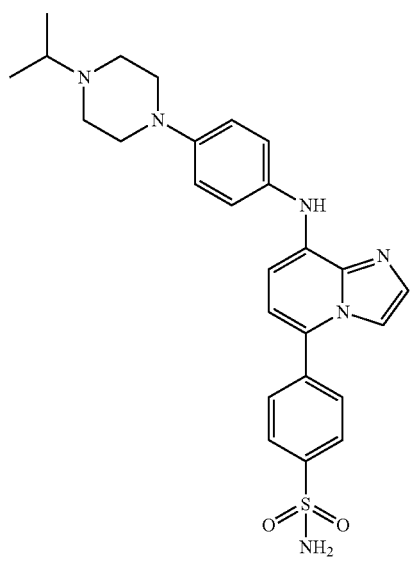
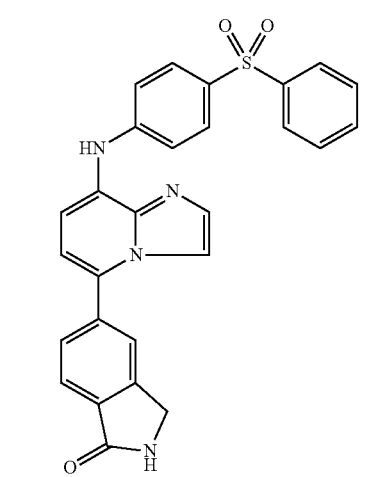
96
-continued
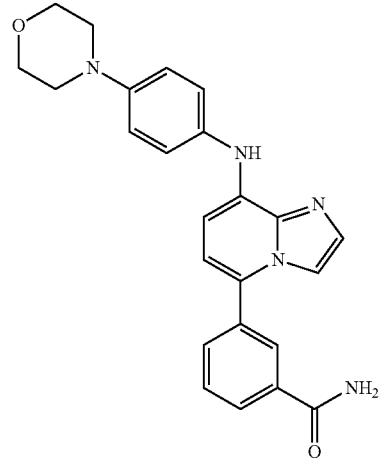
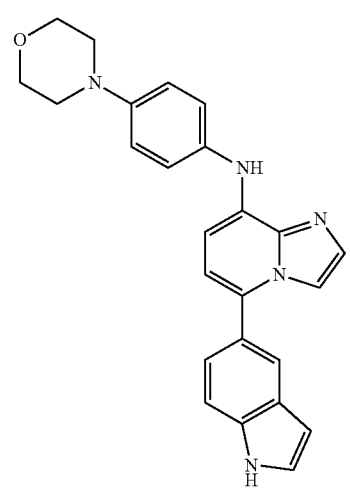
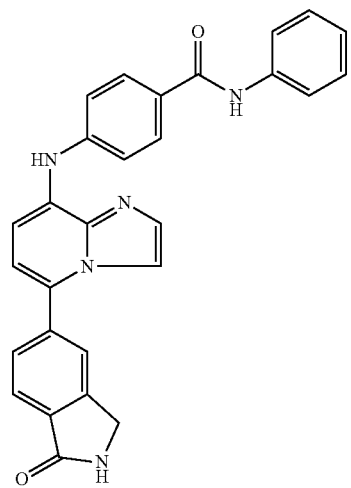

97
-continued
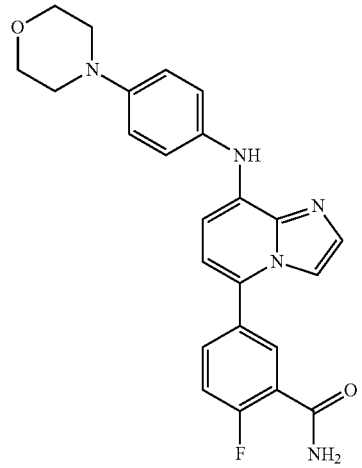
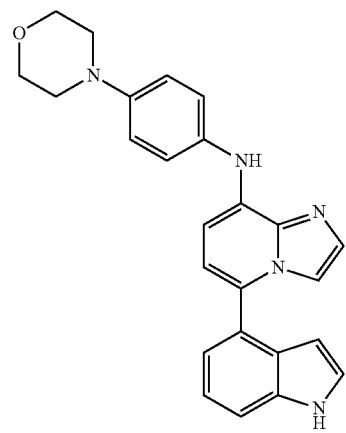
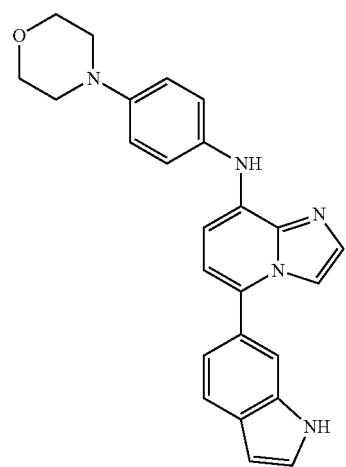
98
-continued
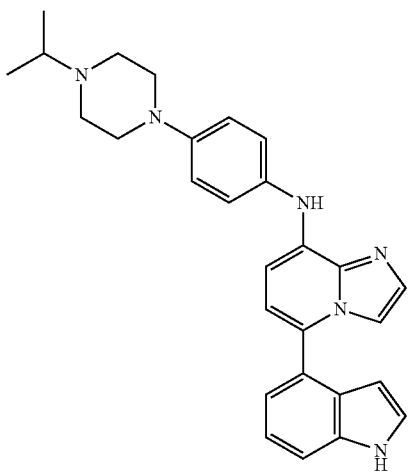
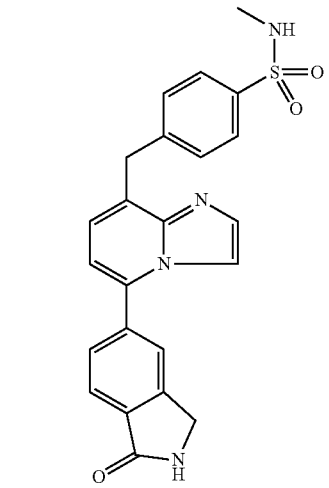
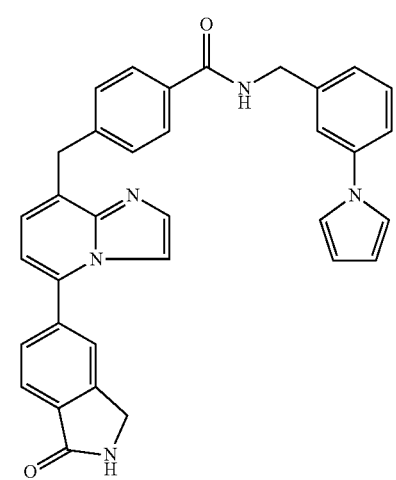

99
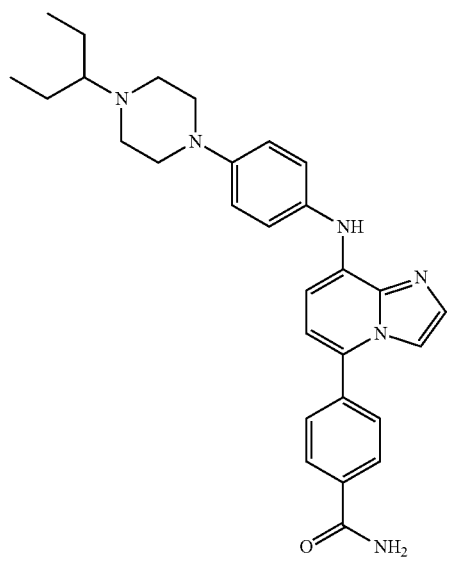
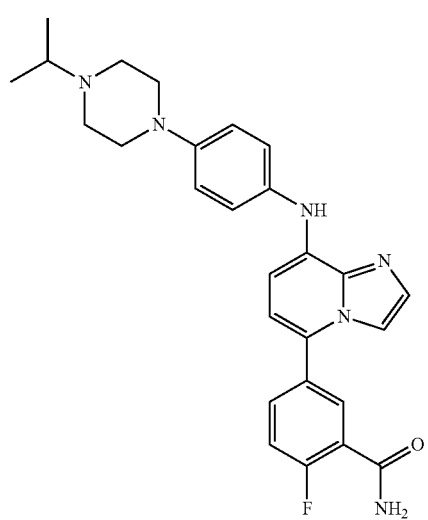
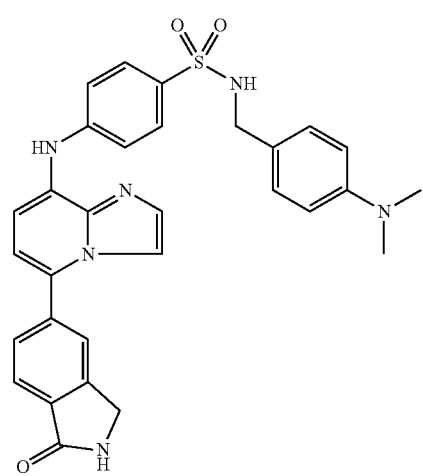
100
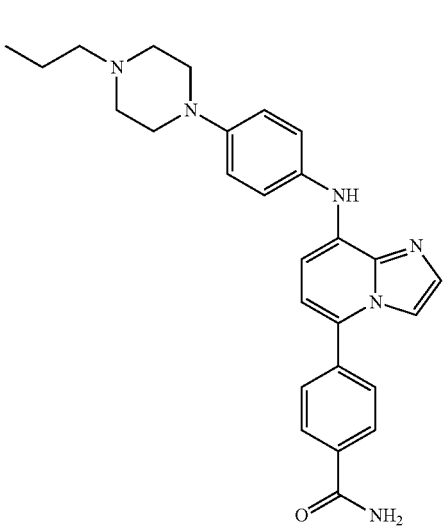
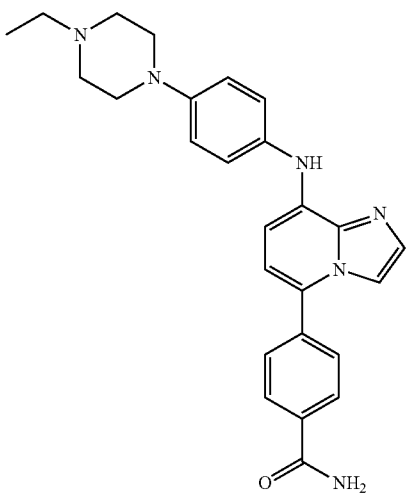
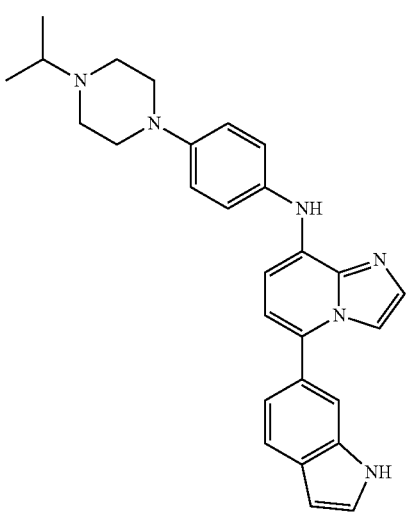

101
-continued
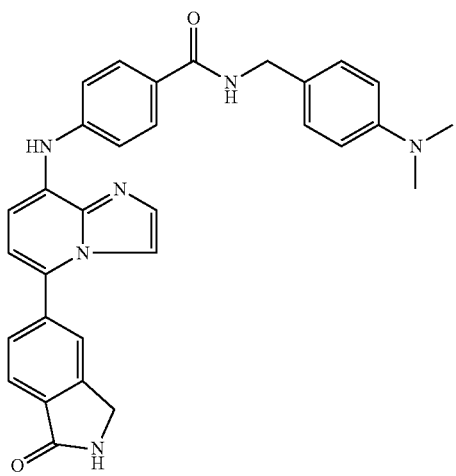
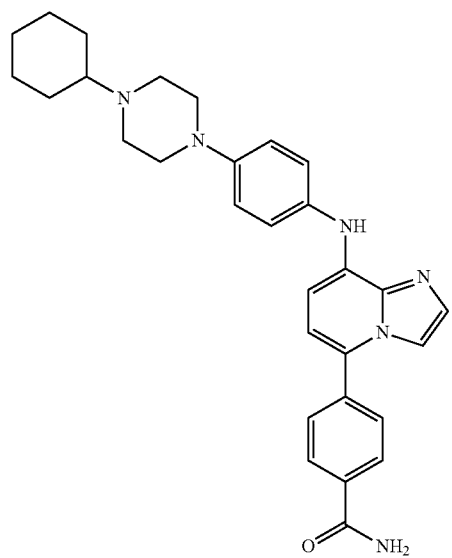
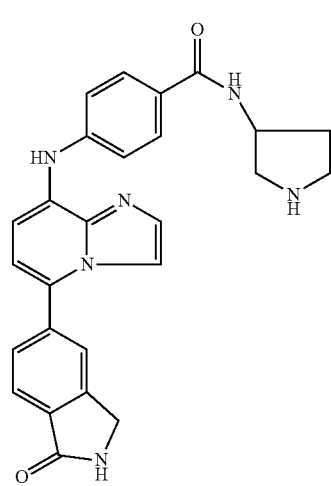
102
-continued
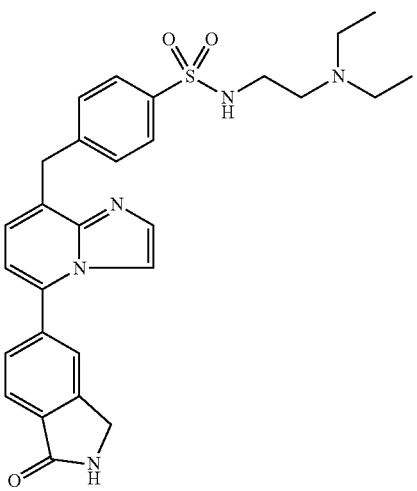
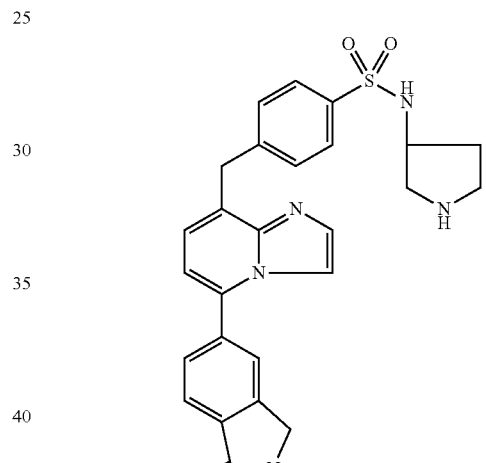
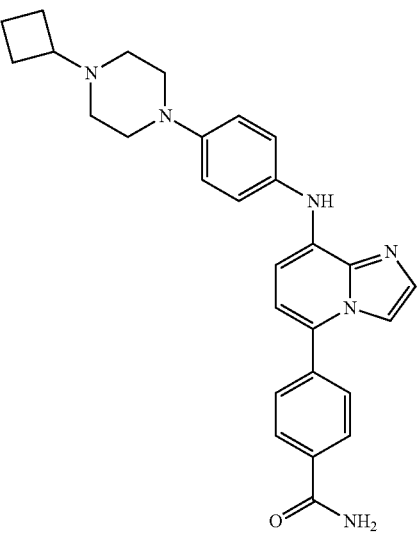

103
-continued
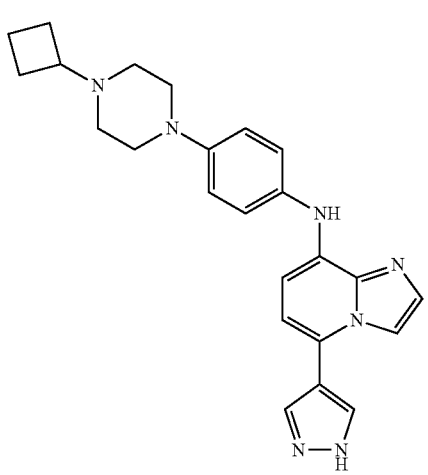
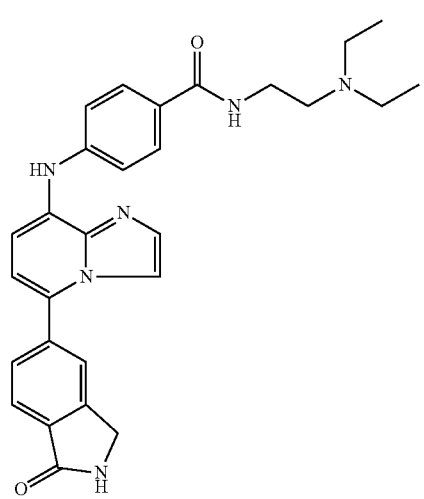
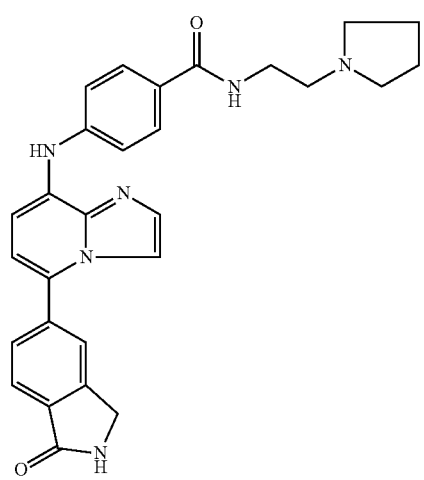
104
-continued
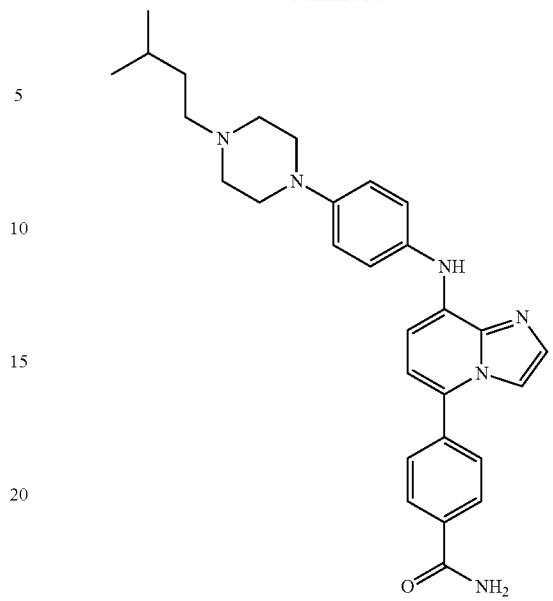
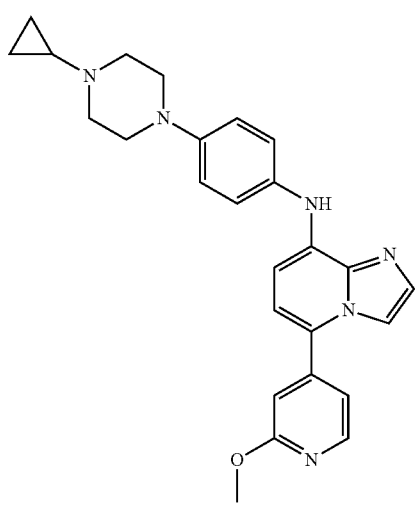
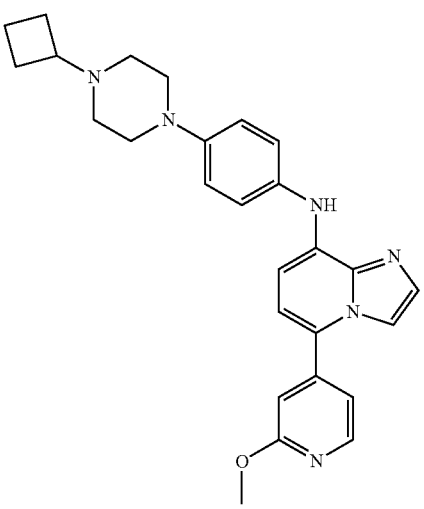

105
-continued
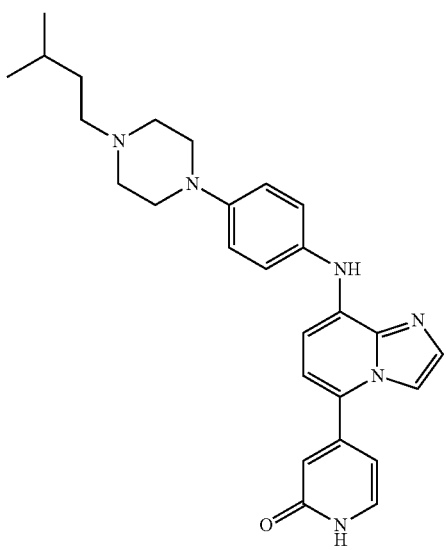
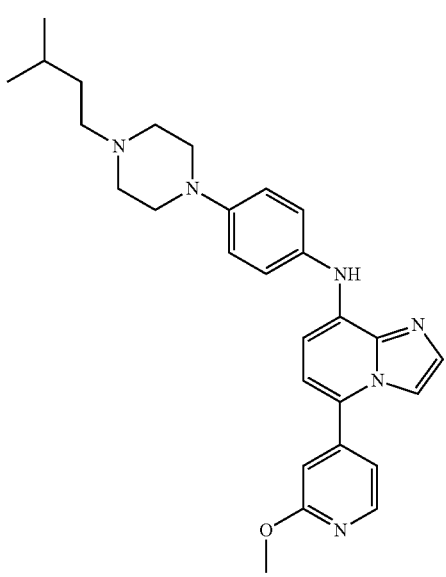
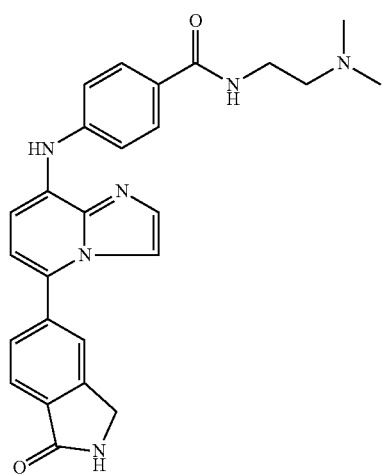
106
-continued
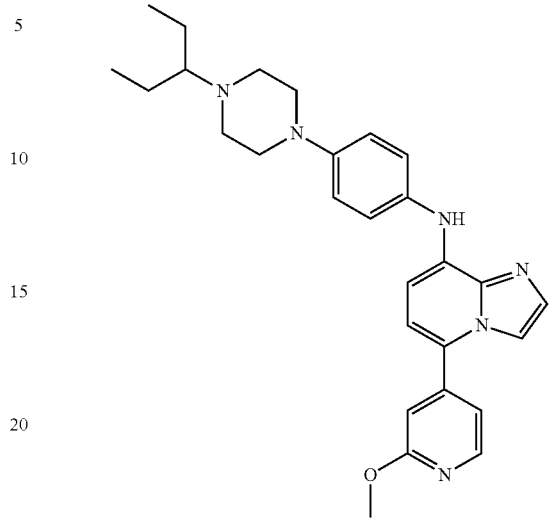
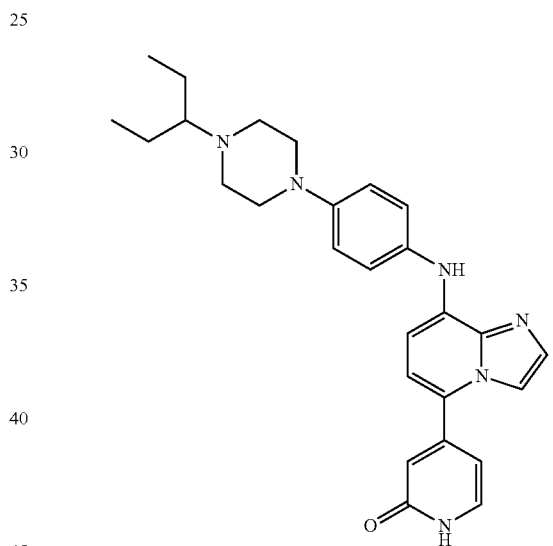
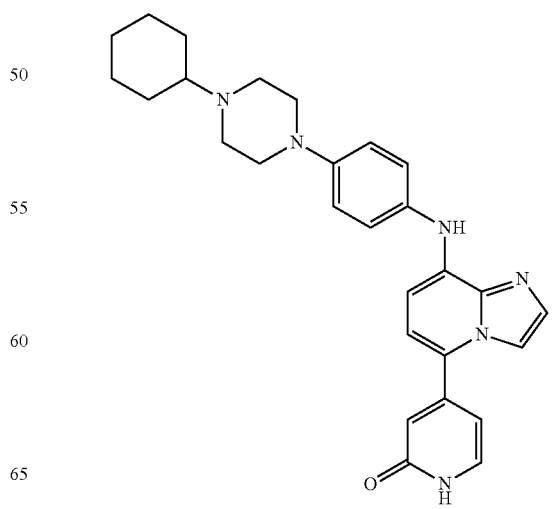

107
-continued
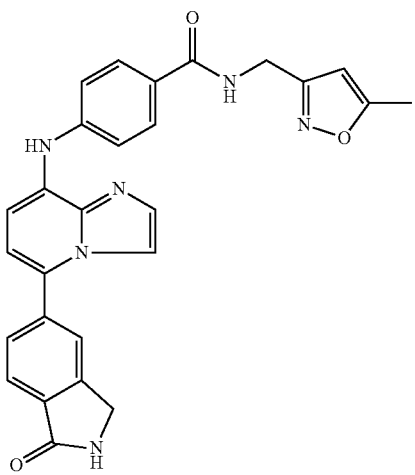
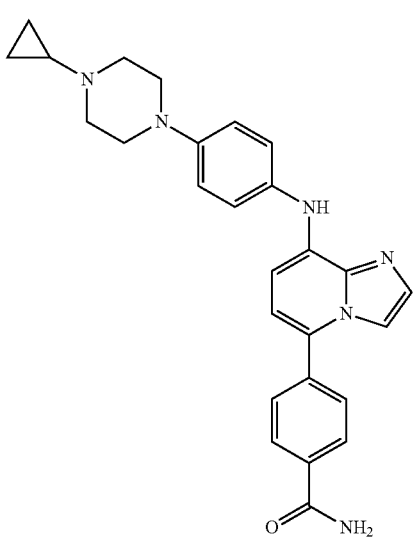
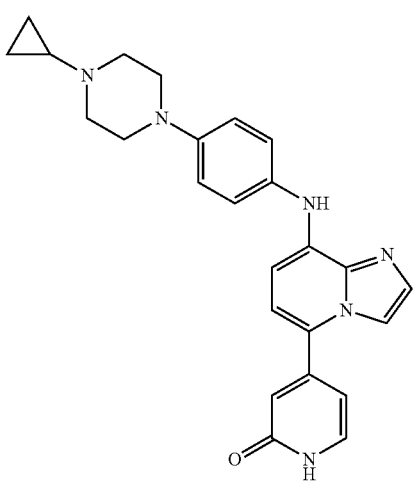
108
-continued
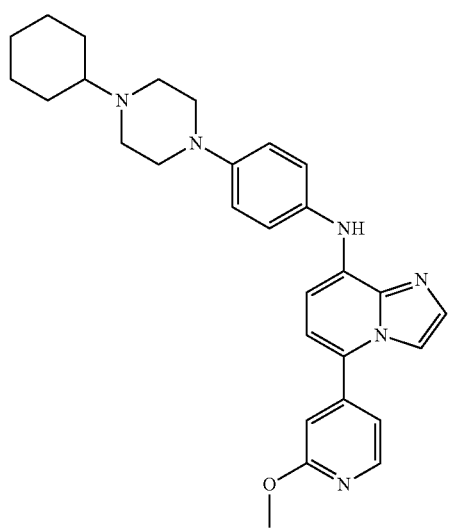
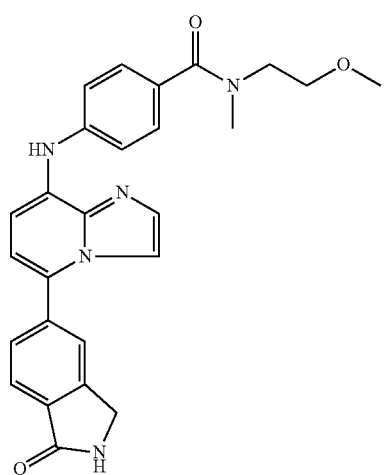
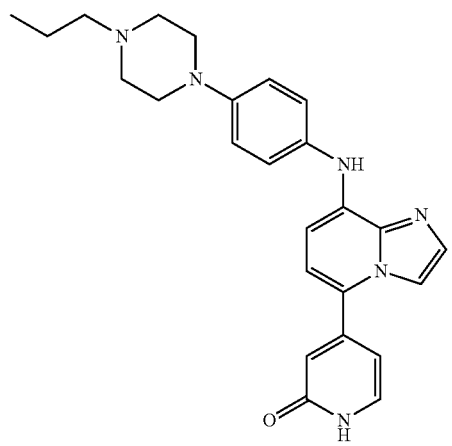

-continued
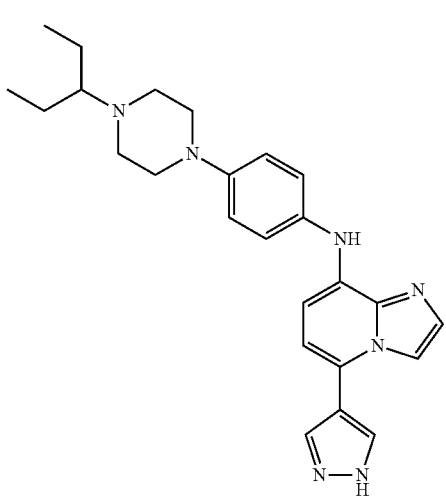
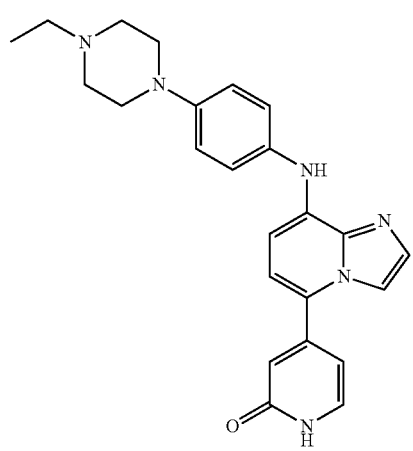
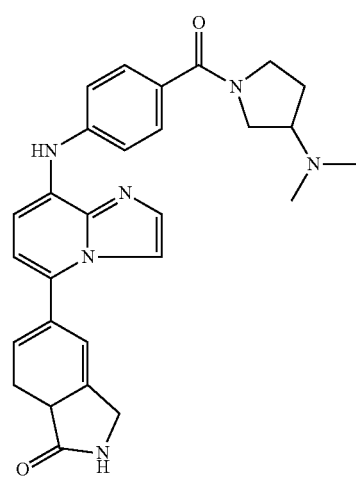
-continued
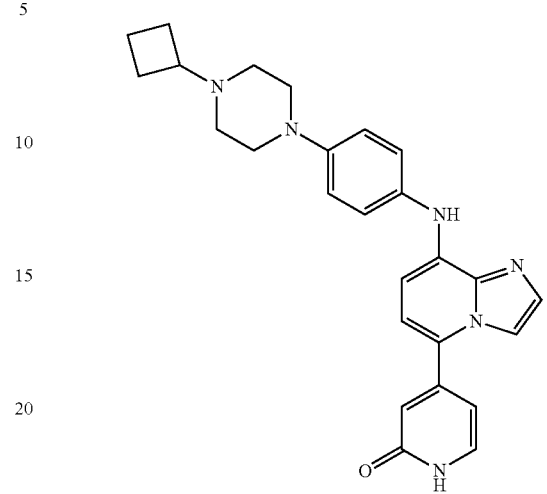
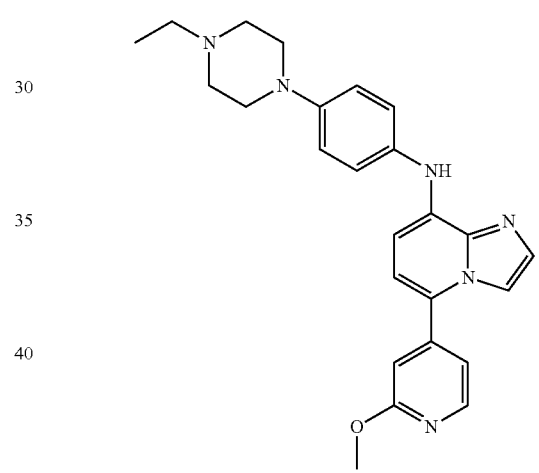
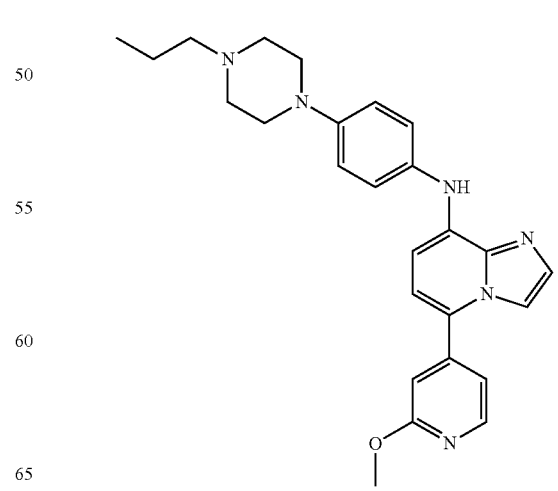

111
-continued
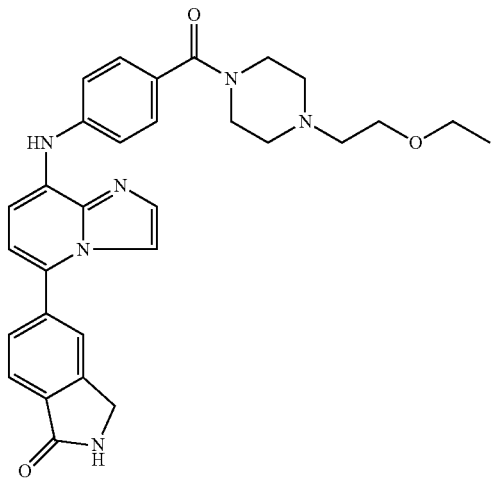
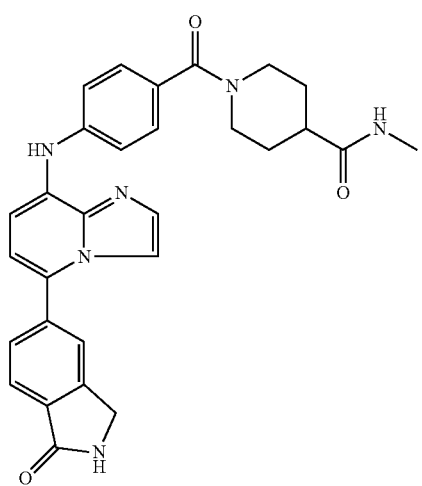
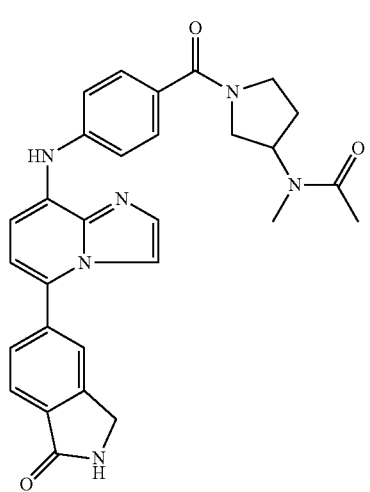
112
-continued
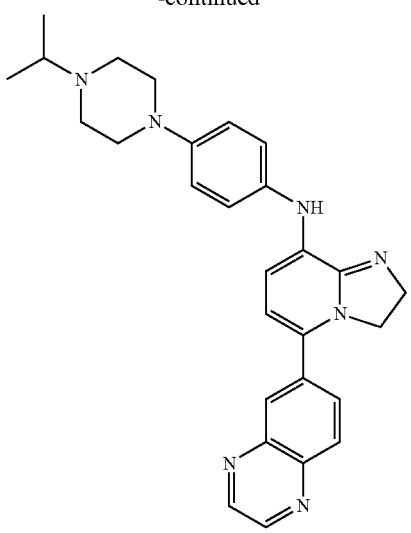
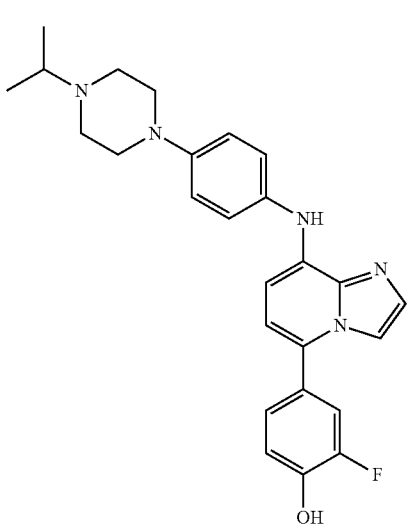
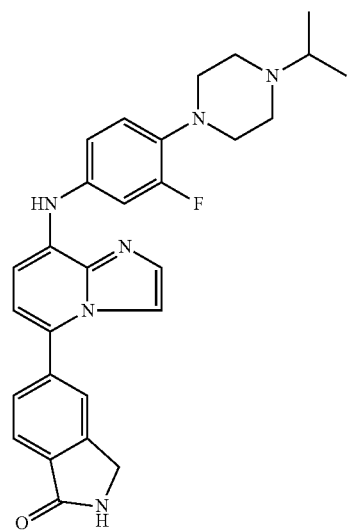

113
-continued
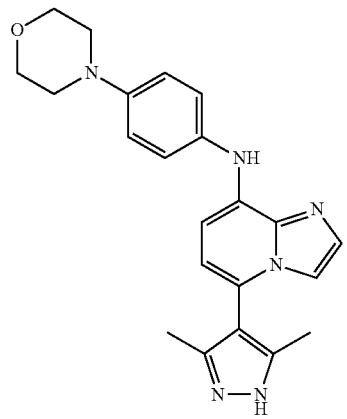
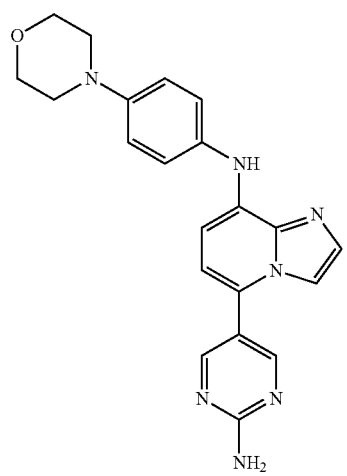
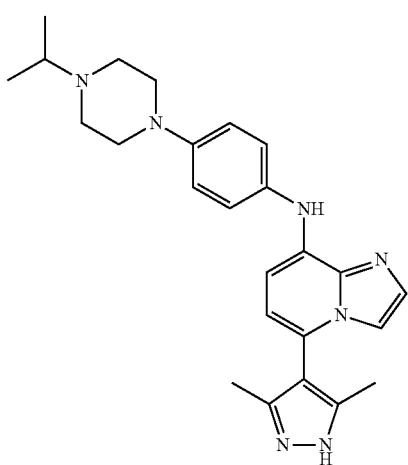
114
-continued
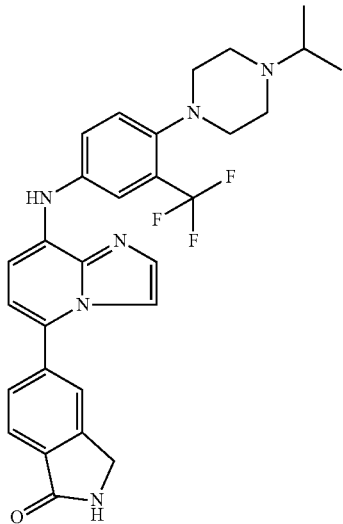
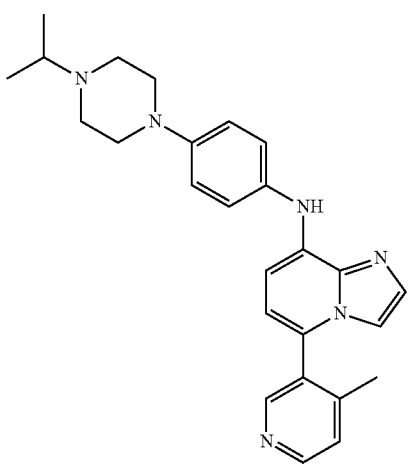
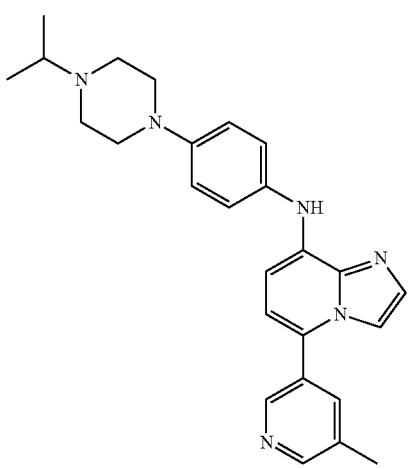

115
-continued
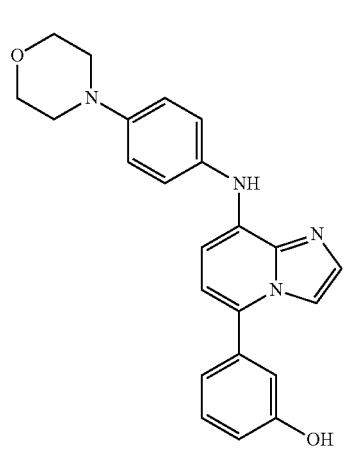
116
-continued
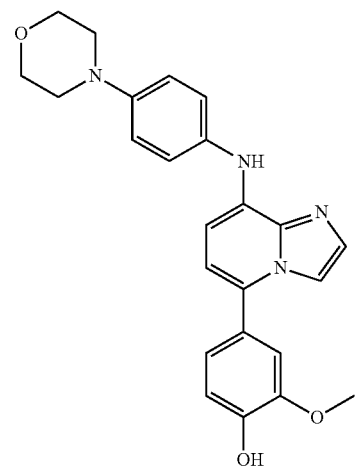
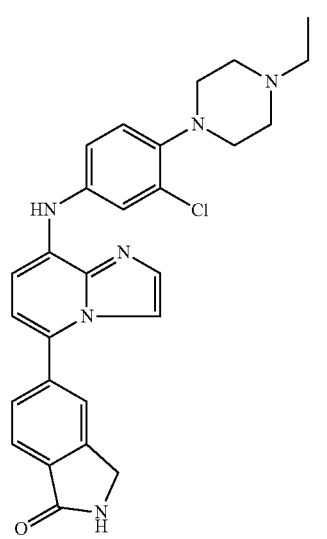
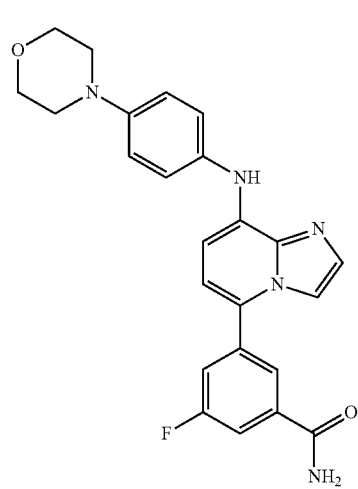
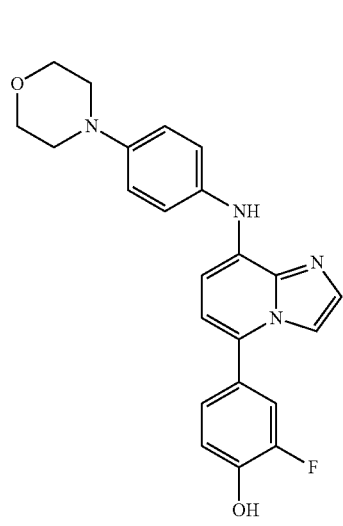
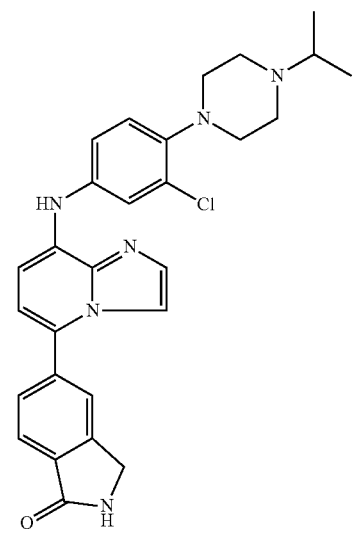

117
-continued
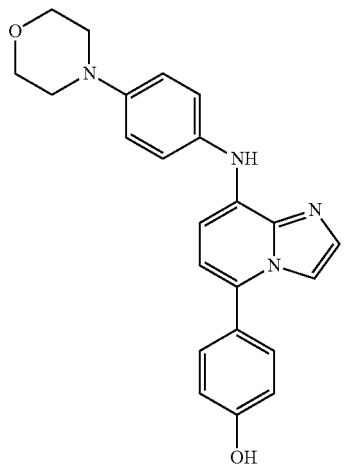
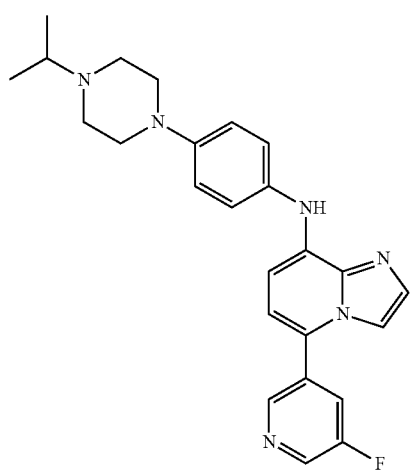
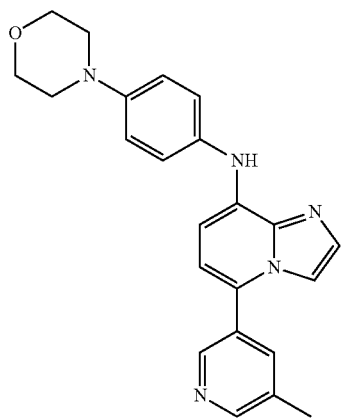
118
-continued
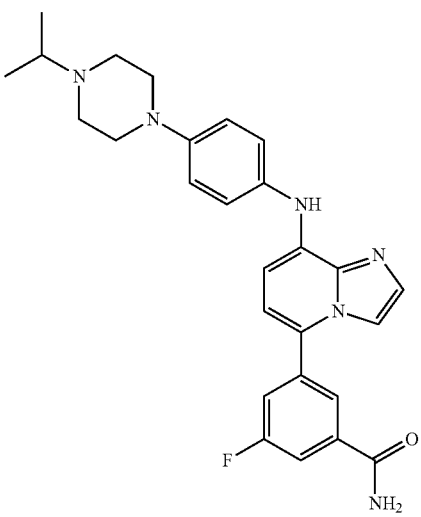
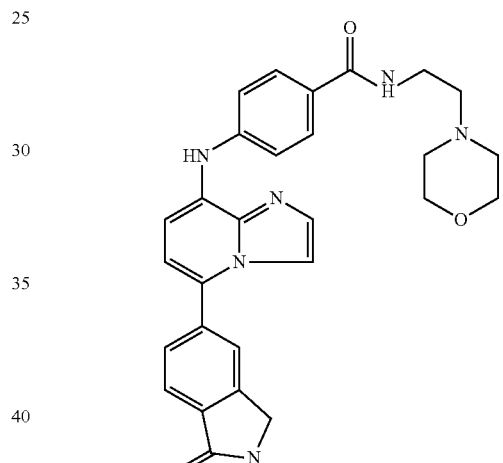
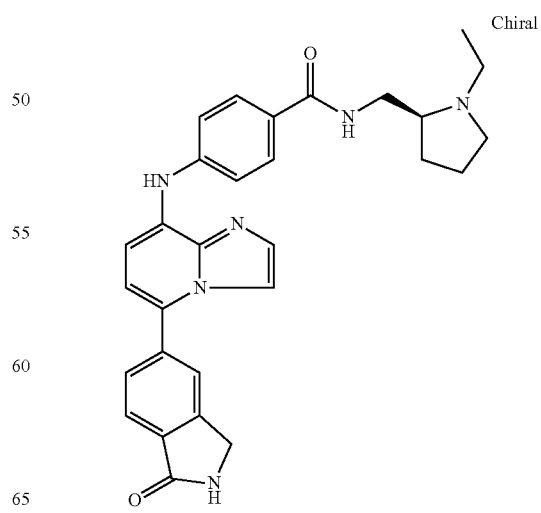

119
-continued
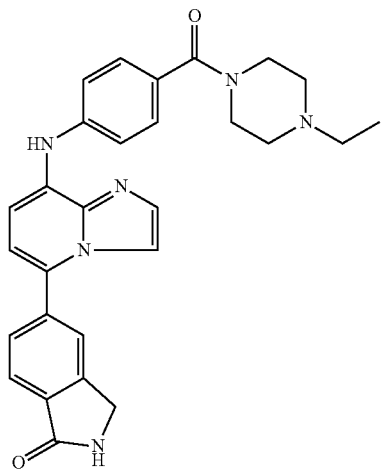
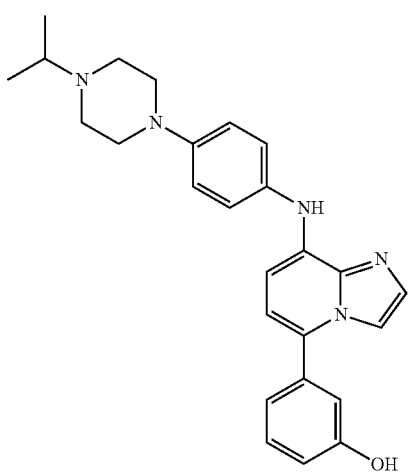
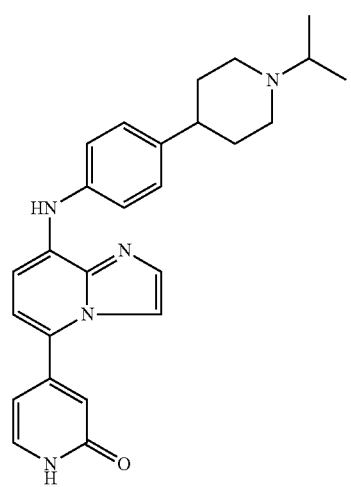
120
-continued
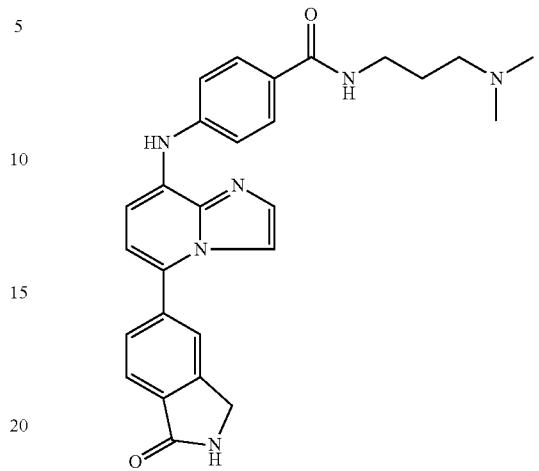
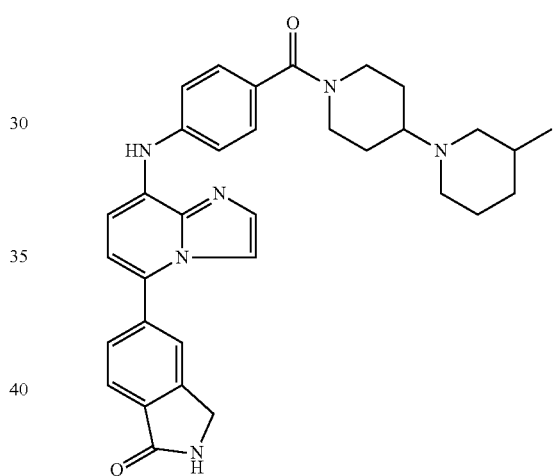
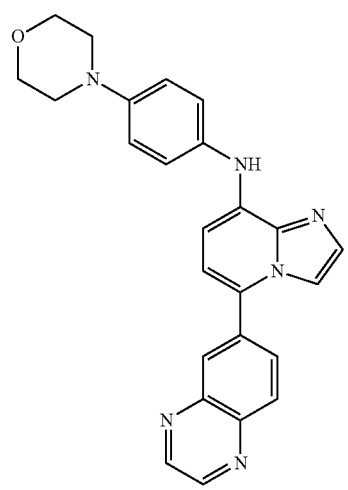

121
-continued
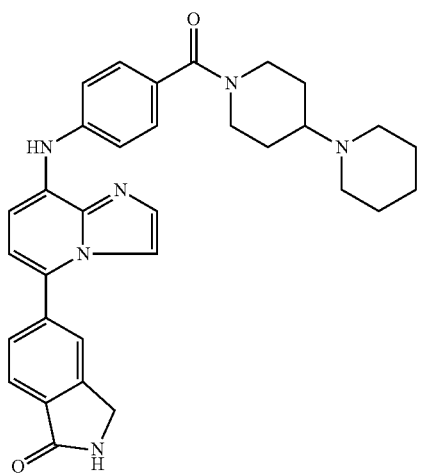
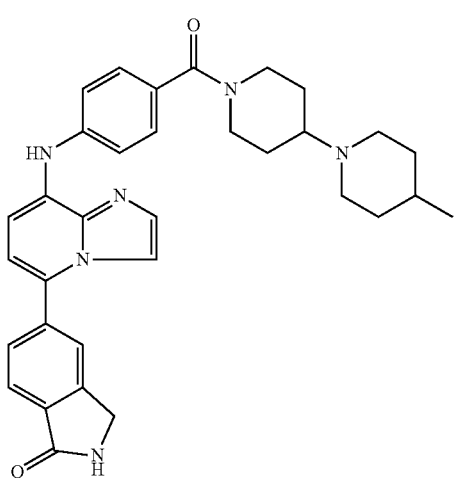
122
-continued
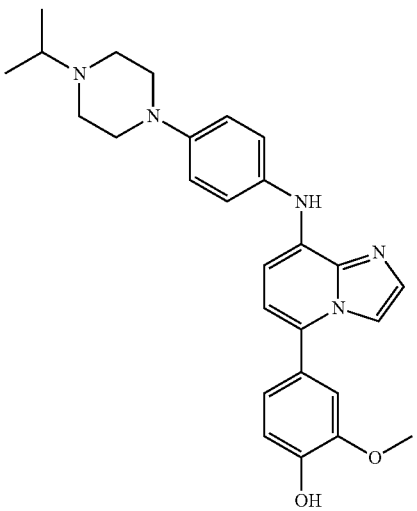
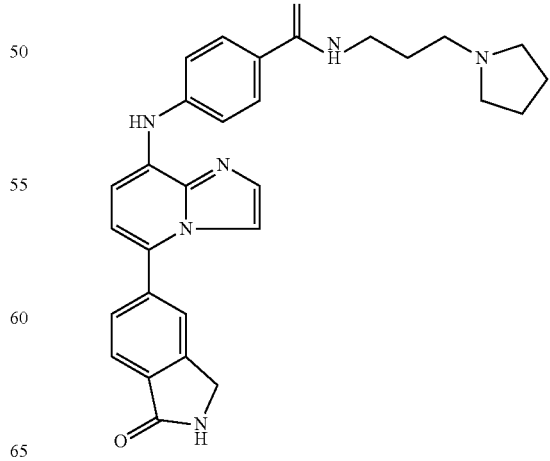

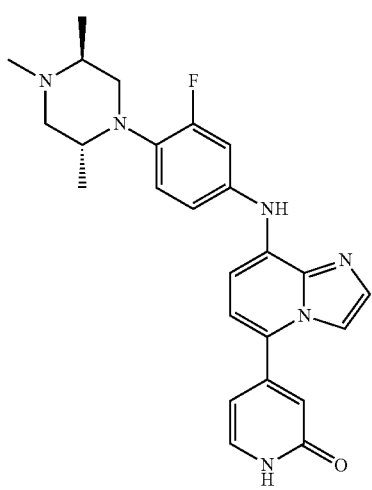
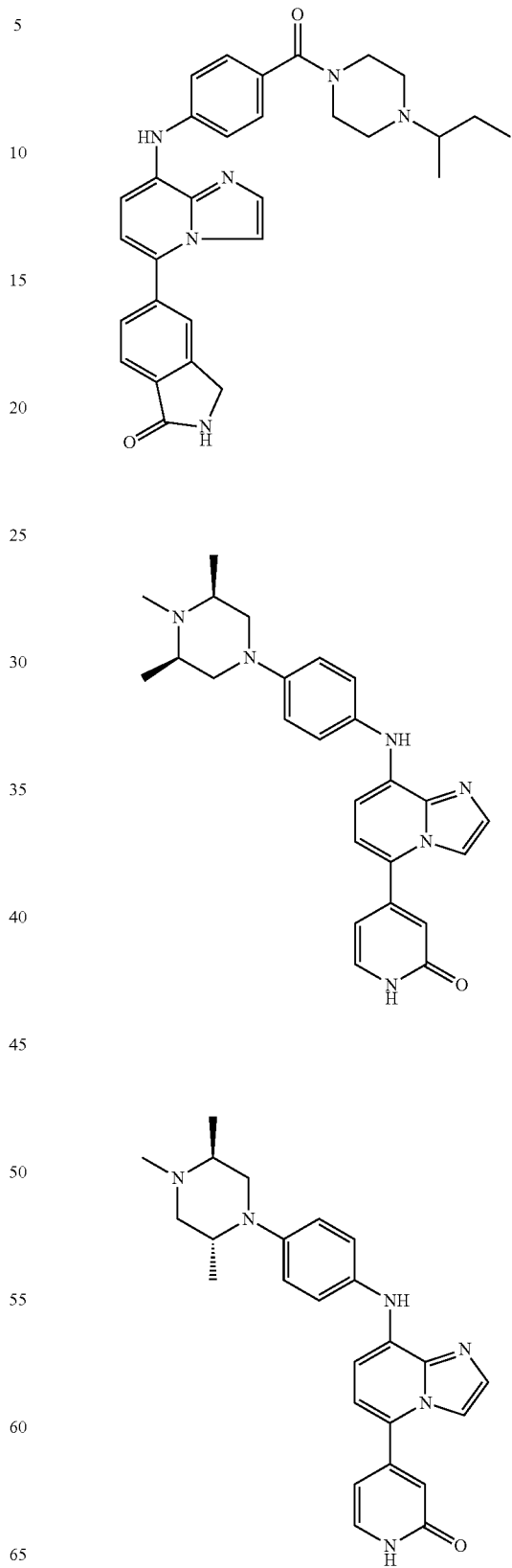

125
-continued
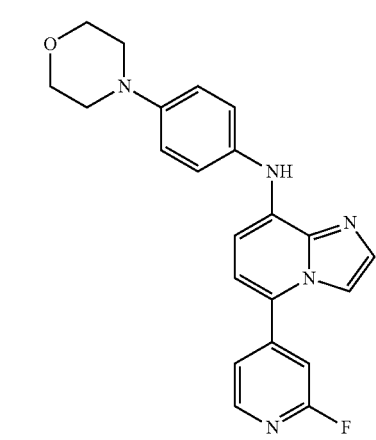
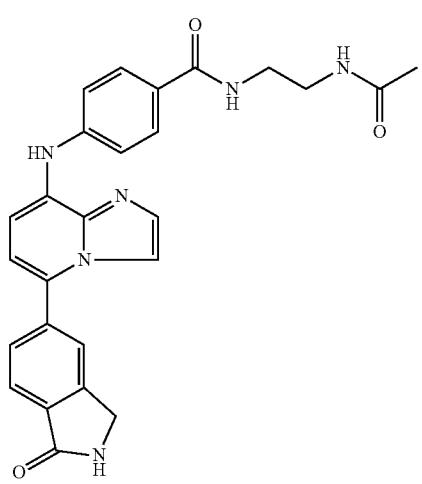
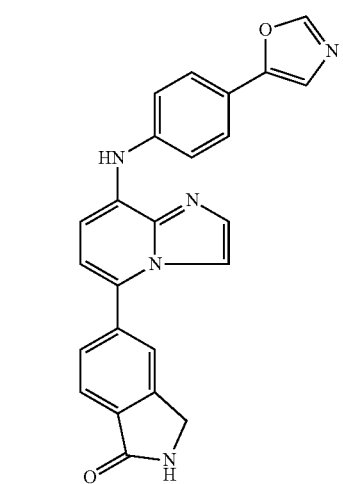
126
-continued
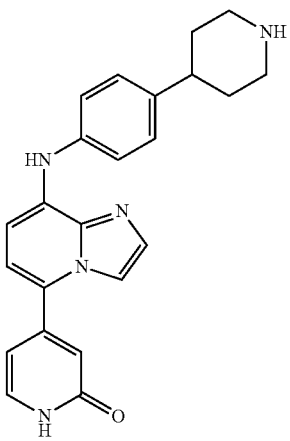
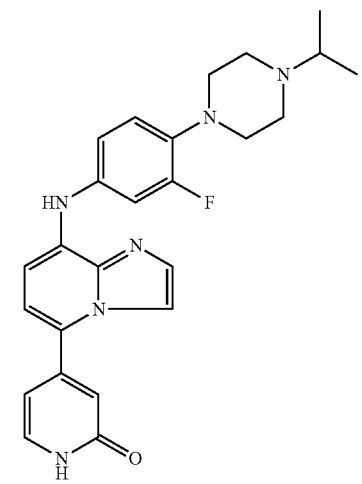
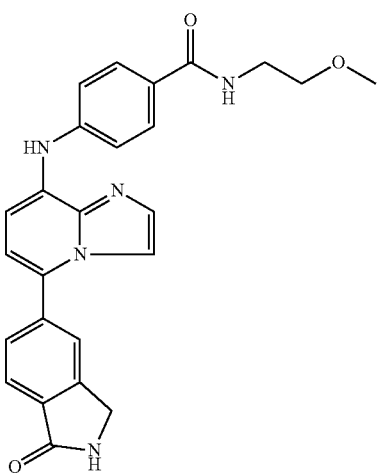

127
-continued
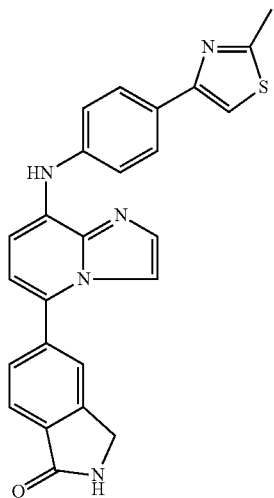
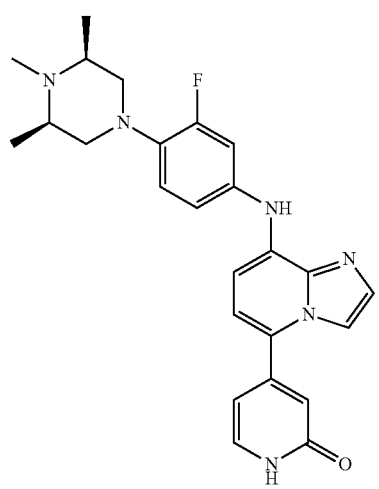
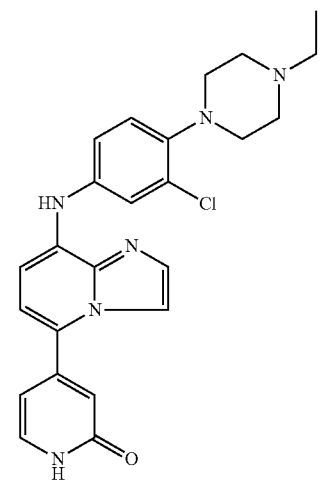
128
-continued
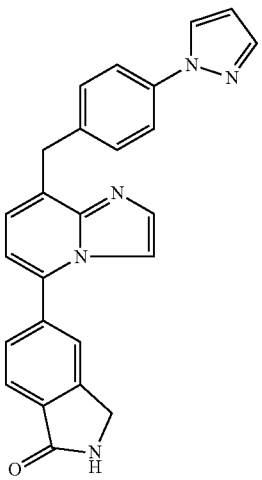
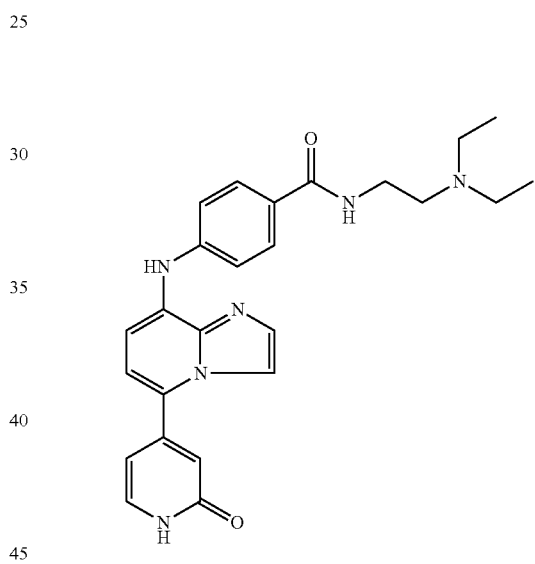

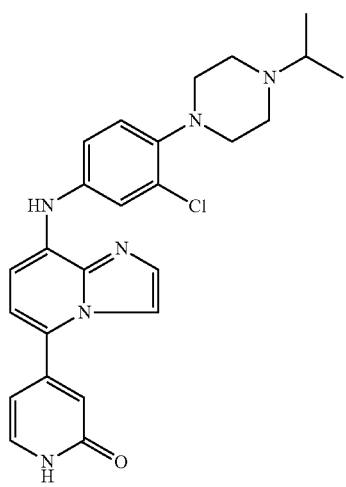
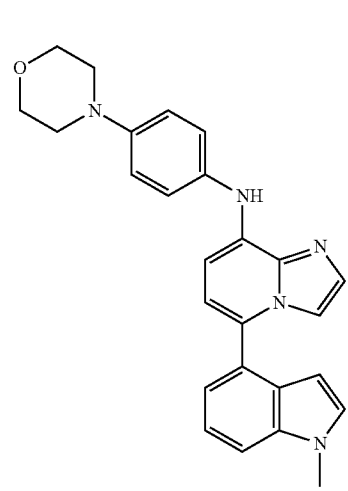
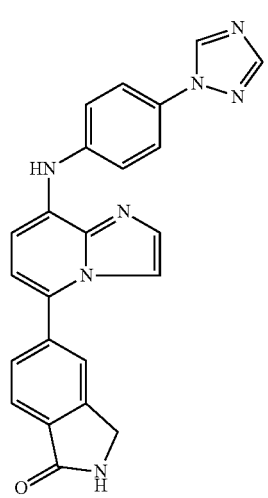
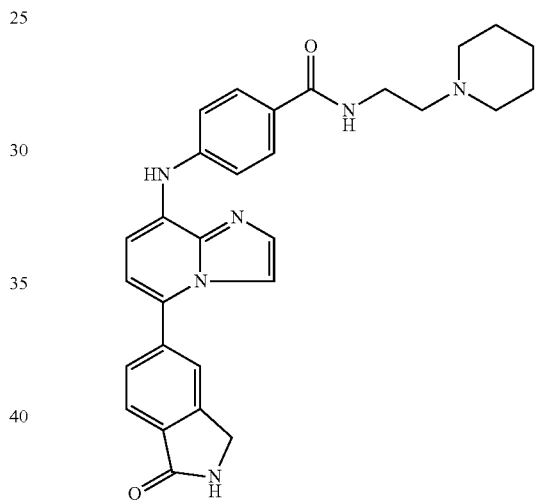
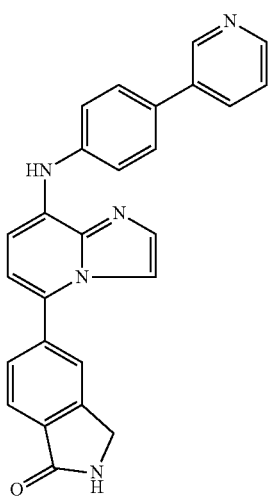
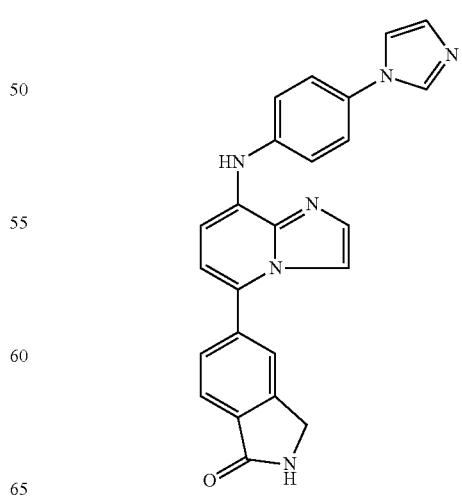

131
-continued
132
-continued
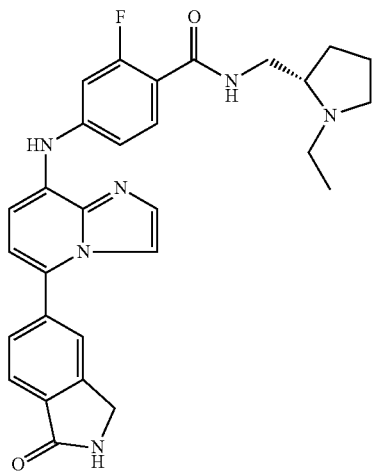
Chiral
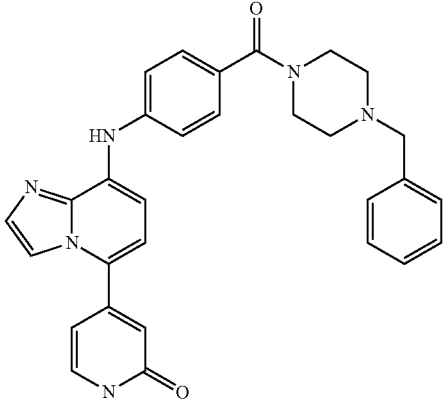
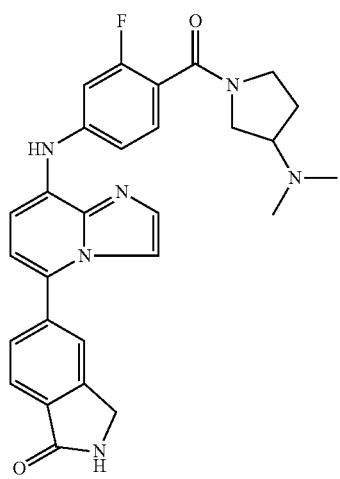
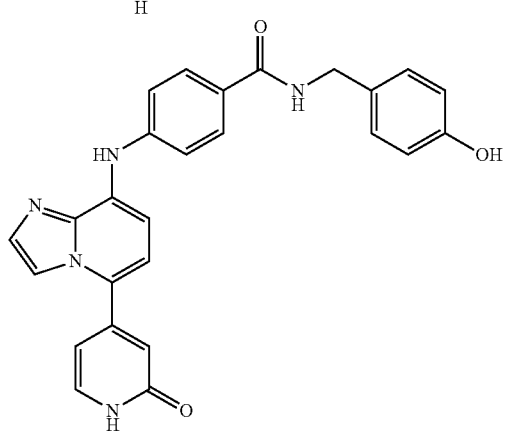
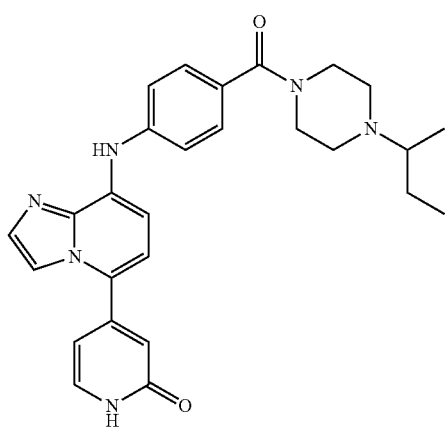
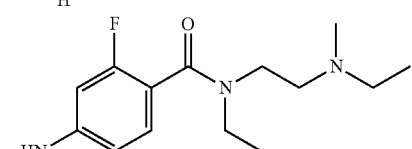
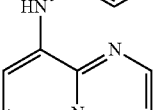
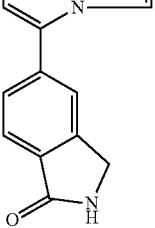
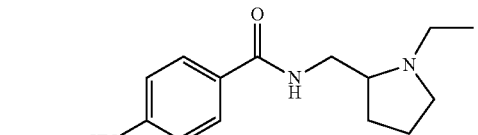
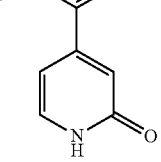

133
-continued
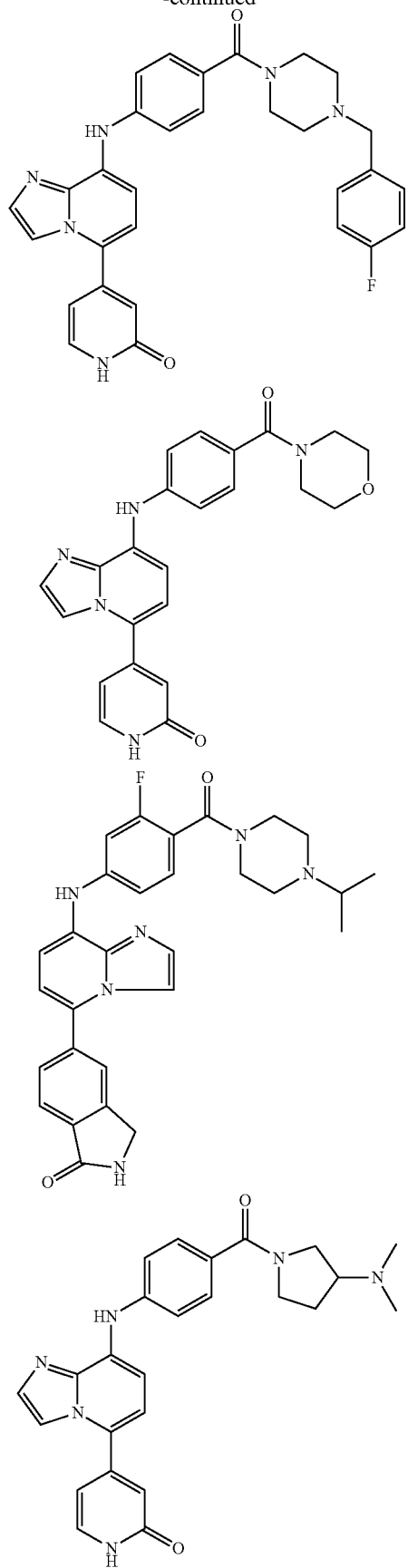
134
-continued
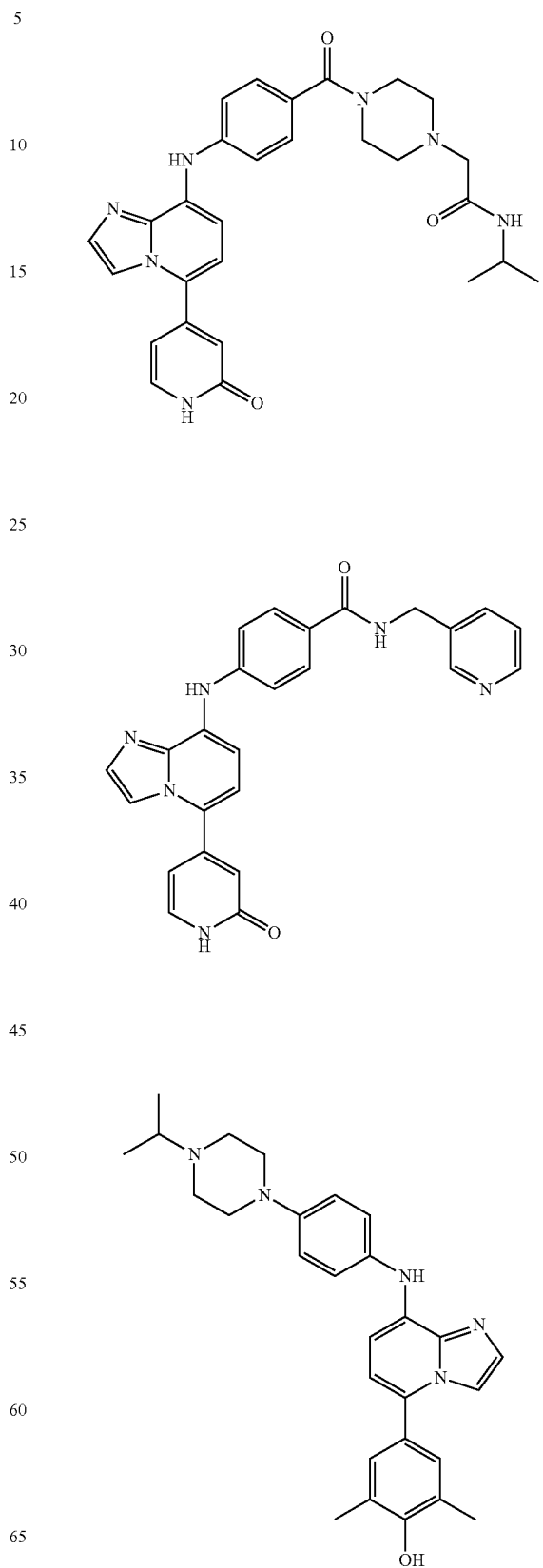

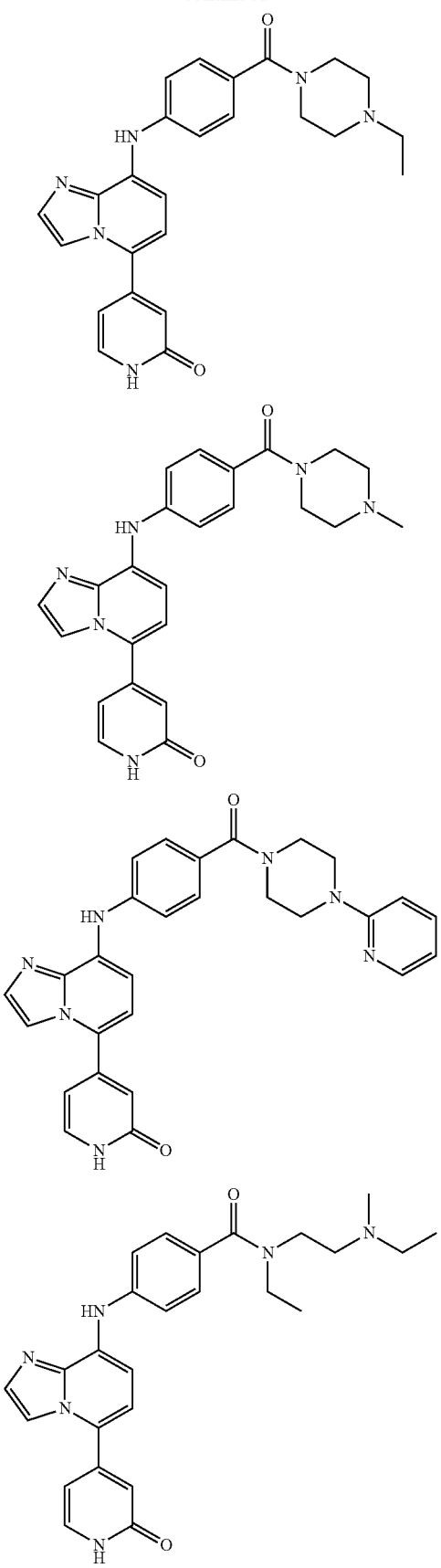

137
-continued
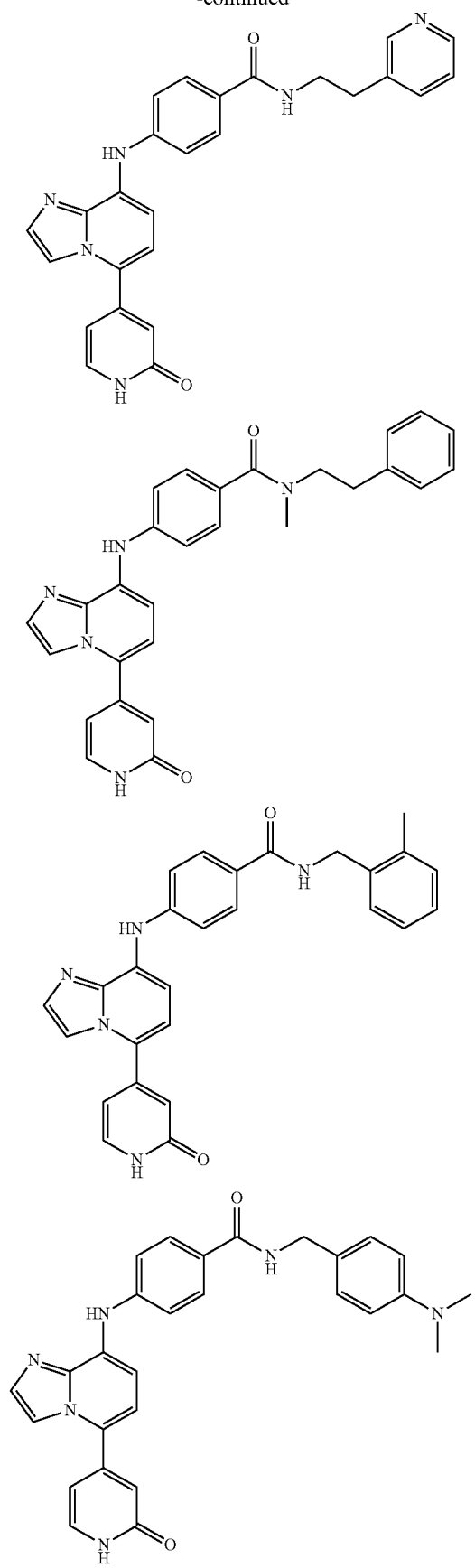
138
-continued
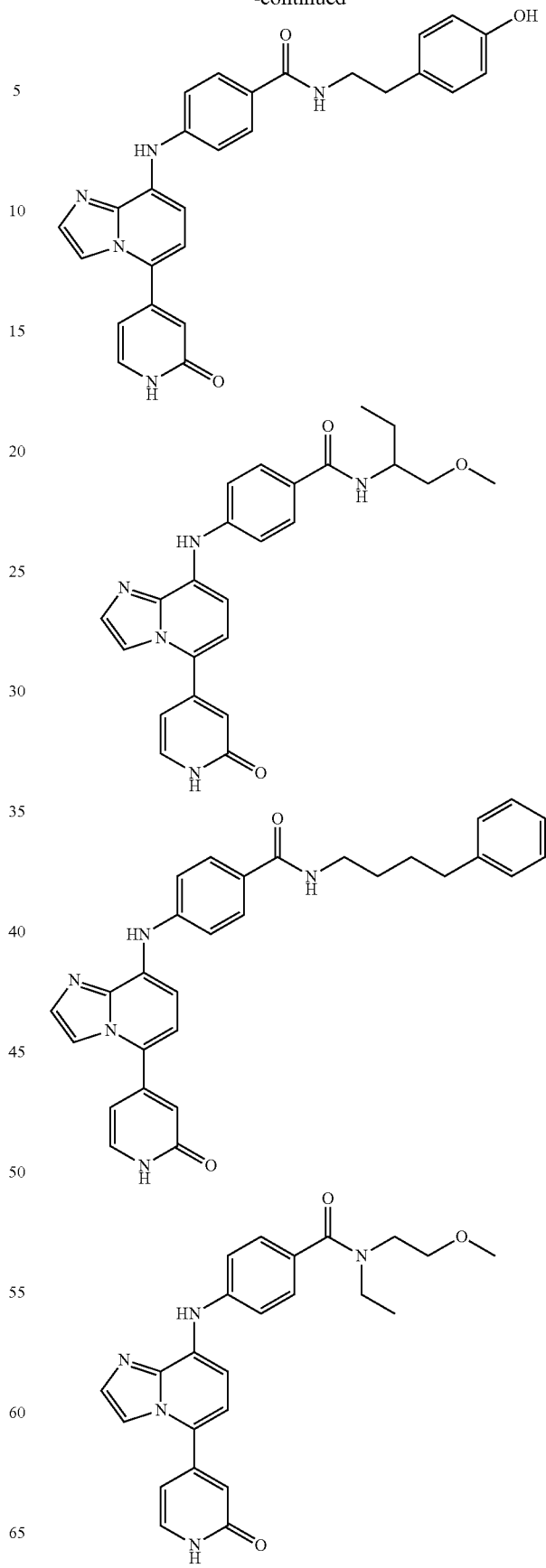

139
-continued
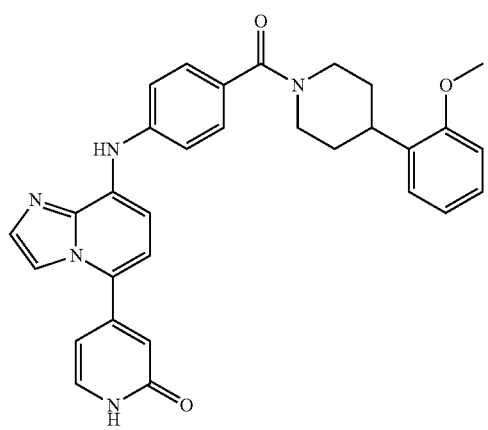
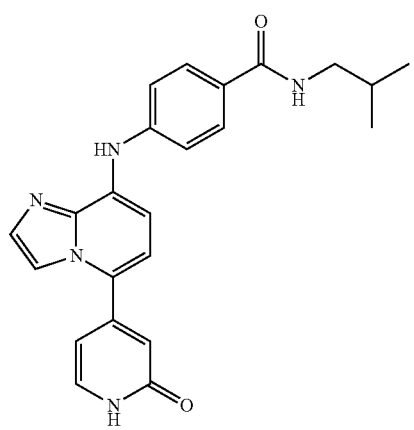
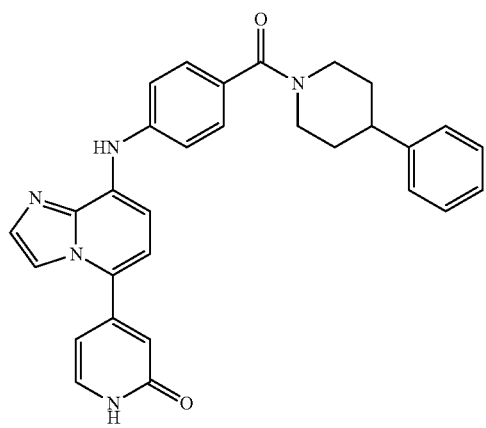
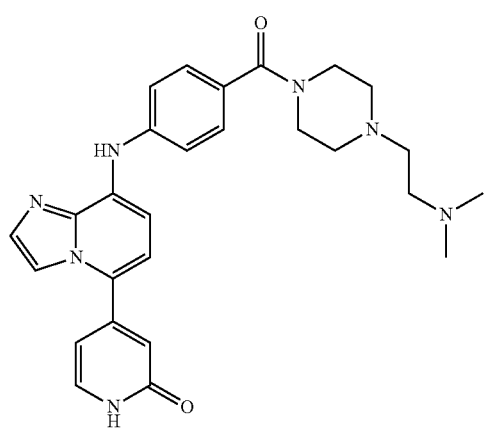
140
-continued
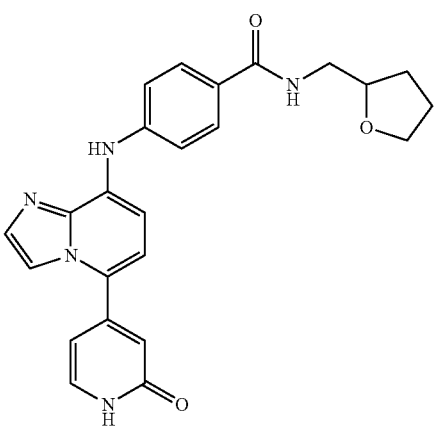
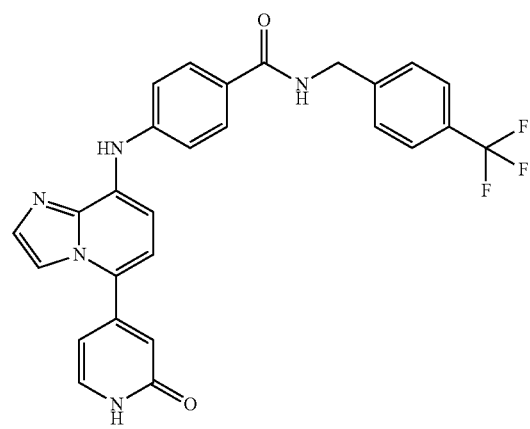
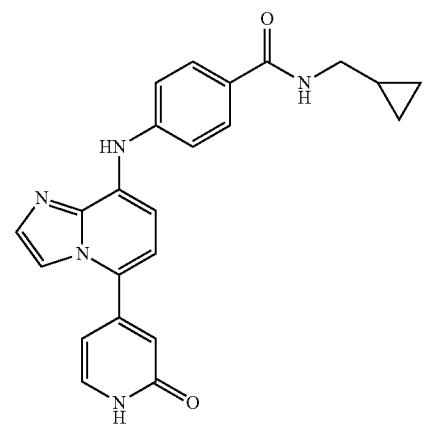
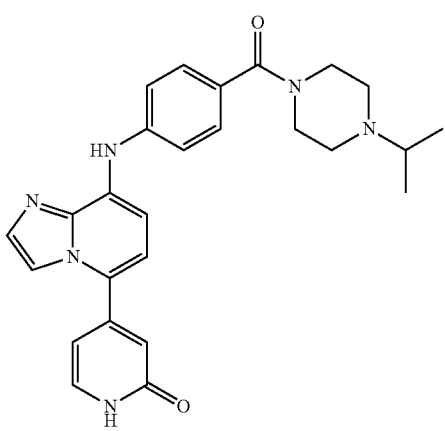

141
-continued
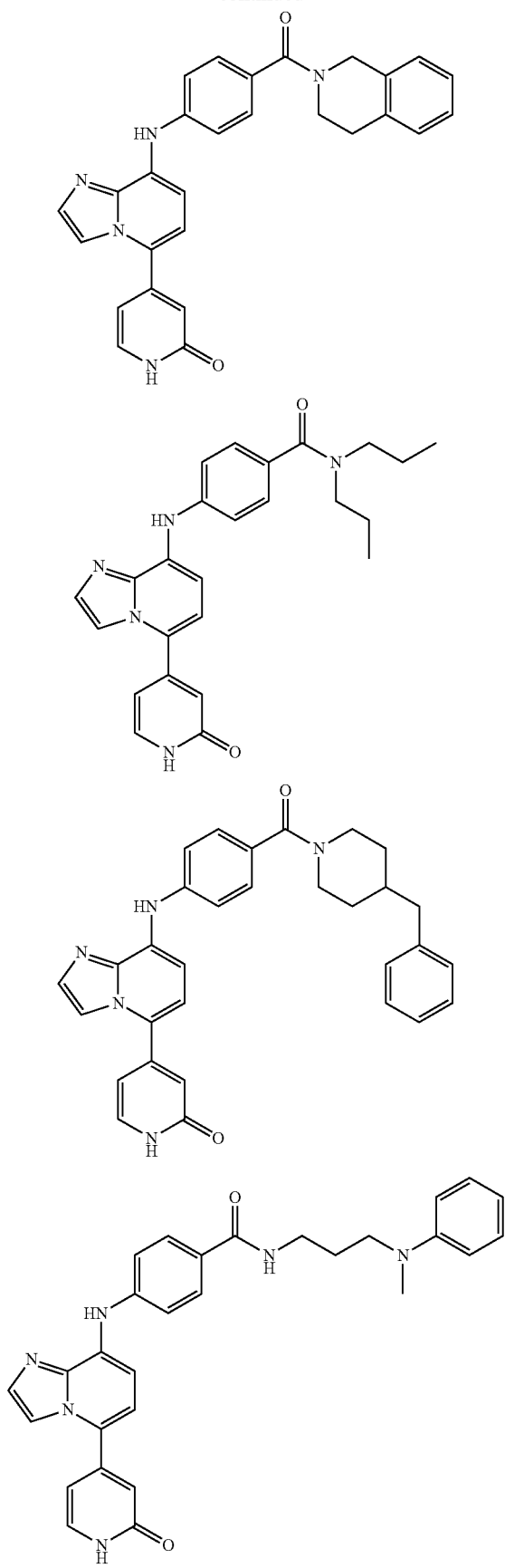
142
-continued
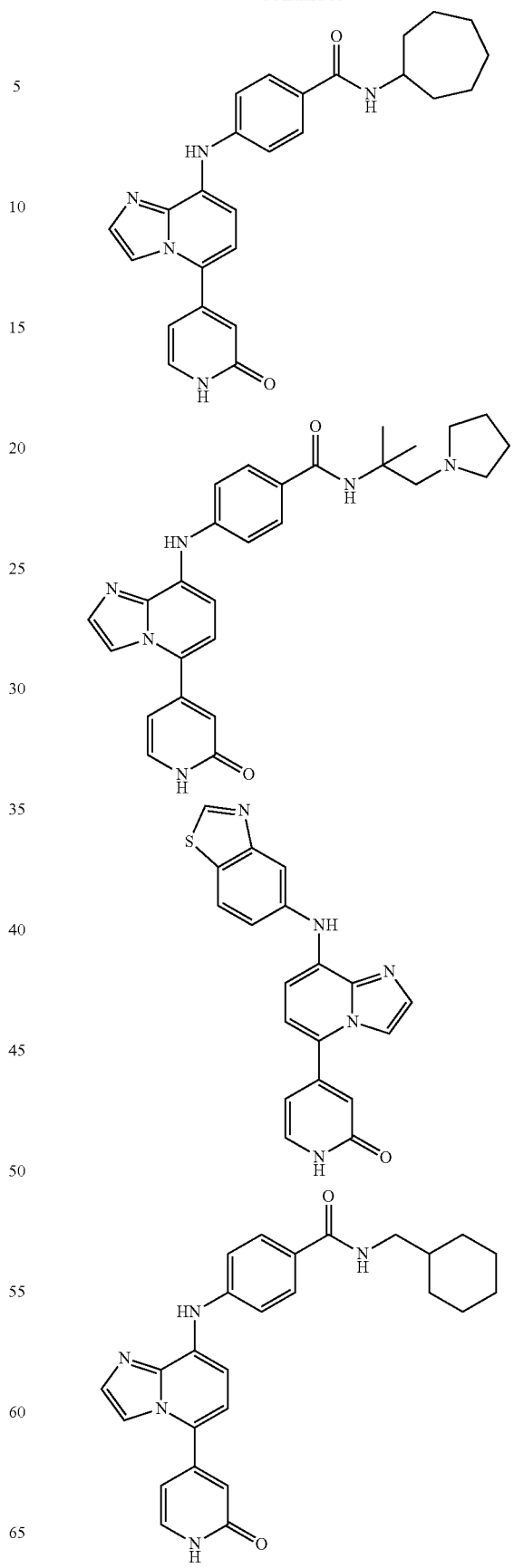

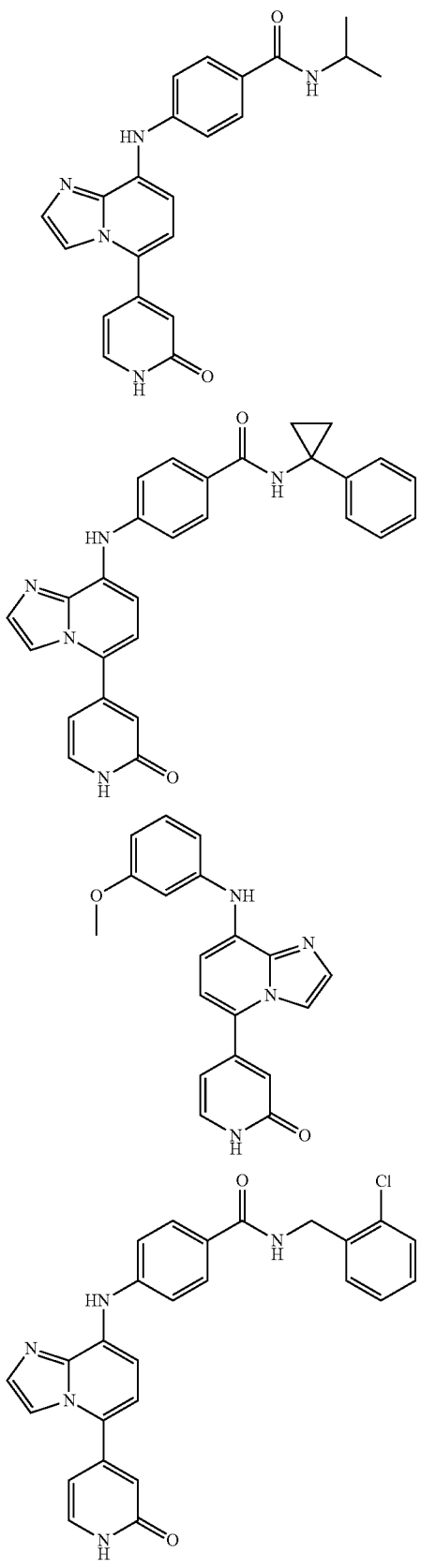
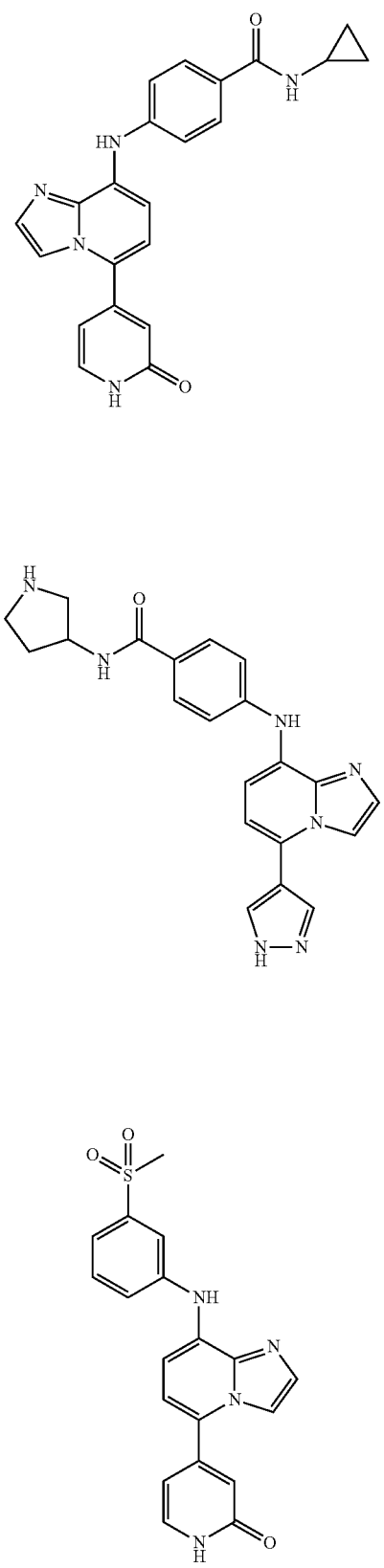

145
-continued
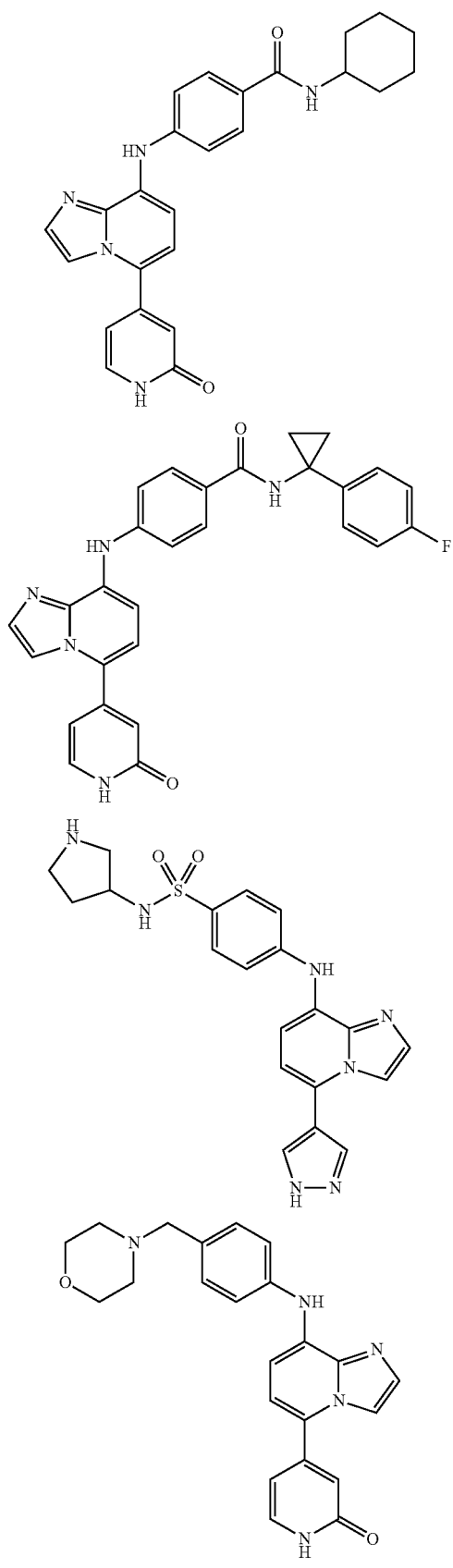
146
-continued
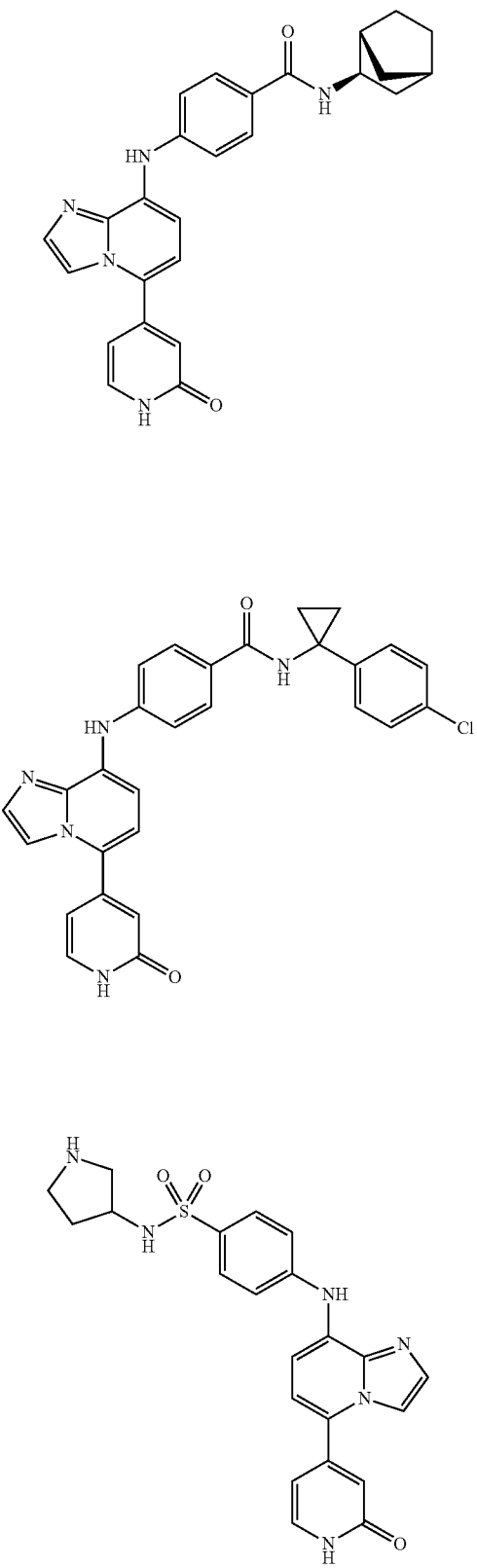

147
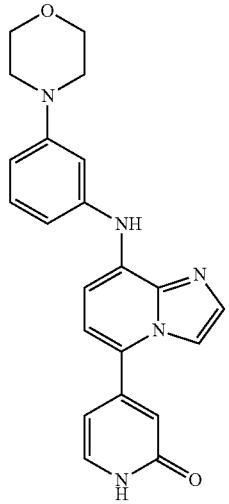
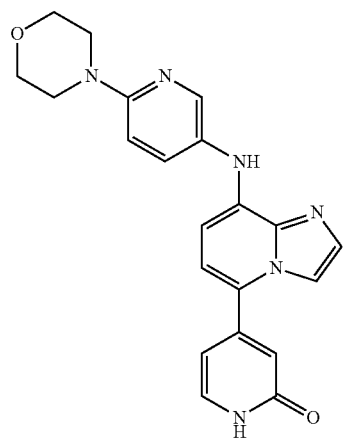
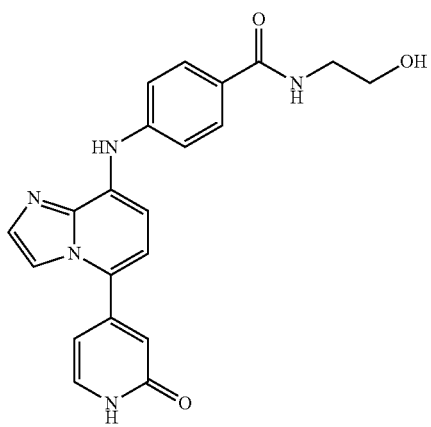
148
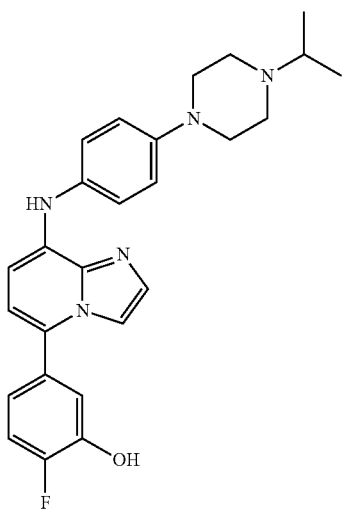
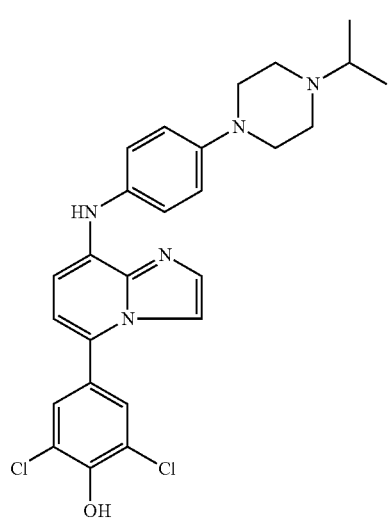
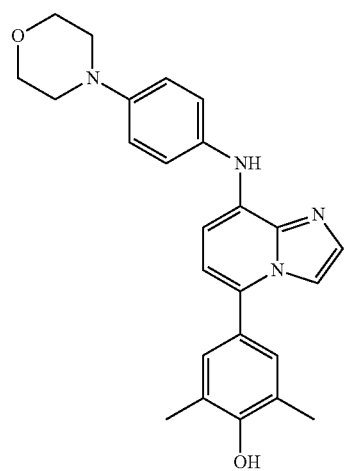

149
-continued
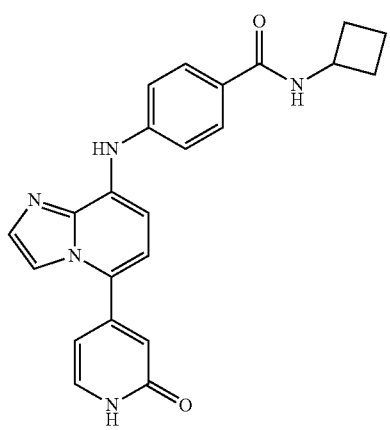
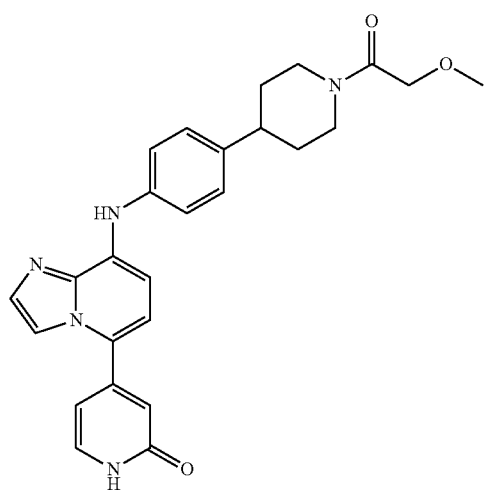
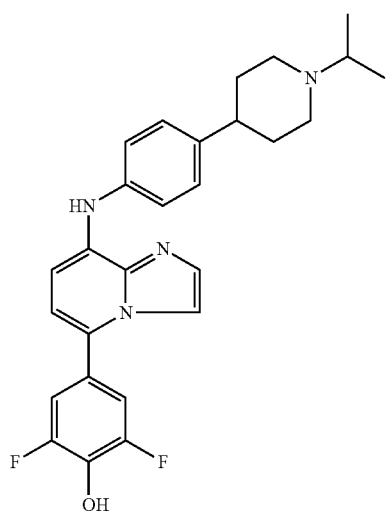
150
-continued
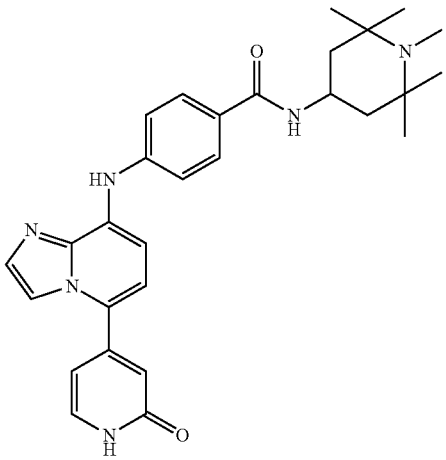
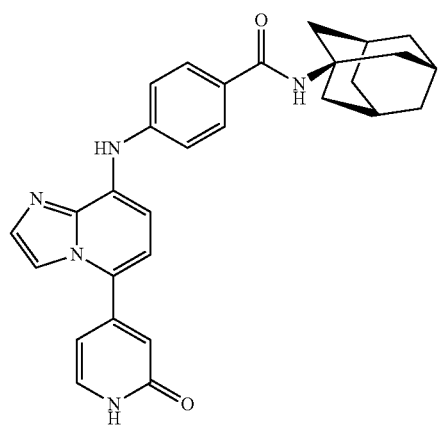
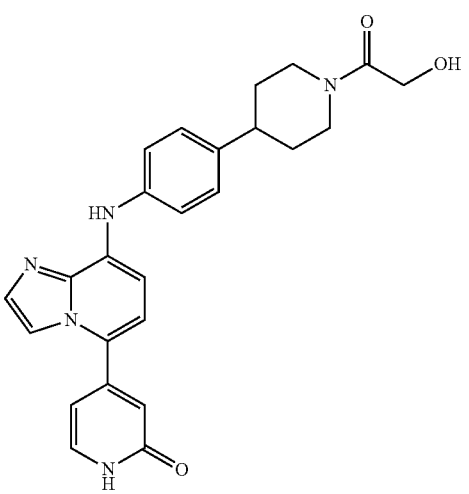
In particularly preferred embodiments of the invention include the following compounds of Formula I and pharmaceutically acceptable salts, solvates or prodrugs thereof:

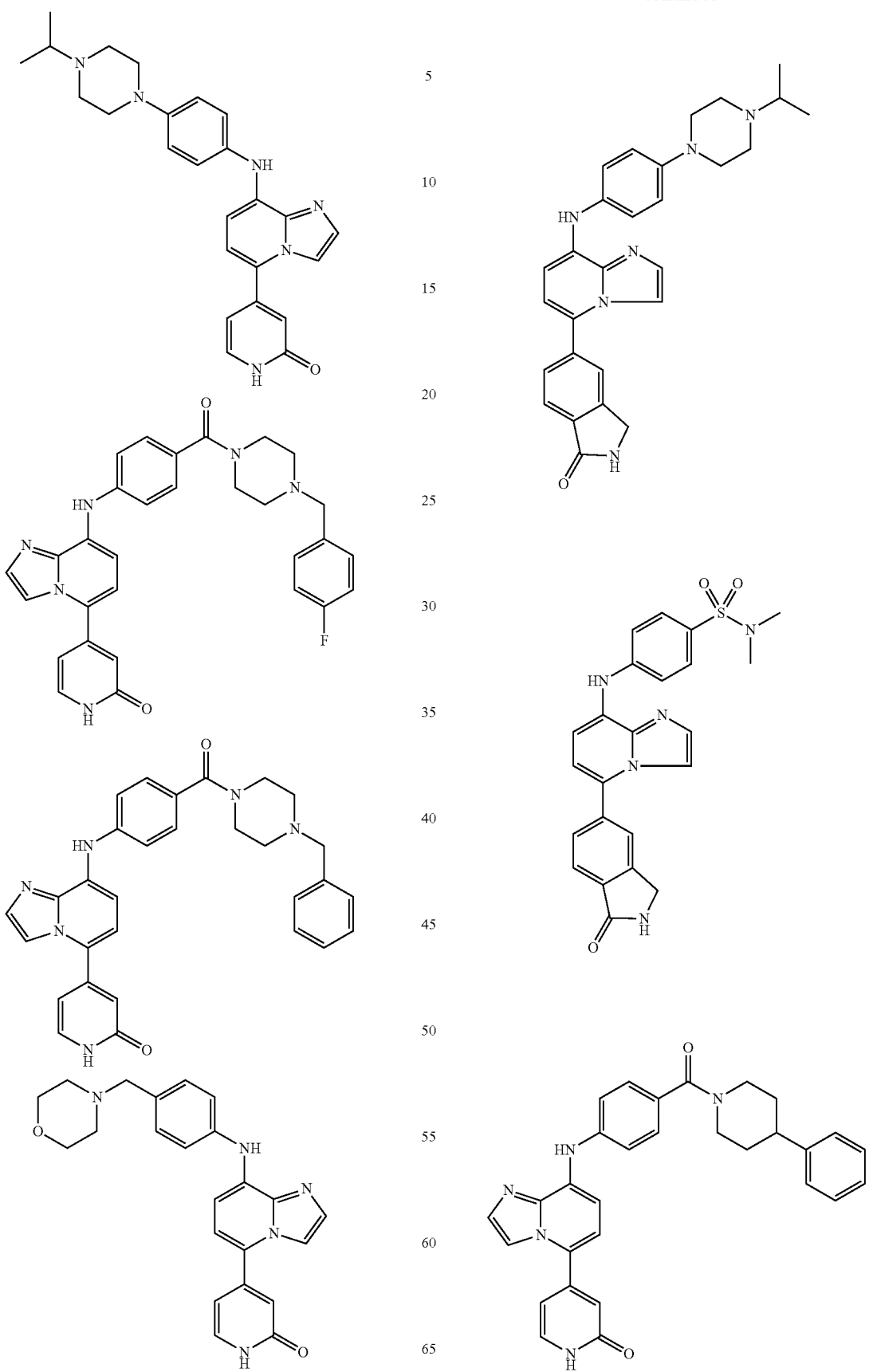

153
-continued
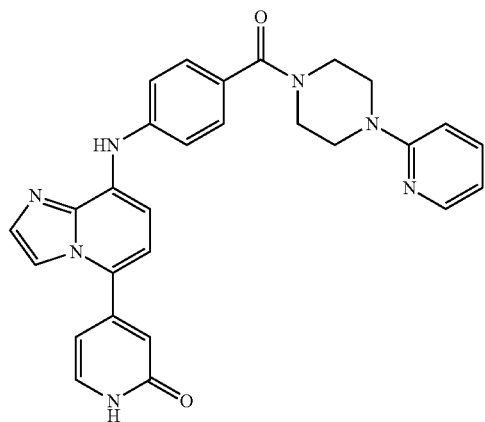
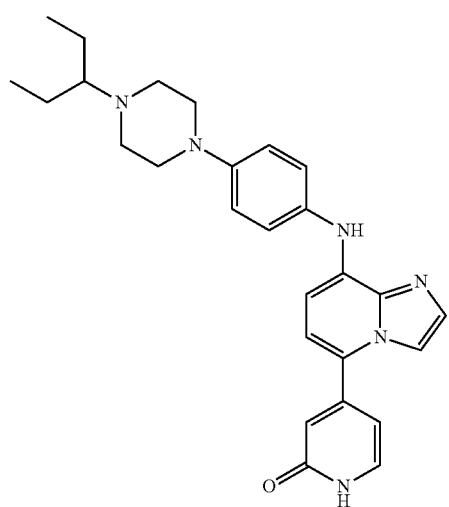
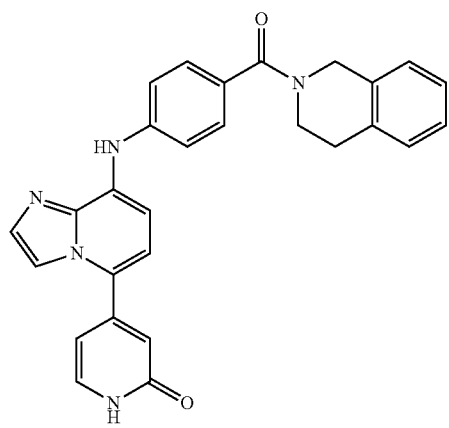
154
-continued
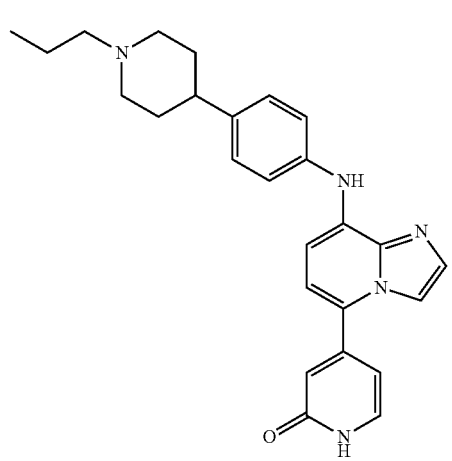
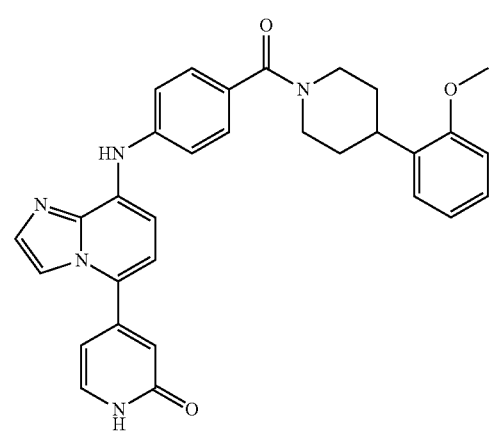
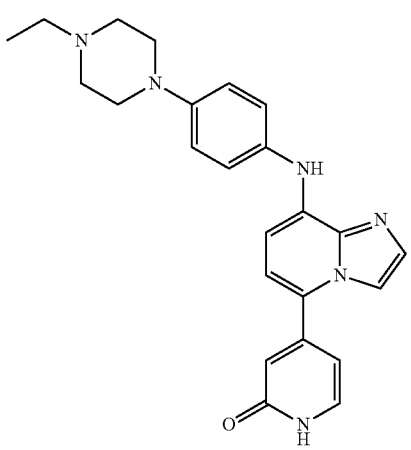

155
-continued
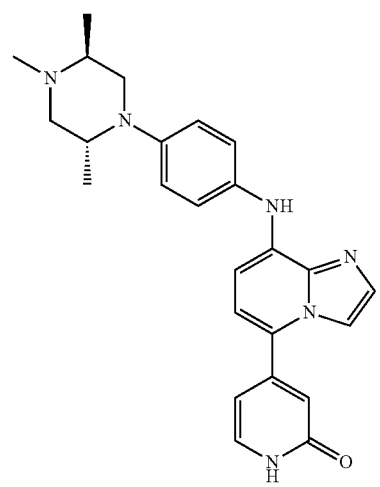
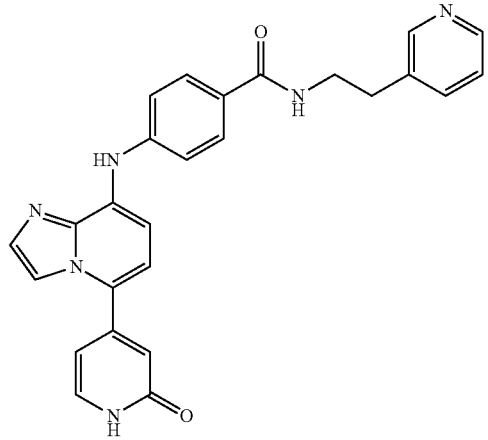
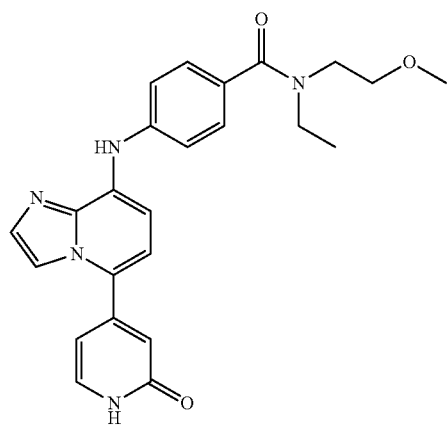
156
-continued
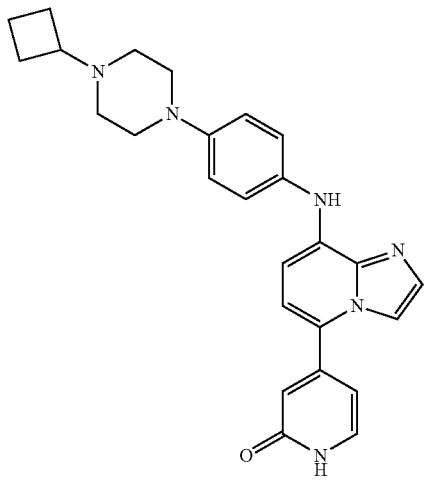
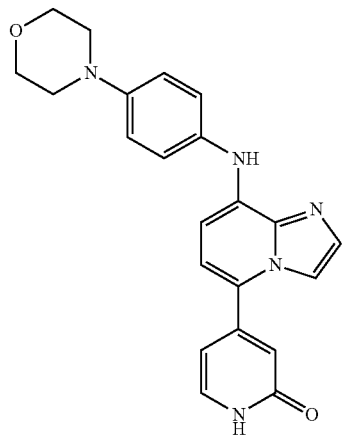
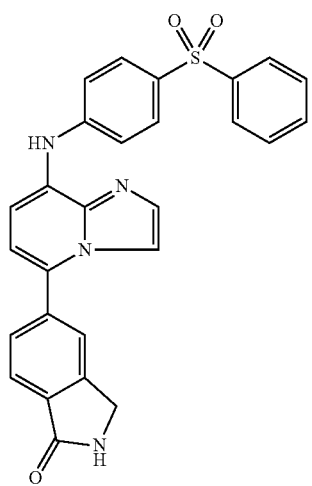

157
-continued
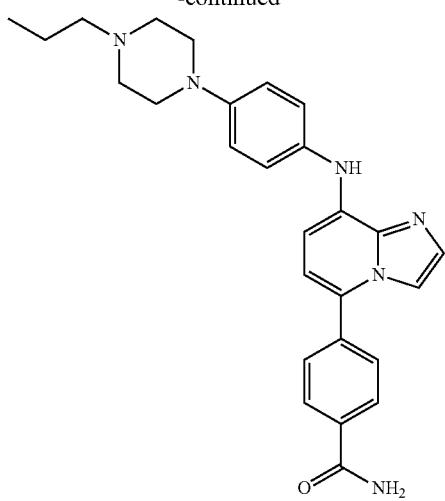
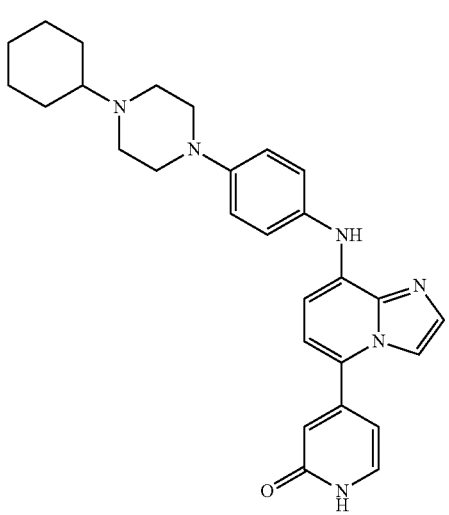
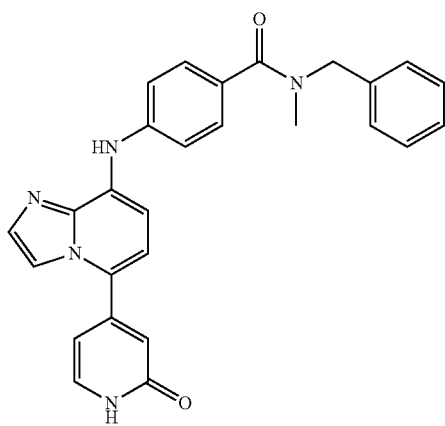
158
-continued
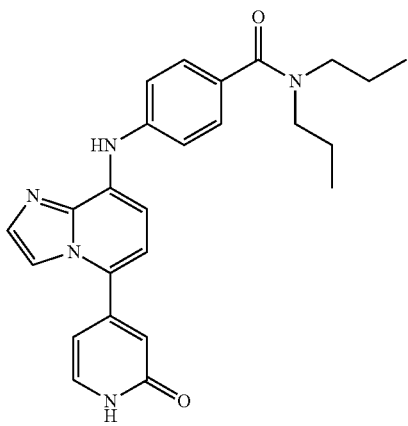
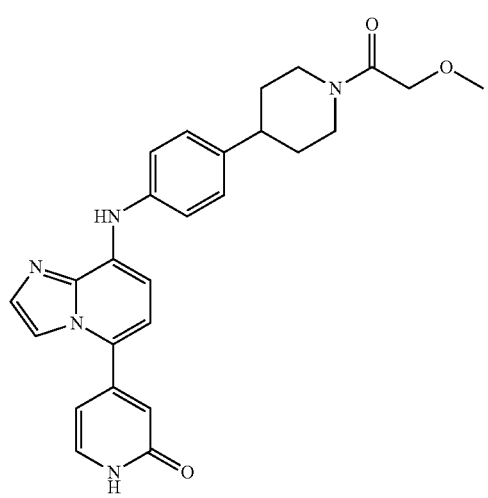
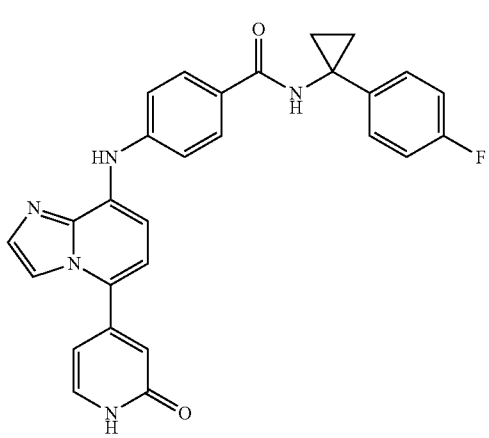

-continued
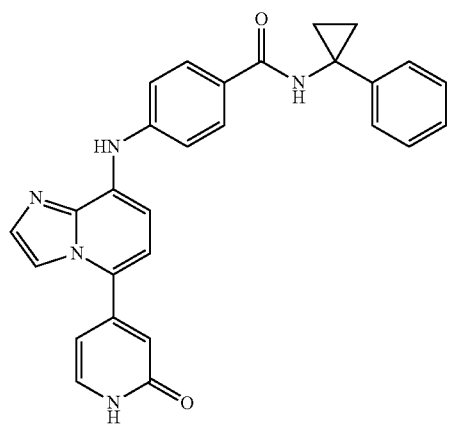
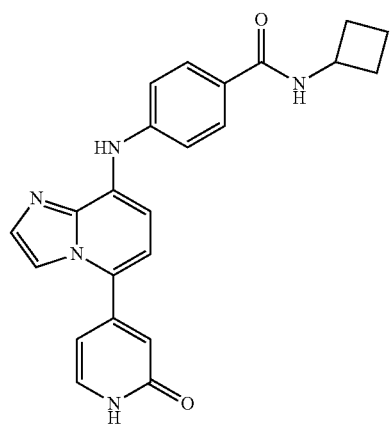
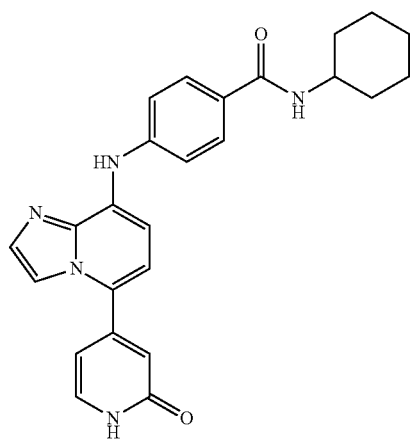
-continued
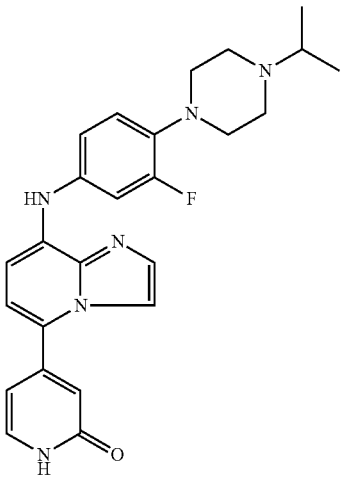
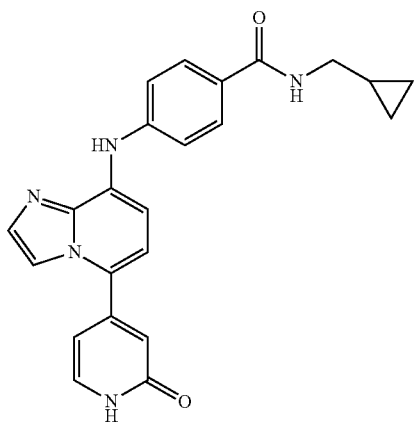
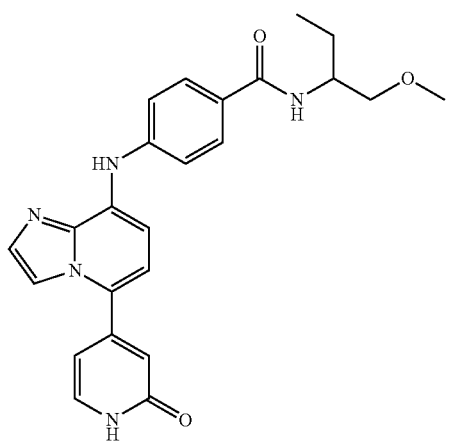

161
-continued
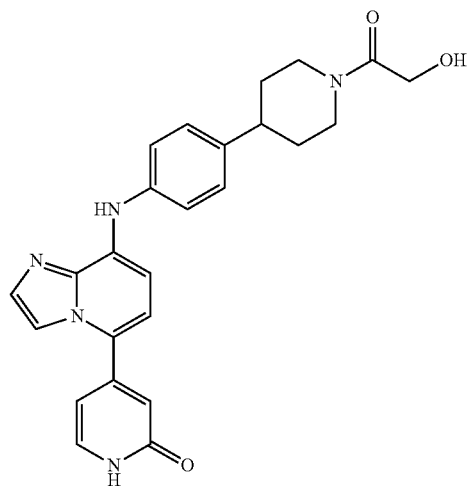
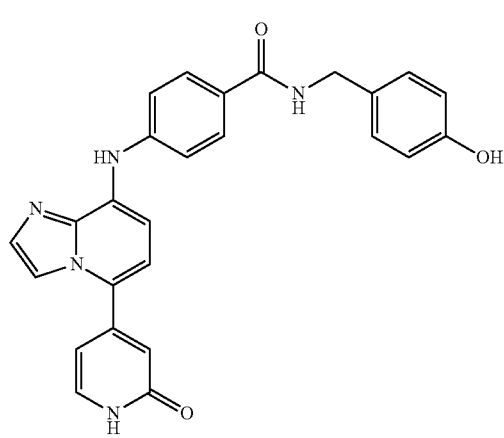
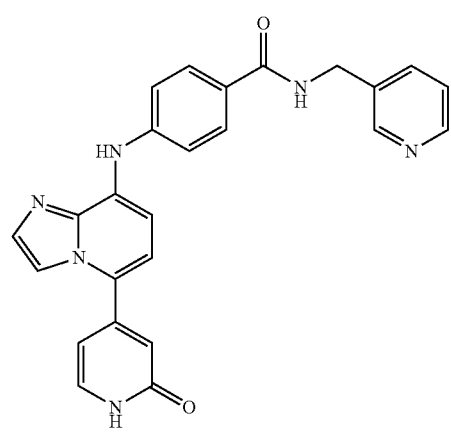
162
-continued
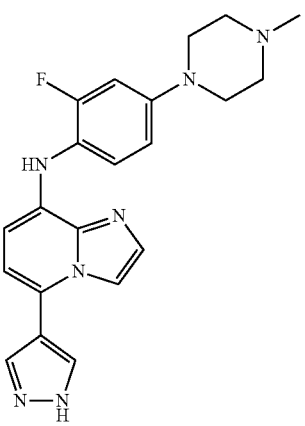
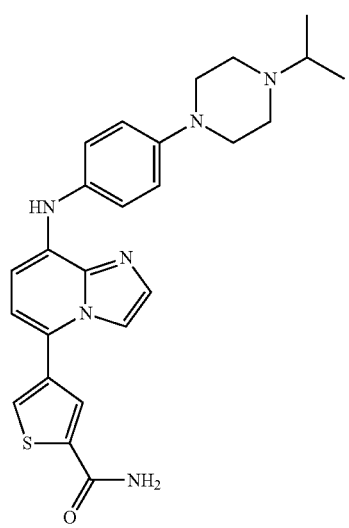
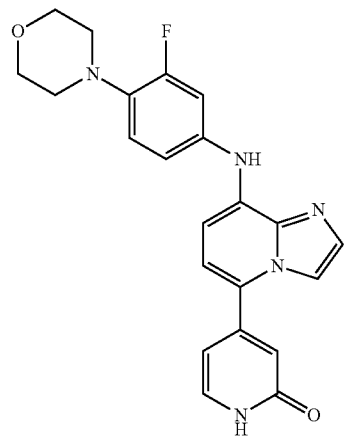

163
-continued
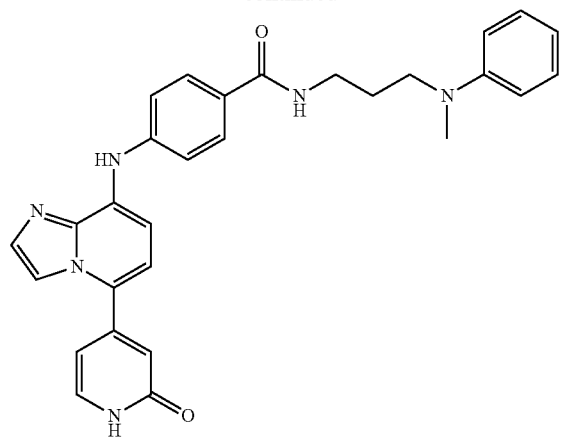
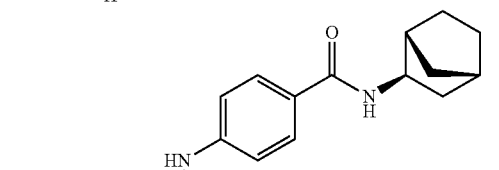
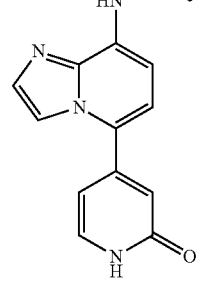
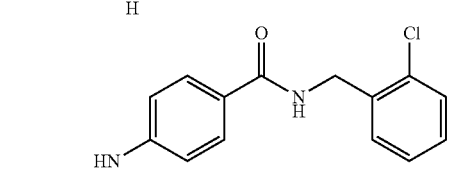
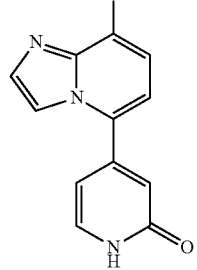
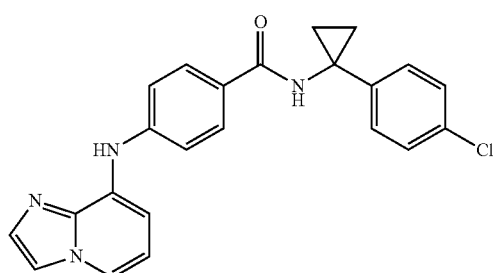
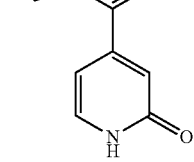
164
-continued
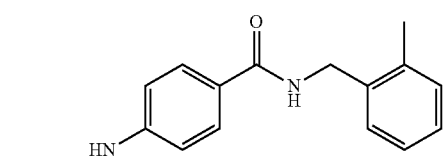
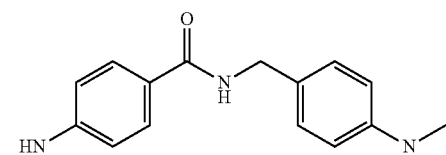
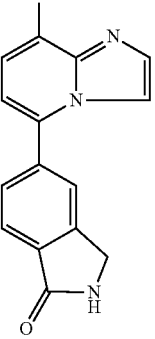
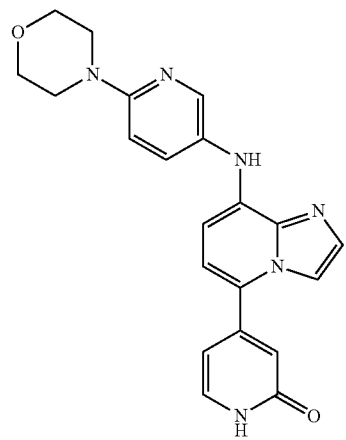

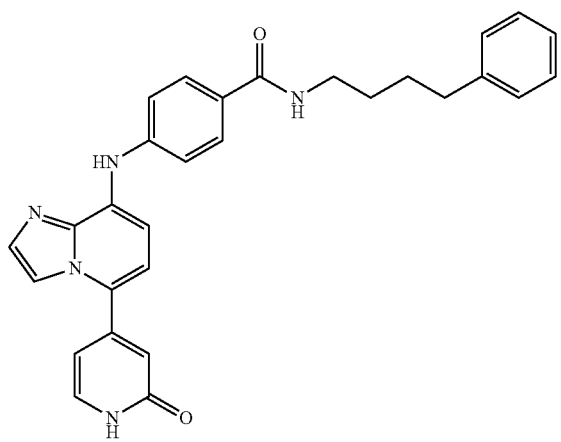
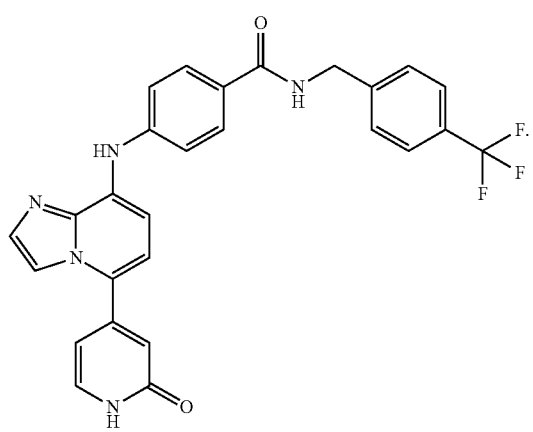
In yet another embodiment, the compound is according to any one of compounds as listed in Table A.
In yet another embodiment, the compound is selected from:
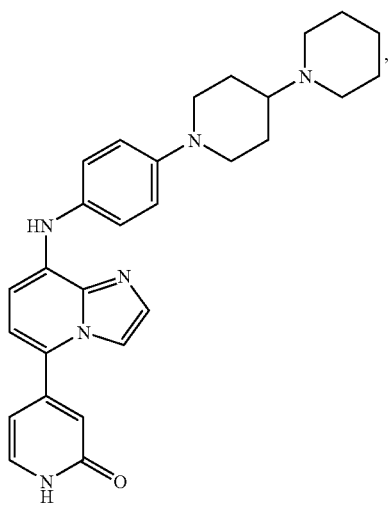
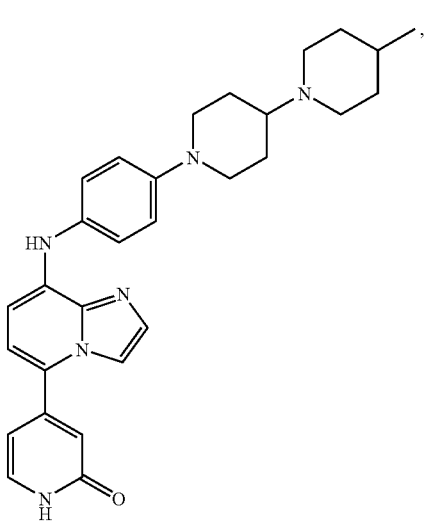
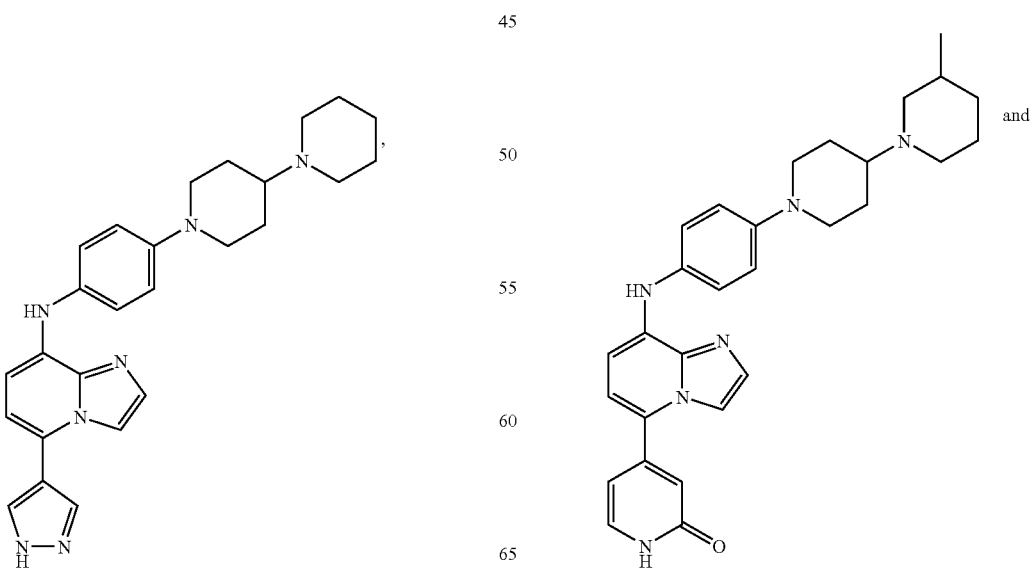

-continued

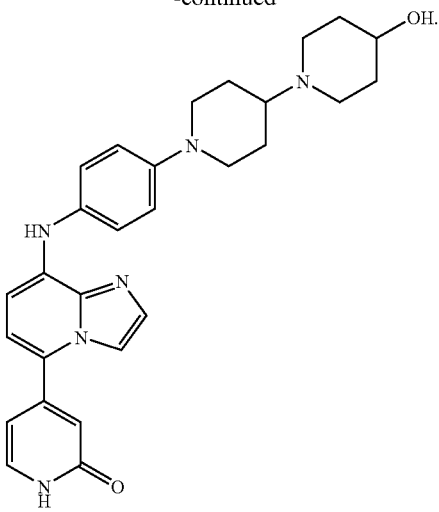

A compound for use according to the invention may contain one or more asymmetric carbon atoms and may exist in racemic and optically active forms. It will be understood by a person of skill in the art that the present invention includes both the racemic mixture and each enantiomer in isolated form. A compound according to an embodiment of the invention may be in trans or cis form.

The present invention also extends to a prodrug of a compound according to an embodiment of the invention such as an ester or amide thereof. A prodrug is a compound that may be converted under physiological conditions or by solvolysis to a compound according to an embodiment of the invention or to a pharmaceutically acceptable salt of a compound according to an embodiment of the invention. A prodrug may be inactive when administered to a subject but is converted in vivo to an active compound of the invention. "Pharmaceutically acceptable prodrugs" as used herein refers to those prodrugs of the compounds useful in the present invention, which are, within the scope of sound medical judgment, suitable for use in contact with the tissues of patients with undue toxicity, irritation, allergic response commensurate with a reasonable benefit/risk ratio, and effective for their intended use of the compounds of the invention. The term "prodrug" means a compound that is transformed in vivo to yield an effective compound useful in the present invention or a pharmaceutically acceptable salt, hydrate or solvate thereof. The transformation may occur by various mechanisms, such as through hydrolysis in blood. The compounds bearing metabolically cleavable groups have the advantage that they may exhibit improved bioavailability as a result of enhanced solubility and/or rate of absorption conferred upon the parent compound by virtue of the presence of the metabolically cleavable group, thus, such compounds act as prodrugs. A thorough discussion is provided in Design of Prodrugs, H. Bundgard, ed., Elsevier (1985); Methods in Enzymology; K. Widder et al, Ed., Academic Press, 42, 309-396 (1985); A Textbook of Drug Design and Development, Krogsgaard-Larsen and H. Bundgard, ed., Chapter 5; "Design and Applications of Prodrugs" 113-191 (1991); Advanced Drug Delivery Reviews, H. Bundgard, 8, 1-38, (1992); J. Pharm. Sci., 77,285 (1988); Chem. Pharm. Bull., N. Nakeya et al, 32, 692 (1984); Pro-drugs as Novel Delivery Systems, T. Higuchi and V. Stella, 14 A.C.S. Symposium Series, and Bioreversible Carriers in Drug Design, E. B. Roche, ed., American Pharmaceutical Association and Pergamon Press, 1987, which are incorporated herein by reference.

The present invention relates also to a method of treatment or prevention of inflammatory diseases, which comprises administering to a subject in need thereof, a therapeutically effective amount of compound of the invention.

The present invention relates also to a method of treatment or prevention of inflammatory diseases, which comprises administering to a subject in need thereof, a therapeutically effective amount of an inhibitor of TAK1 according to Formula I, II, or III.

Another aspect of the present method invention relates to a method of treatment or prophylaxis of a condition characterized by abnormal MMP1 expression, which comprises administering a therapeutically effective amount of a compound which inhibits MMP1 expression according to Formula I, II, or III.

A further aspect of the present method invention is a method of treatment or prophylaxis of a condition selected from diseases involving degradation of extra-cellular matrix, which comprises administering a therapeutically effective MMP1 expression-inhibiting amount of a compound according to Formula I, II, or III.

A yet further aspect of the present method invention is a method of treatment or prophylaxis of a condition selected from diseases involving abnormal cellular expression of MMP1, which comprises administering a therapeutically effective MMP expression-inhibiting amount of a compound according to Formula I, II, or III.

A special embodiment of the present method invention is a method of treatment or prevention of RA, which comprises administering to a subject in need thereof, a therapeutically effective amount of a compound according to Formula I, II, or III.

This invention also relates to the use of the present compounds in the manufacture of a medicament for treatment or prophylaxis of a condition prevented, ameliorated or eliminated by administration of an inhibitor of TAK1 which is a compound of the invention, or a condition characterized by abnormal collagenase activity, or a condition selected from diseases involving inflammation, most preferably in for the treatment of rheumatoid arthritis.

Administration of the compound of the present invention to the subject patient includes both self-administration and administration by another person. The patient may be in need of treatment for an existing disease or medical condition, or may desire prophylactic treatment to prevent or reduce the risk for diseases and medical conditions affected by a disturbance in bone metabolism. The compound of the present invention may be delivered to the subject patient orally, transdermally, via inhalation, injection, nasally, rectally or via a sustained release formulation.

A preferred regimen of the present method comprises the administration to a subject in suffering from a disease condition characterized by inflammation, of an effective matrix metalloprotease inhibiting amount of a compound of the present invention for a period of time sufficient to reduce the abnormal levels of extracellular matrix degradation in the patient, and preferably terminate, the self-perpetuating processes responsible for said degradation. A special embodiment of the method comprises administering of an effective MMP1 expression-inhibiting amount of a compound of the present invention to a subject patient suffering from or susceptible to the development of rheumatoid arthritis, for a period of time sufficient to reduce or prevent, respectively, collagen and bone degradation in the joints of said patient, and preferably terminate, the self-perpetuating processes responsible for said degradation. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A preferred therapeutically effective amount of the compound of the present invention to administer to a subject patient is about 0.1 mg/kg to about 10 mg/kg administered from once to three times a day. For example, an effective regimen of the present method may administer about 5 mg to about 1000 mg of said compound of the present invention from once to three times a day. It will be understood, however, that the specific dose level for any particular subject patient will depend upon a variety of factors including the age, body weight, general health, sex, diet, time of administration, route of administration, rate of excretion, drug combination and the severity of the particular inflammatory condition. A consideration of these factors is well within the purview of the ordinarily skilled clinician for the purpose of determining the therapeutically effective or prophylactically effective dosage amount needed to prevent, counter, or arrest the progress of the condition.

Compounds of the invention can be incorporated into pharmaceutical compositions suitable for administration. Such compositions typically comprise at least one compound of the invention and at least one pharmaceutically acceptable carrier. As used herein the language "pharmaceutically acceptable carrier" is intended to include solid carriers such as lactose, magnesium stearate, terra alba, sucrose, talc, stearic acid, gelatin, agar, pectin, acacia or the like; and liquids such as vegetable oils, arachis oil and sterile water, or the like, any and all solvents, dispersion media, coatings, antibacterial and antifungal agents, isotonic and absorption delaying agents, and the like, compatible with pharmaceutical administration. This listing of pharmaceutically acceptable carriers is not to be construed as limiting. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum mono stearate and gelatin.

Sterile injectable solutions can be prepared by incorporating the active compound (e.g., a compound according to an embodiment of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

A compound according to an embodiment of the invention may be provided as a salt, preferably as a pharmaceutically acceptable salt of compounds of formula I. Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl)aminomethane; and the like.

Salts of compounds according to an embodiment of the invention may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

The present invention will now be described in detail with reference to specific examples of compounds and methods for their production. Within this specification embodiments have been described in a way that enables a clear and concise specification to be written, but it will be appreciated that embodiments may be variously combined or separated without parting from the invention.

EXAMPLES

LC-MS/UV/ELS analysis was performed on instrumentation consisting of Shimadzu LC-10AD vp series HPLC pumps and dual wavelength UV detector, a Gilson 215 autosampler, a Sedex 75c evaporative light scattering (ELS) detector, and a PE/Sciex API 150EX mass spectrometer. The ELS detector was set to a temperature of 40° C. and a $N_2$ pressure of 3.3 atm. The gain setting on the ELS detector was varied as necessary, in order to keep the output signal within a quantifiable range. The Turbo IonSpray source was employed on the API 150 with an ion spray voltage of 5 kV, a temperature of 300° C., and orifice and ring voltages of 5 V and 175 V respectively. Positive ions were scanned in Q1 from 160 to 650 m/z. 5.0 µL injections were performed for each sample, on either a 4.6×50 mm or 4.6×100 mm Phenomenex Gemini 5 µm C18 column. Two analyses of each crude compound were carried out with different mobile modifiers in order to identify the best system for preparative separation. The first mobile phase system consisted of 10.0 mM ammonium carbonate in HPLC grade water (A) and neat HPLC grade acetonitrile (B). The second system consisted of 0.1% formic acid in HPLC grade water (A) and 0.075% formic acid in HPLC grade acetonitrile (B). These mobile phases were approximately pH 8.5 and 3.8 respectively. Gradients used with each method are shown in Tables 1 and 2. Various issues arose during purification and analysis of these compounds, including apparent degradation under basic conditions, and lack of retention under acidic conditions. Therefore, several different methods were employed.

As above, crude product analyses were done in both ammonium carbonate and formic acid, with the gradients listed in Tables 1 and 2 respectively. Analysis of collected fractions was performed with formic acid with the gradients listed in Table 2. Final product analysis was carried out using one of the gradients listed in Tables 1, 2, 3, 4 or 5.

Analytical data were processed and analyzed using proprietary automation routines, including integration via PE/Sciex Anlayst software, and organization of data via Microsoft Excel. Correlation was performed between MS and UV chromatograms through the creation of an extracted ion chromatogram (XIC) for the mass of interest with a width of 1.0 m/z. The intensity of a peak in the XIC was required to be at least 1,000,000 counts per scan (cps) in order to be identified as representing the designed compound. The retention time of this XIC peak was then compared to the integration of the UV chromatogram, and the purity assigned as representative of the designed product, if the offset of the UV peak from the XIC retention time was 0.06 minutes.

TABLE 1

Analytical Gradient

| Time (min) | Flow (mL/min) | % A | % B |
|---|---|---|---|
| 0.00 | 2.0 | 98 | 2 |
| 1.00 | 2.0 | 90 | 10 |
| 5.00 | 2.0 | 0 | 100 |
| 5.80 | 2.0 | 0 | 100 |
| 6.00 | 2.0 | 98 | 2 |
| 7.00 | 2.0 | 98 | 2 |

TABLE 2

HCOOH Gradient (Crude/Fraction/Final)

| Time (min) | Flow (mL/min) | % A | % B |
|---|---|---|---|
| 0.00 | 2.0 | 95 | 5 |
| 4.00 | 2.0 | 0 | 100 |
| 5.80 | 2.0 | 0 | 100 |
| 6.00 | 2.0 | 95 | 5 |
| 7.00 | 2.0 | 95 | 5 |

TABLE 3

(NH$_4$)$_2$CO$_3$ Gradient (Crude/FInal)

| Time (min) | Flow (mL/min) | % A | % B |
|---|---|---|---|
| 0.00 | 2.0 | 95 | 5 |
| 4.00 | 2.0 | 5 | 95 |
| 5.80 | 2.0 | 5 | 95 |
| 6.00 | 2.0 | 95 | 5 |
| 7.00 | 2.0 | 95 | 5 |

TABLE 4

HCOOH Gradient (Final)

| Time (min) | Flow (mL/min) | % A | % B |
|---|---|---|---|
| 0.00 | 2.0 | 95 | 5 |
| 5.00 | 2.0 | 0 | 100 |
| 7.80 | 2.0 | 0 | 100 |
| 8.00 | 2.0 | 95 | 5 |
| 9.50 | 2.0 | 95 | 5 |

TABLE 5

HCOOH Gradient (Final)

| Time (min) | Flow (mL/min) | % A | % B |
|---|---|---|---|
| 0.00 | 2.0 | 95 | 5 |
| 1.00 | 2.0 | 95 | 5 |
| 5.00 | 2.0 | 0 | 100 |
| 5.80 | 2.0 | 0 | 100 |
| 6.00 | 2.0 | 95 | 5 |
| 7.00 | 2.0 | 95 | 5 |

Synthetic Preparation of Compounds of the Invention

A compound according to the present invention can be produced by any methods known to a person of skill in the art, including, but not limited to the methods as described in the following examples.

1. Synthetic Examples

A: General Procedure to Form Imidazolopyridines

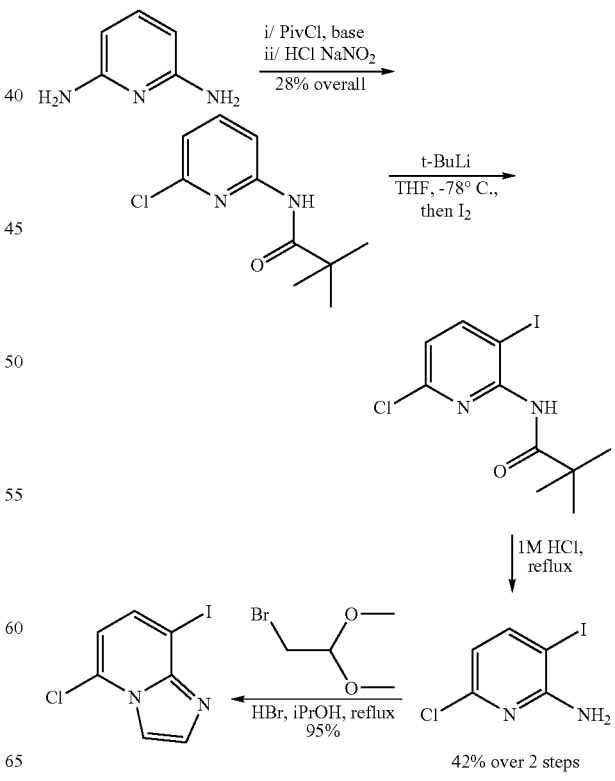

A.1: Pivaloyldiaminopyridine

To a solution of 2,6-diaminopyridine (10 g, 91.743 mmol) and triethylamine (11.14 g, 110.091 mmol, 1.2 equiv.) in DCM (100 mL) at 0° C. is added dropwise a solution of pivaloyl chloride (12.11 g, 100.917 mmol, 1.1 equiv.) in DCM (50 mL) over 2 hours. After completion of the addition the mixture is allowed to warm to room temperature over 30 minutes, at which point LC-MS shows full conversion to the desired material. The mixture is filtered to remove the triethylammonium chloride, and the solvent is removed under vacuum to afford a solid that is not processed further.

A.2: 2-chloro-6-pivaloylaminopyridine

The pivaloyldiamino pyridine is then added to a concentrated HCl solution pre-cooled to 0° C., and stirred until a clear solution is formed. This solution is further cooled to between −15 and −20° C. and a cold solution of NaNO$_2$ (19 g, 275.229 mmol, 1.5 equiv.) in water (50 mL) is added dropwise over 2 hours. On completion of the addition, the reaction is left to stir at −10° C. for 1 hour and allowed to warm up to room temperature over 1 hour. Ice is then added to the reaction mixture and a 10M NaOH solution is added to adjust the pH to 9-10. The resulting solution is finally extracted with dichloromethane, dried over Na$_2$SO$_4$ to afford after solvent removal 11.03 g of 2-chloro-6-pivaloylaminopyridine as a solid).

A.3: 6-Chloro-3-iodo-pyridin-2-ylamine

A solution of 2-chloro-6-pivaloylaminopyridine (10.5 g, 49.528 mmol) in THF (150 mL) is prepared under N$_2$ and cooled to −80° C. t-BuLi 1M in pentane (108.962 mmol, 2.2 equiv.) is added carefully via an addition funnel under rigorously anhydrous conditions, over 1 hour. Once the addition is complete, the mixture is kept at −80° C. for 3 hours, at which point a solution of iodine (15.1 g, 59.431 mmol, 1.2 equiv.) in 50 mL THF under N$_2$, is added slowly in one portion. After the addition, the cooling bath is removed and the reaction mixture allowed to warm up to room temperature under stirring for 2 hours. Finally the reaction mixture is quenched by slowly adding 50 mL of 1M HCl. The mixture is then concentrated under vacuum to remove part of the THF, and the residue is partitioned between EtOAc and water. A 10% sodium thiosulfate solution is added until no further decolourisation occurred and that 2 clear phases are visible. The aqueous layer is extracted with EtOAc, the organic layers are gathered, washed with brine, dried over Na$_2$SO$_4$, and solvent is removed to afford an oil titrating 65% of the desired material. This crude is refluxed in 100 mL of 1M HCl and is refluxed for 5 hours at which point the depivaloylated product is completely formed. The pH is adjusted to 12 by slow addition of NaHCO$_3$ and extracted with DCM. The organic layer is concentrated and columned using 7/3 DCM/Cyclohexane as the eluent (R$_f$ 9/21) to afford the title compound as an oil which solidified on standing.

A.4: 5-Chloro-8-iodo-imidazo[1,2-a]pyridine 2-amino-3-iodo-6-chloropyridine (2 g, 7.874 mmol) is taken up in isopropanol (30 mL) under N$_2$. Diethoxy-2-bromoacetal (2.5 mL, 15.748 mmol, 2 equiv.) is added to the suspension followed by HBr 48% (2 mL). The resulting mixture is then refluxed for 12 h and cooled down to room temperature. The mixture is partly concentrated under vacuum and the resulting slurry is taken up in diethyl ether which causes the precipitation of a solid that is separated by filtration and washed with little amounts of diethyl ether to afford the desired material as a powder.

B: General Procedure of Buchwald Coupling

Palladium acetate (28.26 mg, 0.125 mmol, 5 mol %) and rac-BINAP (78.39 mg, 0.125 mmol, 5 mol %) are premixed in toluene (30 mL) under nitrogen, at room temperature for 30 minutes. The iodo-arene (700 mg, 2.518 mmol) is then added at room temperature and stirred until complete dissolution. Cs$_2$CO$_3$ (4102.1 mg, 12.589 mmol, 5 equiv.) is added followed by 4-(N-Methylpiperazino)aniline (577.12 mg, 3.021 mmol, 1.2 equiv.) and the resulting suspension is further stirred at room temperature for 10 minutes. The reaction vessel is then mounted with a condenser under nitrogen and the reaction is allowed to proceed at reflux for 4 hours at which point no starting material is visible by LC-MS. The residue is then adsorbed on silica and columned using 90/10 EtOAc/MeOH as the eluting system (R$_f$=0.1) to afford 960 mg of the desired compound.

C: General Procedure for Suzuki Coupling

PdCl$_2$(dppf) (0.013 mmol, 10 mol %) and the chloroarene (0.127 mmol) are premixed under nitrogen in 4/1 mixture of dioxane/water (3 mL). Potassium carbonate (0.255 mmol, 2 equiv.) and the boronic acid (0.382 mmol, 3 equiv.) are finally added and the vessel is sealed. The reaction is then allowed to proceed at 90° C. until no starting material is left by LC-MS. Additional boronic acid may be added to complete the reaction. Once the reaction is finished, the reaction mixture is adsorbed on silica and columned using typically a 95/5 to 90/10 DCM/MeOH gradient to afford the desired products.

D: General Method (1) for Synthesizing Compounds of the Invention

A compound according to the present invention can be produced according to the following scheme.

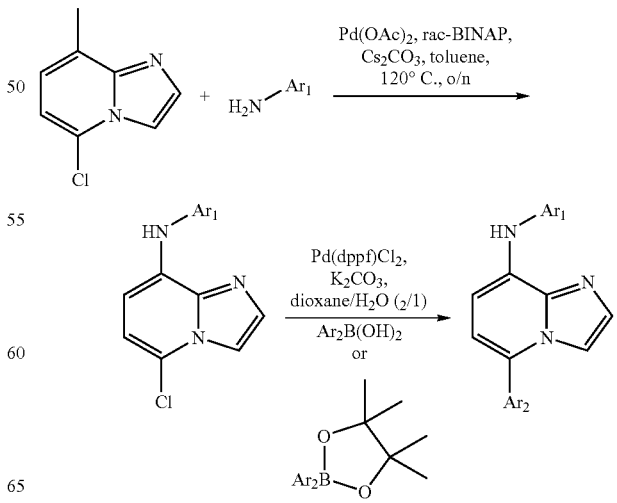

D.1: N-(2-Diethylamino-ethyl)-4-nitro-benzene-sulfonamide

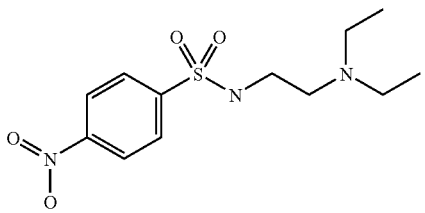

A solution of 4-nitrobenzenesulfonyl chloride (500 mg, 2.35 mmol), 2-diethylaminoethylamine (300 mg, 0.363 mL, 2.59 mmol) and triethylamine (262 mg, 0.359 mL, 2.59 mmol) in $CH_2Cl_2$ (7 mL) was stirred at room temperature for 18 hours. The mixture is then diluted with dichloromethane, and washed with brine. The organic layers is dried ($MgSO_4$) and the solvent is removed under reduced pressure to yield the title compound, which is used as such for the next step.

D.2: 4-Amino-N-(2-diethylamino-ethyl)-benzene-sulfonamide

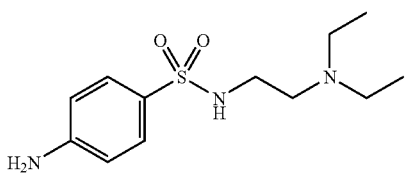

To a solution of N-(2-diethylamino-ethyl)-4-nitro-benzenesulfonamide (200 mg, 0.664 mmol) and ammonium formate (377 mg, 5.980 mmol) in EtOH/EtOAc (1/1: 8 mL) under nitrogen was added Pd/C 10% (35.3 mg, 0.033 mmol). The mixture is refluxed overnight until completion of the reaction. After filtration through a celite plug, the solvent is removed under reduced pressure to yield the title compound, which is used as such for the next step.

D.3: 4-Amino-N-(4-dimethylamino-benzyl)-benzenesulfonamide

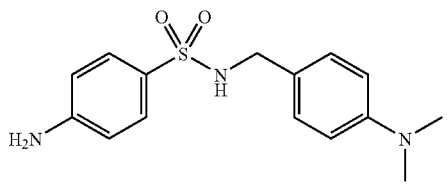

To a solution of N-(4-dimethylamino-benzyl)-4-nitro-benzenesulfonamide (472 mg, 1.409 mmol), prepared as described in D.1, in MeOH (10 ml) under nitrogen was added Pd/C 10% (74.92 mg, 0.007 mmol). The system was purged with hydrogen and let stirred overnight under an atmosphere of hydrogen. After filtration through a celite plug, the solvent is removed under reduced pressure to yield the title compound, which is used as such for the next step.

D.4: 4-Amino-N-pyrrolidin-3-yl-benzenesulfonamide

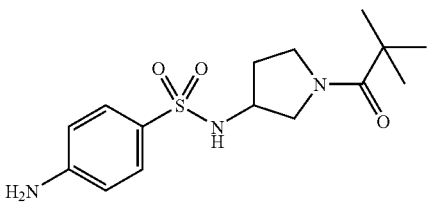

4-Amino-N-[1-(2,2-dimethyl-propionyl)-pyrrolidin-3-yl]-benzenesulfonamide may be prepared using methods as described under D.3 above.

D.5: 1-Isopropyl-4-(4-nitro-phenyl)-piperazine

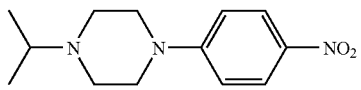

To a solution of 4-fluoronitrobenzene (5.00 g, 35.4 mmol) in THF (50 mL), 1-isopropylpiperazine (4.54 g, 35.4 mmol) and $K_2CO_3$ (7.35 g, 53.2 mmol) are added. The reaction mixture is stirred at room temperature overnight. The solvent is removed under reduced pressure and the residue is partitioned between EtOAc and water. The organic layer is washed with brine, dried ($MgSO_4$), filtered and the solvent is removed under reduced pressure. The crude compound is purified by silica gel column chromatography using 99:1 and 98:2 DCM:$NH_3$ (7 M in MeOH) to give the title compound (8.2 g, 94%).

D.6: 4-(4-Isopropyl-piperazin-1-yl)-phenylamine

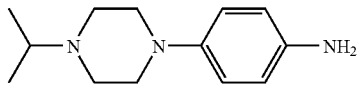

To a solution of 1-isopropyl-4-(4-nitro-phenyl)-piperazine (8.3 g, 33.2 mmol) in MeOH (120 mL) is added tin (II) dichloride dihydrate (37.4 g, 0.165 mol). The mixture is cooled using a water bath and conc. HCl is added (36 mL). The reaction is stirred at room temperature overnight. After removing the methanol, the resultant solution is basified using conc. NaOH (pH 11). The water phase is extracted with diethyl ether. The combined organic layer are dried ($MgSO_4$), filtered and the solvent is removed under reduced pressure to afford the title compound (6.4 g, 88%).

D.7: 3-Chloro-4-(4-isopropyl-piperazin-1-yl)-phenylamine

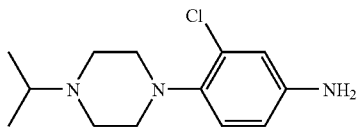

To a solution of 1-(2-chloro-4-nitro-phenyl)-4-isopropyl-piperazine (1.500 g, 5.30 mmol), prepared according to example 5, in MeOH (20 mL) is added zinc dust (1.039 g, 15.90 mmol) followed by ammonium formate (1.002 g, 15.90 mmol). The reaction is stirred at room temperature. Once the reaction is finished, the reaction mixture is filtrated and concentrated. The mixture is taken up in dichloromethane and washed with water. The combined organic layers are dried (MgSO$_4$) and the solvent is removed under reduced pressure to yield the title compound, which is used as such for the next step.

D.8: 3-Fluoro-4-(4-isopropyl-piperazin-1-yl)-phenylamine

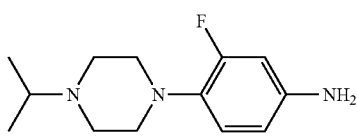

The title compound is prepared using methods as described for D.7 above.

D.9: 4-(4-Isopropyl-piperazin-1-yl)-3-trifluoromethyl-phenylamine

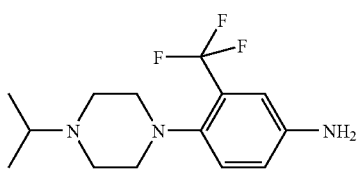

The title compound is prepared using methods as described under D.7 above.

D.10: 4-(1-Isopropyl-piperidin-4-yl)-phenylamine

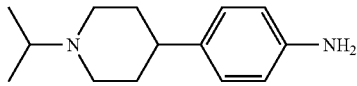

To a solution of 1-isopropyl-4-(4-nitro-phenyl)-piperidine (2.405 g, 9.698 mmol), prepared according to Example 5, in ethanol (100 mL) under nitrogen is added Pd/C 10% (515.9 mg, 0.485 mmol), followed by dropwise addition of hydrazine hydrate (2.427 g, 48.49 mmol). The mixture is refluxed overnight until completion of the reaction. After filtration through a celite plug, the solvent is removed under reduced pressure to yield the title compound, which is used as such for the next step.

D.11. 3-Bromo-2-methyl-benzoic acid methyl ester

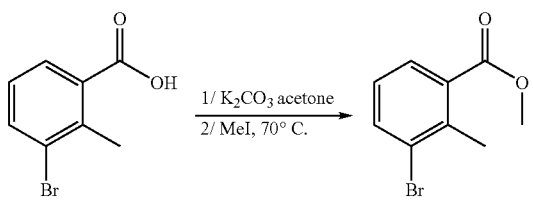

Potassium carbonate (5.46 g, 39.53 mmol) is added to a solution of 3-bromo-2-methyl-benzoic acid (5 g, 23.25 mmol) in acetone (50 mL). The suspension is stirred for 15 minutes at room temperature, then iodomethane (1.74 mL, 27.90 mmol) is added and the mixture is heated to 70° C. for 2.5 hours. The reaction mixture is filtered and evaporated to dryness. The crude product is purified by chromatography on a 50 g Isolute Flash Si II column, eluting with ethyl acetate/cyclohexane (5:95) to yield the title compound.

D.12. 3-Bromo-2-bromomethyl-benzoic acid methyl ester

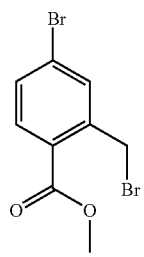

3-Bromo-2-methyl-benzoic acid methyl ester (2.0 g, 8.73 mmol) is dissolved in carbon tetrachloride (35 mL). The solution is kept under an inert atmosphere by bubbling nitrogen through the mixture while benzoyl peroxide (106 mg, 0.44 mmol) and N-bromosuccinimide (1.55 g, 8.73 mmol) are added. The mixture is purged with vacuum and nitrogen, and is then refluxed at 90° C. for 2 hours. The reaction mixture is cooled to 0° C. and filtered. The filtrate is evaporated to yield the title compound, which is used as such for the next step.

D.13. 4-Bromo-2,3-dihydro-isoindol-1-one

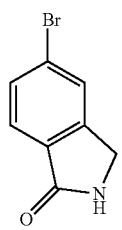

In a 25 mL microwave tube 3-bromo-2-bromomethyl-benzoic acid methyl ester is dissolved in methanol (15 mL) and mixed with 7.0M methanolic ammonia (6.3 mL) and 17.0M aqueous ammonia (7.3 mL). The microwave tube is sealed and the mixture is stirred overnight at room temperature. The precipitate formed is filtered out and washed with cold water, then dried under vacuum to afford the title compound.

D.14. 4-(4,4,5,5-Tetramethyl-[1,3,2]dioxaborolan-2-yl)-2,3-dihydro-isoindol-1-one

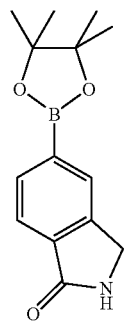

Bis(diphenylphosphino)ferrocene-palladium(II) dichloride (50 mg, 0.06 mmol) is mixed with potassium acetate (600 mg, 6.14 mmol) and bis(pinacolato)diboron (572 mg, 2.25 mmol) in a 5 mL microwave tube. The tube is purged 3 times with vacuum and nitrogen before adding a nitrogen degassed solution of 4-bromo-2,3-dihydro-isoindol-1-one (434 mg, 2.05 mmol) in 1,4-dioxane. Nitrogen is bubbled for 5 minutes through the mixture, and then the tube is sealed and heated to 85° C. for 16 hours. The reaction mixture is cooled to room temperature and filtered through a celite pad. The filtrate is evaporated to yield the title compound, which is used as such for the next step.

E: General Method (2) for Synthesizing Compounds of the Invention

A compound according to the present invention can be produced according to the following scheme.

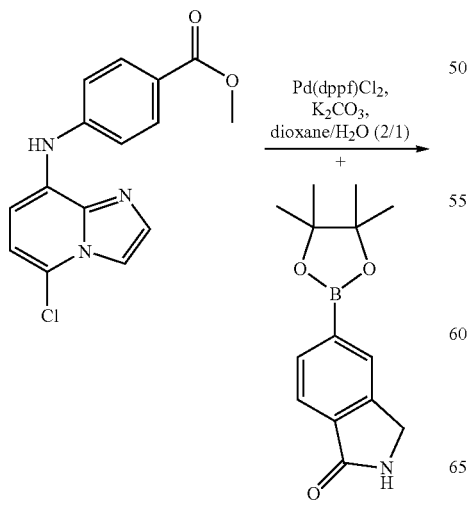

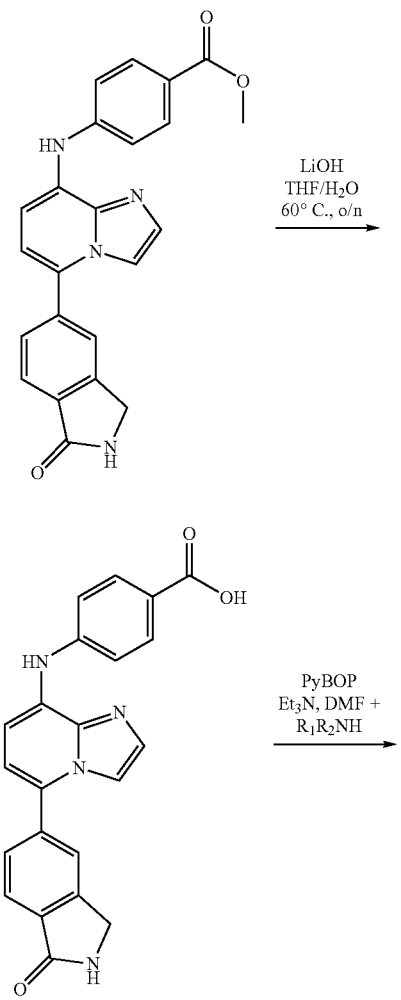

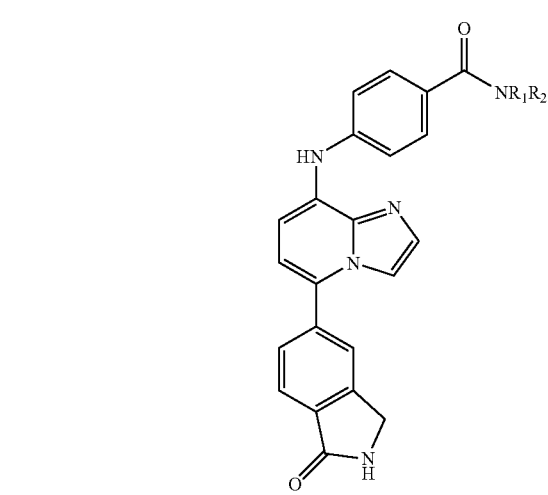

F: General Method (3) for Synthesizing Compounds of the Invention

A compound according to the present invention can be produced according to the following scheme.

G: General Method (4) for Synthesizing Compounds of the Invention
A compound according to the present invention can be produced according to the following scheme.
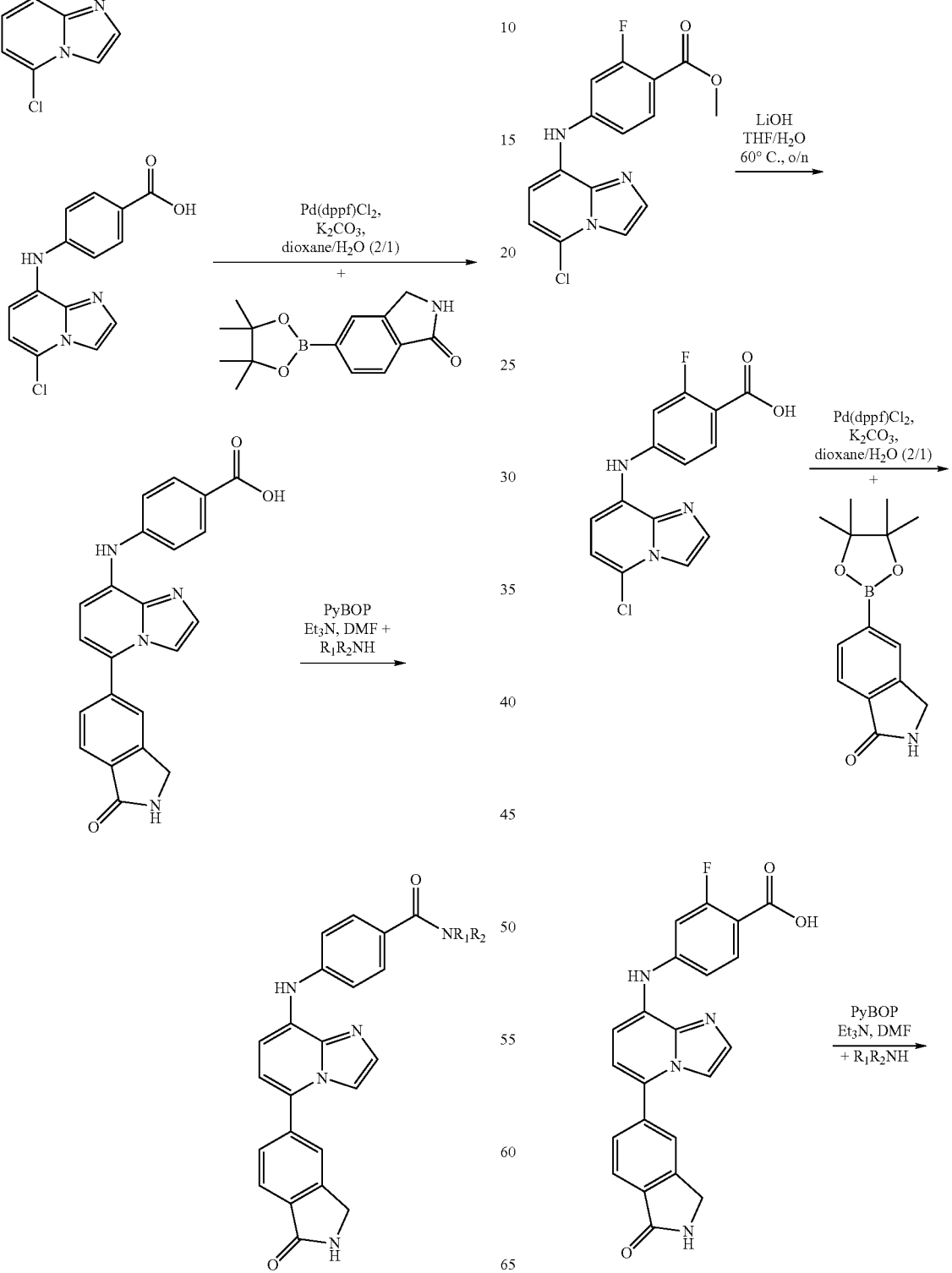

-continued

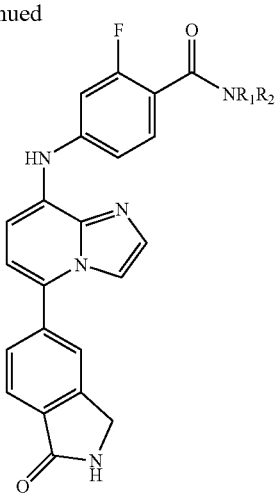

Specific Examples of the Synthesis of Compounds of the Invention

Compound 1: 4-[8-(4-Morpholin-4-yl-phenylamino)-imidazo[1,2-a]pyridin-5-yl]-benzamide

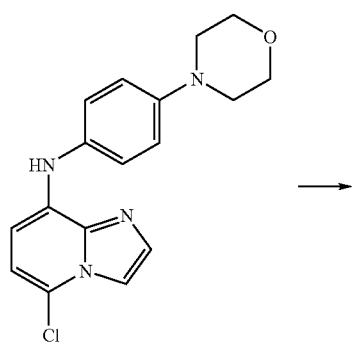

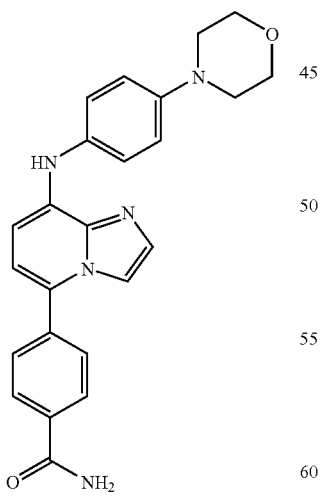

Pd(dppf)Cl$_2$.CH$_2$Cl$_2$ (19 mg, 0.020 mmol) is added to dioxane/water (4:1, 2 mL) in a microwave tube and the mixture is stirred vigorously under N$_2$ for 15 minutes. (5-Chloro-imidazo[1,2-a]pyridin-8-yl)-(4-morpholin-4-yl-phenyl)-amine (75 mg, 0.23 mmol), 4-carbamoylphenylboronic acid (113 mg, 0.68 mmol) and potassium carbonate (95 mg, 0.68 mmol) are then added, the tube is flushed with N$_2$ and sealed. The mixture is stirred and heated in a sand bath at 140° C. for sixteen hours. Analysis by LCMS indicates that considerable starting material remained.

Further Pd(dppf)Cl$_2$.CH$_2$Cl$_2$ (10 mg, 0.01 mmol) and boronic acid (60 mg, 0.35 mmol) are added and the tube is irradiated in the microwave for 30 minutes at 140° C. The mixture is cooled, evaporated onto silica (~1 g) and purified by chromatography on a 20 g silica column (1%-10% MeOH in CH$_2$Cl$_2$) to afford the target compound as a solid (30 mg). NMR and LC-MS data are used to confirm the structure and purity of the compound.

Compound 2: (4-Morpholin-4-yl-phenyl)-[5-(1H-pyrazol-4-yl)-imidazo[1,2-a]pyridin-8-yl]-amine

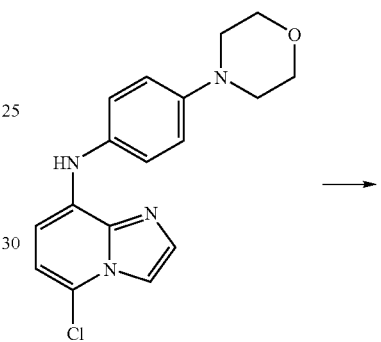

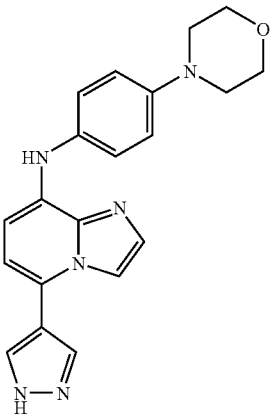

Pd(dppf)Cl$_2$.CH$_2$Cl$_2$ (19 mg, 0.020 mmol) is added to dioxane/water (4:1, 2 mL) in a microwave tube and the mixture is stirred vigorously under N$_2$ for 15 minutes. (5-Chloro-imidazo[1,2-a]pyridin-8-yl)-(4-morpholin-4-yl-phenyl)-amine (75 mg, 0.23 mmol), pyrazole-4-boronic acid (77 mg, 0.68 mmol) and potassium carbonate (95 mg, 0.68 mmol) are then added, the tube is flushed with N$_2$ and sealed. The mixture is stirred and heated in a sand bath at 140° C. for sixteen hours. Analysis by LCMS indicates that considerable starting material remains.

Further Pd(dppf)Cl$_2$.CH$_2$Cl$_2$ (15 mg, 0.02 mmol) and boronic acid (60 mg, 0.35 mmol) are added and the tube is irradiated in the microwave for 30 minutes at 140° C. The mixture is cooled, evaporated onto silica (~1 g) and purified by chromatography on a 20 g silica column (2%-8% MeOH in CH$_2$Cl$_2$) to afford the target compound as a solid (21 mg). NMR and LC-MS data are used to confirm the structure and purity of the compound.

Compound 3: 4-{8-[4-(4-Methyl-piperazin-1-yl)-phenylamino]-imidazo[1,2-a]pyridin-5-yl}-benzamide

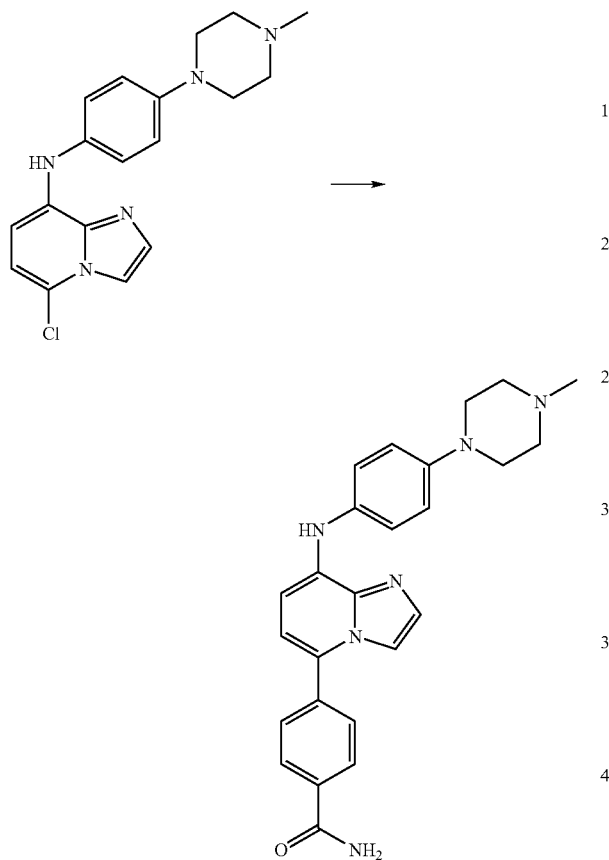

Pd(dppf)Cl$_2$.CH$_2$Cl$_2$ (19 mg, 0.020 mmol) is added to dioxane/water (4:1, 2 mL) in a microwave tube and the mixture is stirred vigorously under N$_2$ for 15 minutes. (5-Chloro-imidazo[1,2-a]pyridin-8-yl)-[4-(4-methyl-piperazin-1-yl)-phenyl]-amine (78 mg, 0.23 mmol), 4-carbamoylphenylboronic acid (113 mg, 0.68 mmol) and potassium carbonate (95 mg, 0.68 mmol) are then added, the tube is flushed with N$_2$ and sealed. The mixture is stirred and heated in a sand bath at 140° C. for sixteen hours. Analysis by LCMS indicates that considerable starting material remains.

Further Pd(dppf)Cl$_2$.CH$_2$Cl$_2$ (15 mg, 0.02 mmol) and boronic acid (90 mg, 0.55 mmol) are added and the tube is irradiated in the microwave for 30 minutes at 140° C. The mixture is cooled, evaporated onto silica (~1 g) and partially purified by chromatography on a 20 g silica column (5%-20% MeOH in CH$_2$Cl$_2$). The material obtained is absorbed onto Celite and purified on a C-18 reverse-phase column (10 g) eluting with 30% to 80% MeOH in water, containing 1M NH$_3$, to afford the target compound as a solid (10 mg). NMR and LC-MS data are used to confirm the structure and purity of the compound.

Compound 4: [4-(4-Methyl-piperazin-1-yl)-phenyl]-[5-(1H-pyrazol-4-yl)-imidazo[1,2-a]pyridin-8-yl]-amine

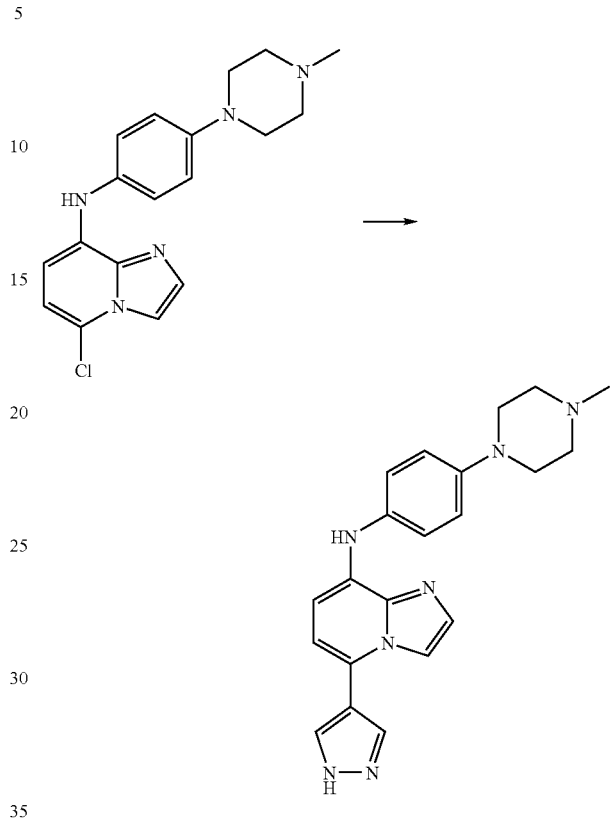

Pd(dppf)Cl$_2$.CH$_2$Cl$_2$ (19 mg, 0.020 mmol) is added to dioxane/water (4:1, 2 mL) in a microwave tube and the mixture is stirred vigorously under N$_2$ for 15 minutes. (5-Chloro-imidazo[1,2-a]pyridin-8-yl)-[4-(4-methyl-piperazin-1-yl)-phenyl]-amine (75 mg, 0.23 mmol), pyrazole-4-boronic acid (77 mg, 0.68 mmol) and potassium carbonate (95 mg, 0.68 mmol) are then added, the tube is flushed with N$_2$ and sealed. The mixture is stirred and heated in a sand bath at 140° C. for sixteen hours. Analysis by LCMS indicates that considerable starting material remains.

Further Pd(dppf)Cl$_2$.CH$_2$Cl$_2$ (15 mg, 0.02 mmol) and boronic acid (60 mg, 0.35 mmol) are added and the tube is irradiated in the microwave for 30 minutes at 140° C. The mixture is cooled, evaporated onto silica (~1 g) and partially purified by chromatography on a 20 g silica column (2%-8% MeOH in CH$_2$Cl$_2$). The residue is absorbed onto Celite and passed through a C-18 reverse-phase column (5 g), eluting with 30%-100% MeOH in water (all 1M in NH$_3$). The material is then purified by preparative HPLC and the HCl salt generated to afford, after lyophillisation, 4 mg of solid. NMR and LC-MS data are used to confirm the structure and purity of the compound.

Further compounds were synthesised using the methods described in detail above.

Compound 5: [3-Fluoro-4-(4-isopropyl-piperazin-1-yl)-phenyl]-[5-(1H-pyrazol-4-yl)-imidazo[1,2-a]pyridin-8-yl]-amine Compound 6: [4-(4-Isopropyl-piperazin-1-yl)-phenyl]-[5-(1H-pyrazol-4-yl)-imidazo[1,2-a]pyridin-8-yl]-amine Compound 7: [2-Fluoro-4-(4-methyl-piperazin-1-yl)-phenyl]-[5-(1H-pyrazol-4-yl)-imidazo[1,2-a]pyridin-8-yl]amine Compound 8: 4-{8-[4-(4-Isopropyl-piperazin-1-yl)-phenylamino]-imidazo[1,2-a]pyridin-5-yl}-thiophene-2-carboxylic acid amide Compound 9: 4-{8-[3-Fluoro-4-(4-isopropyl-piperazin-1-yl)-phenylamino]-imidazo[1,2-a]pyridin-5-yl}-thiophene-2-carboxylic acid amide Compound 10: 4-{8-[4-(4-Isopropyl-piperazin-1-yl)-phenylamino]-imidazo[1,2-a]pyridin-5-yl}-benzamide Compound 11: 4-{8-[3-Fluoro-4-(4-isopropyl-piperazin-1-yl)-phenylamino]-imidazo[1,2-a]pyridin-5-yl}-benzamide Compound 12: 5-{8-[4-(4-Isopropyl-piperazin-1-yl)-phenylamino]-imidazo[1,2-a]pyridin-5-yl}-2,3-dihydro-isoindol-1-one 12.1 (5-Chloro-imidazo[1,2-a]pyridin-8-yl)-[4-(4-isopropyl-piperazin-1-yl)-phenyl]-amine

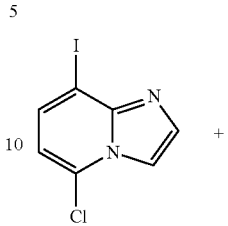

| Compound | Structure | Name | $t_R$ (min), (LCMS method)* | M.W. | Ion found |
|---|---|---|---|---|---|
| 6* | 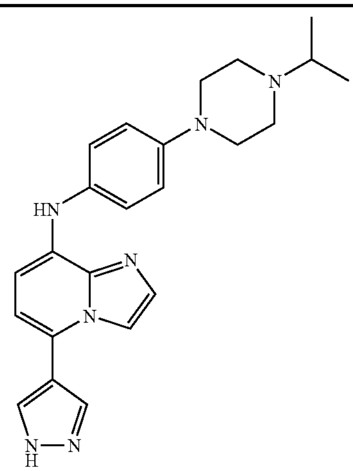 | [4-(4-Isopropyl-piperazin-1-yl)-phenyl]-[5-(1H-pyrazol-4-yl)-imidazo[1,2-a]pyridin-8-yl]-amine | 1.37 | 401.2 | 402.3 (MH)+ |
| 10* | 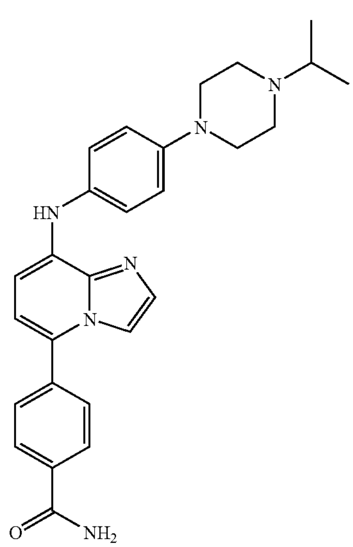 | 4-{8-[4-(4-Isopropyl-piperazin-1-yl)-phenylamino]-imidazo[1,2-a]pyridin-5-yl}-benzamide | 1.57 | 454.2 | 455.1 (MH)+ |

-continued

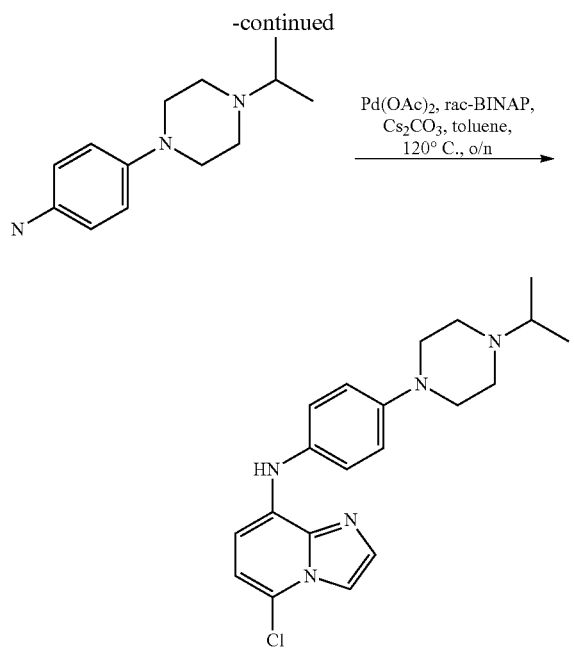

Palladium acetate (4.67 mg, 0.021 mmol) and rac-BINAP (12.95 mg, 0.021 mmol) are sonicated in toluene (4.5 mL) under nitrogen, at room temperature for 5 minutes in a microwave tube. 5-Chloro-8-iodo-imidazo[1,2-a]pyridine (116 mg, 0.417 mmol), Cs$_2$CO$_3$ (679.7 mg, 2.09 mmol) and 4-(4-isopropyl-piperazin-1-yl)-phenylamine (109.59 mg, 0.502 mmol) are then added at room temperature. The reaction mixture is then allowed to proceed at reflux for 16 hours at which point no starting material is visible by LC-MS. After concentration, the mixture is diluted in dichloromethane, and washed with 10% aqueous citric acid solution. The aqueous phase is then basified to pH 7 with saturated aqueous NaHCO$_3$, and extracted with dichloromethane. The combined organic layers are dried (MgSO$_4$) and the solvent is removed under reduced pressure to yield title compound, which is used as such for the next step.

Compound 12.2: 5-{8-[4-(4-Isopropyl-piperazin-1-ye-phenylamino]-imidazo[1,2-a]pyridin-5-yl}-2,3-dihydro-isoindol-1-one

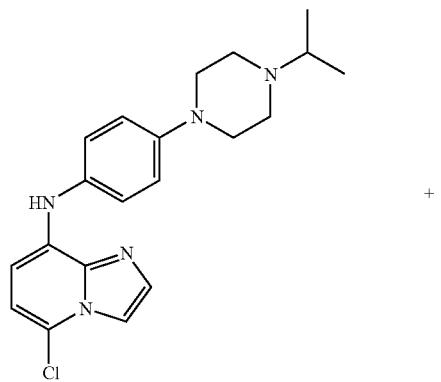

+

-continued

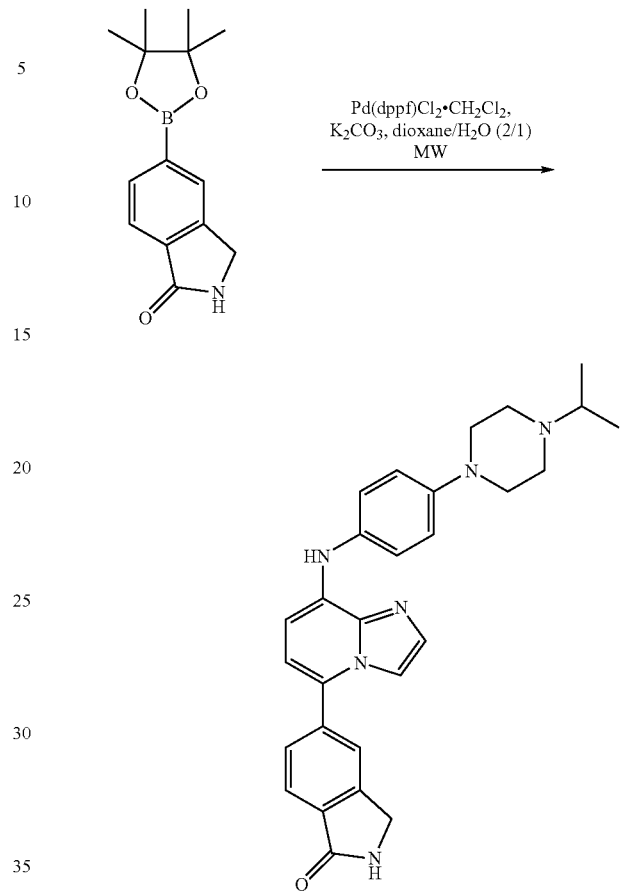

PdCl$_2$(dppf) (16.73 mg, 0.020 mmol), (5-Chloro-imidazo[1,2-a]pyridin-8-yl)-[4-(4-isopropyl-piperazin-1-yl)-phenyl]-amine (76.0 mg, 0.206 mmol), potassium carbonate (56.91 mg, 0.419 mmol) and 4-(4,4,5,5-Tetramethyl-[1,3,2]dioxaborolan-2-yl)-2,3-dihydro-isoindol-1-one (106.66 mg, 0.419 mmol) are added in a microwave tube. The tube is flushed with N$_2$ before adding a 2/1 mixture of dioxane/water (1.0 mL). The vessel is sealed and is irradiated in the microwave for 20 minutes at 140° C. heated in the microwave. Additional boronic acid may be added to complete the reaction. Once the reaction is finished, the reaction mixture is concentrated, diluted with dichloromethane, and washed with water. The combined organic layers are dried (MgSO$_4$) and the solvent is removed under reduced. The crude product is purified by reverse phase HPLC to yield the title compound.

tR: 0.80 min (2 min_LC)

Ion (found): 467 (M+H)+

HPLC purity %: 98

Compounds 13-31

These compounds shown in the table below are prepared using methods similar to those described for compound 12 (irradiation in microwave varied from 120 to 140° C.) via General Method (1) as described above, and are purified either by chromatography on Isolute Flash Si II column or by preparative reverse phase HPLC.

| Compound No. | Structure | Compound name | tR (min), (LCMS method) | M.W. | Ion found |
|---|---|---|---|---|---|
| 13 | 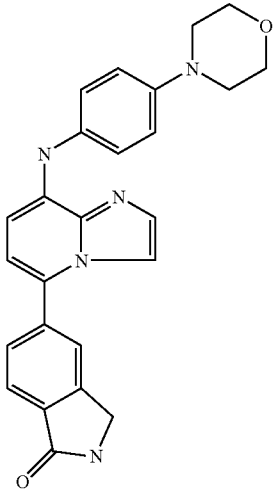 | 5-(8-(4-morpholinophenylamino)imidazo[1,2-a]pyridin-5-yl)isoindolin-1-one | 0.83 (2 min_lc) | 425.49 | 426 (M + H)+ |
| 14 | 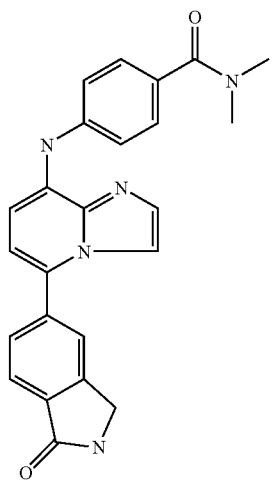 | N,N-dimethyl-4-(5-(1-oxoisoindolin-5-yl)imidazo[1,2-a]pyridin-8-ylamino)benzamide | 0.84 (2 min_lc) | 411.46 | 412 (M + H)+ |
| 15 | 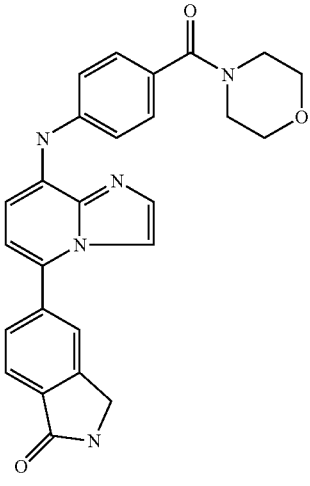 | 5-(8-(4-(morpholine-4-carbonyl)phenylamino)imidazo[1,2-a]pyridin-5-yl)isoindolin-1-one | 0.84 (2 min_lc) | 453.50 | 454 (M + H)+ |

-continued

| Compound No. | Structure | Compound name | tR (min), (LCMS method) | M. W. | Ion found |
|---|---|---|---|---|---|
| 16 | 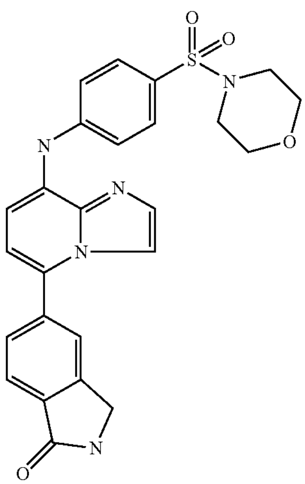 | 5-(8-(4-(morpholinosulfonyl)phenylamino)imidazo[1,2-a]pyridin-5-yl)isoindolin-1-one | 0.91 (2 min_lc) | 489.55 | 490 (M + H)+ |
| 17 | 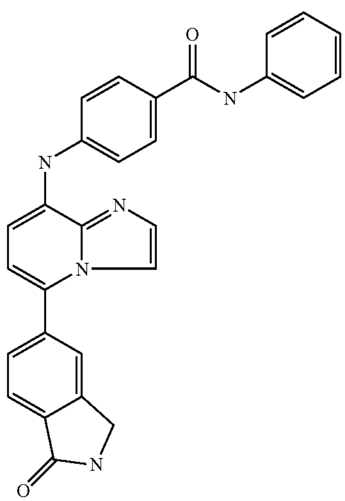 | 4-(5-(1-oxoisoindolin-5-yl)imidazo[1,2-a]pyridin-8-ylamino)-N-phenylbenzamide | 1.01 (2 min_lc) | 459.51 | 460 (M + H)+ |
| 18 | 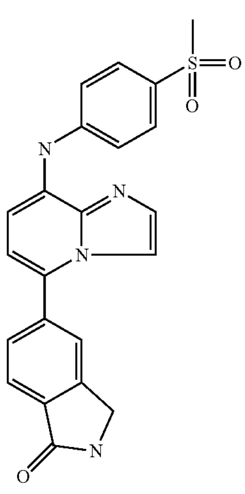 | 5-(8-(4-(methylsulfonyl)phenylamino)imidazol[1,2-a]pyridin-5-yl)isoindolin-1-one | 0.81 (2 min_lc) | 418.48 | 419 (M + H)+ |

-continued

| Compound No. | Structure | Compound name | tR (min), (LCMS method) | M. W. | Ion found |
|---|---|---|---|---|---|
| 19 | 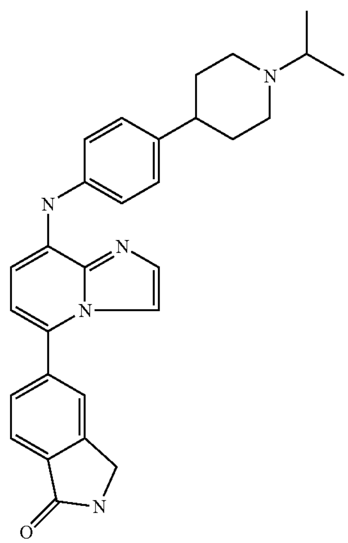 | 5-(8-(4-(1-isopropylpiperidin-4-yl)phenylamino)imidazo[1,2-a]pyridin-5-yl)isoindolin-1-one | 0.80 (2 min_lc) | 465.6 | 466 (M + H)+ |
| 20 | 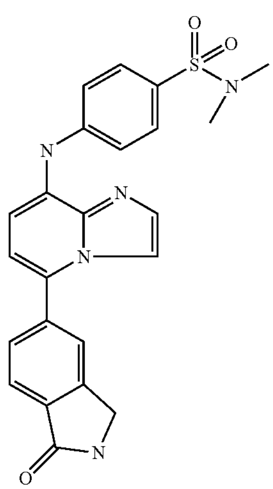 | N,N-dimethyl-4-(5-(1-oxoisoindolin-5-yl)imidazo[1,2-a]pyridin-8-ylamino)benzenesulfonamide | 0.86 (2 min_lc) | 447.52 | 448 (M + H)+ |
| 21 | 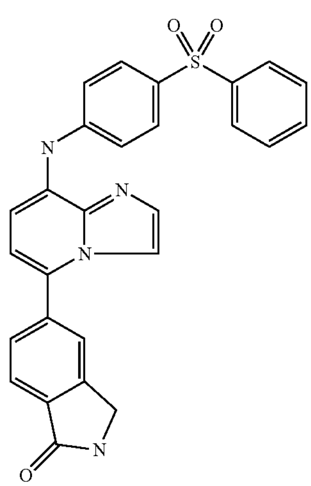 | 5-(8-(4-(phenylsulfonyl)phenylamino)imidazo[1,2-a]pyridin-5-yl)isoindolin-1-one | 0.98 (2 min_lc) | 480.55 | 481 (M + H)+ |

-continued

| Compound No. | Structure | Compound name | tR (min), (LCMS method) | M. W. | Ion found |
|---|---|---|---|---|---|
| 22 | 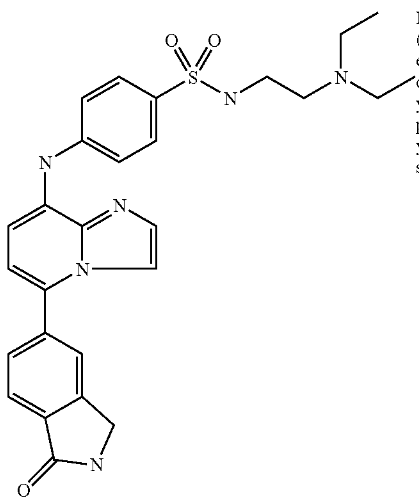 | N-(2-(diethylamino)ethyl)-4-(5-(1-oxoisoindolin-5-yl)imidazol[1,2-a]pyridin-8-ylamino)benzene sulfonamide | 0.79 (2 min_lc) | 518.64 | 519 (M + H)+ |
| 23 | 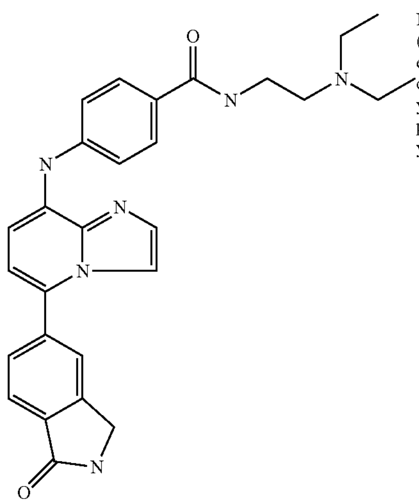 | N-(2-(diethylamino)ethyl)-4-(5-(1-oxoisoindolin-5-yl)imidazol[1,2-a]pyridin-8-ylamino)benzamide | 0.77 (2 min_lc) | 482.59 | 483 (M + H)+ |
| 24 | 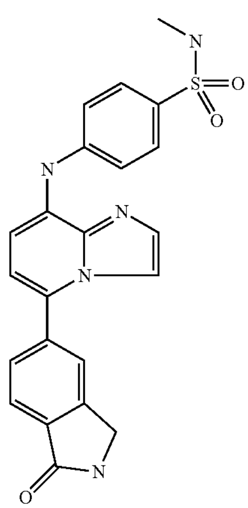 | N-methyl-4-(5-(1-oxoisoindolin-5-yl)imidazo[1,2-a]pyridin-8-ylamino)benzene sulfonamide | 0.80 (2 min_lc) | 433.49 | 434 (M + H)+ |

| Compound No. | Structure | Compound name | tR (min), (LCMS method) | M. W. | Ion found |
|---|---|---|---|---|---|
| 25 | 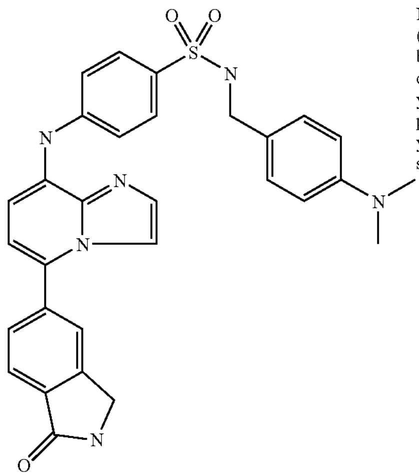 | N-(4-(dimethylamino)benzyl)-4-(5-(1-oxoisoindolin-5-yl)imidazo[1,2-a]pyridin-8-ylamino)benzenesulfonamide | 0.80 (2 min_lc) | 552.66 | 553 (M + H)+ |
| 26 | 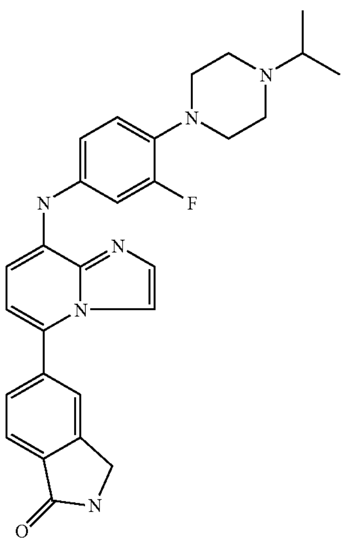 | 5-(8-(3-fluoro-4-(4-isopropylpiperazin-1-yl)phenylamino)imidazo[1,2-a]pyridin-5-yl)isoindolin-1-one | 0.78 (2 min_lc) | 484.58 | 485 (M + H)+ |
| 27 | 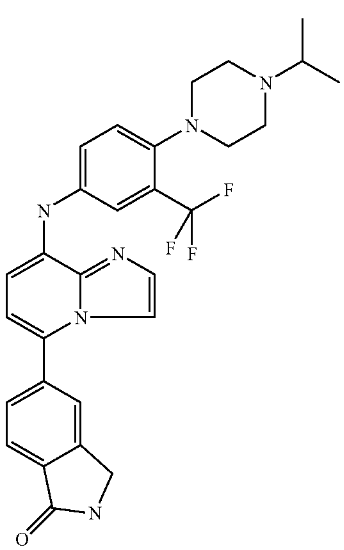 | 5-(8-(4-(4-isopropylpiperazin-1-yl)-3-(trifluoromethyl)phenylamino)imidazo[1,2-a]pyridin-5-yl)isoindolin-1-one | 0.87 (2 min_lc) | 534.59 | 535 (M + H)+ |

-continued

| Compound No. | Structure | Compound name | tR (min), (LCMS method) | M. W. | Ion found |
|---|---|---|---|---|---|
| 28 | 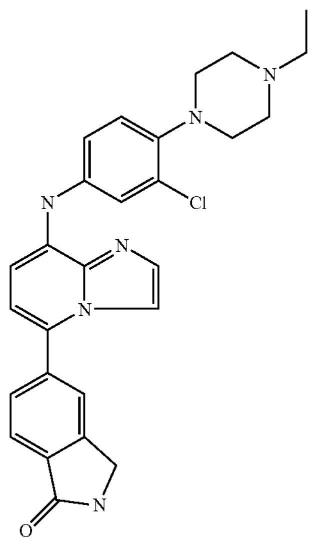 | 5-(8-(3-chloro-4-(4-ethylpiperazin-1-yl)phenylamino)imidazol[1,2-a]pyridin-5-yl)isoindolin-1-one | 0.79 (2 min_lc) | 487.01 | 487 $(M + H)^+$ |
| 29 | 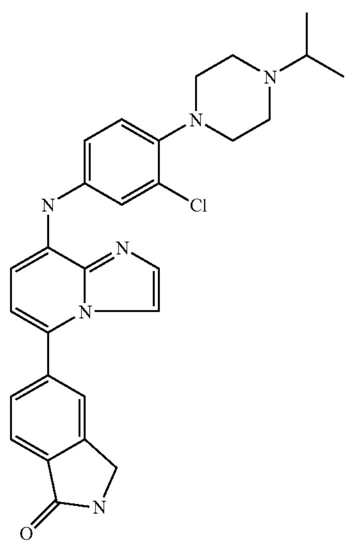 | 5-(8-(3-chloro-4-(4-isopropylpiperazin-1-yl)phenylamino)imidazo[1,2-a]pyridin-5-yl)isoindolin-1-one | 0.82 (2 min_lc) | 501.03 | 501 $(M + H)^+$ |
| 30 | 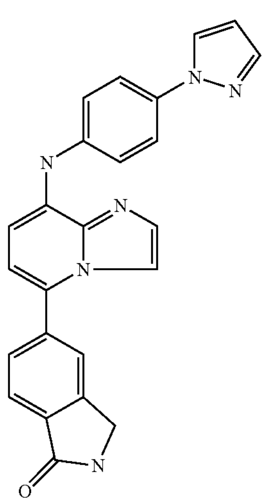 | 5-(8-(4-(1H-pyrazol-1-yl)phenylamino)imidazo[1,2-a]pyridin-5-yl)isoindolin-1-one | 0.93 (2 min_lc) | 406.45 | 407 $(M + H)^+$ |

-continued

| Compound No. | Structure | Compound name | tR (min), (LCMS method) | M. W. | Ion found |
|---|---|---|---|---|---|
| 31 | 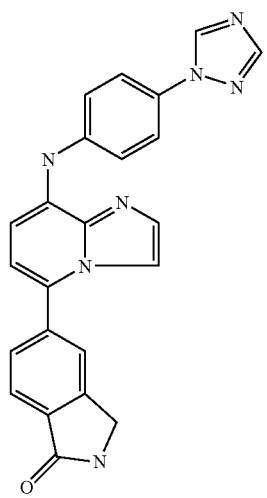 | 5-(8-(4-(1H-1,2,4-triazol-1-yl)phenylamino)imidazo[1,2-a]pyridin-5-yl)isoindolin-1-one | 0.82 (2 min_lc) | 407.44 | 408 (M + H)+ |

Compound 32: 4-(5-(1-oxoisoindolin-5-yl)imidazo[1,2-a]pyridin-8-ylamino)-N-(pyrrolidin-3-yl)benzene sulfonamide

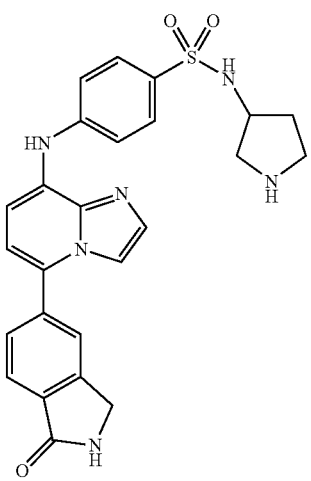

3-{4-[5-(1-oxo-2,3-dihydro-1H-isoindol-5-yl)-imidazo[1,2-a]pyridin-8-ylamino]-benzenesulfonylamino}-pyrrolidine-1-carboxylic acid tert-butyl ester (16 mg, 0.027 mmol), prepared using methods as described for compound 12, is suspended in a 4M solution of HCl in dioxane (0.5 mL) and the mixture is stirred under nitrogen at room temperature for 16 hours. The mixture is concentrated under reduced pressure. The crude product is purified by reverse phase HPLC to yield the title compound.

tR: 0.73 min (2 min_LC)

Ion (found): 489 (M+H)+

Compound 33. 5-(8-(4-(1,4'-bipiperidine-1'-carbonyl)phenylamino)imidazo[1,2-a]pyridin-5-yl)-isoindolin-1-one 33.1 4-[5-(1-oxo-2,3-dihydro-1H-isoindol-5-yl)-imidazo[1,2-a]pyridin-8-ylamino]-benzoic acid

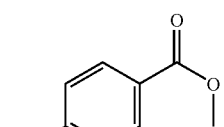 LiOH THF/H2O 60° C., o/n

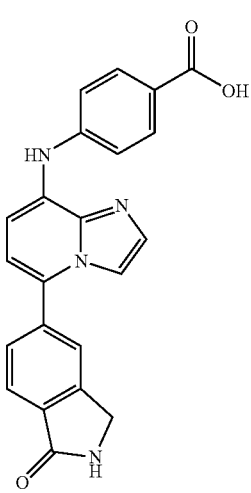

Crude 4-[5-(1-oxo-2,3-dihydro-1H-isoindol-5-yl)-imidazo[1,2-a]pyridin-8-ylamino]-benzoic acid methyl ester (500 mg, 1.256 mmol), prepared using methods similar to those described for compound 12, and lithium hydroxide hydrate (263.5 mg, 6.281 mmol) in solution in THF/water (1/1: 10 mL) is stirred at room temperature for 36 hours then heated 4 hours at 60° C. The mixture is concentrated and then acidified to pH 1 with aqueous 2N HCl. The resulting precipitate is filtrated to yield the title compound, which is used as such for the next step.

33.2. 5-(8-(4-(1,4'-bipiperidine-1'-carbonyl)phenylamino)imidazo[1,2-a]pyridin-5-yl)isoindolin-1-one

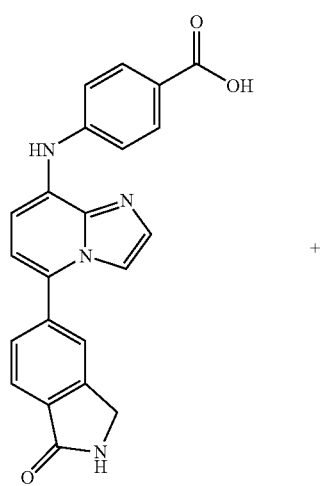

+

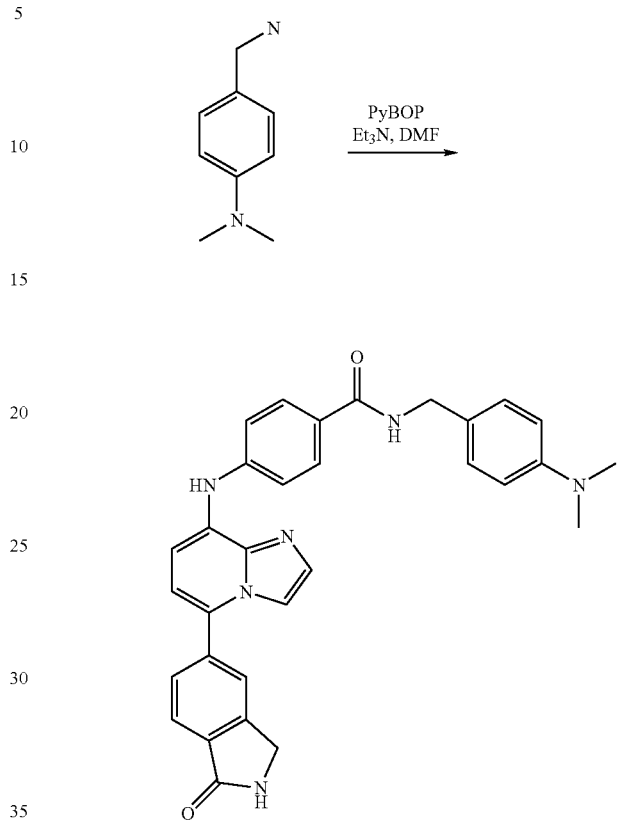

To a solution of 4-[5-(1-oxo-2,3-dihydro-1H-isoindol-5-yl)-imidazo[1,2-a]pyridin-8-ylamino]-benzoic acid (37.0 mg, 0.096 mmol), 4-dimethylaminobenzylamine (15.91 mg, 0.106 mmol) and triethylamine (10.72 mg, 0.047 mL, 0.106 mmol) in dimethylformamide (0.4 mL) under nitrogen is added benzotriazole-1-yl-oxy-tris-pyrrolidino-phosphonium hexafluorophosphate (55.10 mg, 0.106 mmol). The reaction mixture is then stirred at room temperature for 18 hours. The mixture is then diluted with EtOAc and washed with saturated aqueous NaHCO$_3$. The combined organic layers are dried (MgSO$_4$) and the solvent is removed under reduced. The crude product is purified by reverse phase HPLC to yield the title compound.

tR: 0.77 min (2 min_LC)

Ion (found): 517 (M+H)+

Compounds 34-43

These compounds are shown in the table below and are prepared in a similar manner to that described for compound 33, step 2, using General Method (2) as described above, and are purified by preparative reverse phase HPLC.

| Compound No. | Structure | Compound name | tR (min), (LCMS method) | M. W. | Ion found |
|---|---|---|---|---|---|
| 34 | 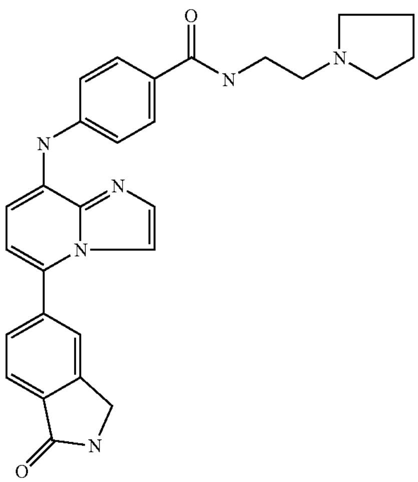 | 4-(5-(1-oxoisoindolin-5-yl)imidazo[1,2-a]pyridin-8-ylamino)-N-(2-(pyrrolidin-1-yl)ethyl)benzamide | 0.73 (2 min_lc) | 480.57 | 481 (M + H)+ |
| 35 | 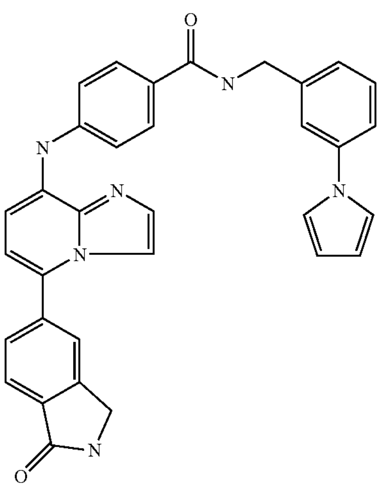 | 4-[5-(1-Oxo-2,3-dihydro-1H-isoindol-5-yl)-imidazol[1,2-a]pyridin-8-ylamino]-N-(3-pyrrol-1-yl-benzyl)-benzamide | 1.07 (2 min_lc) | 538.61 | 539 (M + H)+ |
| 36 | 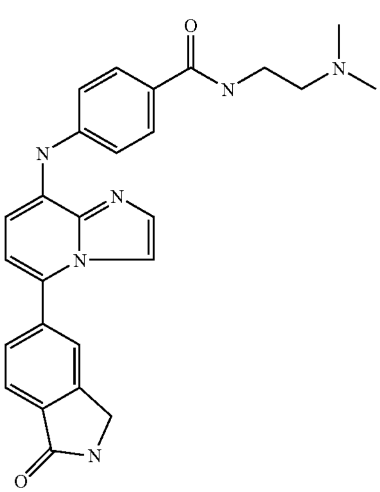 | N-(2-(dimethylamino)ethyl)-4-(5-(1-oxoisoindolin-5-yl)imidazo[1,2-a]pyridin-8-ylamino)benzamide | 0.72 (2 min_lc) | 454.53 | 455 (M + H)+ |

-continued

| Compound No. | Structure | Compound name | tR (min), (LCMS method) | M. W. | Ion found |
|---|---|---|---|---|---|
| 37 | 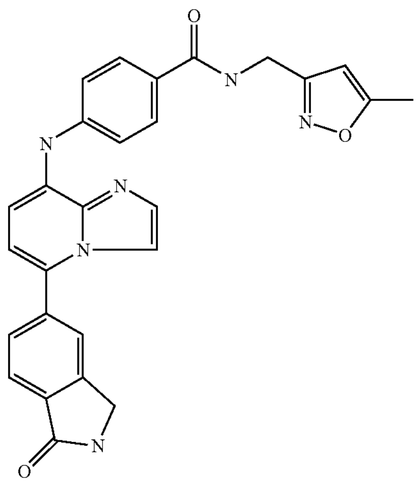 | N-((5-methylisoxazol-3-yl)methyl)-4-(5-(1-oxoisoindolin-5-yl)imidazo[1,2-a]pyridin-8-ylamino)benzamide | 0.77 (2 min_lc) | 478.51 | 479 (M + H)+ |
| 38 | 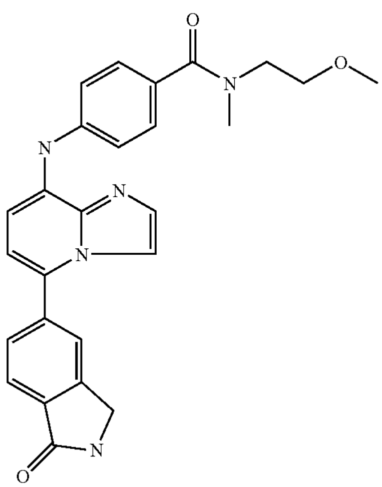 | N-(2-methoxyethyl)-N-methyl-4-(5-(1-oxoisoindolin-5-yl)imidazol[1,2-a]pyridin-8-ylamino)benzamide | 0.84 (2 min_lc) | 455.52 | 456 (M + H)+ |
| 39 | 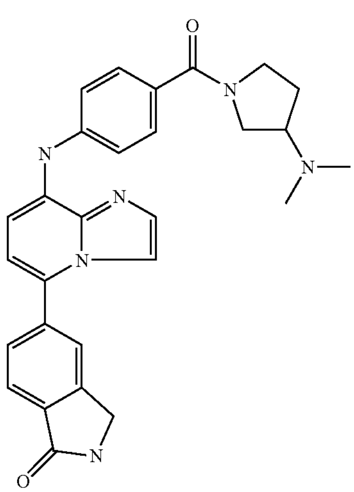 | 5-(8-(4-(3-(dimethylamino)pyrrolidine-1-carbonyl)phenylamino)imidazo[1,2-a]pyridin-5-yl)isoindolin-1-one | 0.70 (2 min_lc) | 480.57 | 481 (M + H)+ |

-continued

| Compound No. | Structure | Compound name | tR (min), (LCMS method) | M. W. | Ion found |
|---|---|---|---|---|---|
| 40 | 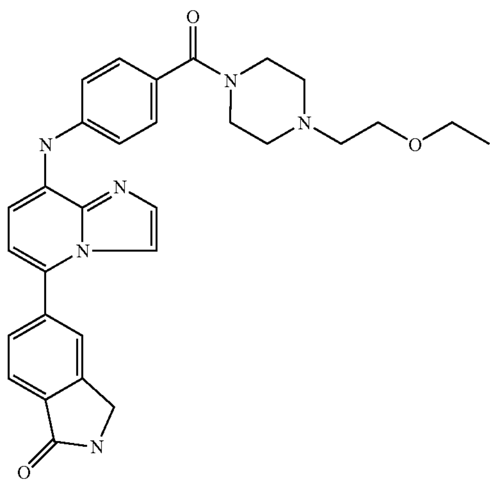 | 5-(8-(4-(4-(2-ethoxy-ethyl)piperazine-1-carbonyl)phenylamino)imidazo[1,2-a]pyridin-5-yl)isoindolin-1-one | 0.75 (2 min_lc) | 524.62 | 525 (M + H)+ |
| 41 | 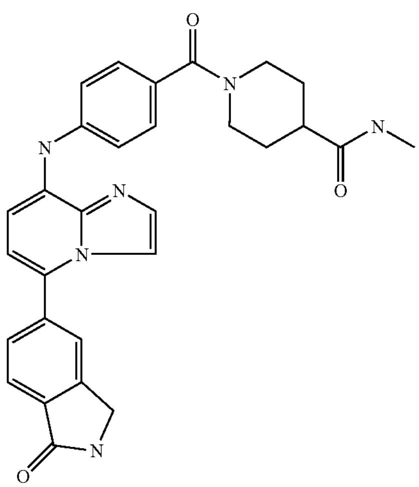 | N-methyl-1-(4-(5-(1-oxoisoindolin-5-yl)imidazo[1,2-a]pyridin-8-ylamino)benzoyl)piperidine-4-carboxamide | 0.77 (2 min_lc) | 508.58 | 509 (M + H)+ |
| 42 | 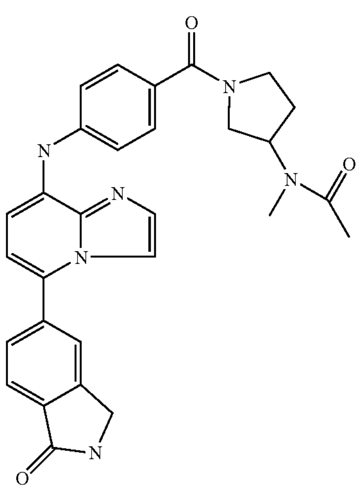 | N-methyl-N-(1-(4-(5-(1-oxoisoindolin-5-yl)imidazo[1,2-a]pyridin-8-ylamino)benzoyl)pyrrolidin-3-yl)acetamide | 0.79 (2 min_lc) | 508.58 | 509 (M + H)+ |

| Compound No. | Structure | Compound name | tR (min), (LCMS method) | M. W. | Ion found |
|---|---|---|---|---|---|
| 43 | 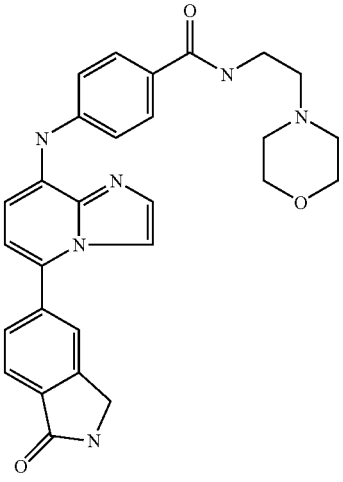 | N-(2-morpholinoethyl)-4-(5-(1-oxoisoindolin-5-yl)imidazo[1,2-a]pyridin-8-ylamino)benzamide | 0.72 (2 min_lc) | 496.57 | 497 (M + H)+ |

Compound 44: 4-[5-(1-oxo-2,3-dihydro-1H-isoindol-5-yl)-imidazo[1,2-a]pyridin-8-ylamino]-N-pyrrolidin-3-yl-benzamide Compound 45. 4-(5-Chloro-imidazo[1,2-a]pyridin-8-ylamino)-benzoic acid

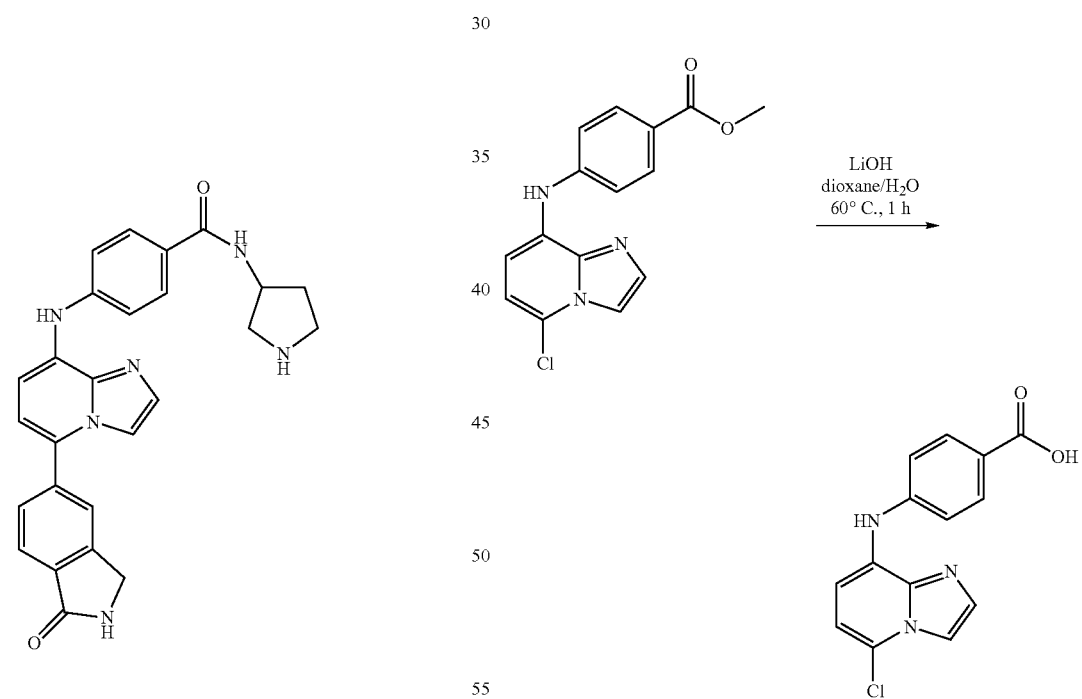

4-[5-(1-Oxo-2,3-dihydro-1H-isoindol-5-yl)-imidazo[1,2-a]pyridin-8-ylamino]-N-pyrrolidin-3-yl-benzamide is prepared using methods similar to those described for compound 33, step 2, followed by deprotection as described for compound 32.

tR: 0.73 min (2 min_LC)

Ion (found): 489 (M+H)+

A mixture of 4-(5-chloro-imidazo[1,2-a]pyridin-8-ylamino)-benzoic acid methyl ester (450 mg, 1.495 mmol), prepared using methods similar to those described for compound 12, step 1, and lithium hydroxide hydrate (250.9 mg, 5.98 mmol) in solution in dioxane/water (2/1: 30 mL) is heated at 60° C. for 2 hours. The mixture is concentrated and then acidified to pH 1 with aqueous 2N HCl. The resulting precipitate is filtrated to yield the title compound, which is used as such for the next step.

Compounds 46-62

These compounds are shown in the table below and are prepared using methods similar to those described for compound 45, using General Method (3) as described above, and are purified either by chromatography on Isolute Flash Si II column or by preparative reverse phase HPLC.

| Compound No. | Structure | Compound Name | tR (min), (LCMS method) | M. W. | Ion found |
|---|---|---|---|---|---|
| 46 | 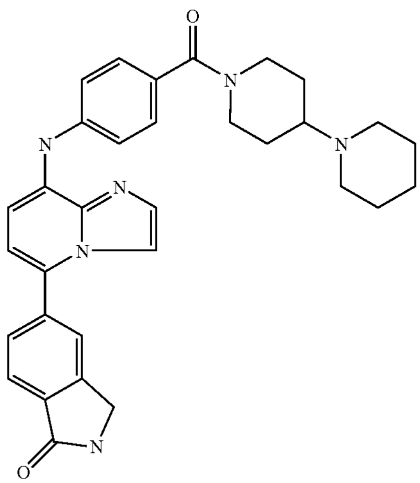 | 5-(8-(4-(1,4'-bipiperidine-1'-carbonyl)phenylamino)imidazo[1,2-a]pyridin-5-yl)isoindolin-1-one | 0.75 (2 min_lc) | 534.66 | 535 (M + H)$^+$ |
| 47 | 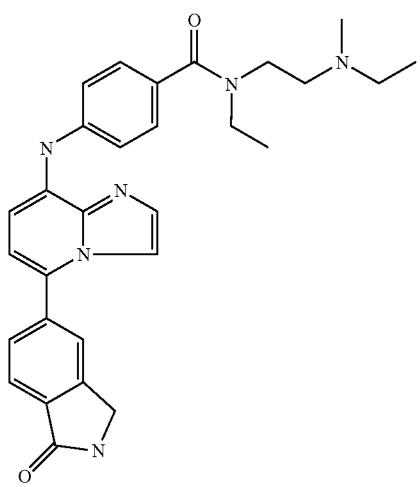 | N-ethyl-N-(2-(ethyl(methyl)amino)ethyl)-4-(5-(1-oxoisoindolin-5-yl)imidazo[1,2-a]pyridin-8-ylamino)benzamide | 0.75 (2 min_lc) | 496.61 | 497 (M + H)$^+$ |
| 48 | 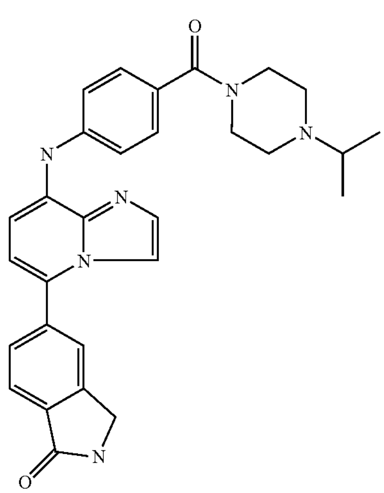 | 5-(8-(4-(4-isopropylpiperazine-1-carbonyl)phenylamino)imidazo[1,2-a]pyridin-5-yl)isoindolin-1-one | 0.73 (2 min_lc) | 494.6 | 495 (M + H)$^+$ |

| Compound No. | Structure | Compound Name | tR (min), (LCMS method) | M. W. | Ion found |
|---|---|---|---|---|---|
| 49 | 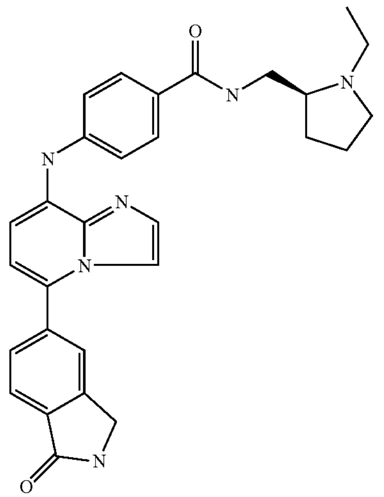 | (S)-N-((1-ethylpyrrolidin-2-yl)methyl)-4-(5-(1-oxoisoindolin-5-yl)imidazo[1,2-a]pyridin-8-ylamino)benzamide | 0.76 (2 min_lc) | 494.6 | 495 (M + H)+ |
| 50 | 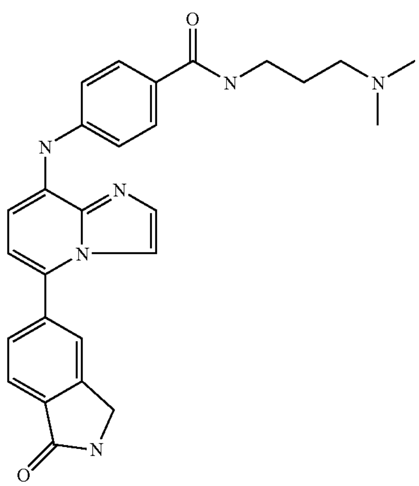 | -(3-(dimethylamino)propyl)-4-(5-(1-oxoisoindolin-5-yl)imidazo[1,2-a]pyridin-8-ylamino)benzamide | 0.73 (2 min_lc) | 468.56 | 469 (M + H)+ |
| 51 | 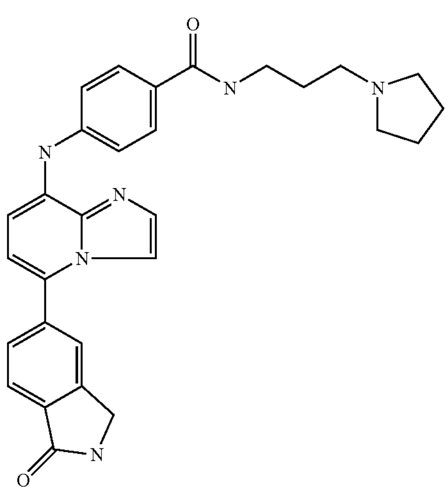 | 4-(5-(1-oxoisoindolin-5-yl)imidazo[1,2-a]pyridin-8-ylamino)-N-(3-(pyrrolidin-1-yl)propyl)benzamide | 0.74 (2 min_lc) | 494.6 | 495 (M + H)+ |

-continued

| Compound No. | Structure | Compound Name | tR (min), (LCMS method) | M. W. | Ion found |
|---|---|---|---|---|---|
| 52 | 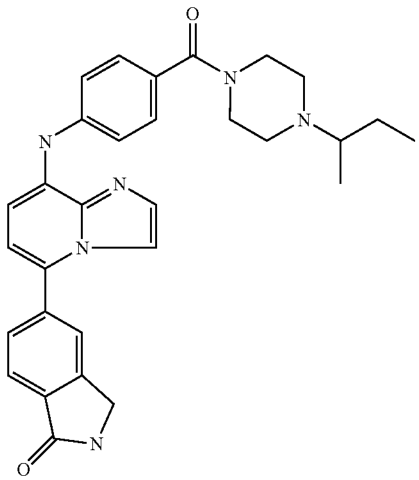 | 5-(8-(4-(4-sec-butylpiperazine-1-carbonyl)phenylamino)imidazo[1,2-a]pyridin-5-yl)isoindolin-1-one | 0.76 (2 min_lc) | 508.63 | 509 (M + H)+ |
| 53 | 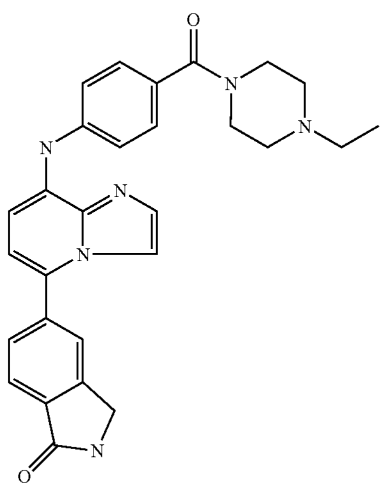 | 5-(8-(4-(4-ethylpiperazine-1-carbonyl)phenylamino)imidazo[1,2-a]pyridin-5-yl)isoindolin-1-one | 0.71 (2 min_lc) | 480.57 | 481 (M + H)+ |
| 54 | 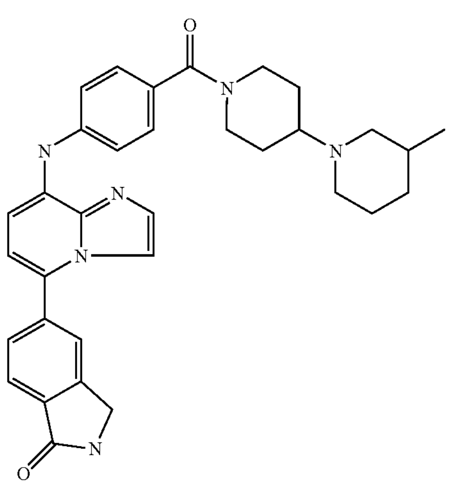 | 5-{8-[4-(3-Methyl-[1,4']bipiperidinyl-1'-carbonyl)-phenylamino]-imidazo[1,2-a]pyridin-5-yl}-2,3-dihydro-isoindol-1-one | 0.79 (2 min_lc) | 548.69 | 549 (M + H)+ |

-continued

| Compound No. | Structure | Compound Name | tR (min), (LCMS method) | M. W. | Ion found |
|---|---|---|---|---|---|
| 55 | 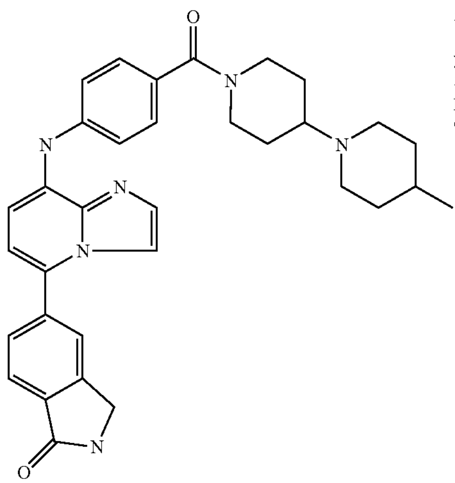 | 5-{8-[4-(4-Methyl-[1,4']bipiperidin yl-1'-carbonyl)-phenylamino]-imidazo[1,2-a]pyridin-5-yl}-2,3-dihydro-isoindol-1-one | 0.79 (2 min_lc) | 548.69 | 549 (M + H)+ |
| 56 | 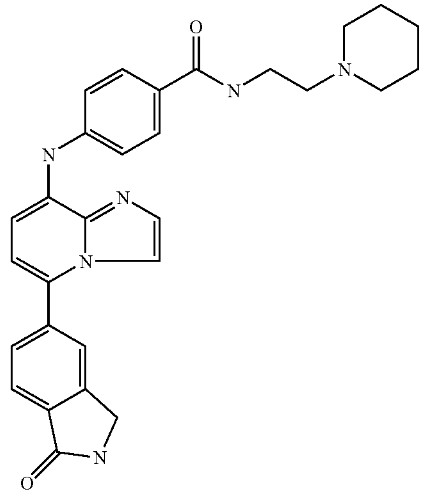 | 4-(5-(1-oxoisoindolin-5-yl)imidazo[1,2-a]pyridin-8-ylamino)-N-(2-(piperidin-1-yl)ethyl)benzamide | 0.76 (2 min_lc) | 494.6 | 495 (M + H)+ |
| 57 | 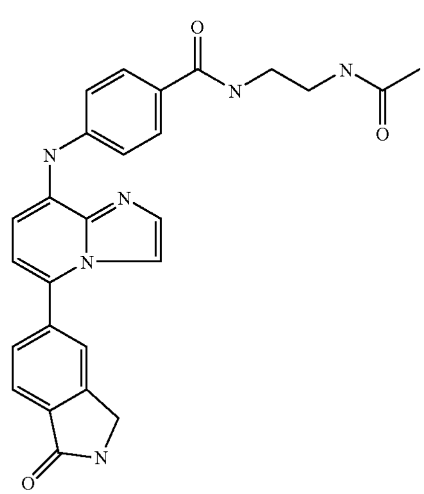 | N-(2-acetamidoethyl)-4-(5-(1-oxoisoindolin-5-yl)imidazo[1,2-a]pyridin-8-ylamino)benzamide | 0.75 (2 min_lc) | 468.52 | 469 (M + H)+ |

-continued

| Compound No. | Structure | Compound Name | tR (min), (LCMS method) | M. W. | Ion found |
|---|---|---|---|---|---|
| 58 | 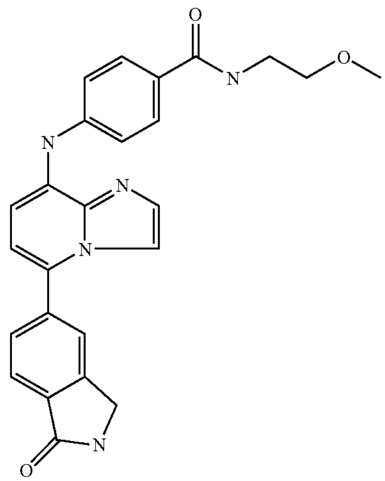 | N-(2-methoxyethyl)-4-(5-(1-oxoisoindolin-5-yl)imidazo[1,2-a]pyridin-8-ylamino)benzamide | 0.81 (2 min_lc) | 441.49 | 442 (M + H)+ |

Compounds 59-62

These compounds are shown in the table below and are prepared using methods similar to those described for compound 33, step 2, and General Method (4) as described above, and are purified by preparative reverse phase HPLC.

| Compound No. | Structure | Compound Name | tR (min), (LCMS method) | M. W. | Ion found |
|---|---|---|---|---|---|
| 59 | 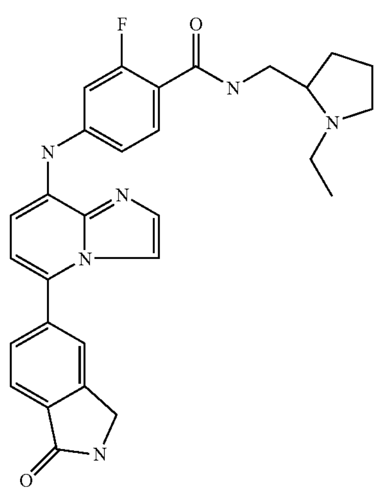 | (S)-N-((1-ethylpyrrolidin-2-yl)methyl)-2-fluoro-4-(5-(1-oxoisoindolin-5-yl)imidazo[1,2-a]pyridin-8-ylamino)benzamide | 0.76 (2 min_lc) | 512.59 | 513 (M + H)+ |

-continued

| Compound No. | Structure | Compound Name | tR (min), (LCMS method) | M.W. | Ion found |
|---|---|---|---|---|---|
| 60 | 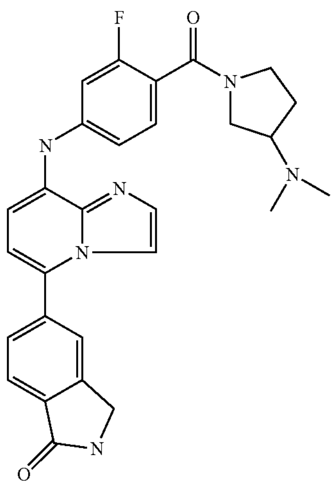 | 5-(8-(4-(3-(dimethylamino)pyrrolidine-1-carbonyl)-3-fluorophenylamino)imidazo[1,2-a]pyridin-5-yl)isoindolin-1-one | 0.71 (2 min_lc) | 498.56 | 499 (M + H)+ |
| 61 | 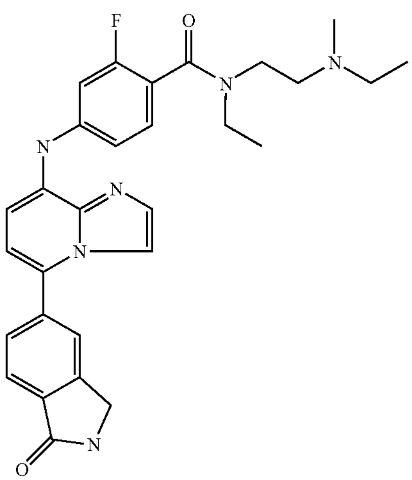 | N-ethyl-N-(2-(ethyl(methyl)amino)ethyl)-2-fluoro-4-(5-(1-oxoisoindolin-5-yl)imidazo[1,2-a]pyridin-8-ylamino)benzamide | 0.76 (2 min_lc) | 514.6 | 515 (M + H)+ |
| 62 | 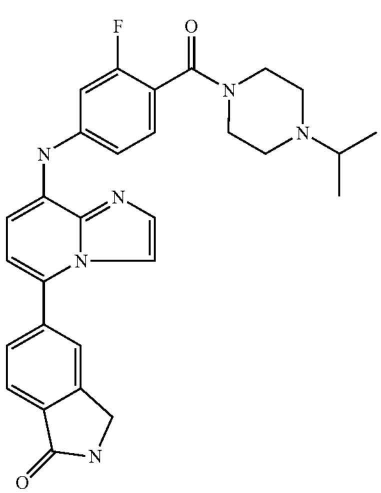 | 5-{8-[4-(4-Isopropyl-piperazine-1-carbonyl)-phenylamino]-imidazo[1,2-a]pyridin-5-yl}-2,3-dihydro-isindol-1-one | 0.74 (2 min_lc) | 512.59 | 513 (M + H)+ |

Compounds 63-105

| Compound No | Structure | tR (min), (LCMS method) | M. W. | Ion found |
|---|---|---|---|---|
| 64 | 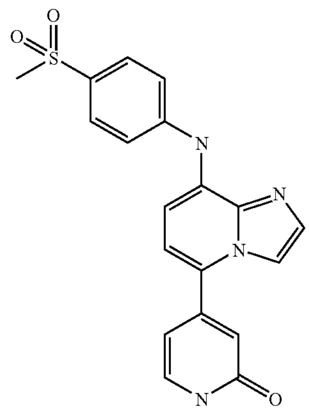 | 0.96 (Table 2) | 380 | 381 |
| 65 | 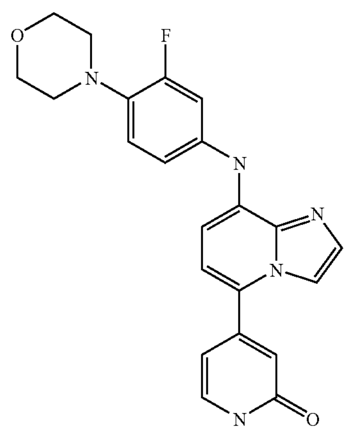 | 1.23 (Table 2) | 405 | 406 |
| 66 | 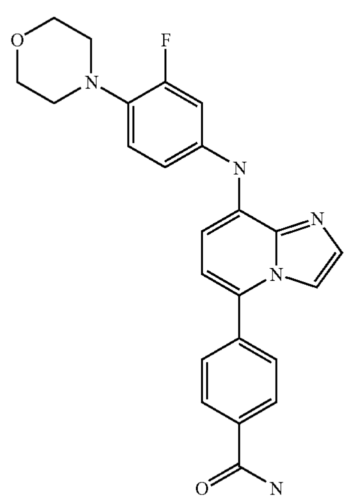 | 1.37 (Table 2) | 431 | 432 |

-continued

| Compound No | Structure | tR (min), (LCMS method) | M. W. | Ion found |
|---|---|---|---|---|
| 67 | 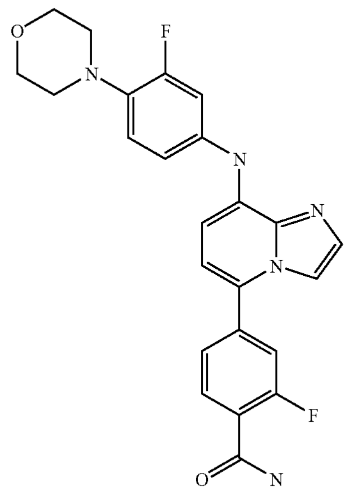 | 1.45 (Table 2) | 449 | 450 |
| 68 | 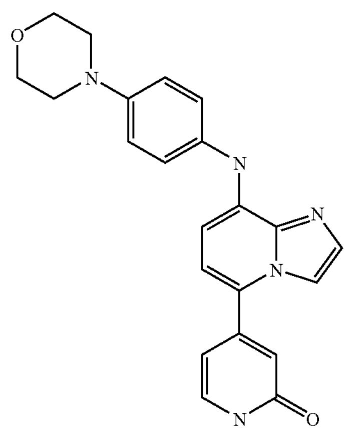 | 2.03 (Table 5) | 387 | 388 |
| 69 | 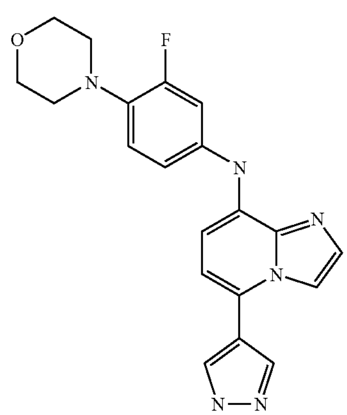 | 2.16 (Table 5) | 378 | 379 |

-continued

| Compound No | Structure | tR (min), (LCMS method) | M. W. | Ion found |
|---|---|---|---|---|
| 70 | 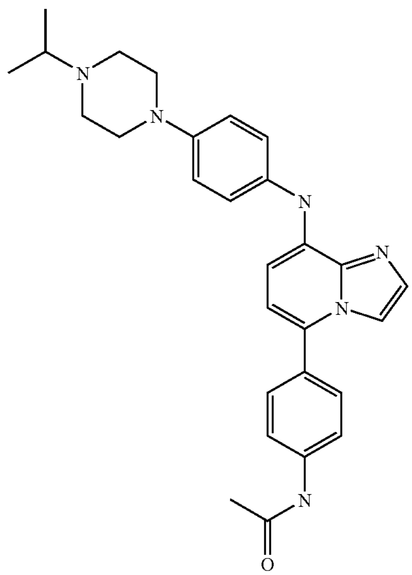 | 1.9 (Table 5) | 468 | 469 |
| 71 | 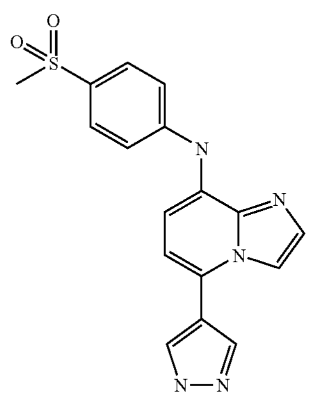 | 1.91 (Table 5) | 353 | 354 |
| 72 | 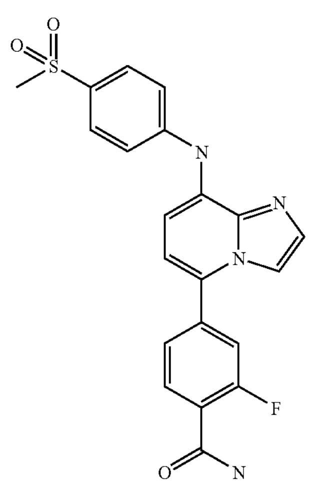 | 2.15 (Table 5) | 424 | 425 |

-continued

| Compound No | Structure | tR (min), (LCMS method) | M. W. | Ion found |
|---|---|---|---|---|
| 73 | 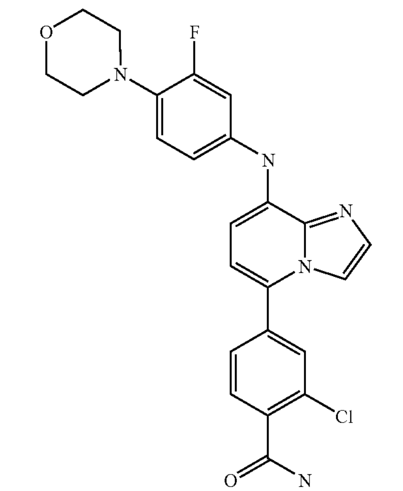 | 2.42 (Table 5) | 465 | 466 |
| 74 | 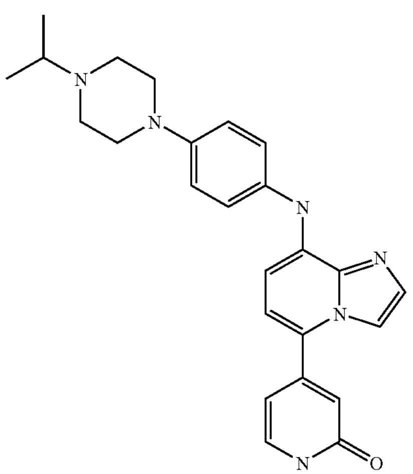 | 0.91 (Table 5) | 428 | 429 |
| 75 | 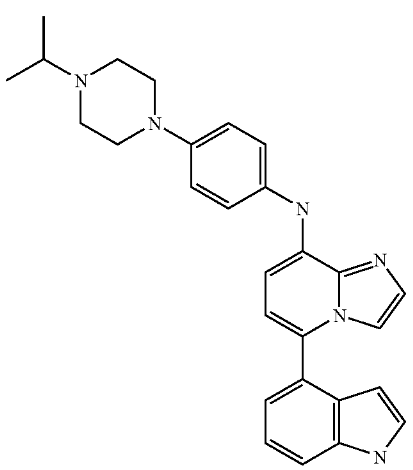 | 1.08 (Table 2) | 450 | 451 |

-continued

| Compound No | Structure | tR (min), (LCMS method) | M. W. | Ion found |
|---|---|---|---|---|
| 76 | 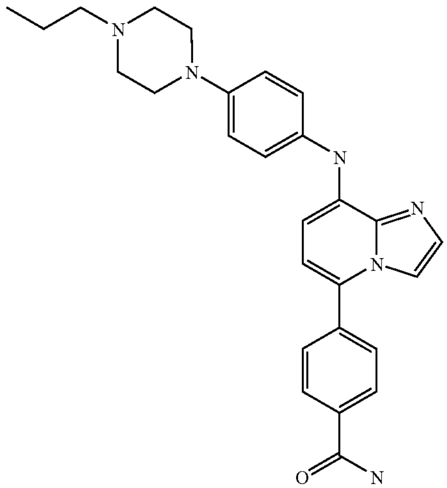 | 1.27 (Table 4) | 454 | 455 |
| 77 | 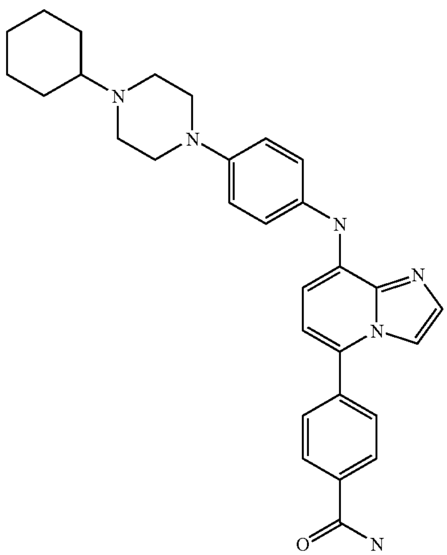 | 1.47 (Table 4) | 494 | 495 |
| 78 | 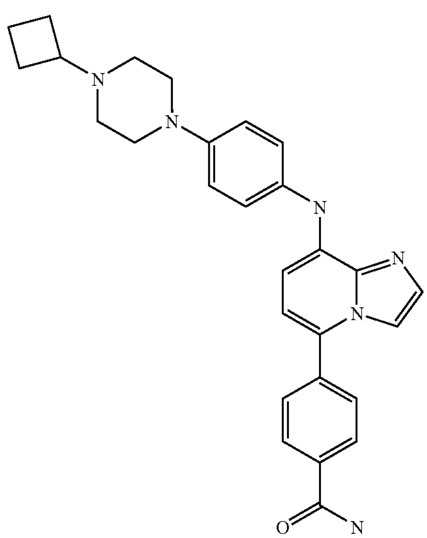 | 1.29 (Table 4) | 466 | 467 |

-continued
| Compound No | Structure | tR (min), (LCMS method) | M. W. | Ion found |
|---|---|---|---|---|
| 79 | 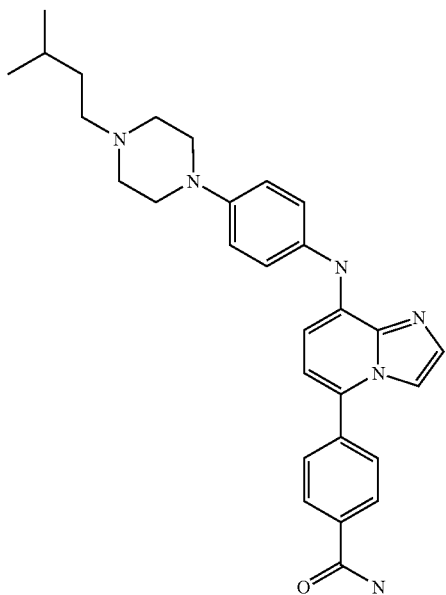 | 1.48 (Table 4) | 482 | 483 |
| 80 | 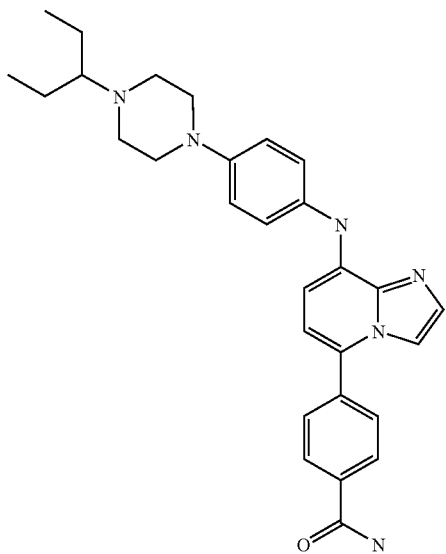 | 1.37 (Table 4) | 482 | 483 |

-continued

| Compound No | Structure | tR (min), (LCMS method) | M.W. | Ion found |
|---|---|---|---|---|
| 81 | 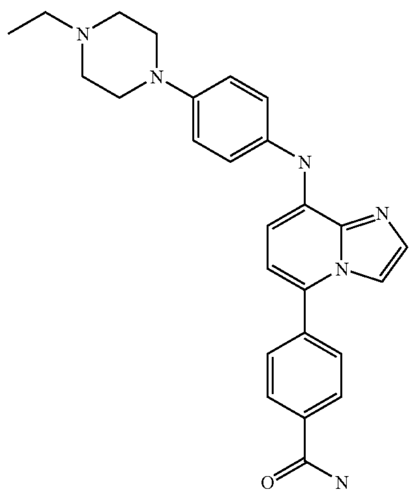 | 1.19 (Table 4) | 440 | 441 |
| 82 | 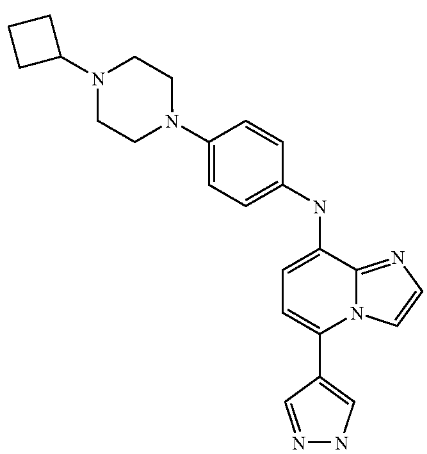 | 1.14 | 413 | 414 |
| 83 | 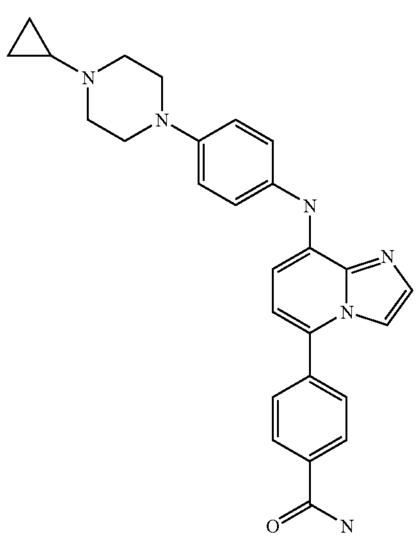 | 1.19 (Table 4) | 452 | 453 |

-continued
| Compound No | Structure | tR (min), (LCMS method) | M. W. | Ion found |
|---|---|---|---|---|
| 84 | 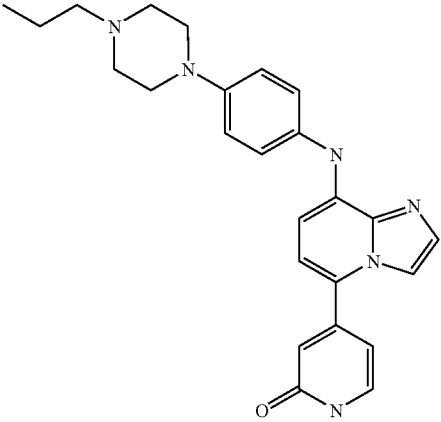 | 2.06 (Table 3) | 428 | 429 |
| 85 | 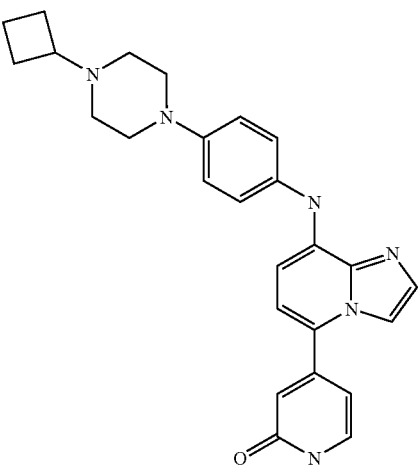 | 1.13 (Table 4) | 440 | 441 |
| 86 | 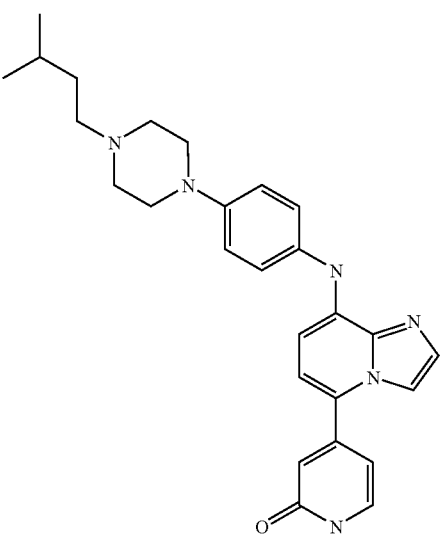 | 1.32 (Table 4) | 456 | 457 |

| Compound No | Structure | tR (min), (LCMS method) | M. W. | Ion found |
|---|---|---|---|---|
| 87 | 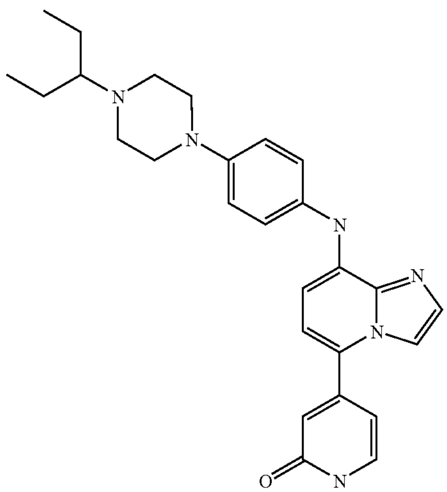 | 1.25 (Table 4) | 456 | 457 |
| 88 | 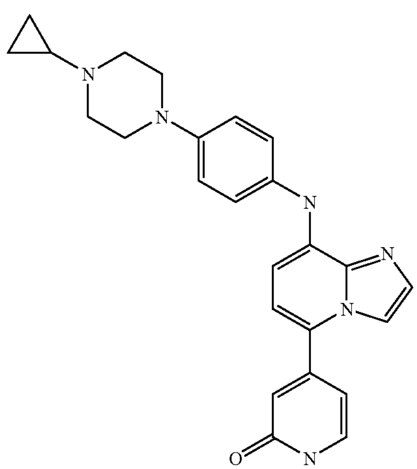 | 2.04 (Table 3) | 426 | 427 |
| 89 | 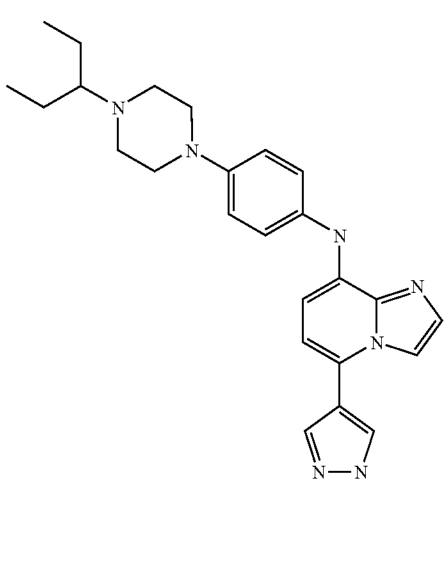 | 1.25 (Table 4) | 429 | 430 |

-continued

| Compound No | Structure | tR (min), (LCMS method) | M. W. | Ion found |
|---|---|---|---|---|
| 90 | 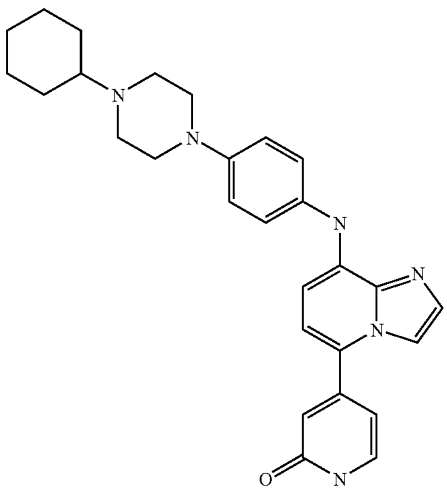 | 1.32 (Table 4) | 468 | 469 |
| 91 | 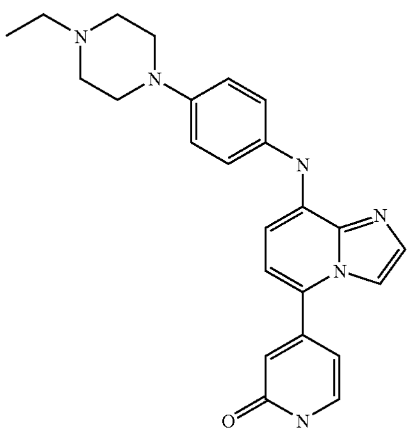 | 1.79 (Table 3) | 414 | 415 |
| 92 | 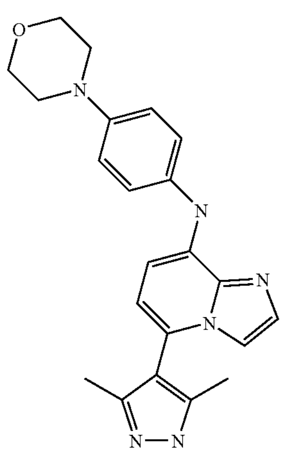 | 1.06 (Table 2) | 388 | 389 |

-continued
| Compound No | Structure | tR (min), (LCMS method) | M. W. | Ion found |
|---|---|---|---|---|
| 93 | 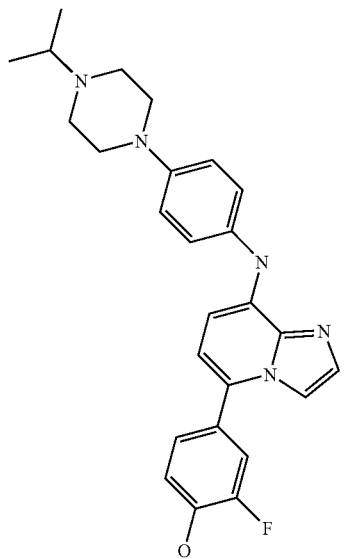 | 0.94 (Table 2) | 445 | 446 |
| 94 | 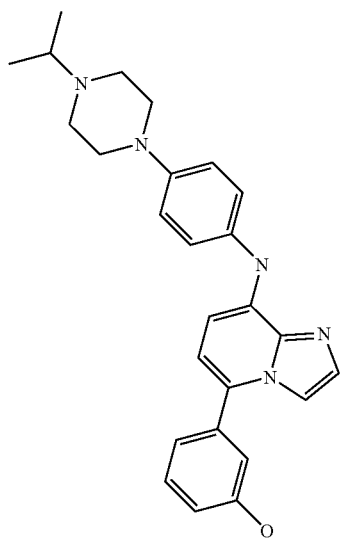 | 0.94 (Table 2) | 427 | 428 |

-continued

| Compound No | Structure | tR (min), (LCMS method) | M. W. | Ion found |
|---|---|---|---|---|
| 95 | 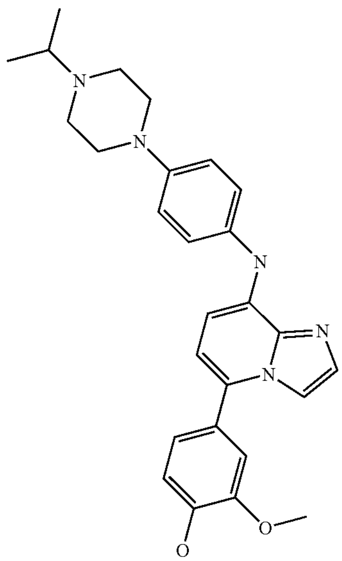 | 0.91 (Table 2) | 457 | 458 |
| 96 | 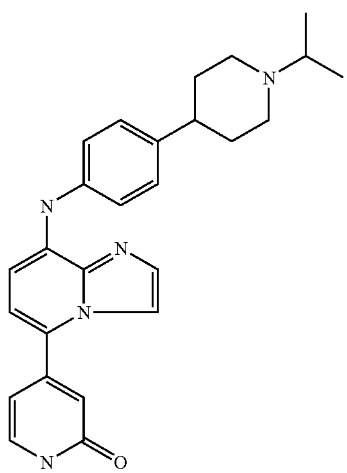 | 0.76 (2 min_lc) | 427.55 | 428 (M + H)+ |
| 97 | 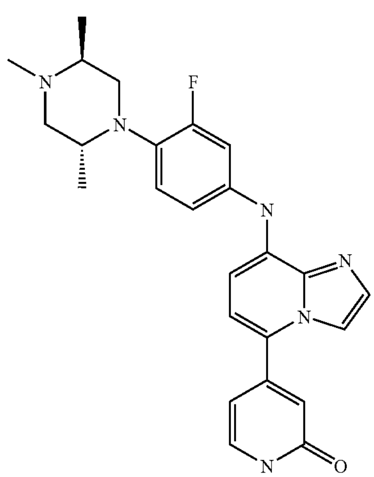 | 1.99 (Table 3) | 446 | 447 |

-continued

| Compound No | Structure | tR (min), (LCMS method) | M. W. | Ion found |
|---|---|---|---|---|
| 98 | 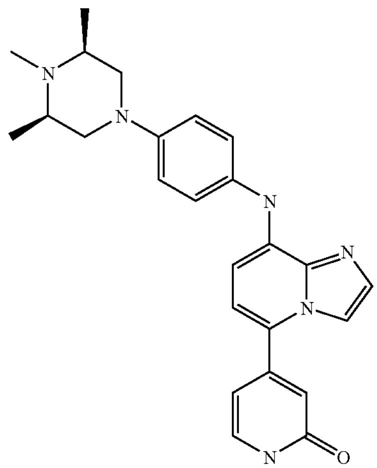 | 1.90 (Table 3) | 428 | 429 |
| 99 | 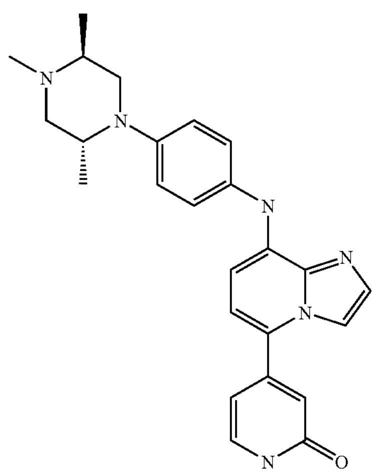 | 1.81 (Table 3) | 428 | 429 |
| 100 | 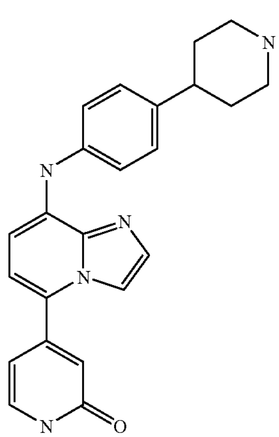 | 1.47 (Table 3) | 385 | 386 |

-continued

| Compound No | Structure | tR (min), (LCMS method) | M. W. | Ion found |
|---|---|---|---|---|
| 101 | 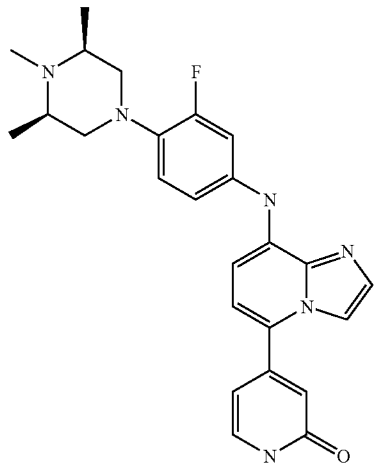 | 2.02 (Table 3) | 446 | 447 |
| 102 | 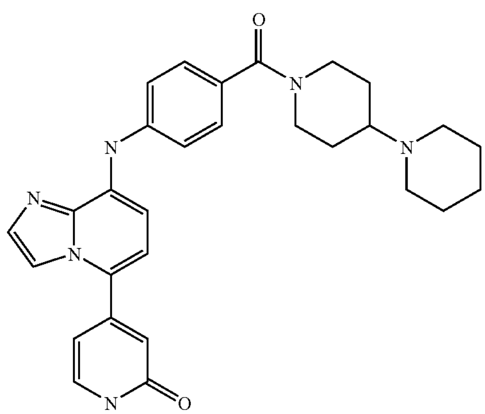 | 1.71 (Table 3) | 496 | 497 |
| 103 | 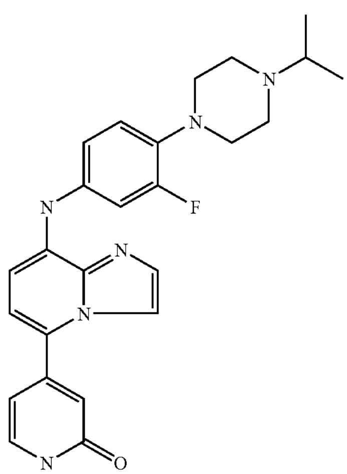 | 1.15 (2 min_lc_NH3) | 446.53 | 447.1 (M + H)+ |

-continued
| Compound No | Structure | tR (min), (LCMS method) | M. W. | Ion found |
|---|---|---|---|---|
| 104 | 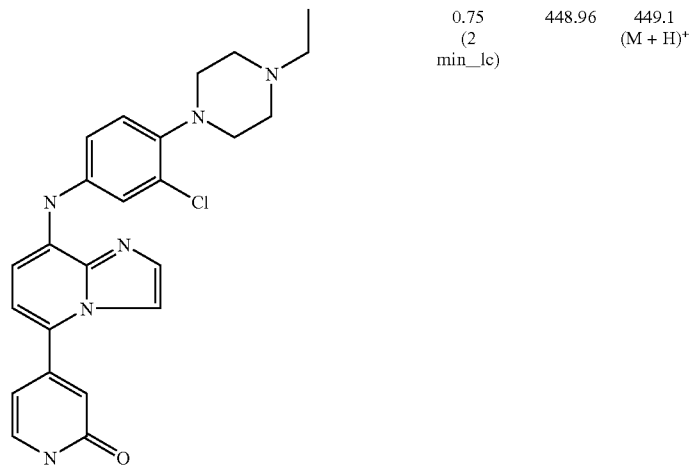 | 0.75 (2 min_lc) | 448.96 | 449.1 (M + H)+ |
| 105 | 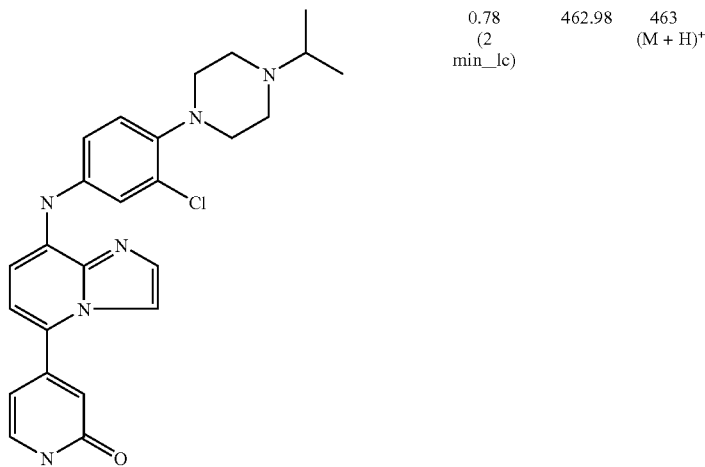 | 0.78 (2 min_lc) | 462.98 | 463 (M + H)+ |

Compounds 106-127

| Compound No. | Structure | Name | Retention time; conditions | MW | Ion found |
|---|---|---|---|---|---|
| 106 | 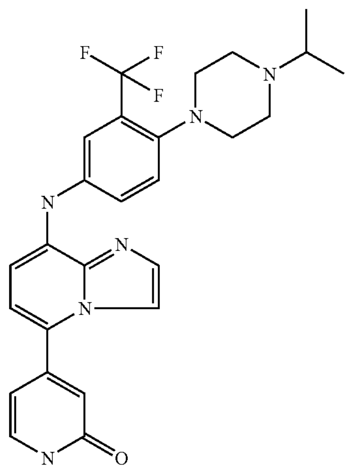 | 4-{8-[4-(4-Isopropyl-piperazin-1-yl)-3-trifluoromethyl-phenylamino]-imidazo[1,2-a]pyridin-5-yl}-1H-pyridin-2-one | 0.85 (2 min_lc) | 496.54 | 497 (M + H)+ |
| 107 | 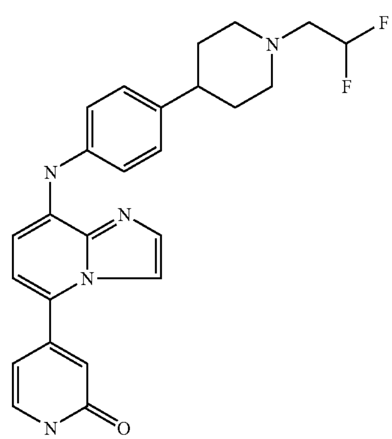 | 4-(8-{4-[1-(2,2-Difluoro-ethyl)-piperidin-4-yl]-phenylamino}-imidazo[1,2-a]pyridin-5-yl)-1H-pyridin-2-one | 0.72 (2 min_lc) | 449.50 | 450 (M + H)+ |
| 108 | 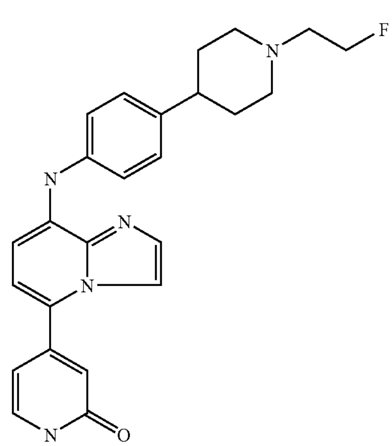 | 4-(8-{4-[1-(2-Fluoro ethyl)-piperidin-4-yl]-phenylamino}-imidazo[1,2-a]pyridin-5-yl)-1H-pyridin-2-one | 0.73 (2 min_lc) | 431.51 | 432 (M + H)+ |

| Compound No. | Structure | Name | Retention time; conditions | MW | Ion found |
|---|---|---|---|---|---|
| 109 | 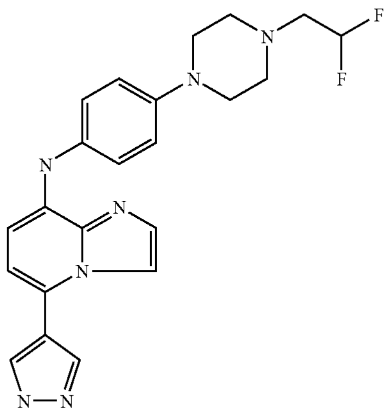 | {4-[4-(2,2-Difluoro-ethyl)-piperazin-1-yl]-phenyl}-[5-(1H-pyrazol-4-yl)-imidazo[1,2-a]pyridin-8-yl]-amine | 0.76 (2 min_lc) | 423.47 | 424 (M + H)+ |
| 110 | 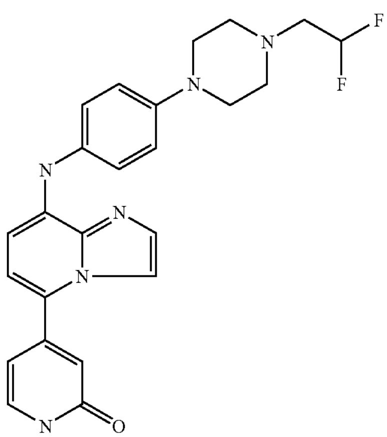 | 4-(8-{4-[4-(2,2-Difluoro-ethyl)-piperazin-1-yl]-phenylamino}-imidazo[1,2-a]pyridin-5-yl)-1H-pyridin-2-one | 0.73 (2 min_lc) | 450.49 | 451 (M + H)+ |
| 111 | 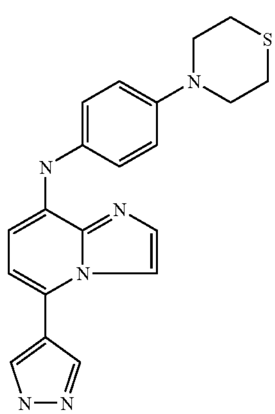 | [5-(1H-Pyrazol-4-yl)-imidazo[1,2-a]pyridin-8-yl]-(4-thiomorpholin-4-yl-phenyl)-amine | 0.81 (2 min_lc) | 376.49 | 377 (M + H)+ |

-continued

| Compound No. | Structure | Name | Retention time; conditions | MW | Ion found |
|---|---|---|---|---|---|
| 112 | 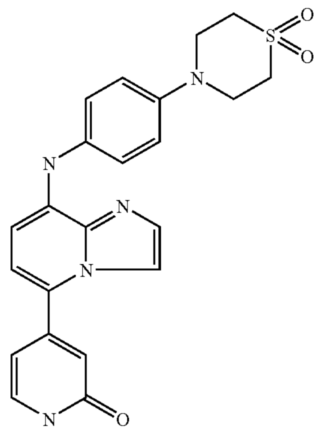 | 4-{8-[4-(1,1-Dioxo-1lambda*6*-thiomorpholin-4-yl)-phenylamino]-imidazo[1,2-a]pyridin-5-yl}-1H-pyridin-2-one | 0.79 (2 min_lc) | 435.51 | 436 (M + H)+ |
| 113 | 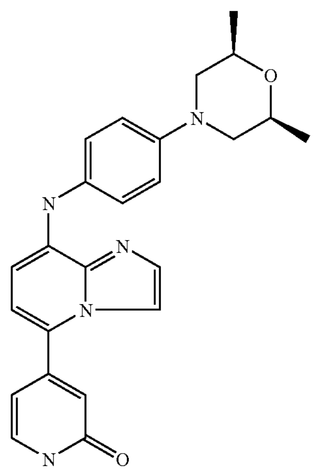 | 4-{8-[4-((2R,6S)-2,6-Dimethyl-morpholin-4-yl)-phenylamino]-imidazo[1,2-a]pyridin-5-yl}-1H-pyridin-2-one | 0.87 (2 min_lc) | 415.5 | 416 (M + H)+ |
| 114 | 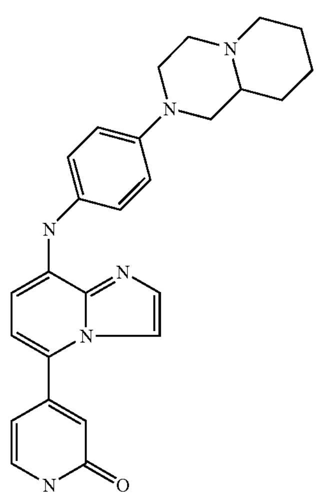 | 4-{8-[4-(Octahydro-pyrido[1,2-a]pyrazin-2-yl)-phenylamino]-imidazo[1,2-a]pyridin-5-yl}-1H-pyridin-2-one | 0.73 (2 min_lc) | 440.55 | 441 (M + H)+ |

-continued

| Compound No. | Structure | Name | Retention time; conditions | MW | Ion found |
|---|---|---|---|---|---|
| 115 | 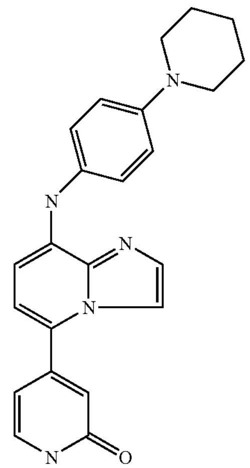 | 4-[8-(4-Piperidin-1-yl-phenylamino)-imidazo[1,2-a]pyridin-5-yl]-1H-pyridin-2-one | 0.71 (2 min_lc) | 385.47 | 386 $(M + H)^+$ |
| 116 | 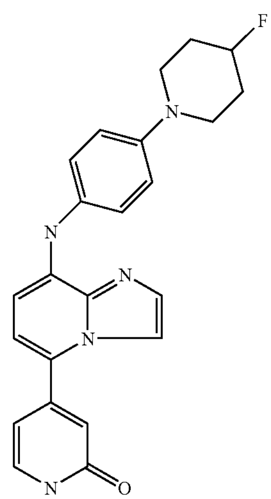 | 4-{8-[4-(4-Fluoro-piperidin-1-yl)-phenylamino]-imidazo[1,2-a]pyridin-5-yl}-1H-pyridin-2-one | 0.74 (2 min_lc) | 403.46 | 404 $(M + H)^+$ |
| 117 | 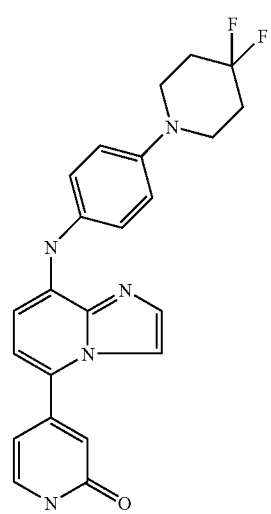 | 4-{8-[4-(4,4-Difluoro-piperidin-1-yl)-phenylamino]-imidazo[1,2-a]pyridin-5-yl}-1H-pyridin-2-one | 0.94 (2 min_lc) | 421.45 | 422 $(M + H)^+$ |

-continued

| Compound No. | Structure | Name | Retention time; conditions | MW | Ion found |
|---|---|---|---|---|---|
| 118 | 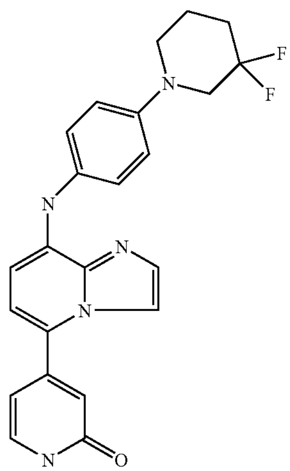 | 4-{8-[4-(3,3-Difluoro-piperidin-1-yl)-phenylamino]-imidazo[1,2-a]pyridin-5-yl}-1H-pyridin-2-one | 1.01 (2 min_lc) | 421.45 | 422 (M + H)+ |
| 119 | 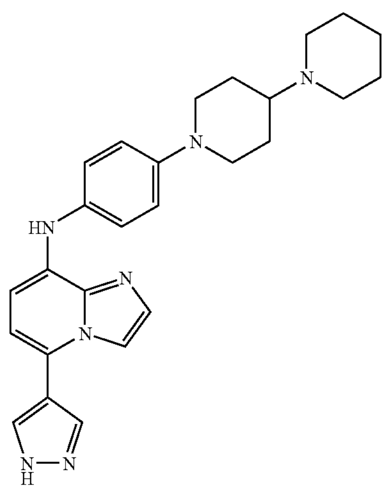 | (4[1,4']Bipiperidinyl-1'-yl-phenyl)-[5-(1H-pyrazol-4-yl)-imidazo[1,2-a]pyridin-8-yl]-amine | 0.73 (a) 1.27 (b) | 441.58 | 442.1 (M + H)+ |
| 120 | 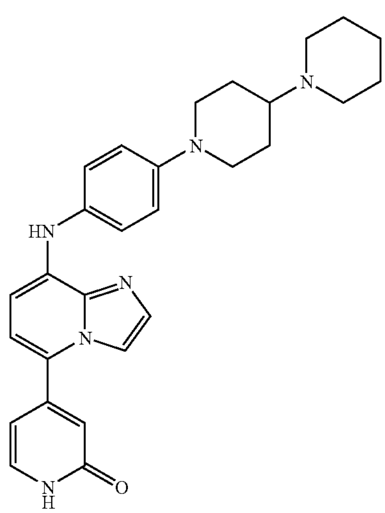 | 4-[8-(4-[1,4']Bipiperidinyl-1'-yl-phenylamino)-imidazo[1,2-a]pyridi-5-yl]-1H-pyridin-2-one | 0.72 (a) 1.20 (b) | 468.60 | 469.1 (M + H)+ |

| Compound No. | Structure | Name | Retention time; conditions | MW | Ion found |
|---|---|---|---|---|---|
| 121 | 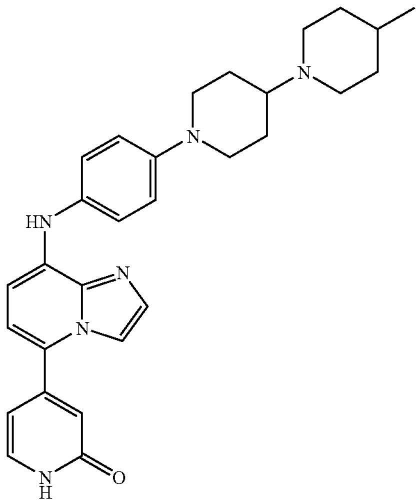 | 4-{8-[4-(4-Methyl-[1,4']bipiperidinyl-1'-yl)-phenylamino]-imidazo[1,2-a]pyridin-5-yl}-1H-pyridin-2-one | 0.72 (a)<br>1.20 (b) | 482.63 | 483.1 (M + H)+ |
| 122 | 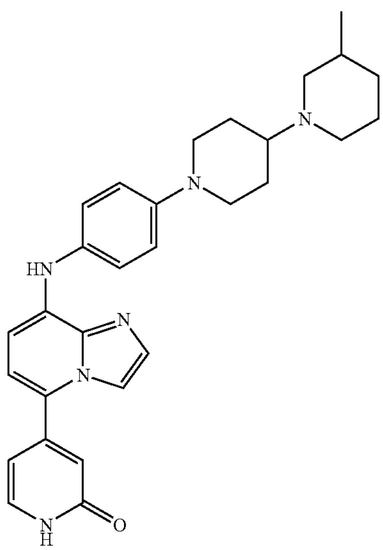 | 4-{8-[4-(3-Methyl-[1,4']bipiperidinyl-1'-yl)-phenylamino]-imidazo[1,2-a]pyridin-5-yl}-1H-pyridin-2-one | 1.28 (b) | 482.63 | 483.1 (M + H)+ |
| 123 | 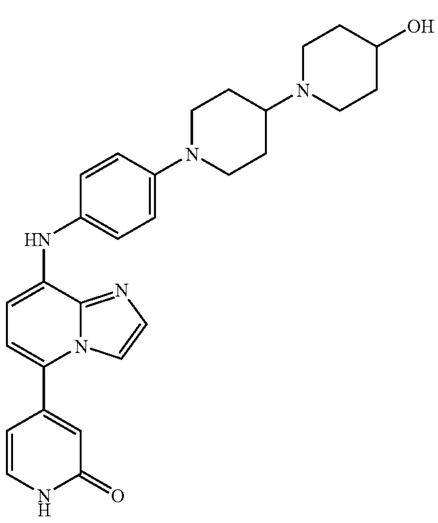 | 4-{8-[4-(4-Hydroxy-[1,4']bipiperidinyl-1'-yl)-phenylamino]-imidazo[1,2-a]pyridin-5-yl}-1H-pyridin-2-one | 0.89 (b) | 401.47 | 402.1 (M + H)+ |

| Compound No. | Structure | Name | Retention time; conditions | MW | Ion found |
|---|---|---|---|---|---|
| 124 | 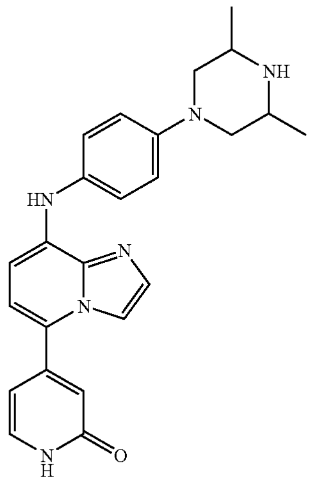 | 4-{8-[4-(3,5-Dimethyl-piperazin-1-yl)-phenylamino]-imidazo[1,2-a]pyridin-5-yl}-1H-pyridin-2-one | 0.96 (b) | 414.51 | 415.0 (M + H)⁺ |
| 125 | 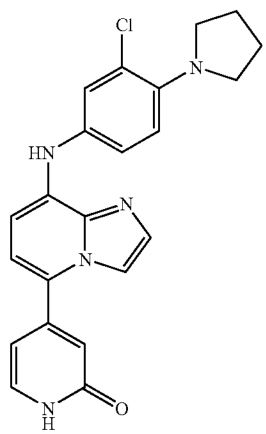 | 4-[8-(3-Chloro-4-pyrrolidin-1-yl-phenylamino)-imidazo[1,2-a]pyridin-5-yl]-1H-pyridin-2-one | 1.26 (b) | 405.89 | 406.0 (M + H)⁺ |
| 126 | 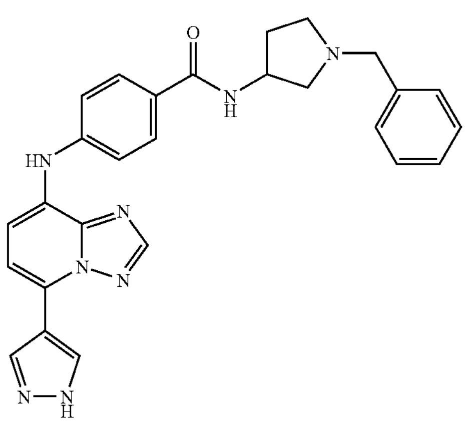 | N-(1-Benzyl-pyrrolidin-3-yl)-4-[5-(1H-pyrazol-4-yl)-[1,2,4]triazolo[1,5-a]pyridin-8-ylamino]-benzamide | 1.13 (b) | 478.56 | 479.1 (M + H)⁺ |

| Compound No. | Structure | Name | Retention time; conditions | MW | Ion found |
|---|---|---|---|---|---|
| 127 | 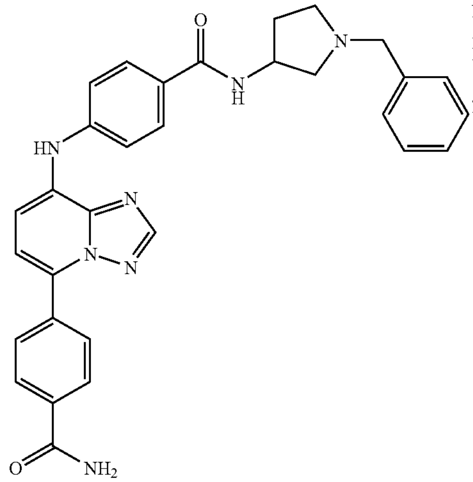 | N-(1-Benzyl-pyrrolidin-3-yl)-4-[5-(1-Benzamide-4-yl)-[1,2,4]triazolo[1,5-a]pyridin-8-ylamino]-benzamide | 1.14 (b) | 531.62 | 532.2 (M + H)+ |

Mass directed preparative HPLC was conducted on a 5 μm Waters XBridge Prep C18 column (100 mm×19 mm ID) using as mobile phase either a mixture of 0.1% TFA in water and acetonitrile (linear gradient), or a mixture of 0.5% NH$_4$OH in water and acetonitrile (linear gradient). Analytical LCMS was conducted on a 1.7 μm Waters Acquity HPLC BEH C18 column (50 mm×2.1 mm ID). The mass spectra were recorded on a Waters Micromass ZQ mass spectrometer using electrospray positive (ES+ve to give MH$^+$ or M(NH$_4$)$^+$ molecular ions) or electrospray negative (ES-ve to give (M−H)$^−$ molecular ion). As used herein, the term "R$_t$" refers to the HPLC retention time, in minutes, associated with the compound using the HPLC method specified. The HPLC methods utilized to obtain the reported retention times are as follows:

Method a: using as mobile phase a mixture of 0.1% TFA in water (solvent A) and CH$_3$CN (solvent B). Flow rate: 0.8 mL/minute. Positive electrospray. Gradient 0-0.25 min 5% B, 0.25-1.50 min linear gradient to 95% B, 1.5-1.75 min 95% B, 1.75-1.80 min linear gradient to 5% B, 1.80-2.00 min 5% B.

Method b: using as mobile phase a mixture of 0.1% NH$_4$OH in water (solvent A) and CH$_3$CN (solvent B). Flow rate: 0.8 mL/minute. Positive electrospray. Gradient 0-0.25 min 5% B, 0.25-1.50 min linear gradient to 95% B, 1.5-1.75 min 95% B, 1.75-1.80 min linear gradient to 5% B, 1.80-2.00 min 5% B.

Method c: using as mobile phase a mixture of 0.1% NH$_4$OH in water (solvent A) and CH$_3$CN (solvent B). Flow rate: 0.8 mL/minute. Positive electrospray. Gradient 0-0.25 min 5% B, 0.25-1.50 min linear gradient to 50% B, 1.5-1.75 min 50% B, 1.75-1.80 min linear gradient to 5% B, 1.80-2.00 min 5% B.

2. Biological Activity Assays

To identify compounds that decrease the ECM-degrading activity of cells, the ECM-degrading activity of cells may be induced to allow proper detection of this activity, and to achieve a clearer read-out. In the context of RA, the cells of choice are mammalian synovial fibroblasts and the triggers that may be used to induce the ECM-degrading activity are cytokines or combination of cytokines relevant in the field of arthritis: for instance TNF-α, IL1β, IL6, OSM, IL17, and MIF1-α. This list is not comprehensive due to the plethora of cytokines potentially involved in the RA pathogenesis (Smolen and Steiner, 2003). To set up an in vitro assay that is as close as possible to the complexity of the pathology, the trigger applied should be a mixture of factors generated by contacting cytokine-producing cells relevant in the field of arthritis, such as monocytes, macrophages, T-cells, and B-cells, with a trigger. The cytokine-producing cells will respond to the contact by producing a complex and unbiased mixture of factors. If the cytokine-producing cell used is also found in a pannus, and the cytokine applied to produce this trigger is found in the synovial fluid of rheumatoid arthritis patients, the mixture of factors ultimately produced will contain part of the factors that are present in the joints of arthritis patients.

Principle of the 'MMP Assay'

Matrix Metallo Proteases (MMPs) possess various physiological roles, as e.g. the maturation of other proteases, growth factors, and the degradation of extra-cellular matrix components. MMP1 is one of the members of the MMP family that is able to degrade native collagen, the main component of bone and cartilage. An increased expression of MMP1 by synovial fibroblasts (SFs) is diagnostic for the progression of the arthritic disease and is predictive for erosive processes in the joint (Cunnane et al., 2001). The expression of MMP1 by SFs can be increased by the activation of SFs with triggers relevant for rheumatoid arthritis, as cytokines like TNF-α or IL1β (Andreakos et al., 2003). Taken together, measurement of the levels of MMP1 produced by activated SFs is a readout that is highly relevant in the context of RA as this event reflects the level of activation of SFs towards an erosive phenotype as it is seen in the pannus.

Compounds that are able to reduce MMP1 expression in activated SFs are thus potential drug candidates for the treatment of RA. Compounds can reduce MMP1 expression because they are inhibiting targets involved in pathways resulting in increased MMP1 expression. One class of targets is kinases. Kinases that are inhibited with reasonable potency by compounds that inhibit MMP1 expression in activated SFs and that can be proven to be involved in MMP1 regulation are likely to be the drug target for the compounds and considered a relevant RA drug target. Proof that a kinase is involved in MMP1 regulation can come from experiments that show that reduced expression and/or activity of a candidate drug target in activated SFs leads to reduction in MMP1 expression by these cells. Several state of the art methods can be used like but not limited to use of siRNA or dominant negatives. In the following examples, the development of an assay, further referred to as 'MMP assay', monitors the MMP1 production by synovial fibroblasts (SFs) in response to diverse activating triggers (Example 2.1). The use of this assay is then described for the testing of compounds and exemplifying that the imidazolopyridine compounds of the present invention are inhibiting MMP1 expression from activated SFs. In a further aspect, we show that the imidazolopyridine compounds of the present invention possess TAK1 inhibiting activity. See Table A.

2.1 Development of the MMP Assay

A 384-well format ELISA for measurement of MMP1 is developed. Various primary antibodies are tested, as well as various ELISA protocols. The following protocol is developed and validated to measure MMP1 levels in SF supernatant in 384 well plates: white Lumitrac 600 384 well plates (Greiner) are coated with 2 µg/mL anti-MMP1 antibody MAB1346 (Chemicon). The antibody is diluted in buffer 40 (1.21 g Tris base (Sigma), 0.58 g NaCl (Calbiochem) and 5 mL 10% $NaN_3$ (Sigma) in 1 L milliQ water and adjusted to pH 8.5). After overnight incubation at 4° C., plates are washed with PBS (80 g NaCl, 2 g KCl (Sigma), 11.5 g $Na_2HPO_4.7H_2O$ and 2 g $KH_2PO_4$ in 10 L milliQ; pH 7.4) and blocked with 100 µL/well Casein buffer (2% Casein (VWR International) in PBS). Next day, casein buffer is removed from ELISA plates and replaced by 50 µL/well EC buffer (4 g casein, 2.13 g $Na_2HPO_4$ (Sigma), 2 g bovine albumin (Sigma), 0.69 g $NaH_2PO_4.H_2O$ (Sigma), 0.5 g CHAPS (Roche), 23.3 g NaCl, 4 mL 0.5 M EDTA pH 8 (Invitrogen), 5 mL 10% $NaN_3$ in 1 L milliQ and adjusted to pH 7.0). 0.25 mM DTT (Sigma) is added to the thawed sample plates. After removal of the EC buffer, 20 µL of sample is transferred to the ELISA plates. After overnight incubation at 4° C. plates are washed twice with PBS and once with PBST (PBS with 0.05% Tween-20 (Sigma)) and incubated with 35 µL/well biotinylated anti-MMP1 antibody solution (R&D). This secondary antibody is diluted in buffer C (0.82 g $NaH_2PO_4.H_2O$, 4.82 g $Na_2HPO_4$, 46.6 g NaCl, 20 g bovine albumin and 4 mL 0.5M EDTA pH 8 in 2 L milliQ and adjusted to pH 7.0) at a concentration of 5 µg/mL. After 2 h of incubation at RT, plates are washed as described above and incubated with 50 µL/well streptavidin-HRP conjugate (Biosource). Streptavidin-HRP conjugate is diluted in buffer C at a concentration of 0.25 µg/mL. After 45 min, plates are washed as described above and incubated for 5 min with 50 µL/well BM Chem ELISA Substrate (Roche). Readout is performed on the Luminoscan Ascent Luminometer (Labsystems) with an integration time of 200 msec or with an Envision reader (Perkin Elmer).

Figure 2:
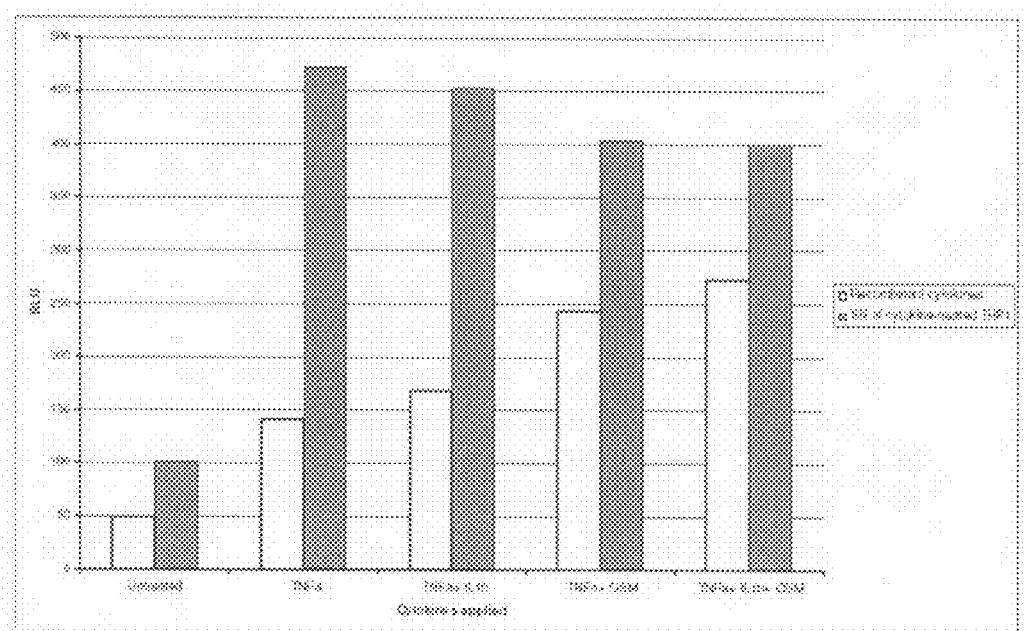
FIG. 2. This chart shows the increased expression of MMP1 in synovial fibroblasts triggered with cytokines involved in rheumatoid arthritis pathology.

The increase of MMP1 expression by SFs upon treatment with cytokines relevant in the field of RA (TNF-α, IL1β and OSM) or a combination thereof is shown in FIG. 2 as white bars. For this experiment, SFs are seeded in 96 well plates, 3,000 cells/well. 24 h later, the medium is changed to M199 medium supplemented with 1% FBS. One day after the medium change, cytokines or combinations thereof are added to the cultures, each cytokine being added to a final concentration of 25 ng/mL. 72 h after cytokine addition, the supernatant is collected and processed in the MMP1 ELISA as described in the protocol given above. In parallel with this experiment, SFs are triggered, using the same protocol, with the supernatant of THP1 cells (2-fold diluted in M199+1% FBS) treated with the same cytokines or combinations of cytokines for 48 h in M199 medium+1% FBS. MMP1 levels for these samples are shown in FIG. 2 as grey bars. The induction of the MMP1 expression by SFs triggered with the supernatants of TNF-α-treated THP1 cells is stronger (>4.5 fold induction) as compared to the SFs triggered with recombinant TNF-α alone (3-fold induction) and almost equals the 5-fold induction obtained by a mixture of 3 purified cytokines (TNF-α, IL1βb, OSM). This result indicates that the supernatant of TNF-α-induced THP1 cells contains, besides TNF-α, additional pro-inflammatory factors that activate SFs towards MMP1 expression. As the role of TNF-α in the RA pathogenesis is validated (TNF-α-blockers as Infliximab and Ethanercept show some efficacy in the treatment of RA patients) and the THP-1 cells are representative for monocytes/macrophages present in the joint of RA patients, the TNF-α-based trigger mixture prepared by contacting THP-1 cells with TNF-α will contain factors present in the joints of RA patients and subsequently is relevant to RA. This TNF-α-based complex trigger, further referred to as the 'complex trigger', will further be used as basis for the 'MMP assay'. For preparing a stock of this 'complex trigger', THP-1 cells are used between passage 8 and 16. THP-1 cells are routinely grown in suspension cultures in RPMI supplemented with 10% heat-inaktivated FBS (Invitrogen). The cultures are diluted twice a week to a cell density of 2E5 cells/mL, avoiding cell density to exceed 1.5E5 cells/mL. For production of the complex trigger mixture, THP1 cells are seeded in M199 medium supplemented with 1% heat-inaktivated FBS at a density of 1E6 cells/ml. Recombinant human TNF-α (PeproTech) is added to final concentration of 50 ng/mL and cells are incubated at 37° C., 5% $CO_2$. After 72 hr, the supernatans was collected by centrifugation, filtered through a 0.22 um Nalgene filter and stored at −80° C. in aliquots till further use. Every new batch of "complex trigger" was characterized for its efficacy at inducing MMP1 expression by SFs.

Figure 3:
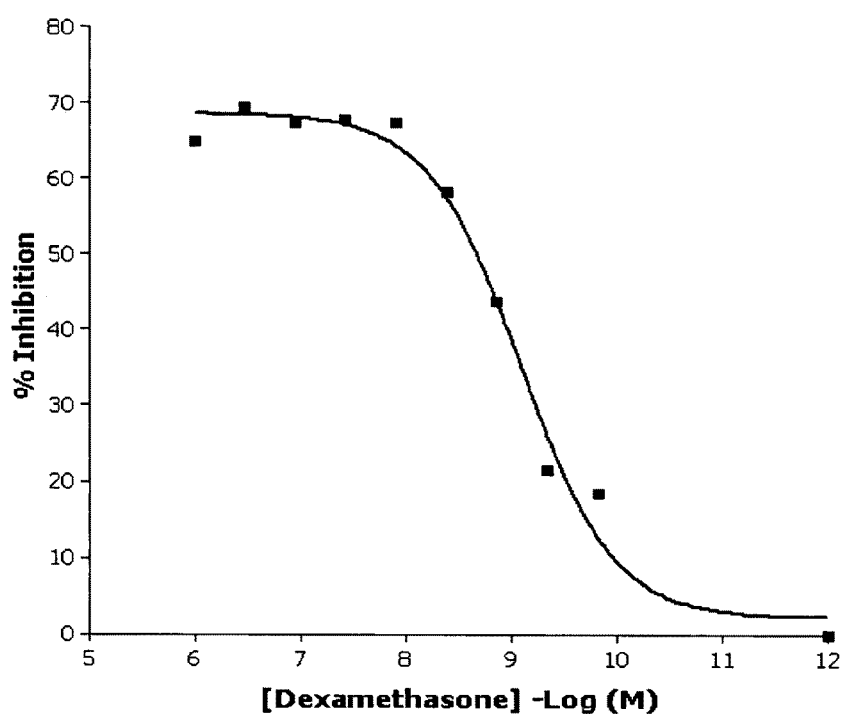
FIG. 3. This graph shows the dose-dependent inhibition of the "TNF-α-based trigger"-induced expression of MMP1 by SFs by a known anti-inflammatory compound.

Inhibition of the activation of SF by the 'complex trigger' is shown using dexamethasone, a potent anti-inflammatory agent that also strongly reduces collagen-induced arthritis in rodents (Yang et al., 2004) (FIG. 3). Dexamethasone is shown to dose-dependently reduce amounts of MMP1 produced by complex trigger activated SFs. SFs are seeded at a density of 3000 cells/well in 96 well plates. 24 hrs after seeding, increasing concentrations of dexamethasone are added to the cells.

After overnight incubation, medium of every well is refreshed with supernatant of THP-1 cells treated with TNF-α (50% diluted in M199+0.5% FBS), and the same concentration of dexamethasone as added the day before. 48 hrs after treatment, the supernatant is collected and subjected to the MMP1 ELISA described above. The addition of dexamethasone clearly reduced the MMP1 expression by SFs, with an $IC_{50}$ value of about 1 nM (see FIG. 3). These data show that the MMP1 expression by activated SFs can be reduced by the addition of a physiologically relevant inhibitor and represent a proof of principle for the 'MMP assay'.

2.2 Compounds of the Present Invention Inhibit MMP1 Expression from Activated SFs SFs were acquired at passage 1 from a commercial supplier (Cell applications, Inc.). SFs are cultured in DMEM supplemented with 10% heat-inactivated FBS, 1× penicillin/streptomycin (Invitrogen) at 37° C., 10% $CO_2$ until passage 6. Aliquots of the cells are frozen and cryopreserved in liquid nitrogen. Starting from a cryopreserved aliquot, cells are further expanded by sub-culturing cells at 1/3 ratio every week. Cells between passage 10 and 12 are routinely used in compound testing according to the following protocol.

Starting from the compound master stocks (all at 10 mM concentration in 100% DMSO) a 3-fold serial dilution is made in 96-well plates in 100% DMSO. Then, plates are further diluted 45-fold in M199 medium supplemented with 1% heat-inactivated FBS to obtain a intermediate work stock.

At day 1, RASFs are seeded in 96 well plates (flat bottom, tissue culture treated, Greiner) at a density of 3000 cells/well in complete synovial growth medium (Cell Applications). Day 5, the medium is completely removed from the cells, and replaced by 81 μL of M199 medium supplemented with 1% heat-inactivated FBS followed by addition of 10 μL compound out of the intermediate work stock. After an incubation period of 90 minutes, which allows the compounds to equilibrate and enter the cells, cells are stimulated with either TNF-α or 'complex trigger'. TNF-α trigger is added in a volume of 10 to obtain final concentration of 10 ng/mL. For that, TNF-α stock (PeproTech) at 10 ng/mL was diluted to 100 ng/mL TNF-α in M199 medium supplemented with 1% FBS. 'Complex trigger' mix is added in a volume of 20 μL to obtain a final concentration of 12.5%. For that, 'complex trigger' mix, is diluted to 80% with M199 medium supplemented with 1% FBS. After incubation for 48 hrs, 20 μL of the cell supernatant is then processed in the MMP1 ELISA as described above, delivering raw data (RLU: relative luminescence units). The following controls are included in the experiments, a maximal signal control, in which the cells are activated by TNF-α (or the complex trigger) but only the 0.2% DMSO vehicle (and thus no compound) is added. This control indicates the maximal level of MMP1 that can be achieved in the test. A minimal signal control is also included in these experiments. Here, cells are not triggered. This control returns the basal MMP1 levels produced by the RASFs. The percent inhibition of the MMP1 expression achieved by the compounds is then calculated based on the RLU data returned by the ELISA with following formula: [[(maximal MMP1 levels−minimal MMP1 levels)−(MMP1 level compound X at concentration Y−minimal MMP1 levels)]/(maximal MMP1 levels−minimal MMP1 levels)]×100. Based on these percent inhibition data obtained in at least two independent experiments for the compounds, compounds are ranked as inactive (−), active (+), more active (++) and strongly active (+++). See Table A.

2.3 In Vitro TAK1 Kinase Assay

For assessing TAK1 inhibition, active TAK1-TAB1 fusion protein was used from Upstate (Cat.No, 14-600). Kinase reactions are set up in 96-well polypropylene plates in 25 μL containing 0.5 mU TAK1-TAB1 fusion protein, 5 μM ATP, 0.01 μCi/mL [$^{33}$P]-γ-ATP, 0.1 mg/mL casein substrate in 1× reaction buffer containing 10 mM MOPS pH 7.0, 1 mM EDTA.

Starting from the compound master stocks (all at 10 mM concentration in 100% DMSO) a 3-fold serial dilution is made in 96-well plates in 100% DMSO. Plates are further diluted 66-fold in $H_2O$ containing 3.5% DMSO, to obtain an intermediate work stock with compounds at 5× the final assay concentration in 5% DMSO.

5 μL of the intermediate stock is transferred into V-bottom 96 well polypropylene plates and 11 μL of Enzyme mix is added. Enzyme mix is made by combining 5 μL 5× reaction buffer (40 mM MOPS pH 7.0, 1 mM EDTA), 5 μL casein (Sigma) diluted in $H_2O$ to 0.5 mg/mL and 1 μL of TAK1-TAB1 fusion protein that was prediluted to 0.5 mU/mL in 1× enzyme dilution buffer (20 mM MOPS pH 7.0, 0.1 mM EDTA, 0.01% Brij-35, 5% glycerol, 1 mM DTT, 1 mg/ml BSA).

The reactions are started by the addition of 9 μL of mixture containing ATP (20.83 uM) and [$^{33}$P]-γ-ATP (0.028 μCi/μL).

The assay is stopped 90 minutes after incubation at 30° C. by the addition of 25 μL phosphoric acid (150 mM). The label incorporated into the casein substrate is separated from labeled unincorporated ATP by filtration onto 96-well filter plates using a harvester device. After 6 washes with 75 mM phosphoric acid, the bottom of the filter plates are sealed, and incorporated label is quantified after addition of 40 μL scintillation fluid using TopCount. Percent inhibition is calculated relative to control reactions which do not contain inhibitor.

Based on these percent inhibition data obtained in at least two independent experiments for the compounds, compounds are ranked using semi-quantitative scores. Table A below lists a number of compounds which have been or can be prepared according to the synthetic methods described herein.

Semi-Quantitative Score:

* >3001 nM

** 1001-3000 nM

*** 101-1000 nM

**** <100 nM

It should be understood that factors such as the differential cell penetration capacity of the various compounds can contribute to discrepancies between the activity of the compounds in the in vitro biochemical and cellular MMP assays.

TABLE A

| Compound No. | Structure | IC$_{50}$/ Score | MMP1/ TNFα (RASF) EC$_{50}$/ Score |
|---|---|---|---|
| 1 | 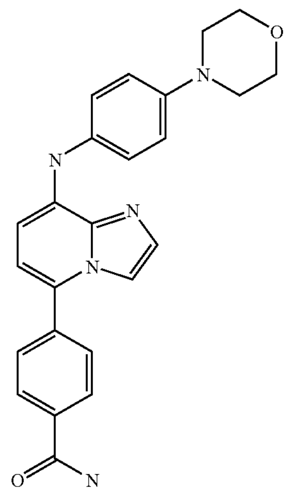 |  | * |
| 2 | 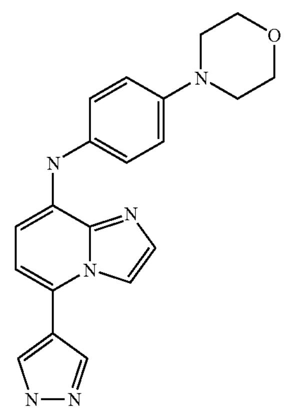 | * | * |
| 3 | 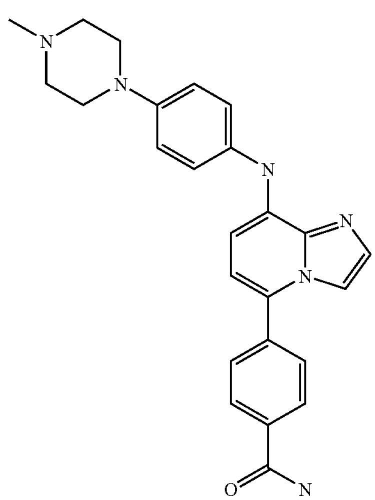 | * | ** |

TABLE A-continued

| Compound No. | Structure | IC$_{50}$/ Score | MMP1/ TNFα (RASF) EC$_{50}$/ Score |
|---|---|---|---|
| 4 | 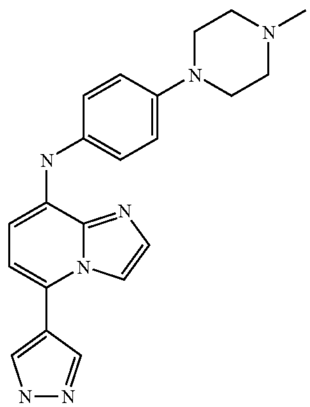 | *** | * |
| 5 | 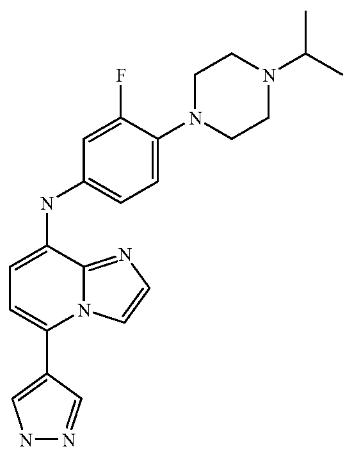 | * |  |
| 6 | 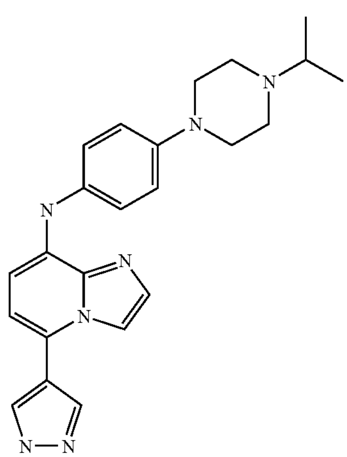 | * | * |

TABLE A-continued
| Compound No. | Structure | IC$_{50}$/ Score | MMP1/ TNFα (RASF) EC$_{50}$/ Score |
|---|---|---|---|
| 7 | 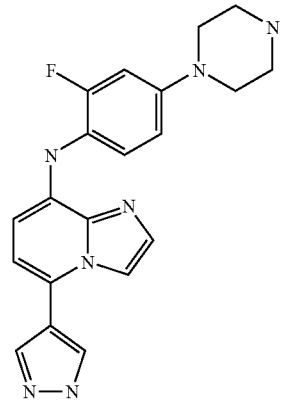 | * | * |
| 8 | 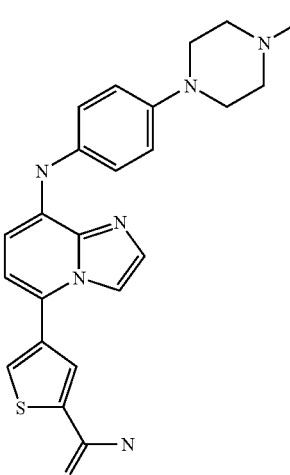 | * | * |
| 9 | 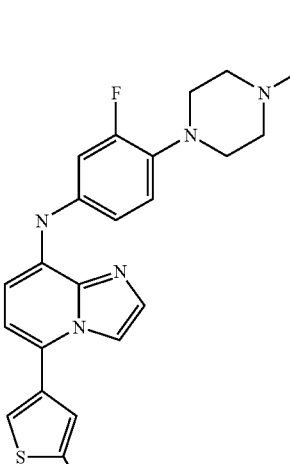 |  |  |

TABLE A-continued
| Compound No. | Structure | IC$_{50}$/ Score | MMP1/ TNFα (RASF) EC$_{50}$/ Score |
|---|---|---|---|
| 10 | 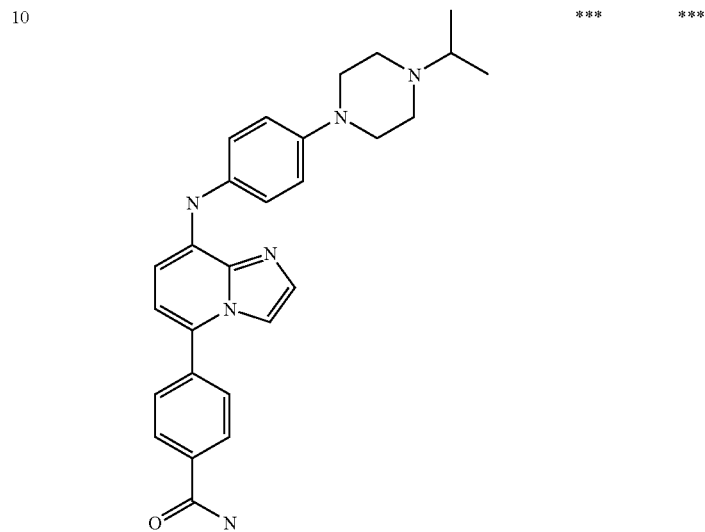 | * | * |
| 11 | 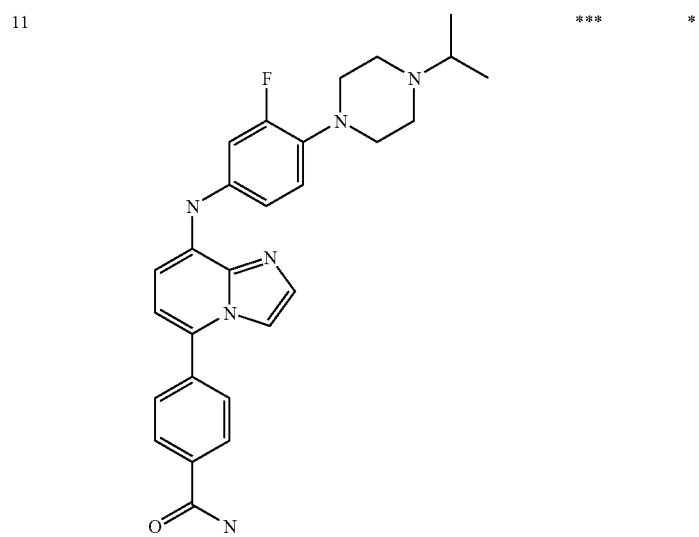 | *** | * |

TABLE A-continued

| Compound No. | Structure | IC$_{50}$/ Score | MMP1/ TNFα (RASF) EC$_{50}$/ Score |
|---|---|---|---|
| 12 | 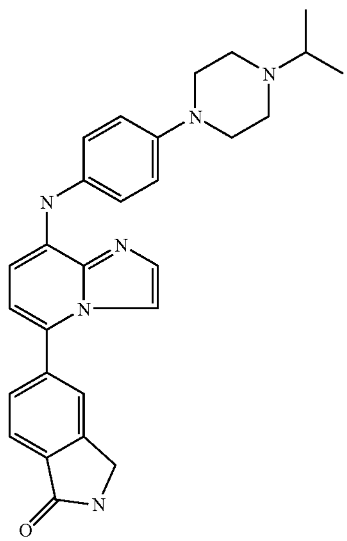 | ** | * |
| 13 | 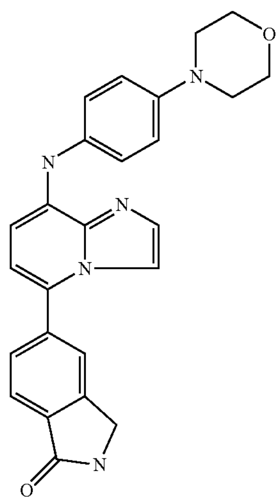 | * |  |
| 14 | 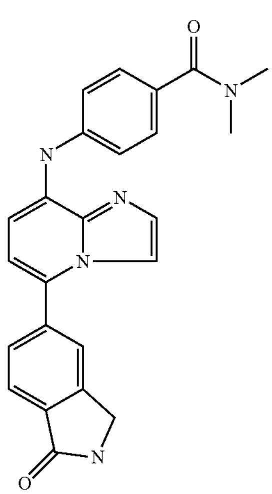 | *** | * |

TABLE A-continued

| Compound No. | Structure | IC$_{50}$/ Score | MMP1/ TNFα (RASF) EC$_{50}$/ Score |
|---|---|---|---|
| 15 | 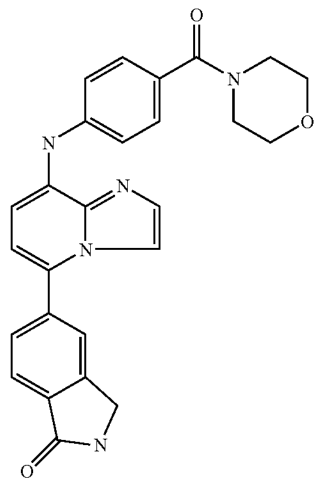 | *** | * |
| 16 | 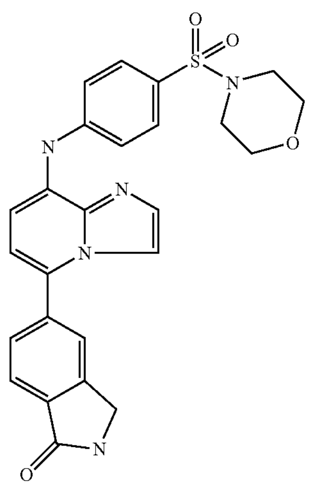 | *** | * |
| 17 | 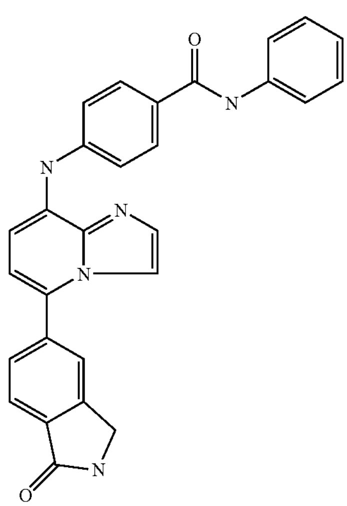 | ** | * |

TABLE A-continued

| Compound No. | Structure | IC$_{50}$/ Score | MMP1/ TNFα (RASF) EC$_{50}$/ Score |
|---|---|---|---|
| 18 | 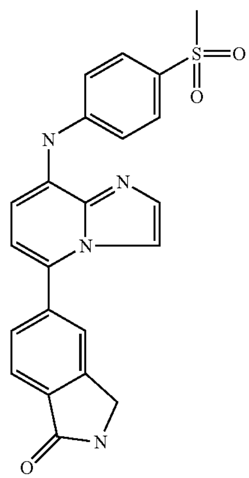 | *** | * |
| 19 | 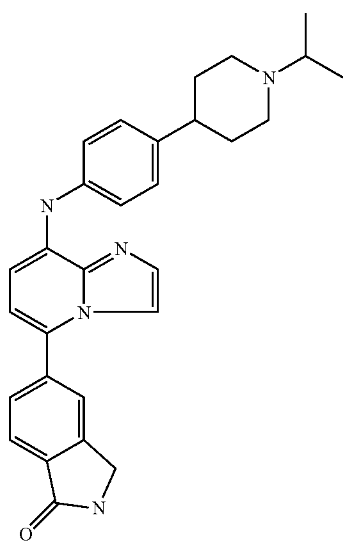 | ** | * |
| 20 | 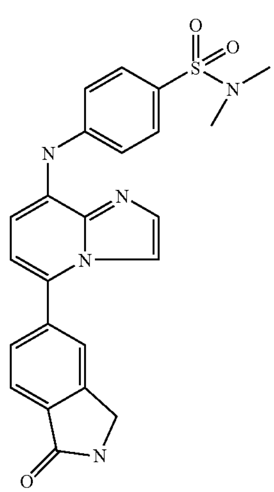 | * | * |

TABLE A-continued

| Compound No. | Structure | IC$_{50}$/ Score | MMP1/ TNFα (RASF) EC$_{50}$/ Score |
|---|---|---|---|
| 21 | 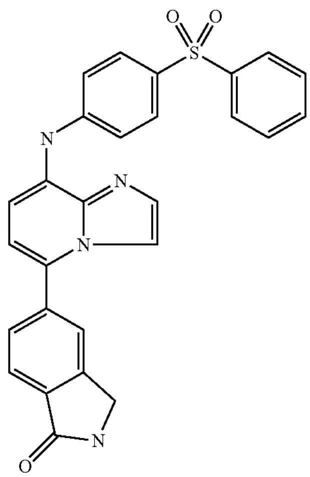 | * | * |
| 22 | 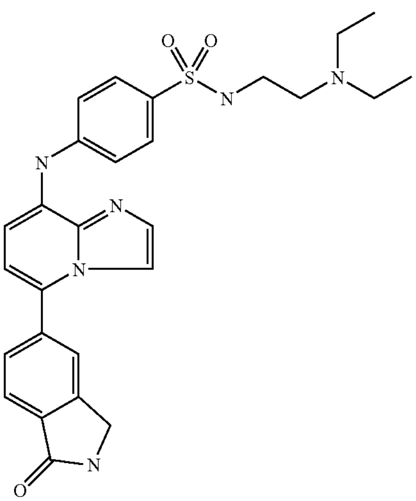 | * |  |
| 23 | 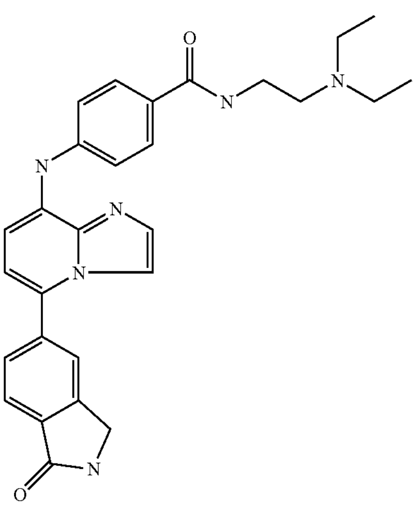 | **** | * |

TABLE A-continued

| Compound No. | Structure | IC$_{50}$/ Score | MMP1/ TNFα (RASF) EC$_{50}$/ Score |
|---|---|---|---|
| 24 | 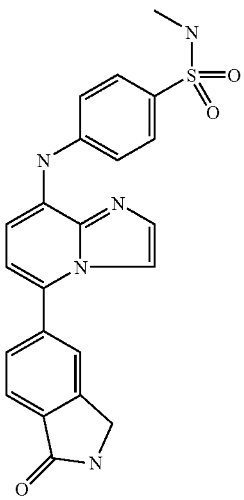 | * |  |
| 25 | 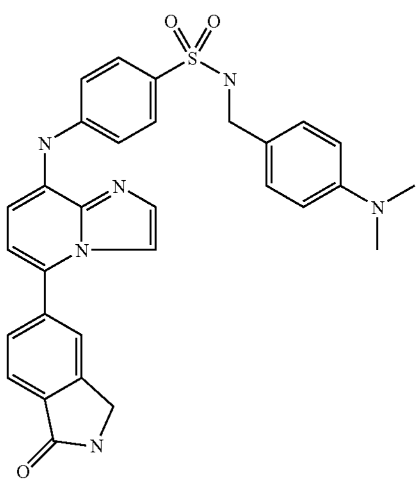 | * |  |
| 26 | 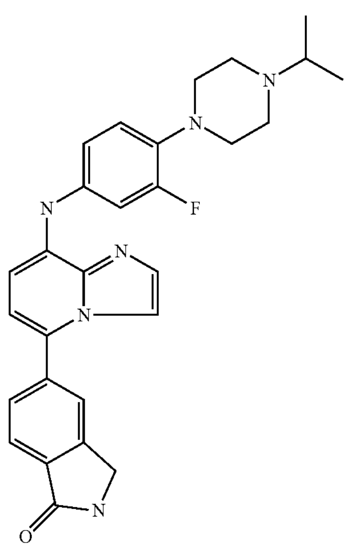 | **** | * |

TABLE A-continued
| Compound No. | Structure | IC$_{50}$/ Score | MMP1/ TNFα (RASF) EC$_{50}$/ Score |
|---|---|---|---|
| 27 | 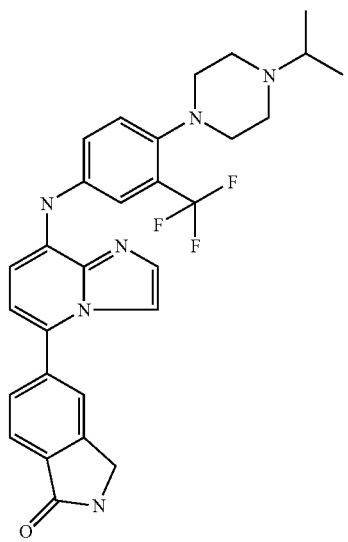 | *** | * |
| 28 | 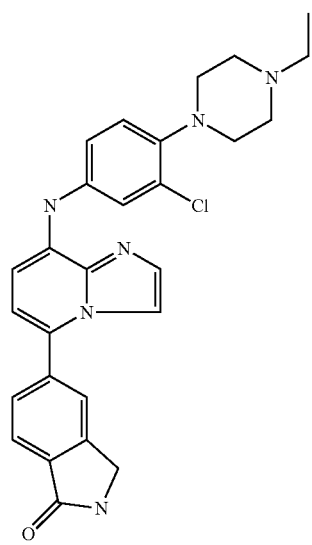 | *** | * |

TABLE A-continued

| Compound No. | Structure | IC$_{50}$/ Score | MMP1/ TNFα (RASF) EC$_{50}$/ Score |
|---|---|---|---|
| 29 | 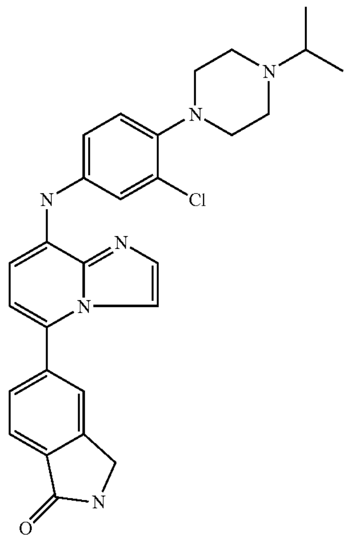 | *** | * |
| 30 | 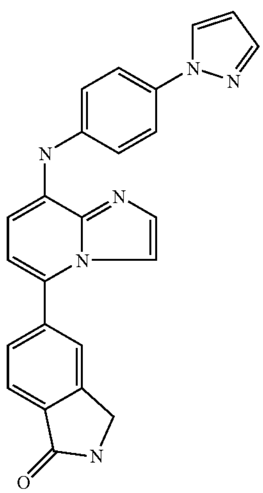 | ** | |
| 31 | 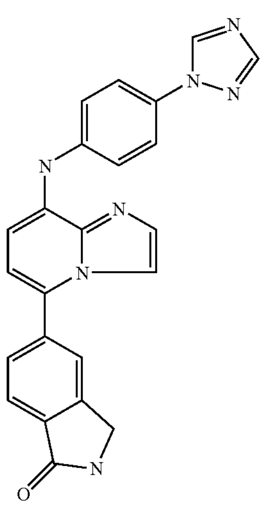 | *** | |

TABLE A-continued

| Compound No. | Structure | IC$_{50}$/ Score | MMP1/ TNFα (RASF) EC$_{50}$/ Score |
|---|---|---|---|
| 32 | 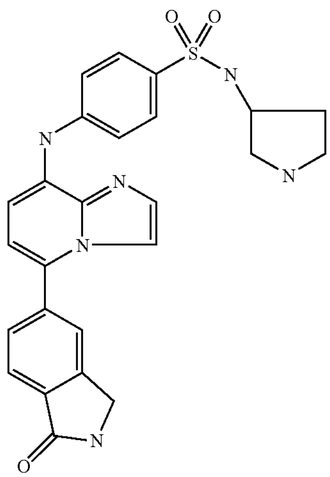 | *** | * |
| 33 | 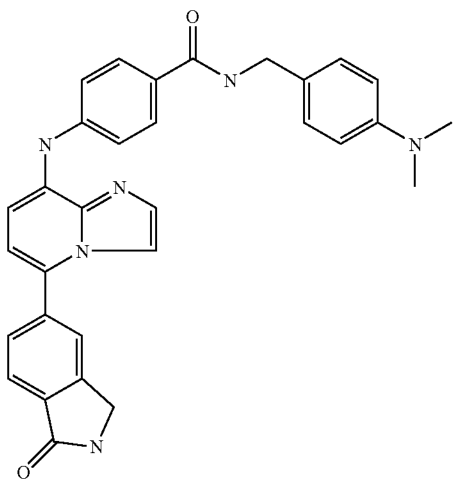 | * | * |
| 34 | 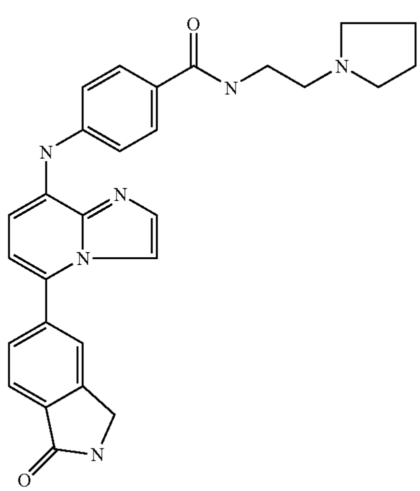 | **** | * |

TABLE A-continued

| Compound No. | Structure | IC$_{50}$/ Score | MMP1/ TNFα (RASF) EC$_{50}$/ Score |
|---|---|---|---|
| 35 | 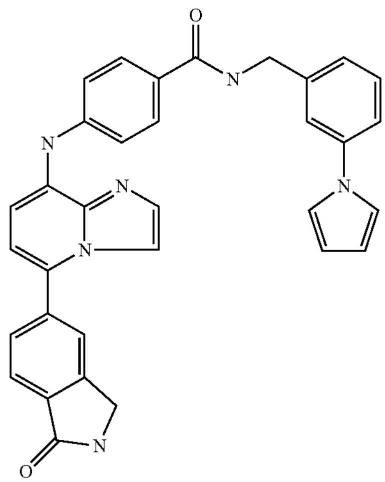 | *** | |
| 36 | 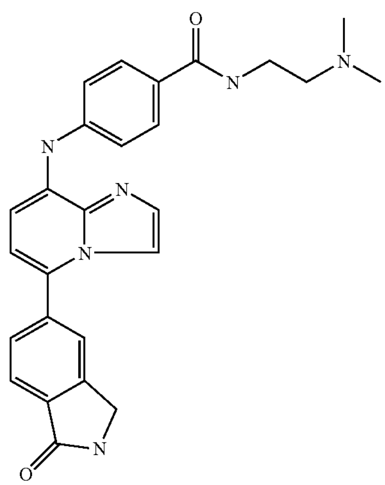 | *** | * |
| 37 | 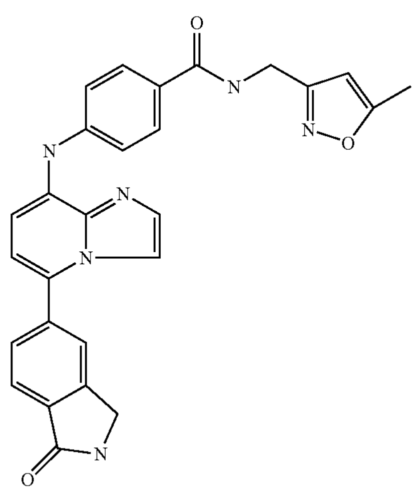 |  |  |

TABLE A-continued

| Compound No. | Structure | IC$_{50}$/ Score | MMP1/ TNFα (RASF) EC$_{50}$/ Score |
|---|---|---|---|
| 38 | 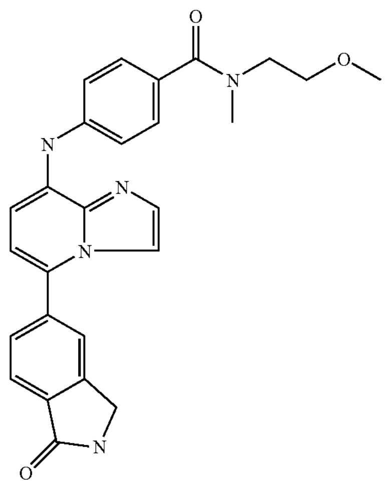 | *** | * |
| 39 | 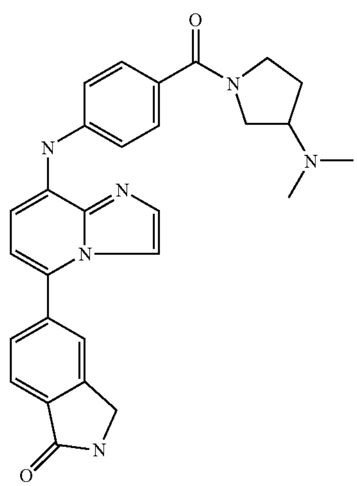 | **** | * |
| 40 | 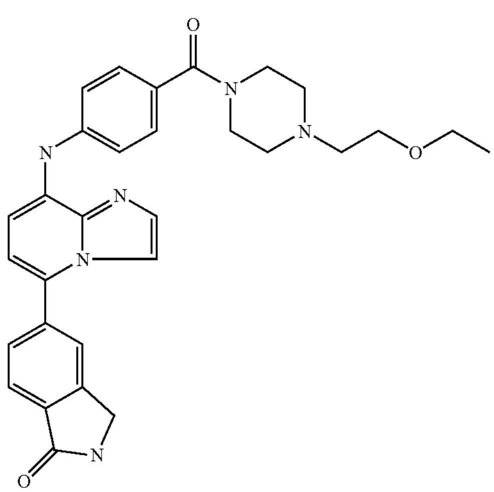 | *** | * |

TABLE A-continued

| Compound No. | Structure | IC$_{50}$/ Score | MMP1/ TNFα (RASF) EC$_{50}$/ Score |
|---|---|---|---|
| 41 | 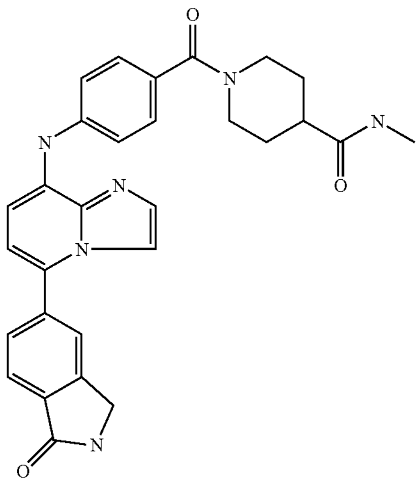 | *** | * |
| 42 | 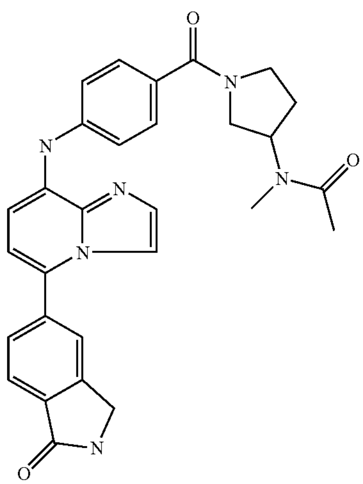 | *** | * |
| 43 | 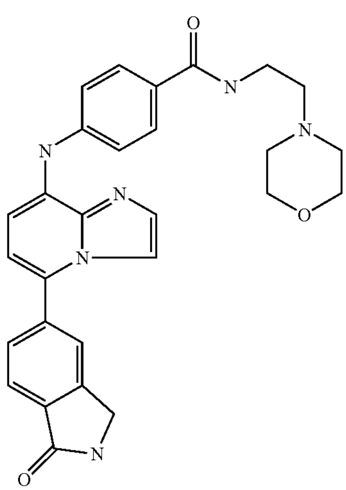 | *** | * |

TABLE A-continued
| Compound No. | Structure | IC$_{50}$/ Score | MMP1/ TNFα (RASF) EC$_{50}$/ Score |
|---|---|---|---|
| 44 | 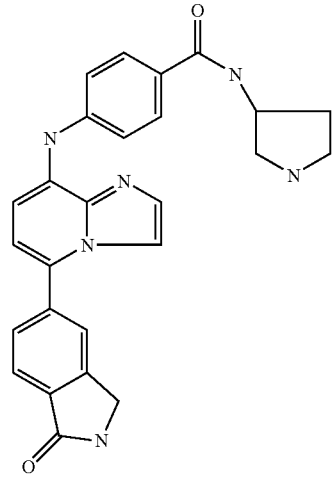 | *** | |
| 46 | 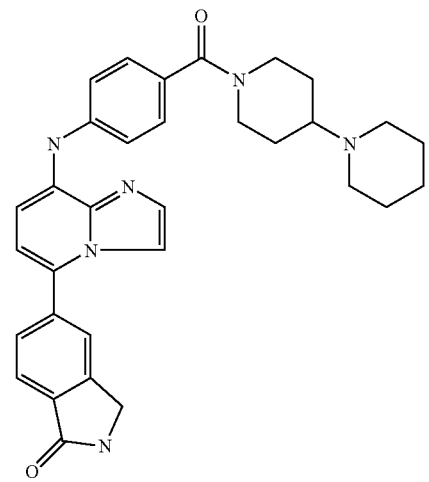 | **** | * |
| 47 | 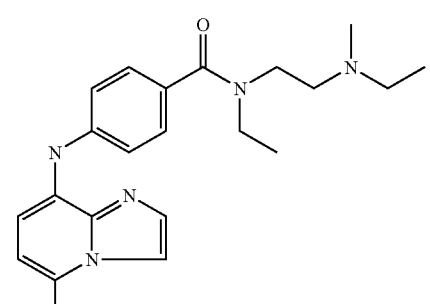 | **** | * |

TABLE A-continued

| Compound No. | Structure | IC$_{50}$/ Score | MMP1/ TNFα (RASF) EC$_{50}$/ Score |
|---|---|---|---|
| 48 | 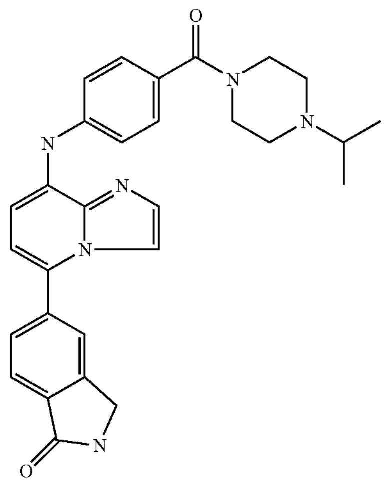 | **** | * |
| 49 | (Chiral) | **** | * |
| 50 | 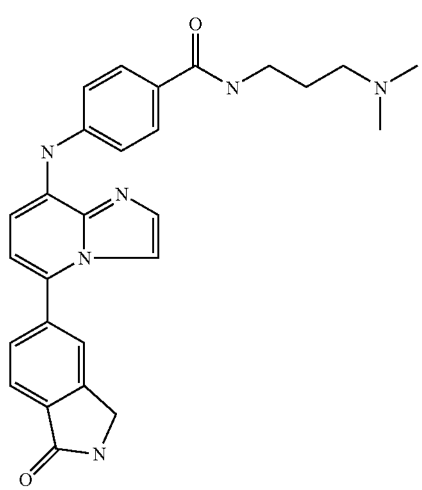 | *** | * |

TABLE A-continued

| Compound No. | Structure | IC$_{50}$/ Score | MMP1/ TNFα (RASF) EC$_{50}$/ Score |
|---|---|---|---|
| 51 | 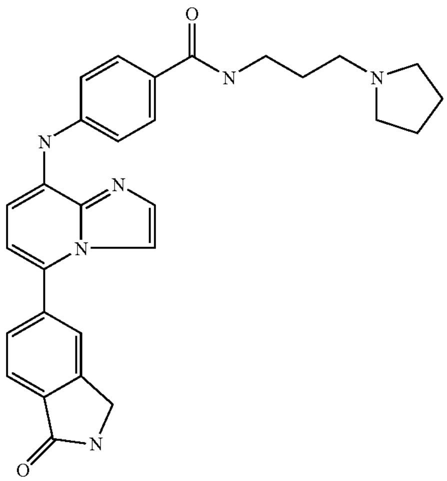 | *** | * |
| 52 | 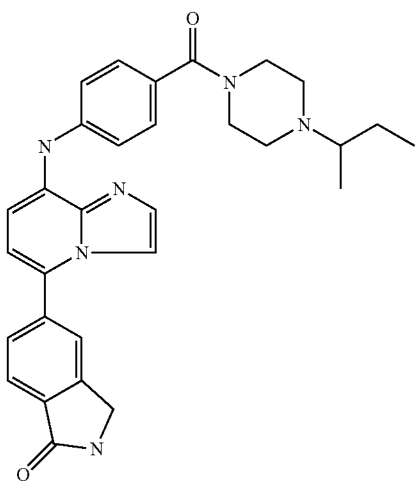 | *** | * |
| 53 | 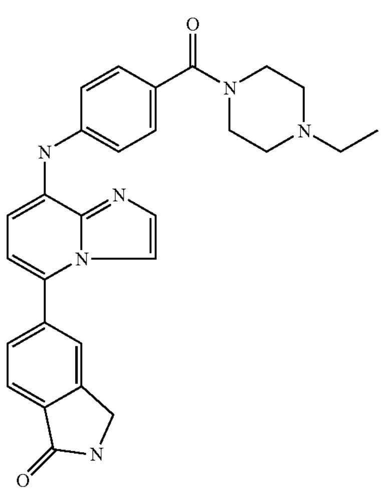 | **** | * |

TABLE A-continued

| Compound No. | Structure | IC$_{50}$/ Score | MMP1/ TNFα (RASF) EC$_{50}$/ Score |
|---|---|---|---|
| 54 | 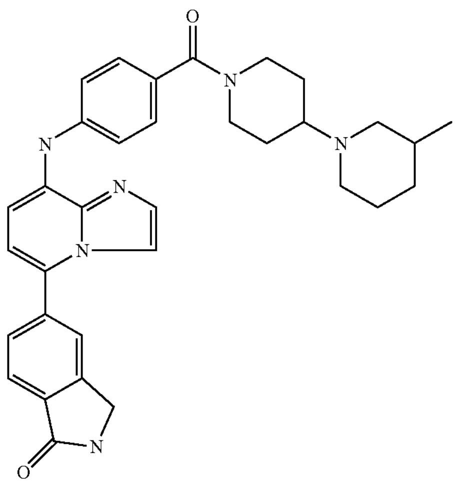 | | *** |
| 55 | 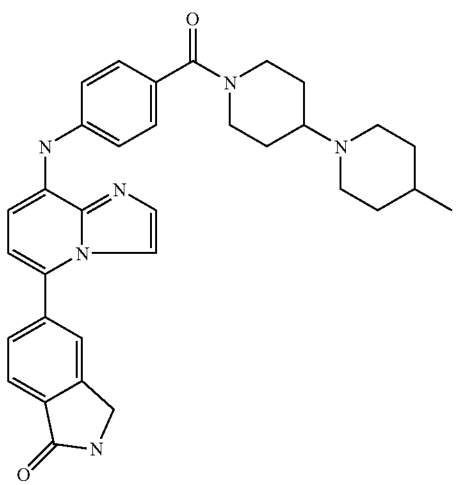 | | *** |
| 56 | 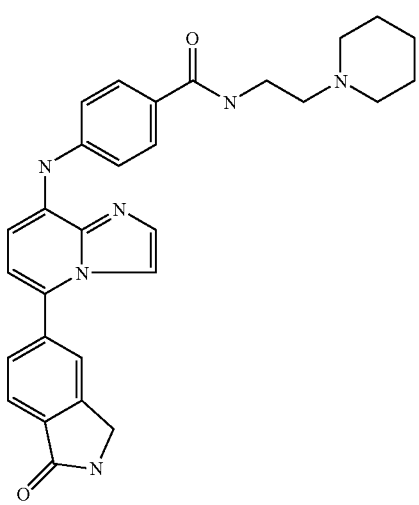 | | *** |

TABLE A-continued

| Compound No. | Structure | IC$_{50}$/ Score | MMP1/ TNFα (RASF) EC$_{50}$/ Score |
|---|---|---|---|
| 57 | 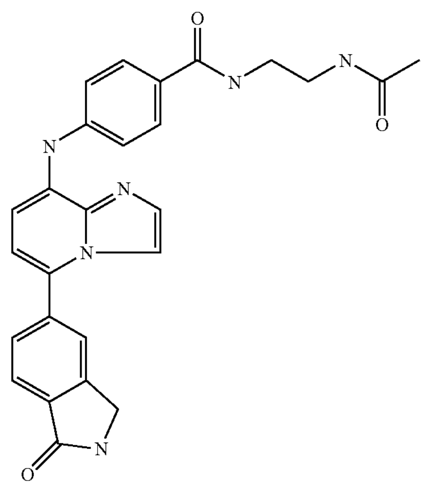 | | *** |
| 58 | 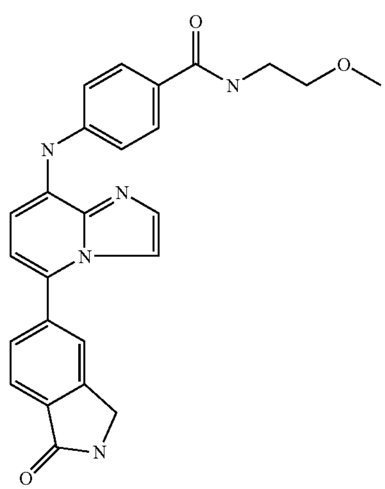 | | *** |
| 59 | 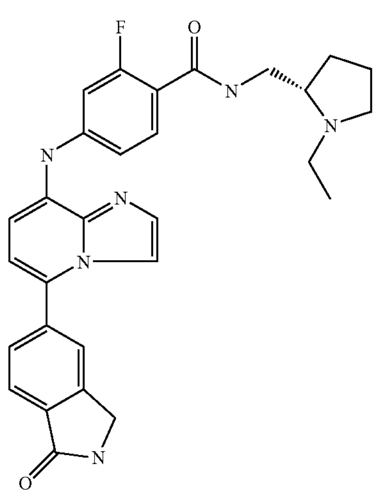 | | *** |

| Compound No. | Structure | IC$_{50}$/ Score | MMP1/ TNFα (RASF) EC$_{50}$/ Score |
| --- | --- | --- | --- |
| 60 | 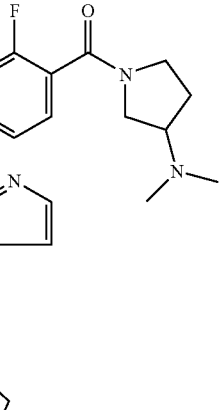 | | |
| 61 | 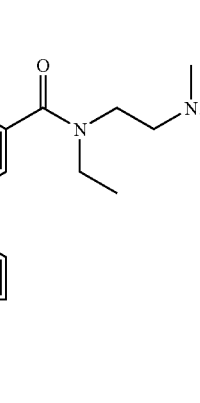 | | |
| 62 | 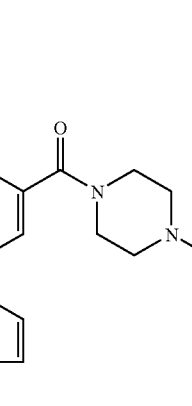 | | |

TABLE A-continued

| Compound No. | Structure | IC$_{50}$/ Score | MMP1/ TNFα (RASF) EC$_{50}$/ Score |
|---|---|---|---|
| 63 | 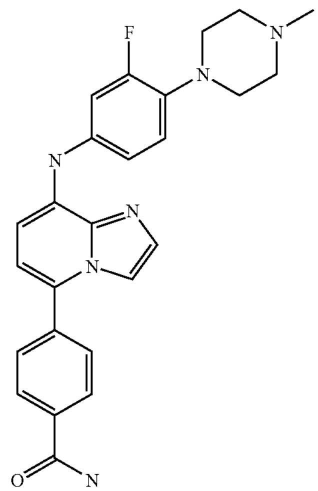 | *** | * |
| 64 | 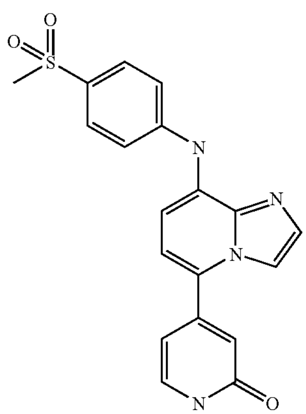 | * |  |
| 65 | 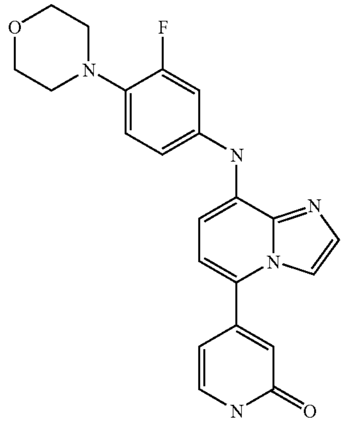 | * | * |

TABLE A-continued

| Compound No. | Structure | IC$_{50}$/ Score | MMP1/ TNFα (RASF) EC$_{50}$/ Score |
|---|---|---|---|
| 66 | 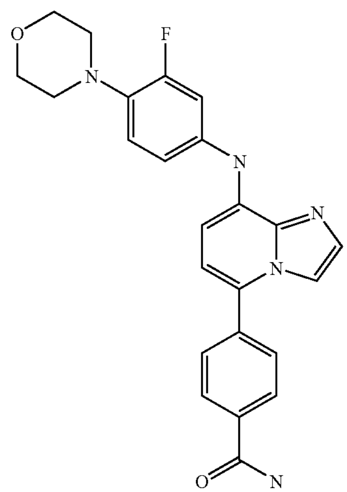 |  | * |
| 67 | 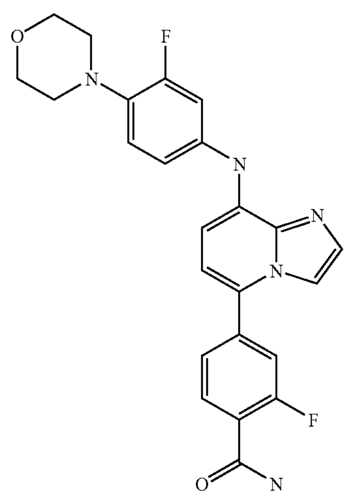 | * | *** |
| 68 | 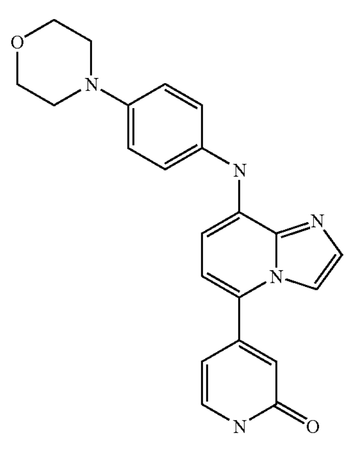 | * | * |

TABLE A-continued

| Compound No. | Structure | IC$_{50}$/ Score | MMP1/ TNFα (RASF) EC$_{50}$/ Score |
|---|---|---|---|
| 69 | 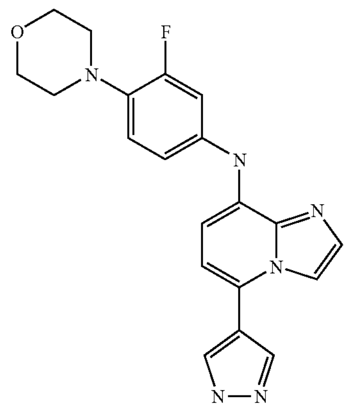 | * |  |
| 70 | 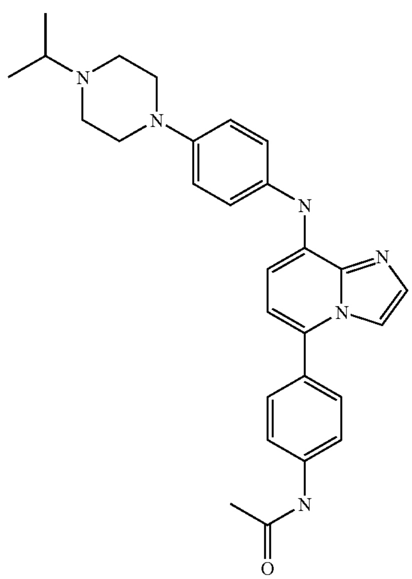 | * | * |
| 71 | 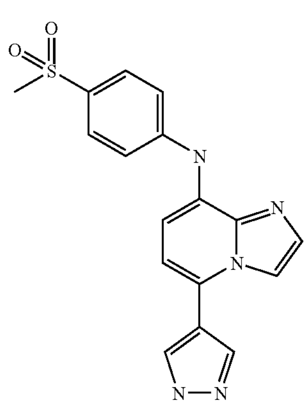 | * |  |

TABLE A-continued

| Compound No. | Structure | IC$_{50}$/ Score | MMP1/ TNFα (RASF) EC$_{50}$/ Score |
|---|---|---|---|
| 72 | 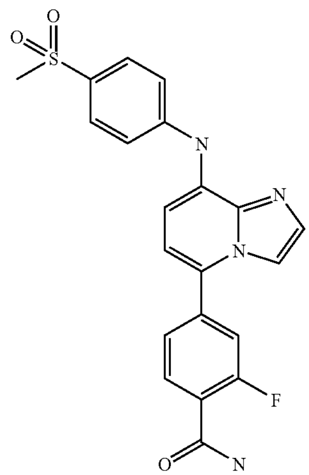 |  |  |
| 73 | 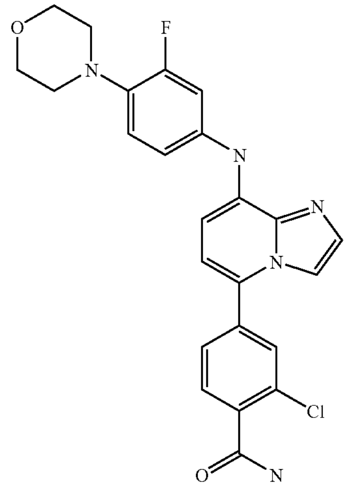 | * | *** |
| 74 | 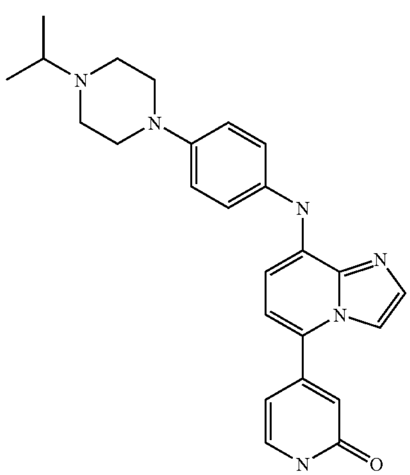 | ** | * |

TABLE A-continued

| Compound No. | Structure | IC$_{50}$/ Score | MMP1/ TNFα (RASF) EC$_{50}$/ Score |
|---|---|---|---|
| 75 | 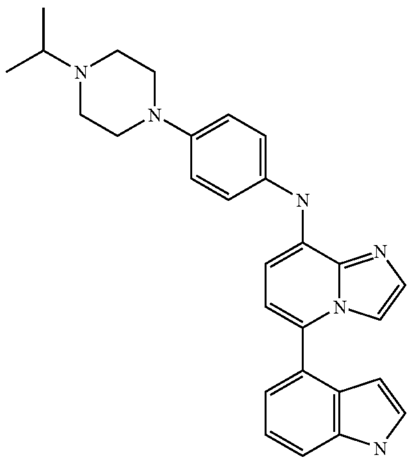 | *** | * |
| 76 | 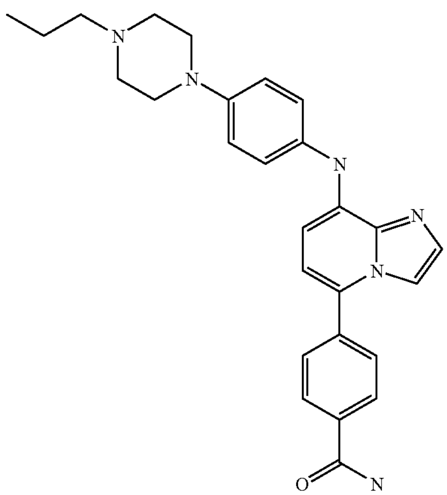 | * | * |
| 77 | 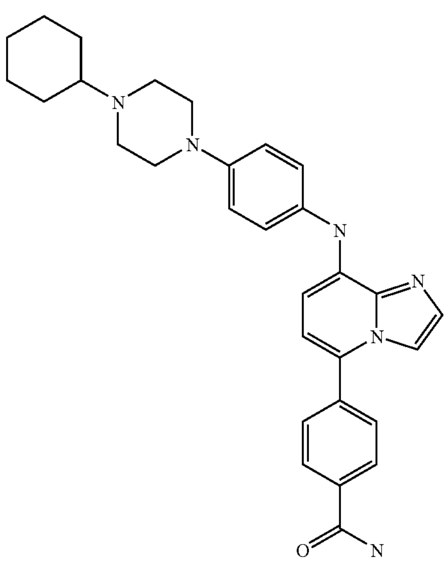 | * |  |

TABLE A-continued
| Compound No. | Structure | IC$_{50}$/ Score | MMP1/ TNFα (RASF) EC$_{50}$/ Score |
|---|---|---|---|
| 78 | 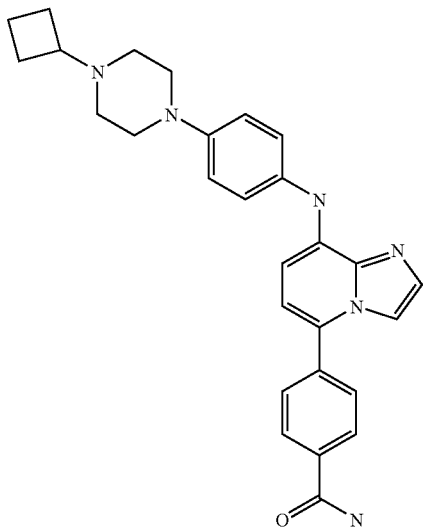 | *** | * |
| 79 | 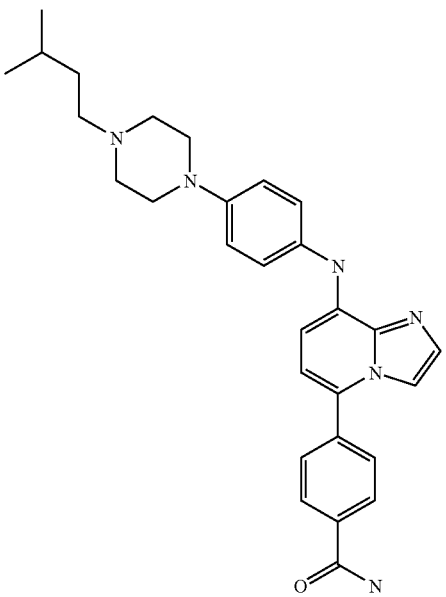 | *** | * |

TABLE A-continued
| Compound No. | Structure | IC$_{50}$/ Score | MMP1/ TNFα (RASF) EC$_{50}$/ Score |
|---|---|---|---|
| 80 | 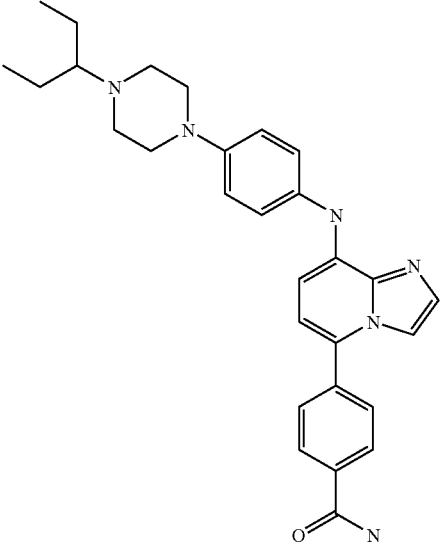 | *** | * |
| 81 | 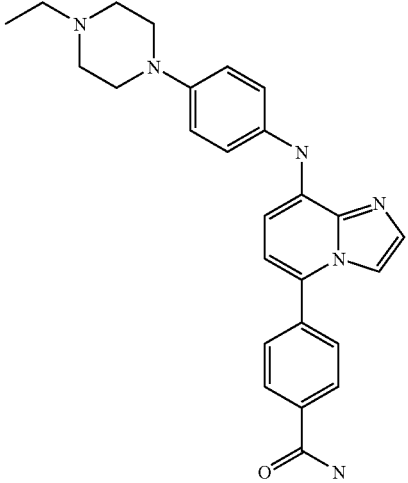 | * |  |
| 82 | 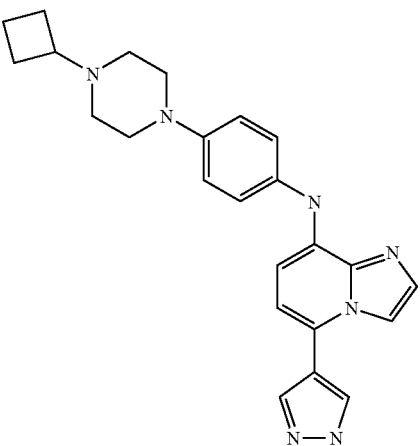 | *** | * |

TABLE A-continued

| Compound No. | Structure | IC$_{50}$/ Score | MMP1/ TNFα (RASF) EC$_{50}$/ Score |
|---|---|---|---|
| 83 | 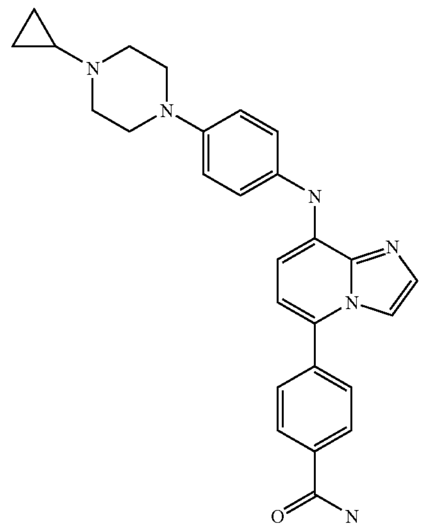 | ** | * |
| 84 | 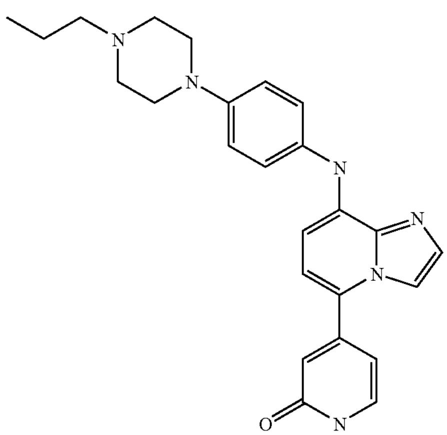 | * | * |
| 85 | 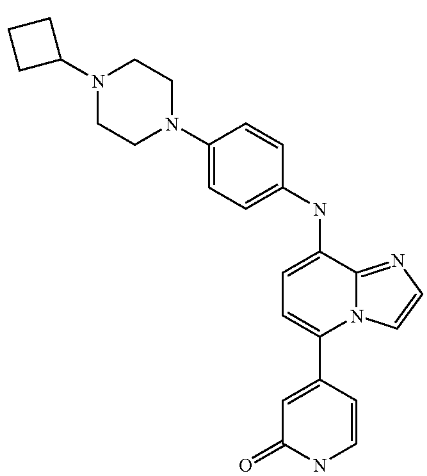 | * | * |

TABLE A-continued

| Compound No. | Structure | IC$_{50}$/ Score | MMP1/ TNFα (RASF) EC$_{50}$/ Score |
|---|---|---|---|
| 86 | 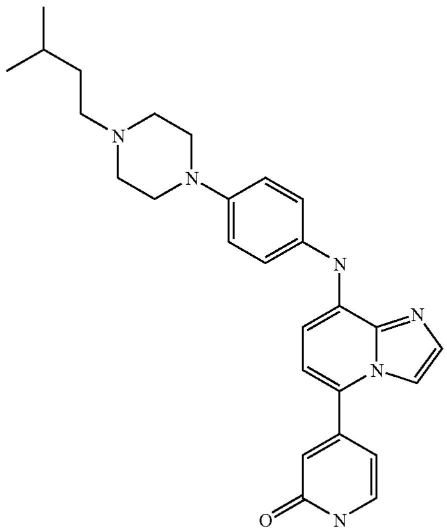 | * |  |
| 87 | 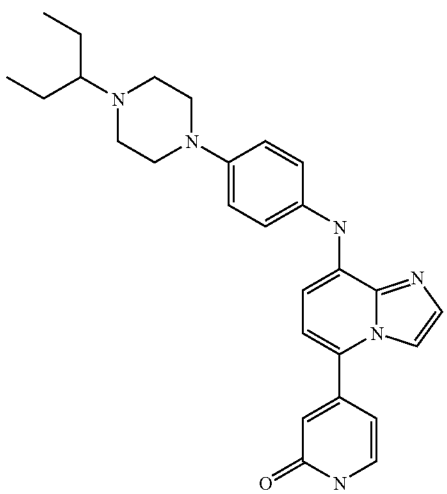 | * | * |
| 88 | 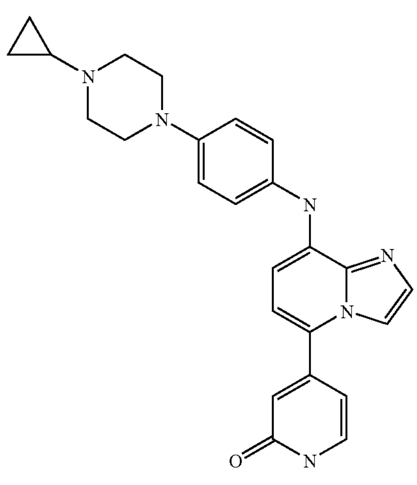 |  |  |

TABLE A-continued

| Compound No. | Structure | IC$_{50}$/ Score | MMP1/ TNFα (RASF) EC$_{50}$/ Score |
|---|---|---|---|
| 89 | 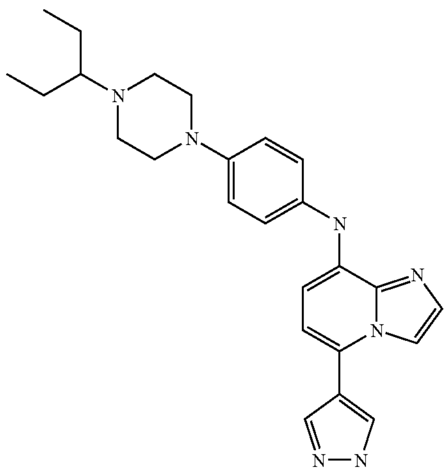 | *** | * |
| 90 | 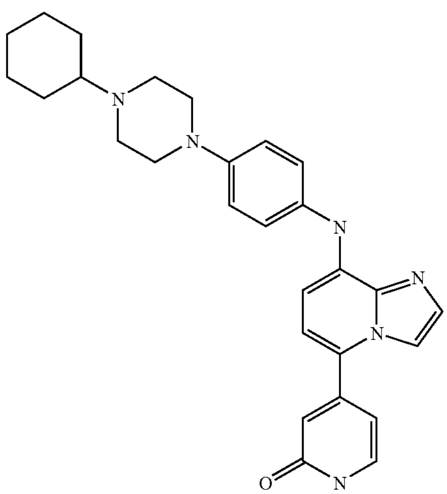 | * | * |
| 91 | 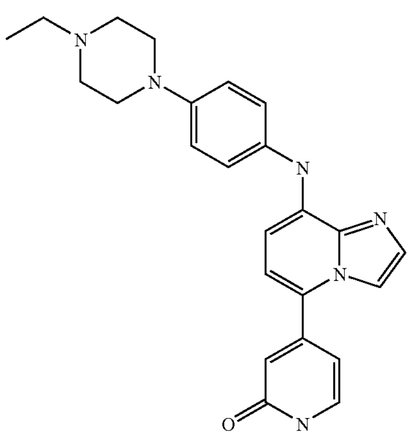 | * | * |

TABLE A-continued
| Compound No. | Structure | IC$_{50}$/ Score | MMP1/ TNFα (RASF) EC$_{50}$/ Score |
|---|---|---|---|
| 92 | 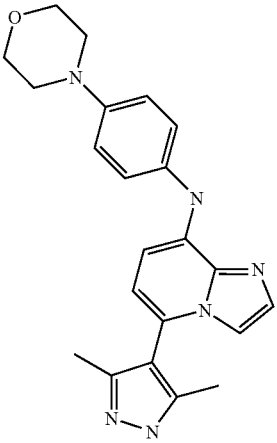 | * | * |
| 93 | 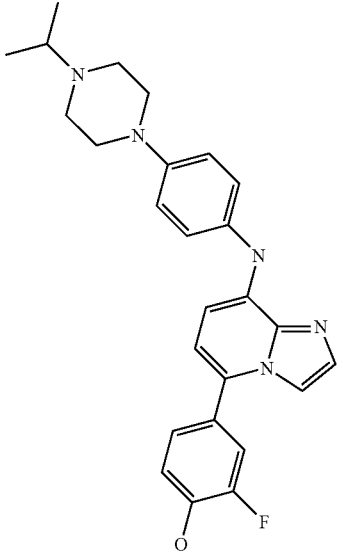 | ** | |
| 94 | 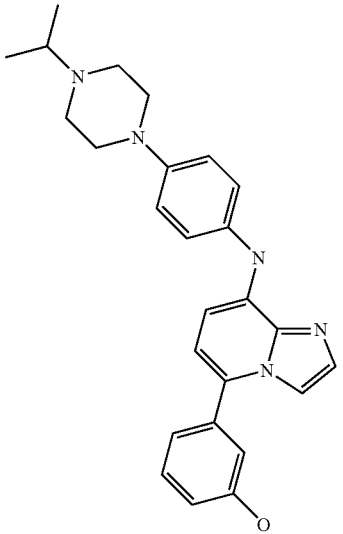 | * | * |

TABLE A-continued

| Compound No. | Structure | IC$_{50}$/ Score | MMP1/ TNFα (RASF) EC$_{50}$/ Score |
|---|---|---|---|
| 95 | 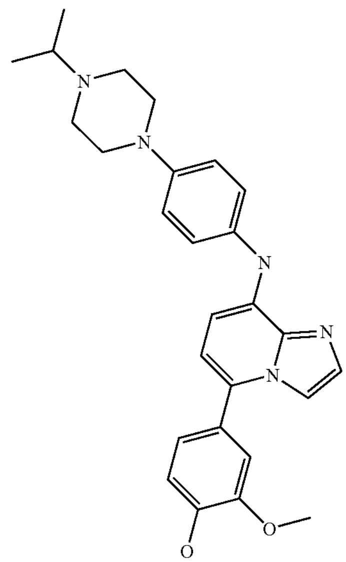 | *** | * |
| 96 | 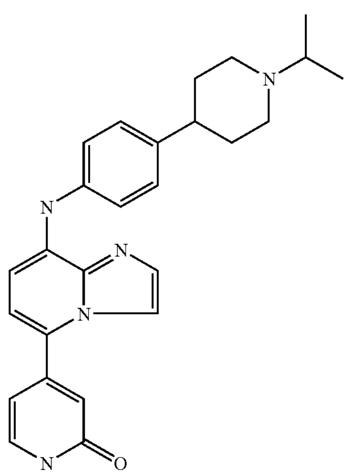 | * |  |
| 97 | 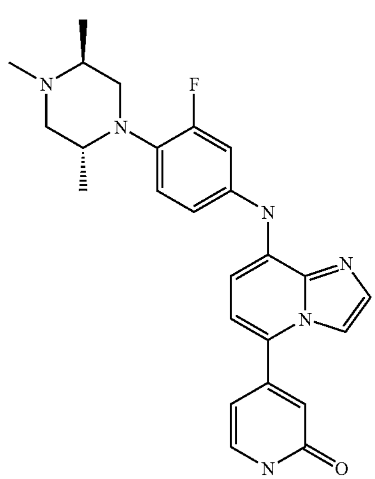 | *** | |

TABLE A-continued

| Compound No. | Structure | IC$_{50}$/ Score | MMP1/ TNFα (RASF) EC$_{50}$/ Score |
|---|---|---|---|
| 98 | 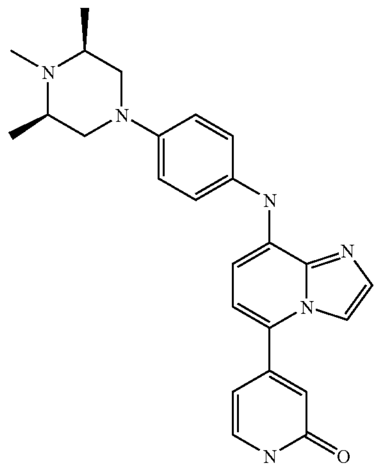 | | *** |
| 99 | 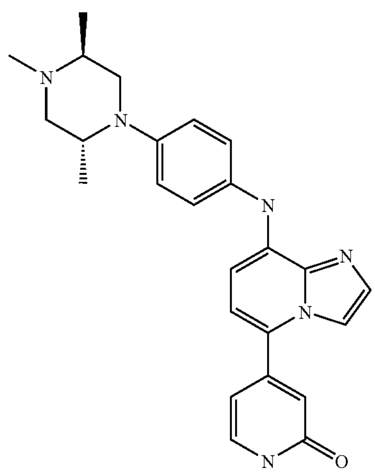 | | *** |
| 100 | 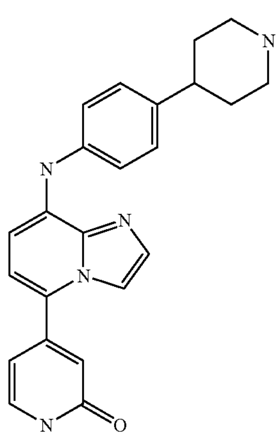 | | *** |

TABLE A-continued

| Compound No. | Structure | IC$_{50}$/ Score | MMP1/ TNFα (RASF) EC$_{50}$/ Score |
|---|---|---|---|
| 101 | 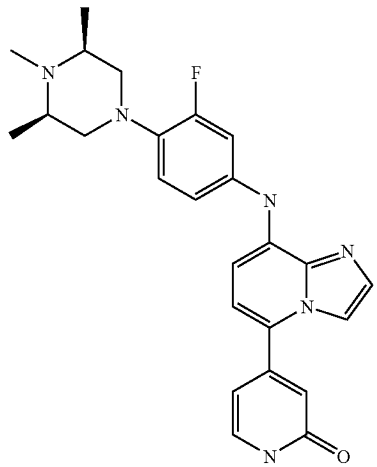 | | *** |
| 102 | 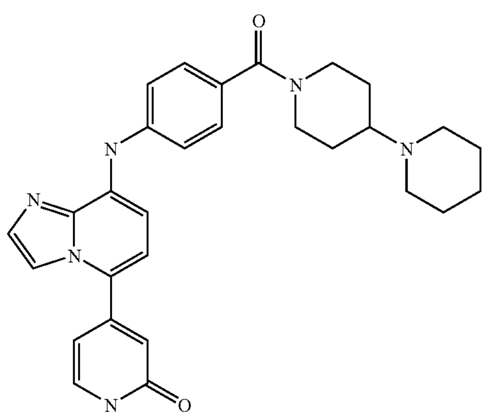 | | **** |
| 103 | 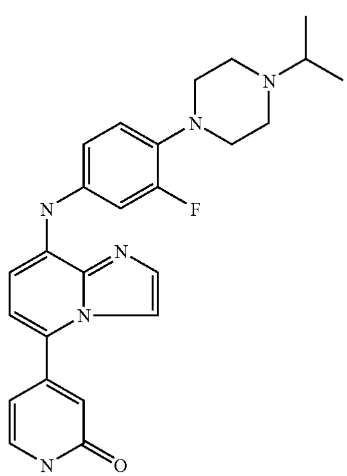 | | *** |

TABLE A-continued

| Compound No. | Structure | IC$_{50}$/ Score | MMP1/ TNFα (RASF) EC$_{50}$/ Score |
|---|---|---|---|
| 104 | 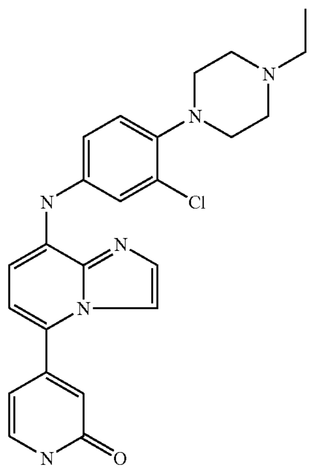 | *** | |
| 105 | 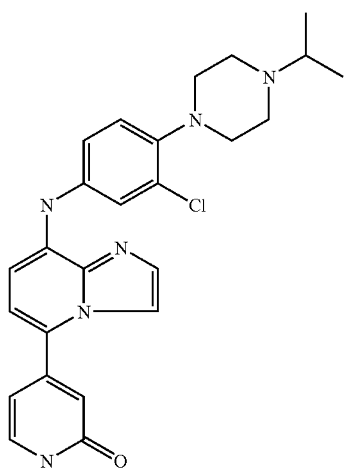 | *** | |
| 106 | 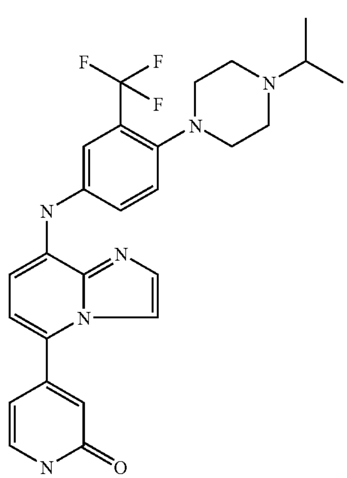 | * | *** |

TABLE A-continued

| Compound No. | Structure | IC$_{50}$/ Score | MMP1/ TNFα (RASF) EC$_{50}$/ Score |
|---|---|---|---|
| 107 | 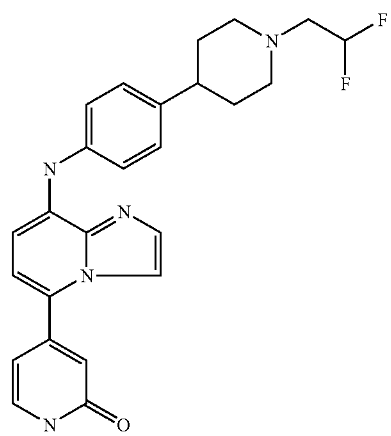 |  |  |
| 108 | 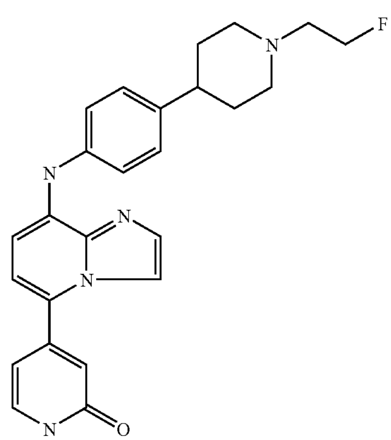 | * |  |
| 109 | 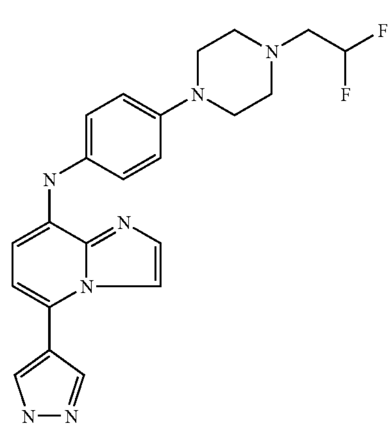 |  | * |

TABLE A-continued

| Compound No. | Structure | IC$_{50}$/ Score | MMP1/ TNFα (RASF) EC$_{50}$/ Score |
|---|---|---|---|
| 110 | 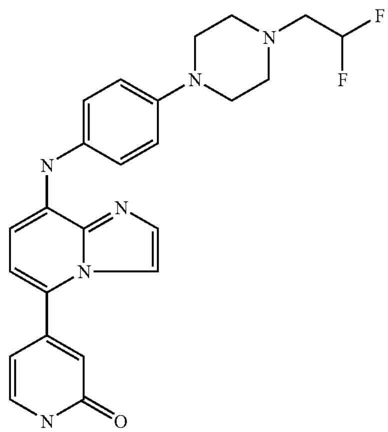 | * | |
| 111 | 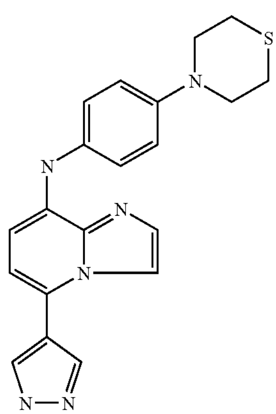 |  | * |
| 112 | 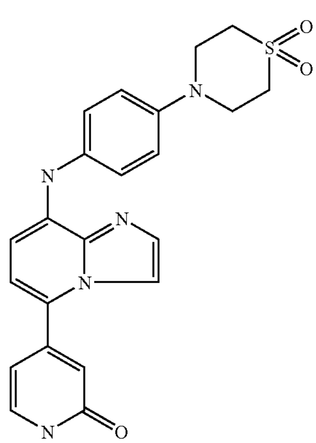 | * | |

TABLE A-continued

| Compound No. | Structure | IC$_{50}$/ Score | MMP1/ TNFα (RASF) EC$_{50}$/ Score |
|---|---|---|---|
| 113 | 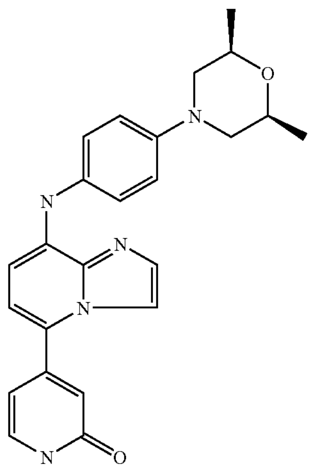 | | ** |
| 114 | 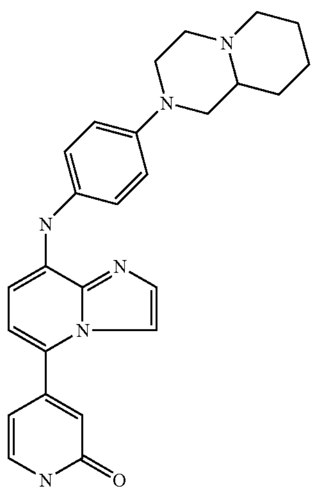 | | *** |
| 115 | 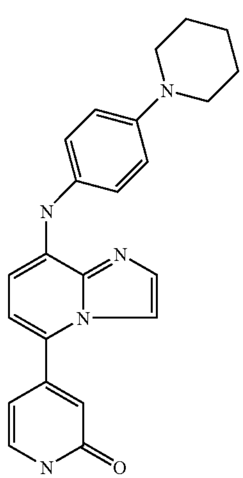 | | ** |

| Compound No. | Structure | IC50/ Score | MMP1/ TNFα (RASF) EC50/ Score |
|---|---|---|---|
| 116 | 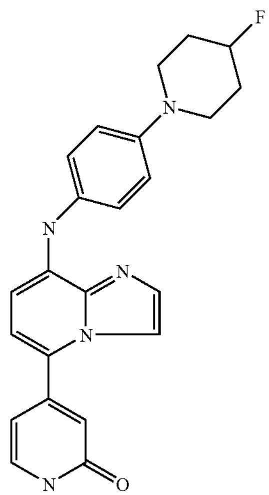 | | ** |
| 117 | 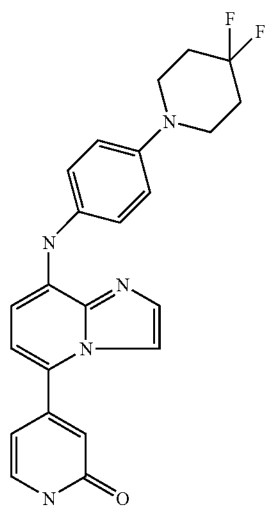 | | * |
| 118 | 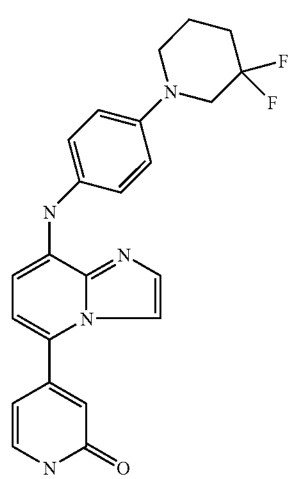 | | * |

TABLE A-continued

| Compound No. | Structure | IC$_{50}$/ Score | MMP1/ TNFα (RASF) EC$_{50}$/ Score |
|---|---|---|---|
| 119 | 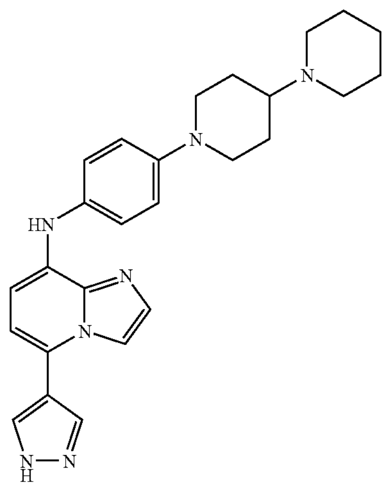 | *** | |
| 120 | 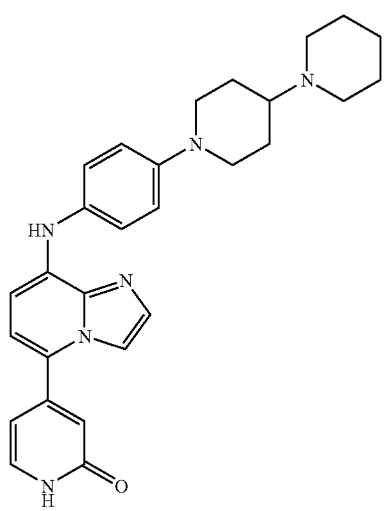 | * | * |
| 121 | 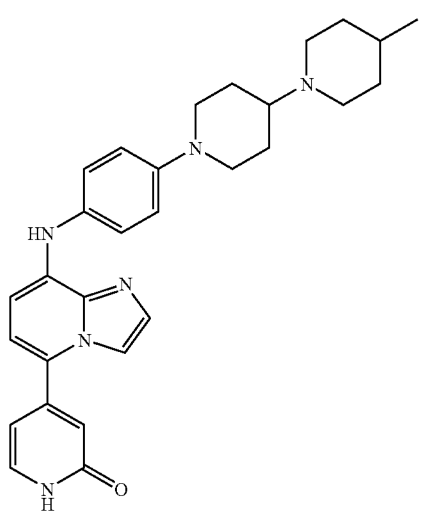 | *** | |

TABLE A-continued

| Compound No. | Structure | IC$_{50}$/ Score | MMP1/ TNFα (RASF) EC$_{50}$/ Score |
|---|---|---|---|
| 122 | 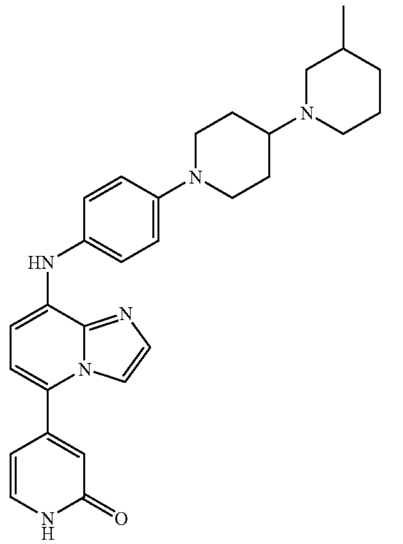 | *** | |
| 123 | 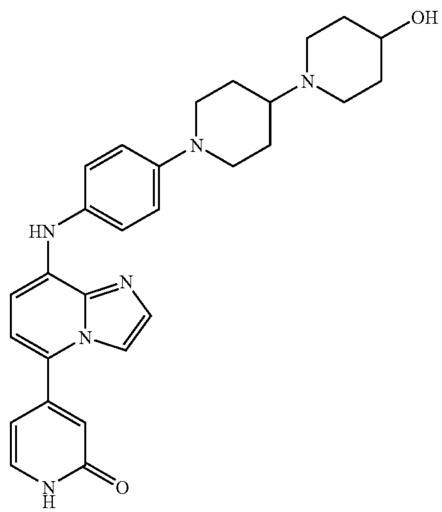 | ** | |
| 124 | 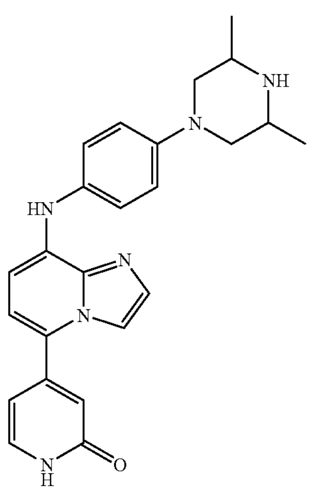 | * |  |

TABLE A-continued

| Compound No. | Structure | IC$_{50}$/ Score | MMP1/ TNFα (RASF) EC$_{50}$/ Score |
|---|---|---|---|
| 125 | 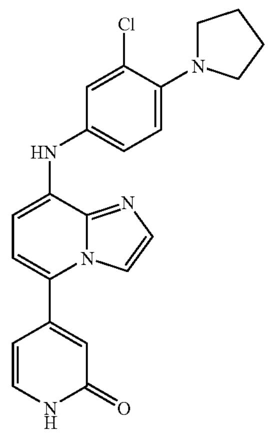 | * | |

REFERENCES

Andreakos E, et al. (2003). Arthritis Rheum. 48: 1901-12.
Blonska M., Shambharkar P B., Kobayashi M., Zhang D., Sakurai H., Su B. and Lin X. (2005) J. Biol. Chem. 280: 43056-43063
Boutros M., Agaisse H. and Perrimon M. (2002) Dev. Cell 13: 711-722
Choy E H, Panayi G S. (2001). N Engl J. Med. 344: 907-16.
Coussens L M, et al. (2002). Science 295: 2387-92.
Creemers E E, et al. (2001). Circ Res. 2001 89:201-10
Cunnane G, et al. (2001). Arthritis Rheum 44: 2263-74.
Dong W., Liu Y., Peng J., Chen L. Zou T. Xiao H., Liu Z., Li W., Bu Y. and Qi, Y. (2006) J. Biol. Chem. 281: 26029-26040
Edwards J. C. W., Szczepanski L., Szechinski J., Filipowicz-Sosnowska A., Emery P., Close D. R., Stevens R. M., Shaw T. (2004) N Engl J. Med. 350:2572-2581.
EMBO J. 23:4780-91.
Firestein G S. (2003). Nature. 423:356-61.
Gapski R, et al. (2004). J Periodontol. 75:441-52.
Gomez-Reino J J, et al. (2003). Arthritis Rheum. 48: 2122-7.
Huang H., Ryu J., Ha J., Chang E J., Kim H J., Kim H M., Kitamura T., Lee Z H. And Kim H H. (2006) Cell Death Differ. 13: 1879-1891
Irie T., Muta T. and Takeshige K. (2000) FEBS Lett. 467: 160-164
Klatt A R., Klinger G., Neumuller O., Eidenmuller B., Wagner I., Achenbach T., Aigner T. and Bartnik E. (2006) Biomedicine & Pharmacotherapy 60: 55-61
Kremer J. M., Westhovens R., Leon M., Di Giorgio E., Alten R., Steinfeld S., Russell A., Dougados M., Emery P., Nuamah I. F., Williams G. R., Becker J.-C., Hagerty D. T., Moreland L. W. (2003) N Engl J. Med. 349:1907-1915.
Lee D M, Weinblatt M E (2001). Lancet. 358: 903-11.
Mizukami J., Takaesu G., Akatsuka H., Sakurai H., Ninomiya-Tsuji J., Matsumoto K. and Sakurai N. (2002) Mol. Cell. Biol. 22: 992-1000
New L, Jiang Y, Han J. (2003) Regulation of PRAK subcellular location by p38 MAP kinases. Mol Biol Cell. 14(6): 2603-16.
Ninomiya-Tsuji J., Kishimoto K., Hiyama A., Inoue J., Cao Z. and Matsumoto K. (1999) Nature 398: 252-256
O'Dell J R, Leff R, Paulsen G, Haire C, Mallek J, Eckhoff P J, Fernandez A, Blakely K, Wees S, Stoner J, Hadley S, Felt J, Palmer W, Waytz P, Churchill M, Klassen L, Moore G. (2002) Arthritis Rheum. 46:1164-70.
O'Dell J R. (2004) Therapeutic strategies for rheumatoid arthritis. N Engl J. Med. 350(25):2591-602.
Reif S, Somech R, Brazovski E, Reich R, Belson A, Konikoff F M, Kessler A. (2005) Digestion. 71:124-130.
Rosenberg G A. (2002). Glia. 39:279-91.
Sakurai H., Miyoshi H., Toriumi W. and Sugita T. (1999) J. Biol. Chem. 274: 10641-10648
Sato S., Sanjo H., Takeda K., Ninomiya-Tsuji J., Yamamoto M., Kawai T., Matsumoto K., Takeuchi O. and Akira S. (2005) Nat. Immunol. 6: 1087-1095
Schanstra J P, et al. (2002). J Clin Invest. 110:371-9.
Seternes O M, Mikalsen T, Johansen B, Michaelsen E, Armstrong C G, Morrice N A, Turgeon B, Meloche S, Moens U, Keyse S M. (2004) Activation of MK5/PRAK by the atypical MAP kinase ERK3 defines a novel signal transduction pathway.
Shi Y, Kotlyarov A, Laabeta K, Gruber A D, Butt E, Marcus K, Meyer H E, Friedrich A, Volk H D, Gaestel M. (2003) Elimination of protein kinase MK5/PRAK activity by targeted homologous recombination. Mol Cell Biol. 23:7732-41.
Shibuya H., Iwata H., Masuyama N., Gotoh Y., Yamaguchi K., Irie K., Matsumoto K., Nishida E. and Ueno N. (1998) EMBO J. 17: 1019-1028
Shim J H., Xiao C., Paschal A E., Bailey S T., Rao P., Hayden M S., Lee K Y., Bussey C., Steckel M., Tanaka N., Yamada G., Akira S., Matsumoto K., Ghosh S. (2005) Genes Dev. 19:2668-2681
Smolen J S, Steiner G. (2003). Nat Rev Drug Discov. 2: 473-88.
St Clair E W, van der Heijde D M, Smolen J S, Maini R N, Bathon J M, Emery P, Keystone E, Schiff M, Kalden J R, Wang B, Dewoody K, Weiss R, Baker D; (2004) Combination of infliximab and methotrexate therapy for early rheumatoid arthritis: a randomized, controlled trial. Arthritis Rheum. 50:3432-43.

Suzuki R, et al. (2004). Treat Respir Med. 3:17-27.
Vidal S., Khush R. S., Leulier F., Tzou P., Nakamura M. and Lemaitre B. (2001) Genes & Dev. 15: 1900-1912.
Wan Y Y., Chi H., Xie M., Schneider M D. And Flavell R A. (2006) Nat. Immunol 7: 851-858
Yamagushi K., Shirakabe K., Shibuya H., Irie K., Oishi I., Ueno N., Taniguchi T., Nishida E. and Matsumoto K. (1995) Science 270: 2008-2011.
Yang Y H, Morand E F, Getting S J, Paul-Clark M, Liu D L, Yona S, Hannon R, Buckingham J C, Perretti M and Flower R J (2004) Arthritis Rheum. 50:976-84.

It will be appreciated by those skilled in the art that the foregoing description is exemplary and explanatory in nature, and is intended to illustrate the invention and its preferred embodiments. Through routine experimentation, an artisan will recognise apparent modifications and variations that may be made without departing from the spirit of the invention. Thus, the invention is intended to be defined not by the above description, but by the following claims and their equivalents.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

We claim:
1. A compound according to formula III:

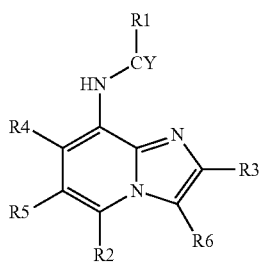

wherein CY—$R^1$ is

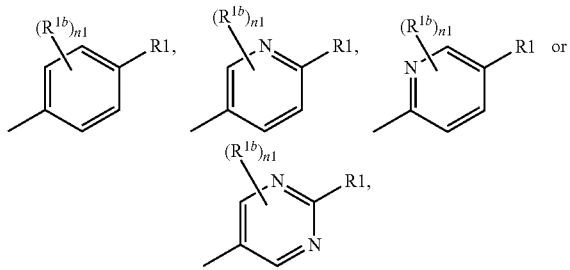

the subscript n1 is 1, 2, 3, or 4; and each $R^{1b}$ is independently selected from hydrogen, $C_1$-$C_6$ alkyl, $C_1$-$C_6$ alkoxy, $C_1$-$C_6$ haloalkyl, $OCF_3$, cyano, and halo;
and $R^1$ is -L-$R^{1a}$; and
wherein
L is selected from a single bond, alkylene, —CO—, and —$SO_2$—;
$R^{1a}$ is selected from $C_1$-$C_6$ alkyl, $C_1$-$C_6$ haloalkyl,
cycloalkyl, unsubstituted, or substituted with $C_1$-$C_6$ alkyl, $C_1$-$C_6$ alkoxy, $C_1$-$C_6$ haloalkyl, hydroxy, $C_1$-$C_6$ haloalkoxy, CN, cycloalkyl, heterocycloalkyl, aryl, heteroaryl, aralkyl, cycloalkylalkyl, or halo,
aryl, unsubstituted, or substituted with $C_1$-$C_6$ alkyl, $C_1$-$C_6$ alkoxy, $C_1$-$C_6$ haloalkyl, hydroxy, cyano, or halo,
heterocycloalkyl unsubstituted, or substituted with $C_1$-$C_6$ alkyl, $C_1$-$C_6$ alkoxy, $C_1$-$C_6$ haloalkyl, hydroxy, $C_1$-$C_6$ haloalkoxy, CN, cycloalkyl, heterocycloalkyl, aryl, heteroaryl, aralkyl, cycloalkylalkyl, or halo,
heteroaryl, unsubstituted or substituted with $C_1$-$C_6$ alkyl, $C_1$-$C_6$ alkoxy, $C_1$-$C_6$ haloalkyl, hydroxy, cyano, or halo,
amino, unsubstituted or substituted with $C_1$-$C_6$ alkyl,
aralkyl, unsubstituted or substituted with $C_1$-$C_6$ alkyl, $C_1$-$C_6$ alkoxy, $C_1$-$C_6$ haloalkyl, hydroxy, or halo,
heteroarylalkyl, unsubstituted or substituted with $C_1$-$C_6$ alkyl, $C_1$-$C_6$ alkoxy, $C_1$-$C_6$ haloalkyl, hydroxy, or halo, and
aminoalkyl;
or $R^1$ is -L-$R^{1a}$; and
L is —CO—, and —$SO_2$—; and
$R^{1a}$ is amino, alkylamino, dialkylamino, cycloalkylamino, cycloalkylalkylamino, arylamino, aralkylamino, heteroarylamino, and heteroarylalkylamino;
$R^2$ is selected from
aryl, unsubstituted or substituted with $C_1$-$C_6$ alkyl, $C_1$-$C_6$ alkoxy, $C_1$-$C_6$ haloalkyl, hydroxy, cyano, carboxamido, or halo, and
heteroaryl, unsubstituted or substituted with $C_1$-$C_6$ alkyl, $C_1$-$C_6$ alkoxy, $C_1$-$C_6$ haloalkyl, hydroxy, cyano, carboxamido, or halo; and
$R^3$, $R^4$, $R^5$, and $R^6$ are independently selected from H, OH, OMe, $OC_2H_5$, F, Cl, Me, Et, $SO_2Me$, $CF_3$ and $OCF_3$.

2. A compound according to formula III:

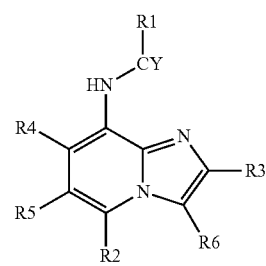

wherein
$R^1$ represents H, halogen, $C_1$-$C_6$ alkyl, $C_1$-$C_6$ alkoxy, $CF_3$, CN,
heterocycloalkyl, unsubstituted, or substituted with $C_1$-$C_6$ alkyl, $C_1$-$C_8$ cycloalkyl, $C_1$-$C_6$ alkoxy, $C_1$-$C_6$ haloalkyl, hydroxy, carboxamido, cyano, or halo,
cycloalkyl, unsubstituted, or substituted with $C_1$-$C_6$ alkyl, $C_1$-$C_6$ alkoxy, $C_1$-$C_6$ haloalkyl, hydroxy, carboxamido, cyano, or halo, monocyclic aryl, unsubstituted, or substituted with $C_1$-$C_6$ alkyl, $C_1$-$C_6$ alkoxy, $C_1$-$C_6$ haloalkyl, hydroxy, carboxamido, cyano, or halo, monocyclic heteroaryl, unsubstituted, or substituted with $C_1$-$C_6$ alkyl, $C_1$-$C_6$ alkoxy, $C_1$-$C_6$ haloalkyl, hydroxy, carboxamido, cyano, or halo, $C(=NH)NR^aR^b$, —$COR^a$, —$OR^a$, —$OC(O)$—$C_1$-$C_6$ alkyl, $(CH_2)_aCOOR^a$, $C(O)NR^aR^b$, $S(O)_2(CH_2)_aN(R^aR^b)$, $SR^a$, $SO(CH_2)_aNR^aR^b$, $S(O)_2$—$R^a$, $SOR^a$, $(CH_2)_aNR^aR^b$, $(CH_2)_aN(R^a)S(O)_2$—$C_1$-$C_6$ alkyl, $(CH_2)_aNR^aS(O)$—$C_1$-$C_6$ alkyl, $NR^aCO$—$R^b$, and $NH$—$CO$—$CO$—$OR^a$; each of which may be optionally substituted with one or more groups selected from H, halogen, OH, $C_1$-$C_6$ alkyl, $NH_2$, $N(C_1$-$C_6$ alkyl)($C_1$-$C_6$-alkyl), heterocycloalkyl, cycloalkyl and $CF_3$;

$R^2$ is selected from aryl, unsubstituted, or substituted with $C_1$-$C_6$ alkyl, $C_1$-$C_6$ alkoxy, $C_1$-$C_6$ haloalkyl, hydroxy, cyano, or halo, and heteroaryl, unsubstituted, or substituted with $C_1$-$C_6$ alkyl, $C_1$-$C_6$ alkoxy, $C_1$-$C_6$ haloalkyl, hydroxy, cyano, or halo;

$R^3$, $R^4$, $R^5$ and $R^6$ are independently selected from H, OH, OMe, $OC_2H_5$, F, Cl, Me, Et, $SO_2Me$, $CF_3$ and $OCF_3$;

$CY$—$R^1$ is

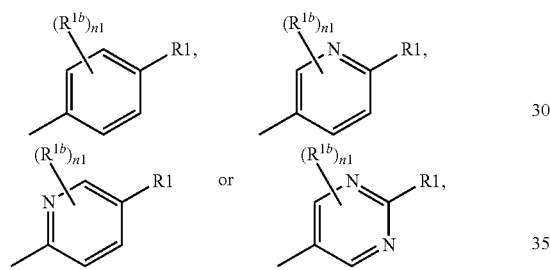

the subscript n1 is 1, 2, 3, or 4; and each $R^{ib}$ is independently selected from hydrogen, $C_1$-$C_6$ alkyl, $C_1$-$C_6$ alkoxy, $C_1$-$C_6$ haloalkyl, cyano, and halo;

$R^a$ and $R^b$ each independently represent H, halogen, $C_1$-$C_6$ alkyl, $(CH_2)_a$—$N(C_1$-$C_6$ alkyl)($C_1$-$C_6$-alkyl), $(CH_2)_a$-monocyclic aryl, $(CH_2)_a$-monocyclic heteroaryl, $(CH_2)_a$-cycloalkyl or $(CH_2)_a$-heterocycloalkyl, each of which may be optionally substituted with one or more groups selected from halogen, —OH, $C_1$-$C_6$ alkyl, $C_1$-$C_6$ alkyl-O—$C_1$-$C_6$ alkyl, $C_1$-$C_6$ alkoxy, —$NH_2$, —$NR^cR^d$, $NR^cCOR^d$, heteroaryl, heterocycloalkyl, or —$CF_3$; or $R^a$ and $R^b$ may, if joined to the same atom, represent together with the nitrogen to which they are attached a heterocycloalkyl group which may be optionally substituted with one or more groups selected from halogen, —OH, $C_1$-$C_6$ alkyl, $C_1$-$C_6$ alkoxy, —$NH_2$, —$NR^cR^d$, —$NR^cCOR^d$, —$C(O)NR^cR^d$, aryl, aralkyl, heteroaryl, cycloalkyl or —$CF_3$;

$R^c$ and $R^d$ each independently represent H, or $C_1$-$C_6$ alkyl; and

"a" is 0, 1, 2 or 3;

or a pharmaceutically acceptable salt, stereoisomers, or tautomers thereof.

3. The compound according to claim 2, wherein CY is selected from unsubstituted phenyl, unsubstituted pyridyl, and unsubstituted pyrimidine.

4. The compound according to claim 2, wherein each of $R^3$, $R^4$ and $R^5$ is H.

5. The compound according to claim 1, wherein the compound is according to formula IIIa, IIIb, IIIc or IIId:

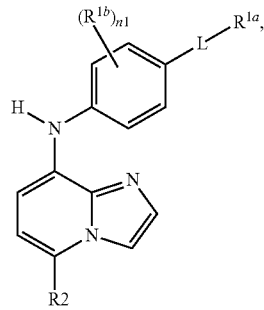

IIIa

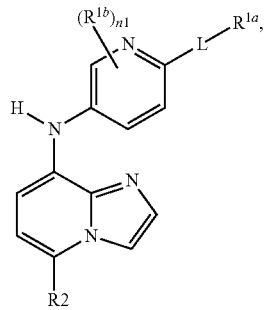

IIIb

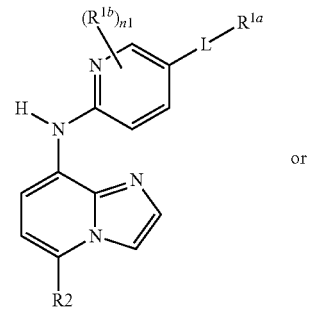

IIIc or

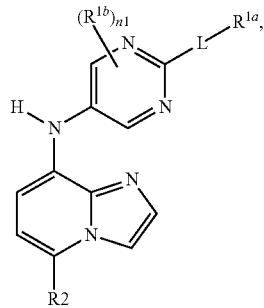

IIId wherein L, $R^{1a}$, and $R^2$ are as defined in claim 1, the subscript n1 is 1, 2, 3 or 4; and each $R^{1b}$ is independently selected from hydrogen, $C_1$-$C_6$ alkyl, $C_1$-$C_6$ alkoxy, $C_1$-$C_6$ haloalkyl, cyano, and halo.

6. The compound according to claim 5, wherein L is —CO— or $SO_2$—; and $R^{1a}$ is amino.

7. The compound according to claim 5, wherein L is —CO— or $SO_2$—; and $R^{1a}$ is alkylamino, dialkylamino, cycloalkylamino, arylamino, aralkylamino, heteroarylamino, and heteroarylalkylamino.

8. The compound according to claim 5, wherein L is a single bond, —CO—, $SO_2$, and —$(CH_2)_{m1}$—; the subscript m1 is selected from 1, 2, 3, or 4; and $R^{1a}$ is

and wherein the ring P is heterocycloalkyl, unsubstituted, or substituted with $C_1$-$C_6$ alkyl, $C_1$-$C_6$ alkoxy, $C_1$-$C_6$ haloalkyl, hydroxy, or halo.

9. The compound according to claim 5, wherein L is a single bond.

10. The compound according to claim 5, wherein L is —CO—.

11. The compound according to claim 2, wherein the compound is according to formula Va, Vb or Vc:

Va

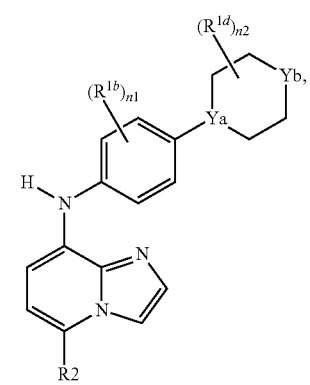

Vb

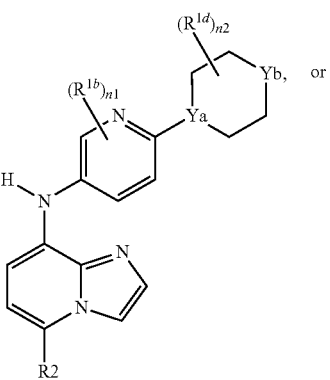

or

Vc

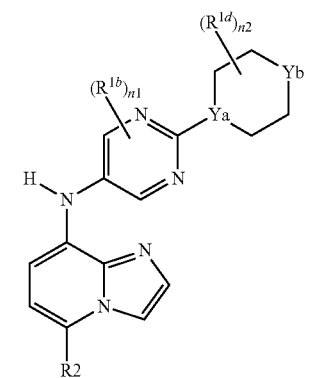

and wherein $R^2$ is as in claim 14, Ya is C or N, Yb is C—$R^{1c}$, O, S, $SO_2$ or N—$R^{1c}$; each $R^{1b}$ is independently selected from H, Me, Et, n-Pr, iso-Pr, Cl, F, CN, OMe, OEt, $CF_3$, $CF_2CF_3$ and $OCF_3$; $R^{1c}$ is hydrogen, alkyl, cycloalkyl or heterocycloalkyl; each $R^{1d}$ is independently selected from H, Me, Et, n-Pr, iso-Pr, Cl, F, CN, OMe, OEt, $CF_3$, $CF_2CF_3$ and $OCF_3$; and each n1 and n2 is independently 1 or 2.

12. A compound according to formula VIa, VIb, VIc, VId, VIe, VIf, VIg, VIh, VIi, VIj, VIk, or VIl:

VIa

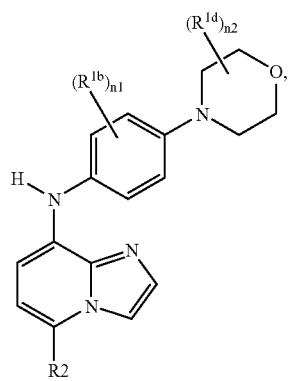

VIb

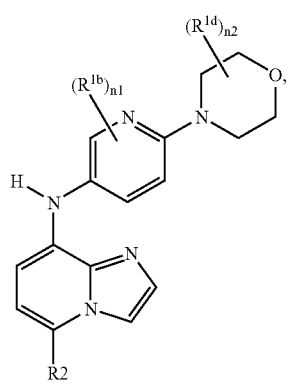

VIc

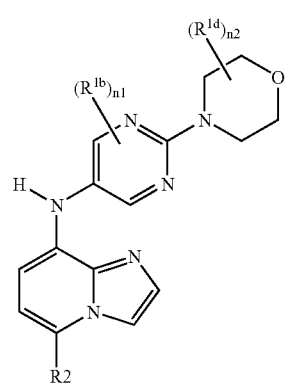

VId

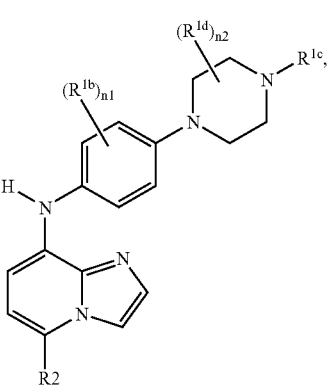

-continued
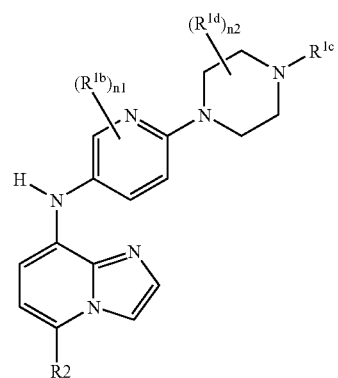
VIe
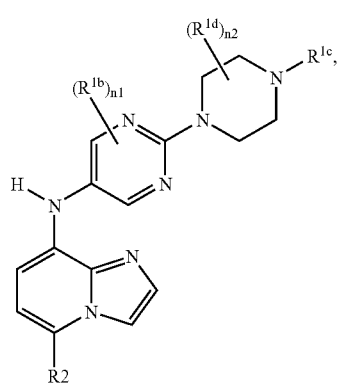
VIf
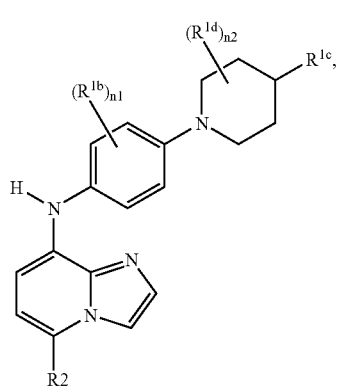
VIg
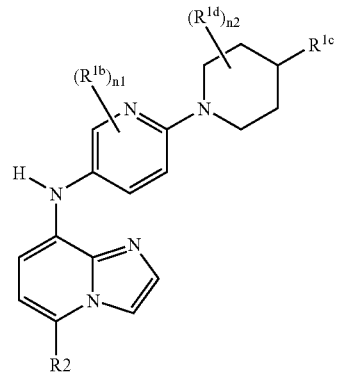
VIh
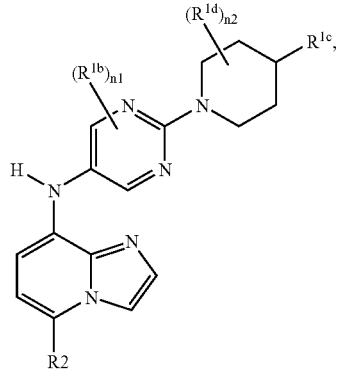
VIi
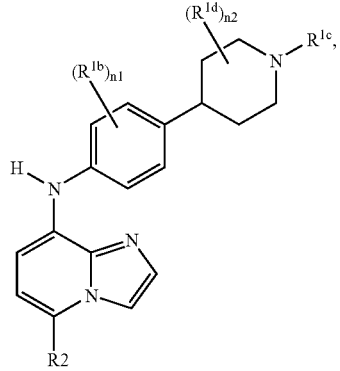
VIj
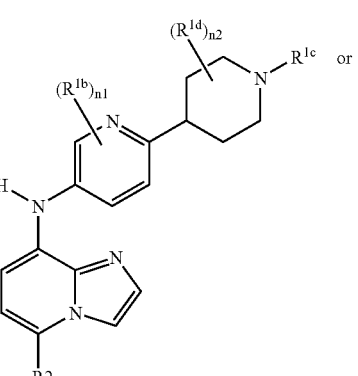
VIk
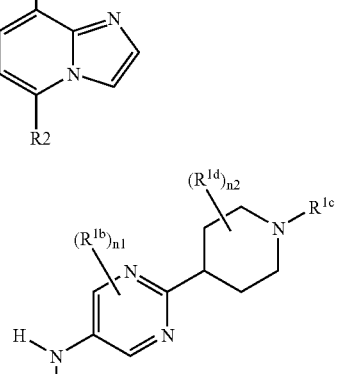
or
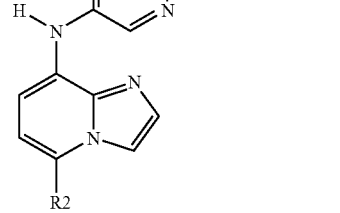
VIl
and wherein $R^2$ is selected from
aryl, unsubstituted or substituted with $C_1$-$C_6$ alkyl, $C_1$-$C_6$ alkoxy, $C_1$-$C_6$ haloalkyl, hydroxy, cyano, carboxamido, or halo, and
heteroaryl, unsubstituted or substituted with $C_1$-$C_6$ alkyl, $C_1$-$C_6$ alkoxy, $C_1$-$C_6$ haloalkyl, hydroxy, cyano, carboxamido, or halo; each $R^{ib}$ is independently selected from H, Me, Et, n-Pr, iso-Pr, Cl, F, CN, OMe, OEt, CF$_3$, CF$_2$CF$_3$ or OCF$_3$; $R^{1c}$ is selected from hydrogen, alkyl or substituted or unsubstituted cycloalkyl or heterocycloalkyl; each $R^{id}$ is independently selected from H, Me, Et, n-Pr, iso-Pr, Cl, F, CN, OMe, OEt, CF$_3$, CF$_2$CF$_3$ or OCF$_3$; and each n1 and n2 is independently 1 or 2.

13. The compound according to claim 2, wherein the compound is according to formula IXa or IXb:

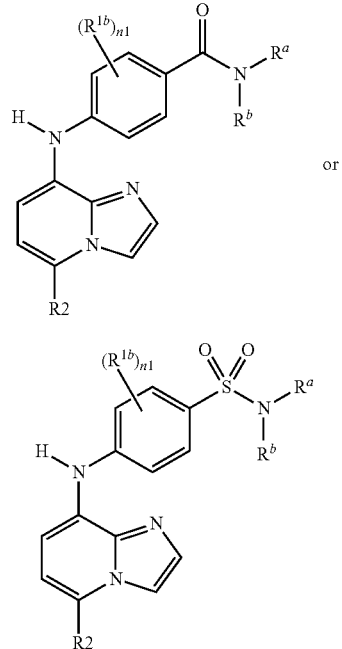

IXa

IXb and wherein $R^{1b}$ is independently selected from hydrogen, C$_1$-C$_6$ alkyl, C$_1$-C$_6$ alkoxy, C$_1$-C$_6$ haloalkyl, cyano, and halo; n1 is 1, 2, 3 or 4; R$^2$ is selected from aryl, unsubstituted, or substituted with C$_1$-C$_6$ alkyl, C$_1$-C$_6$ alkoxy, C$_1$-C$_6$ haloalkyl, hydroxy, cyano, or halo, heteroaryl, unsubstituted, or substituted with C$_1$-C$_6$ alkyl, C$_1$-C$_6$ alkoxy, C$_1$-C$_6$ haloalkyl, hydroxy, cyano, or halo; and;

R$^a$ and R$^b$ each independently represent H, halogen, C$_1$-C$_6$ alkyl, (CH$_2$)$_a$—N(C$_1$-C$_6$ alkyl)(C$_1$-C$_6$-alkyl), (CH$_2$)$_a$-monocyclic aryl, (CH$_2$)$_a$-monocyclic heteroaryl, (CH$_2$)$_a$-cycloalkyl or (CH$_2$)$_a$-heterocycloalkyl, each of which may be optionally substituted with one or more groups selected from halogen, —OH, C$_1$-C$_6$ alkyl, C$_1$-C$_6$ alkyl-O—C$_1$-C$_6$ alkyl, C$_1$-C$_6$ alkoxy, —NH$_2$, —NR$^c$R$^d$, NR$^c$COR$^d$, heteroaryl, heterocycloalkyl, or —CF$_3$; or R$^a$ and R$^b$ may, if joined to the same atom, represent together with the nitrogen to which they are attached a heterocycloalkyl group which may be optionally substituted with one or more groups selected from halogen, —OH, C$_1$-C$_6$ alkyl, C$_1$-C$_6$ alkoxy, —NH$_2$, —NR$^c$R$^d$, —NR$^c$COR$^d$, —C(O)NR$^c$R$^d$, aryl, aralkyl, heteroaryl, cycloalkyl or —CF$_3$;

R$^c$ and R$^d$ each independently represent H, or C$_1$-C$_6$ alkyl; and

"a" is 0, 1, 2 or 3.

14. The compound according to claim 1, wherein R$^2$ is selected from heteroaryl.

15. The compound according to claim 1, wherein R$^2$ is selected from phenyl, pyridyl, indolyl, isoindolyl, pyrrolyl, furanyl, thienyl, pyrazolyl, oxazolyl, and thiazolyl.

16. The compound according to claim 1, wherein R$^2$ is

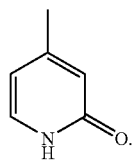

17. The compound according to claim 1, wherein R$^2$ is

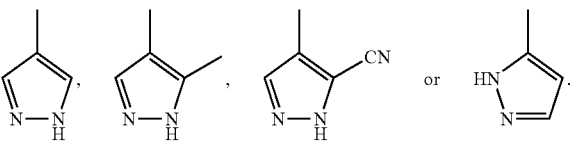

18. A compound according to formula XIa, XIb, XIc, XId, XIe, XIf, XIg, XIh, XIi, XIj, XIk or XIl

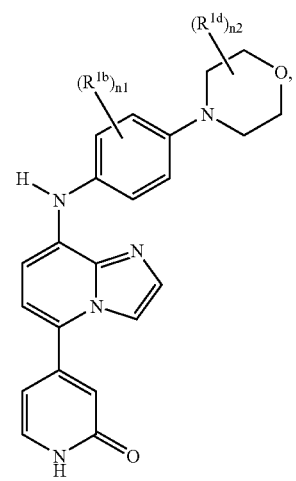

XIa

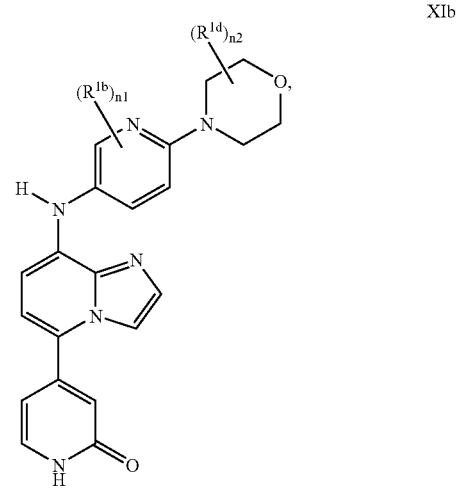

XIb

XIc
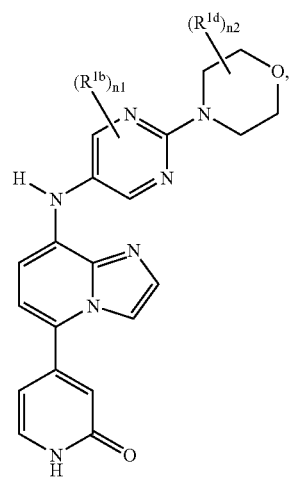
XId
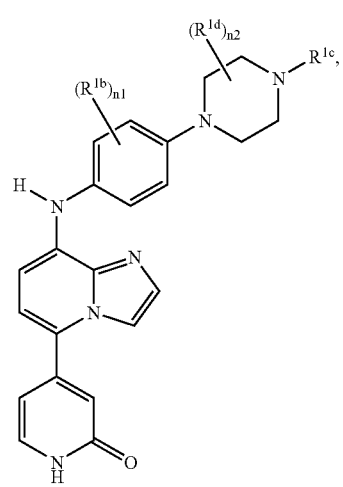
XIe
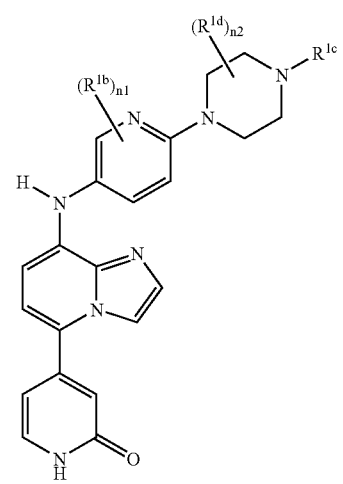
XIf
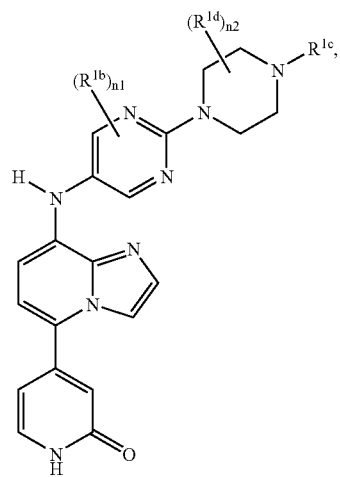
XIg
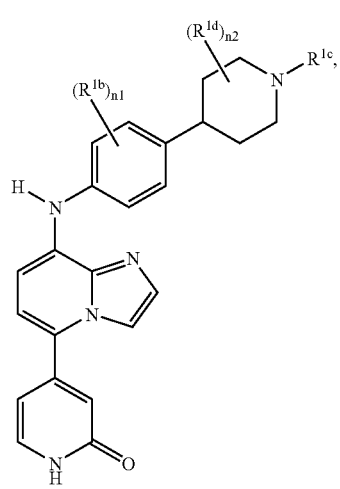
XIh
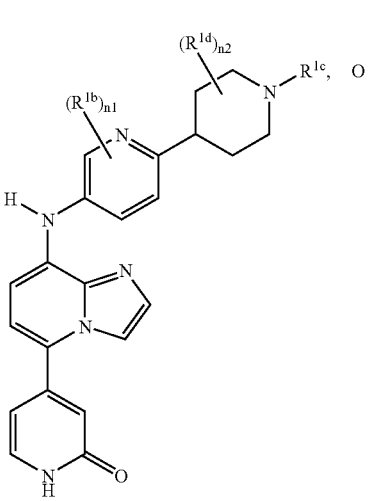

379
-continued

XIi
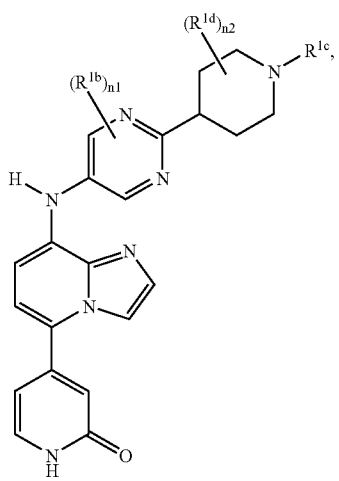

XIj
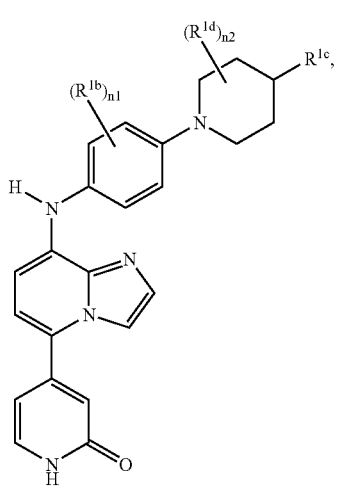

XIk
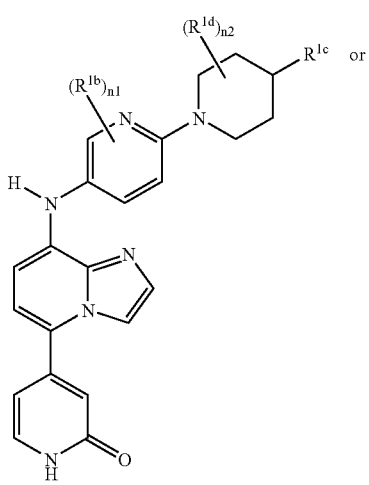

380
-continued

XII
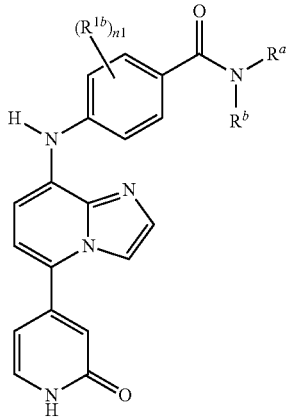

and wherein $R^{1c}$ is hydrogen, alkyl, cycloalkyl, or heterocycloalkyl; each $R^{1b}$ is independently selected from H, Me, Et, n-Pr, iso-Pr, Cl, F, CN, OMe, OEt, $CF_3$, $CF_2CF_3$ and $OCF_3$; each $R^{1d}$ is independently selected from H, Me, Et, n-Pr, iso-Pr, Cl, F, CN, OMe, OEt, $CF_3$, $CF_2CF_3$ and $OCF_3$; and each n1 and n2 is independently selected 1 or 2.

19. The compound according to either of claim 12 or 18, with respect to compounds of formulae VId-VIl, and XIa-XIl wherein $R^{1c}$ is Me, Et, Pr, i-Pr, t-Bu, i-Bu, i-pentyl, cyclopropyl, cyclobutyl, cyclopentyl, cyclohexyl, cyclopropylmethyl or piperidinyl.

20. The compound according to claim 1, wherein the compound is according to formula XIVa, or XIVb:

XIVa or

-continued

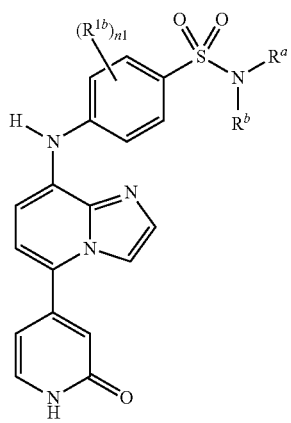

XIVb and wherein $R^{1b}$ is independently selected from hydrogen, $C_1$-$C_6$ alkyl, $C_1$-$C_6$ alkoxy, $C_1$-$C_6$ haloalkyl, cyano, and halo; n1 is 1, 2, 3 or 4; each $R^a$ and $R^b$ is independently selected from hydrogen, $C_1$-$C_6$ alkyl, aryl, aralkyl, heteroaryl, heteroarylalkyl, cycloalkyl, and cycloalkylalkyl.

21. The compound according to claim 13, wherein $R^a$ is H, and $R^b$ is Me, Et, Pr, i-Pr, t-Bu, i-Bu, i-pentyl, cyclopropyl, cyclobutyl, cyclopentyl, cyclohexyl, or cyclopropylmethyl.

22. A compound selected from:

-continued

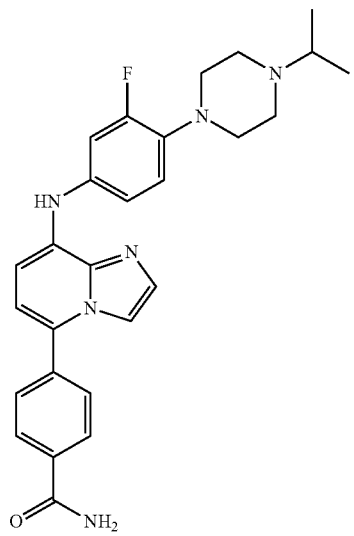

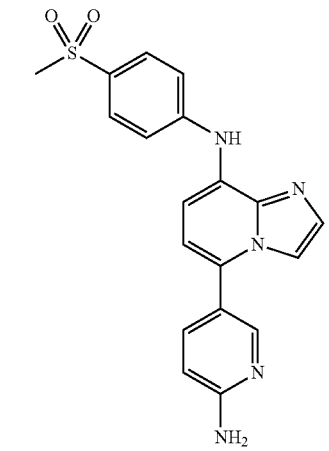

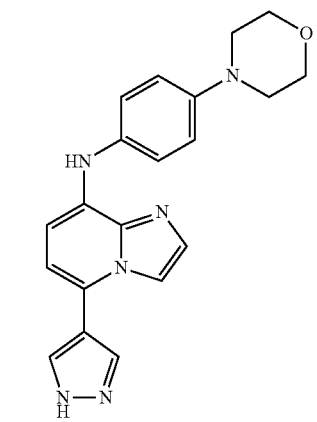

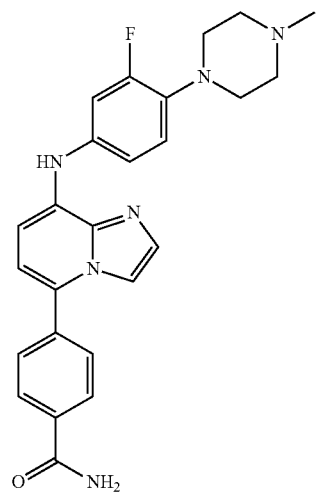
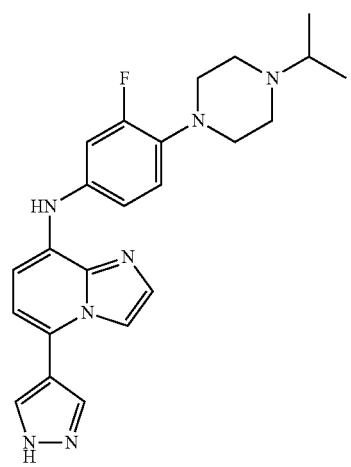
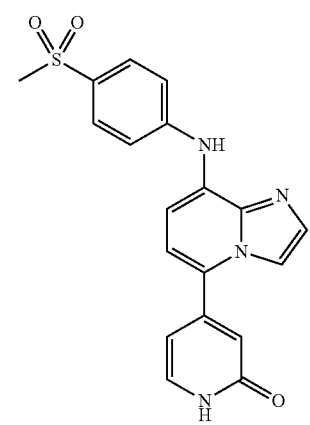
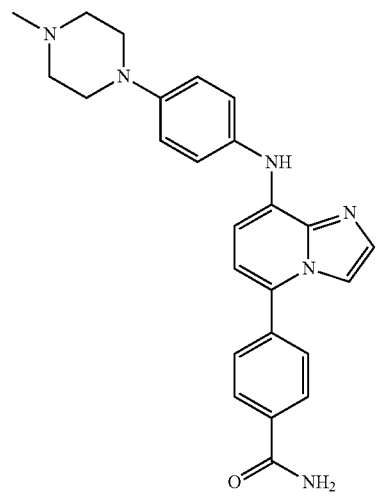
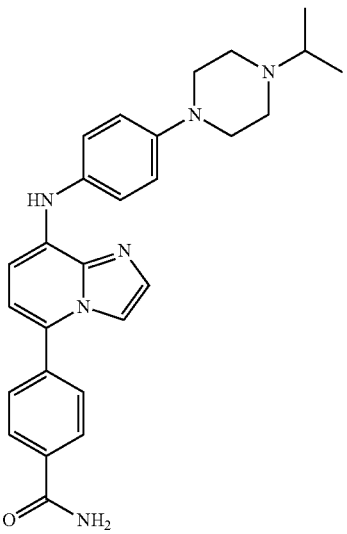
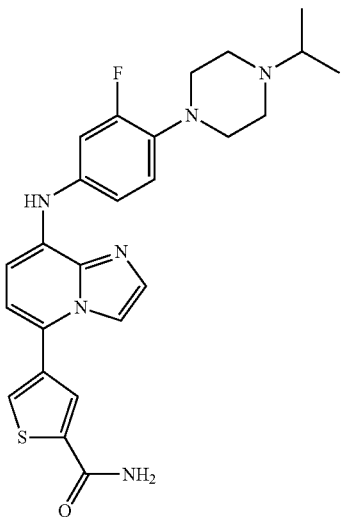

385
-continued
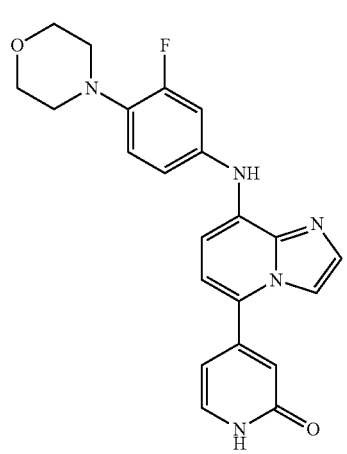
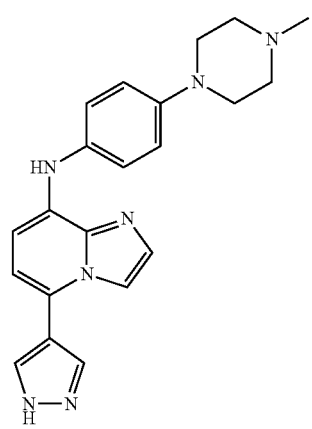
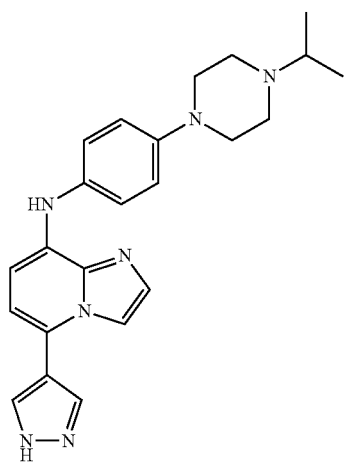
386
-continued
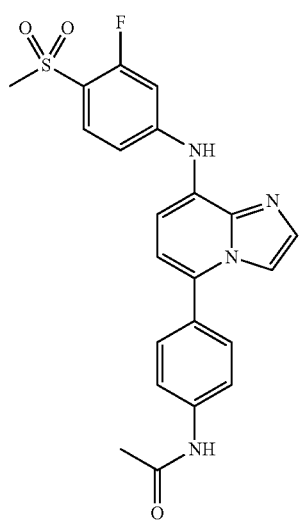
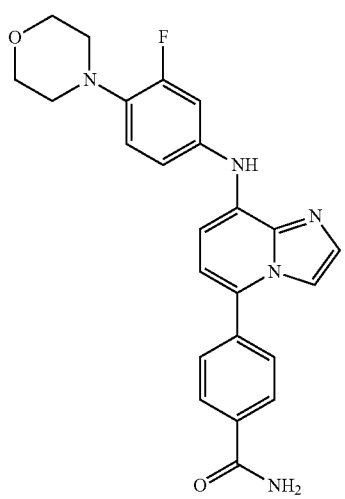
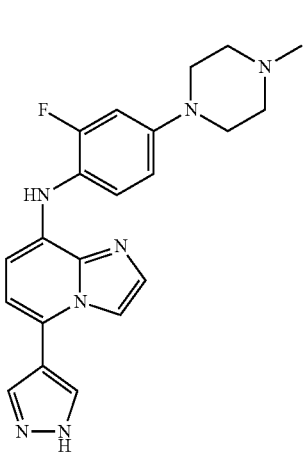

387
-continued
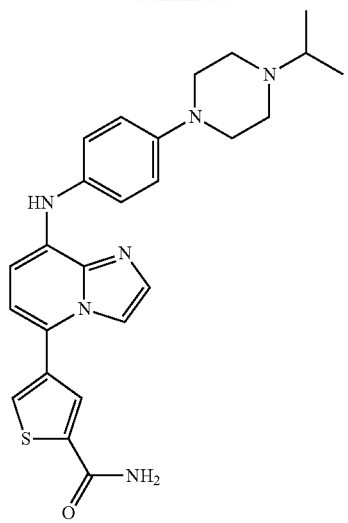
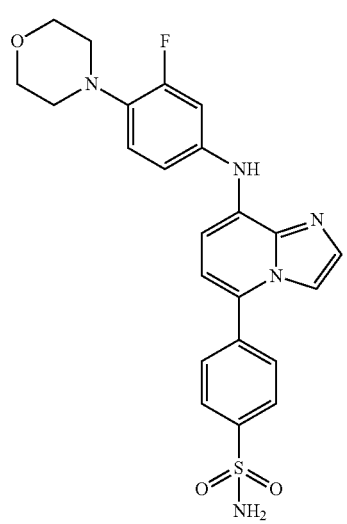
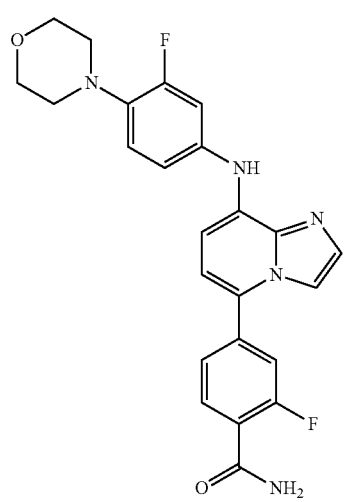
388
-continued
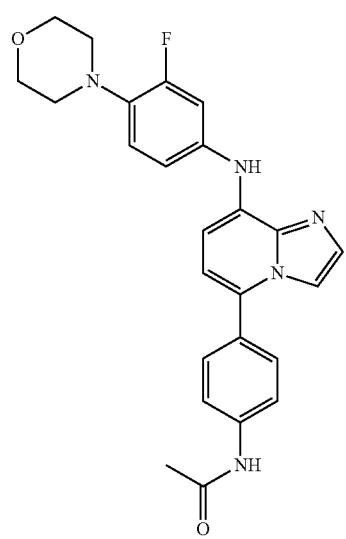
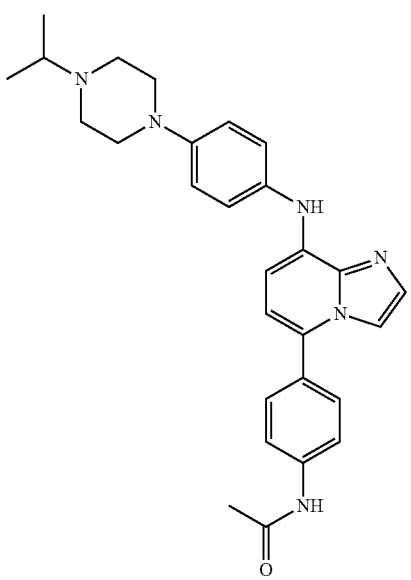
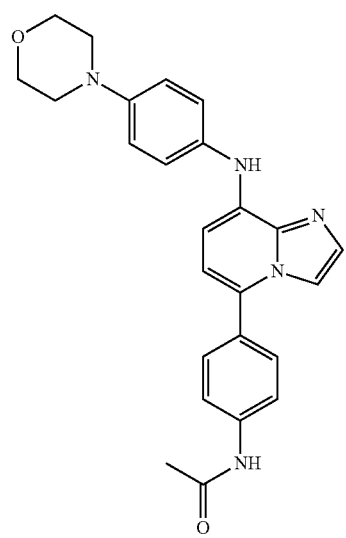

389
-continued
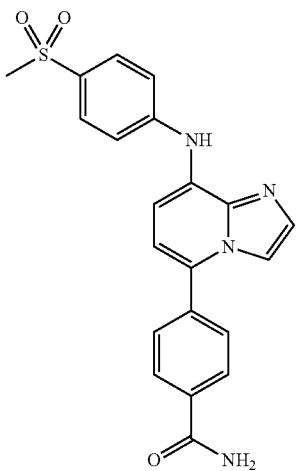
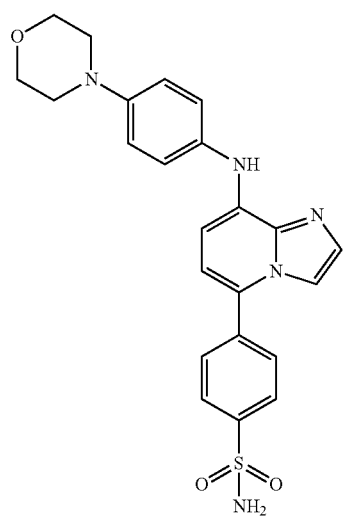
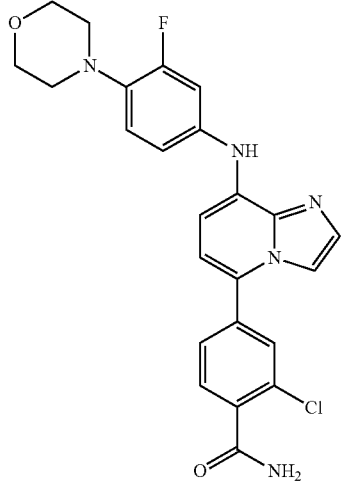
390
-continued
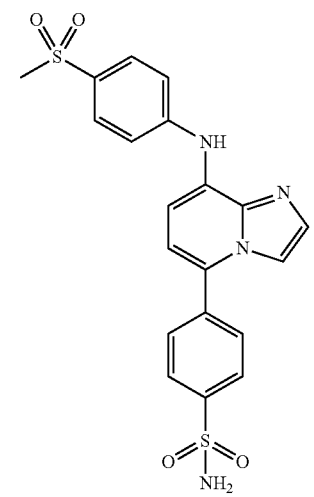
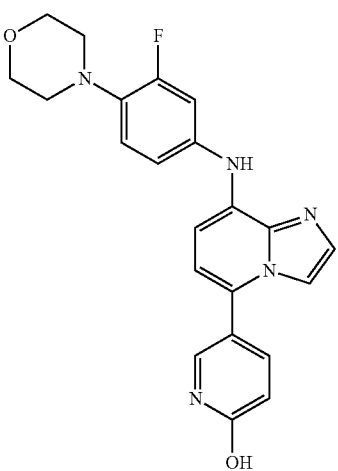

391
-continued
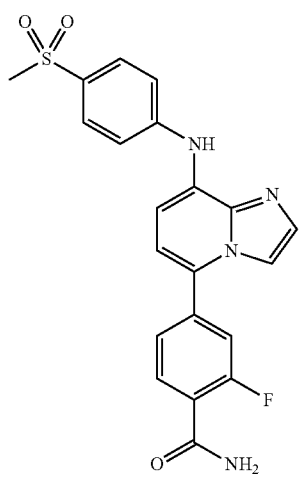
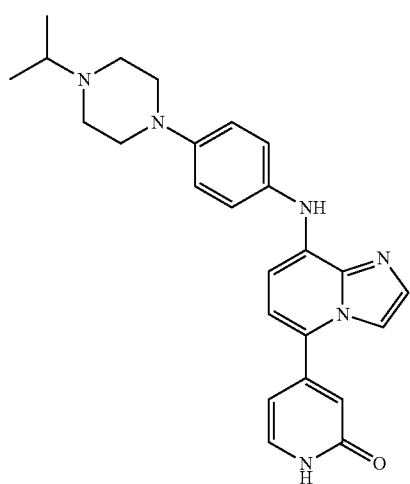
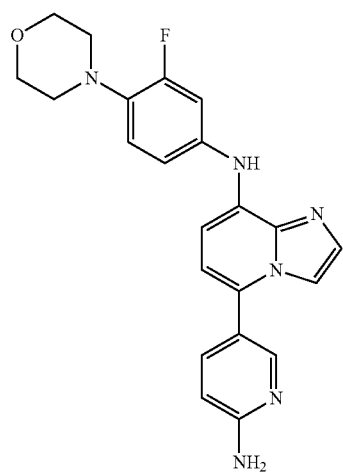
392
-continued
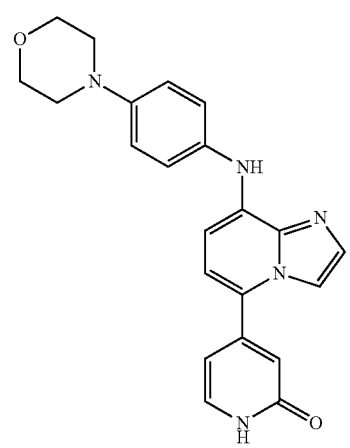
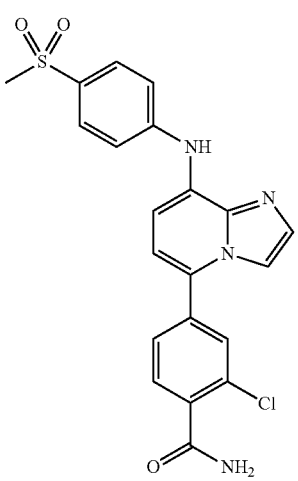

393
-continued
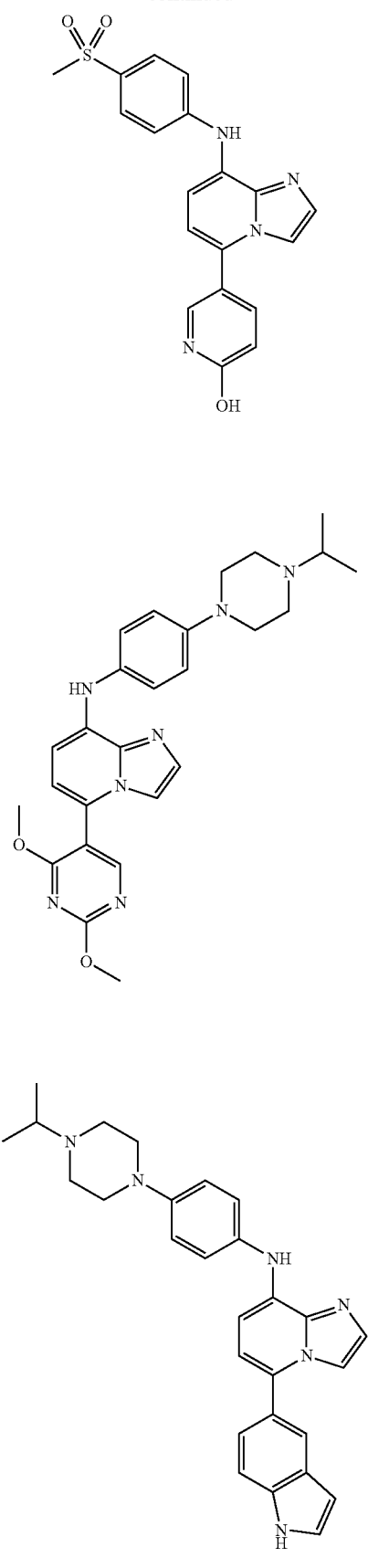
394
-continued
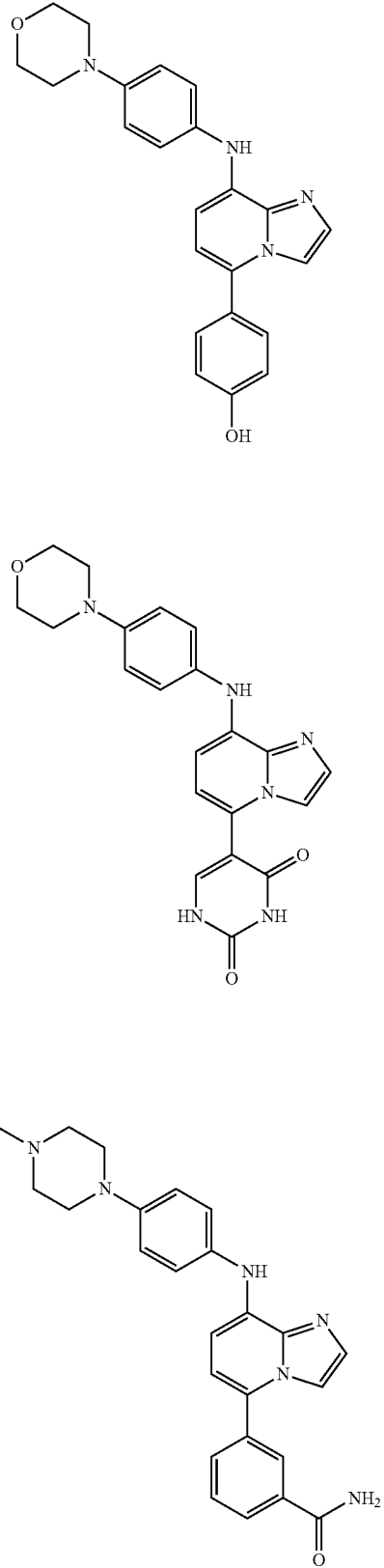

395
-continued
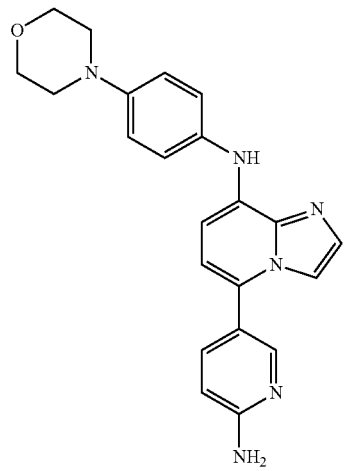
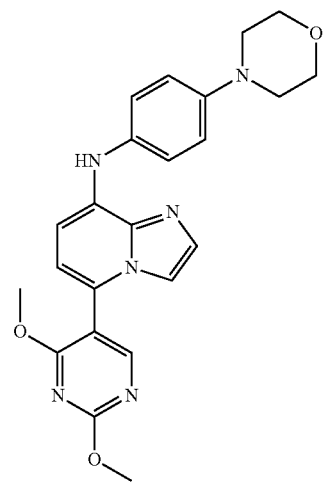
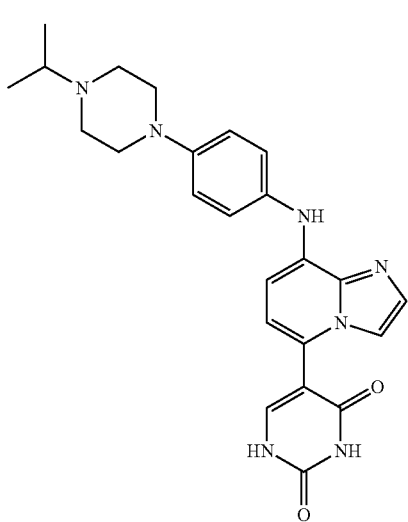
396
-continued
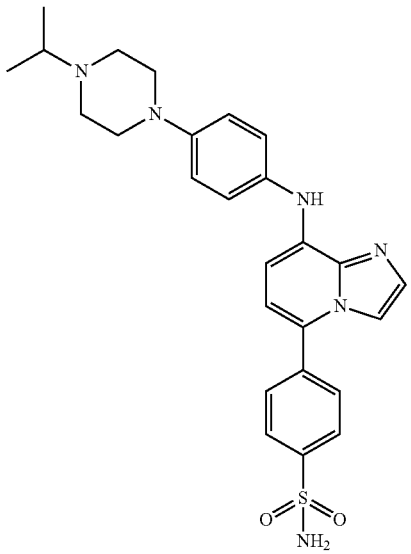
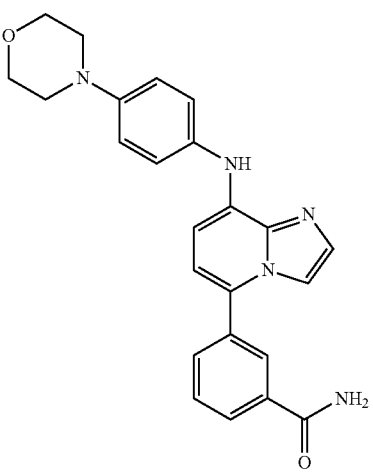

397
-continued
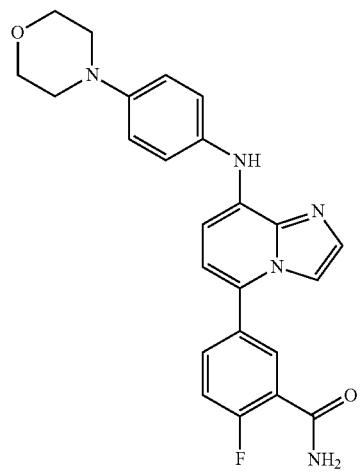
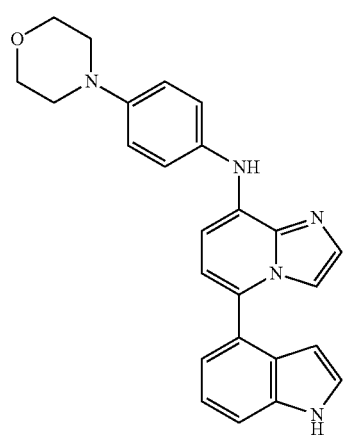
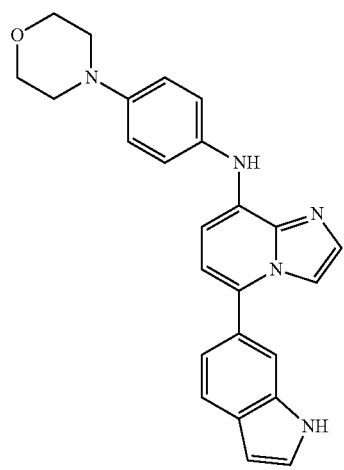
398
-continued
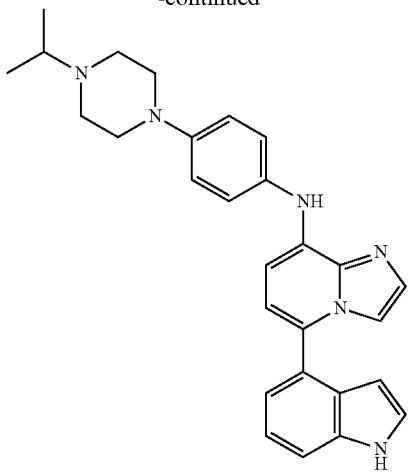
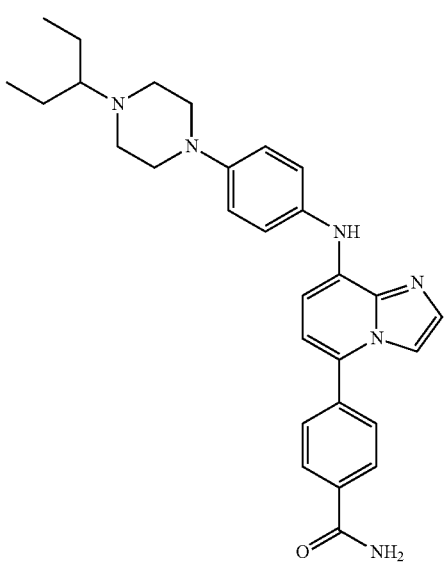
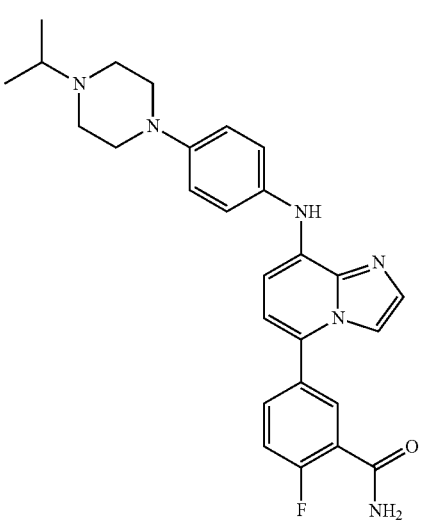

399
-continued
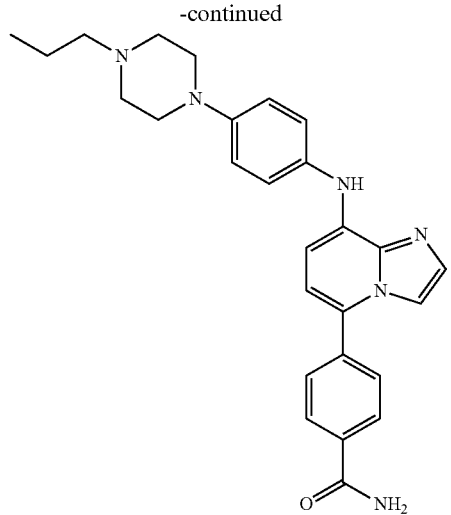
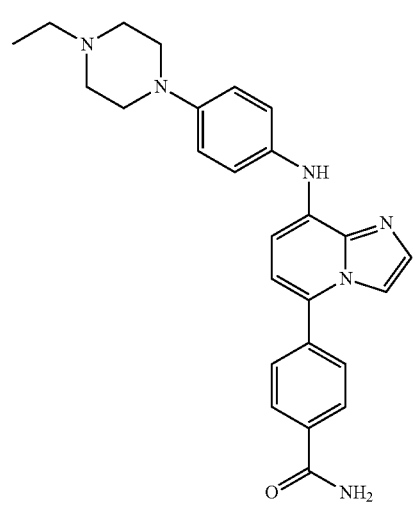
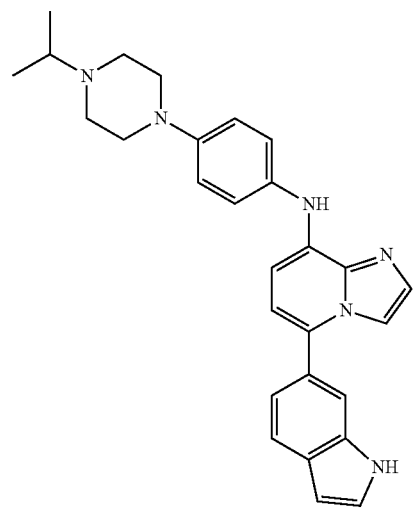
400
-continued
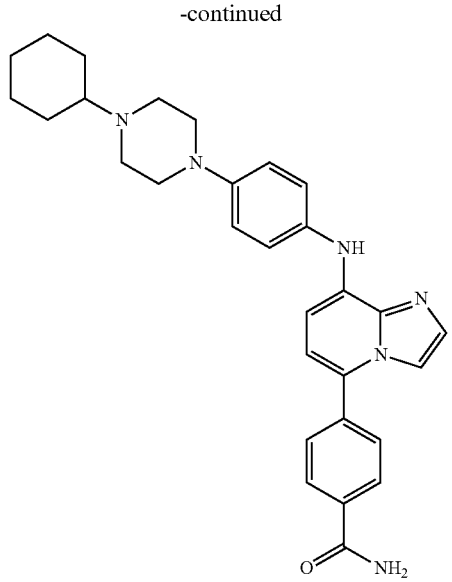
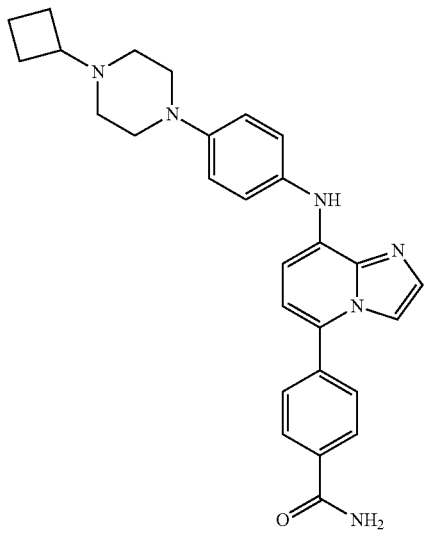
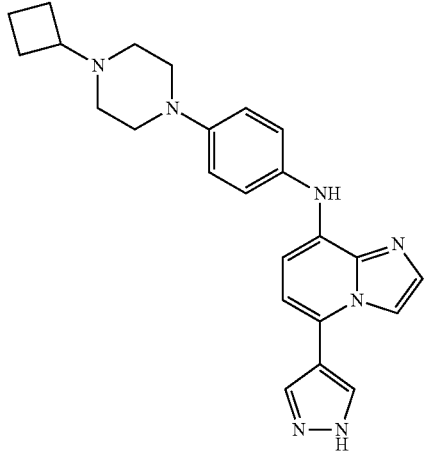

401
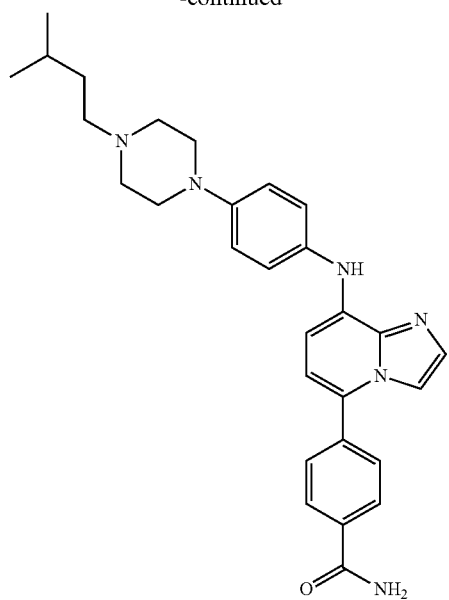
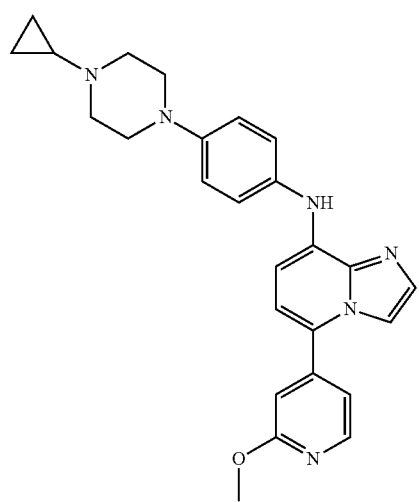
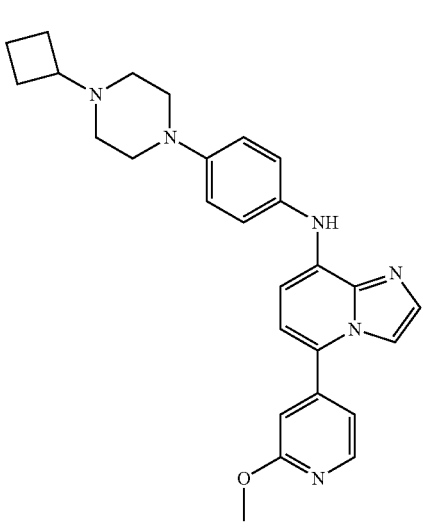
402
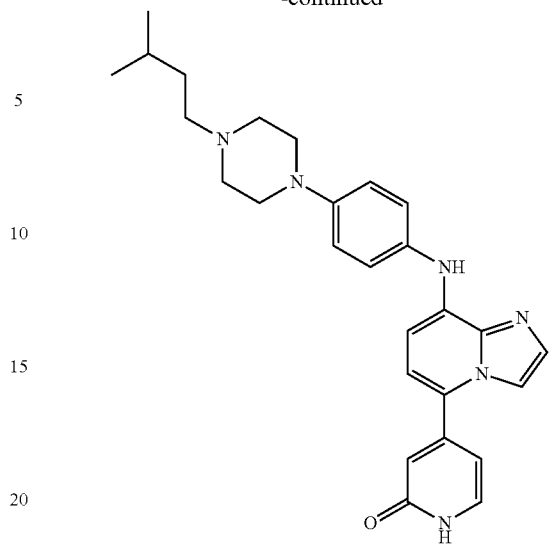
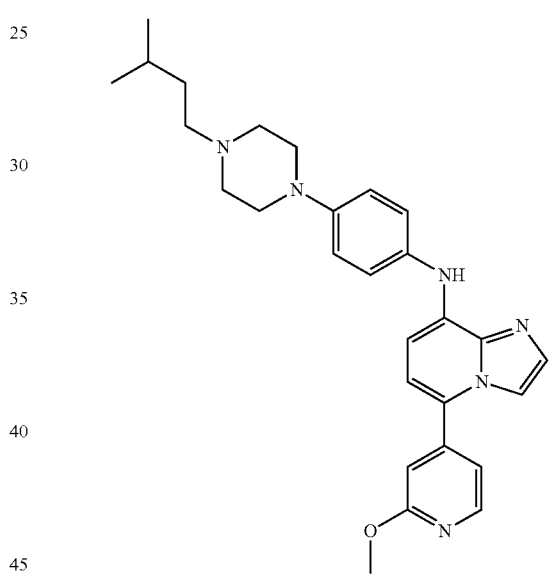
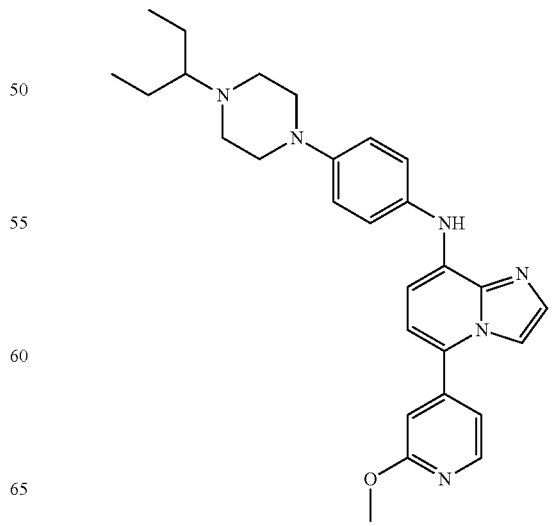

403
-continued
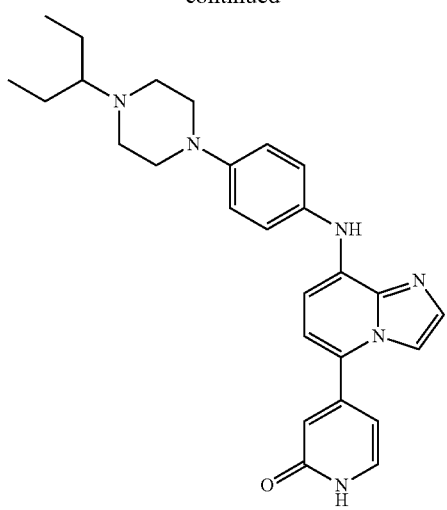
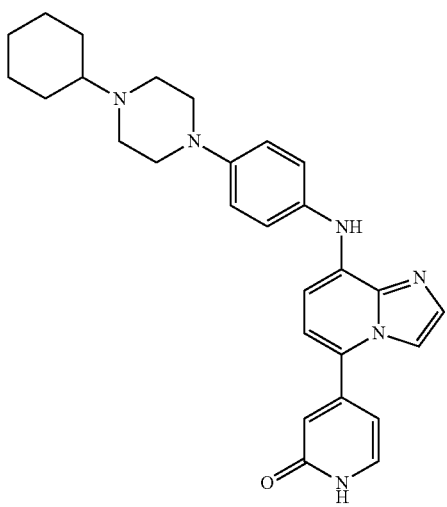
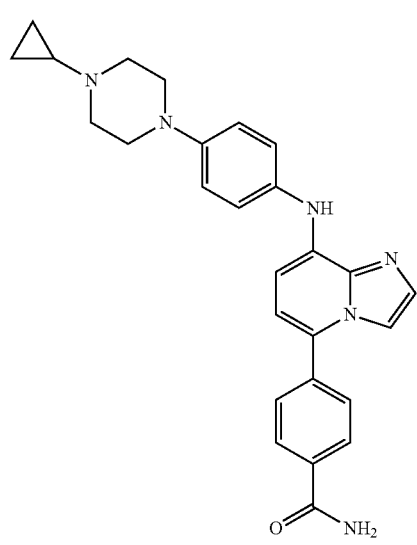
404
-continued
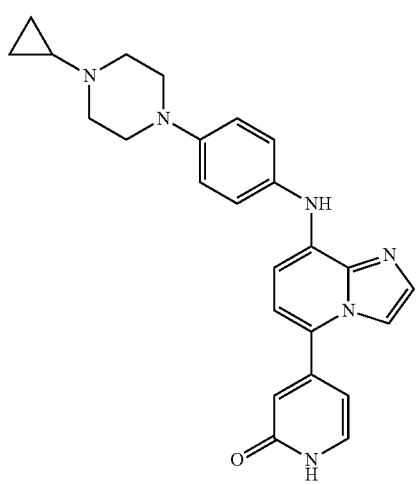
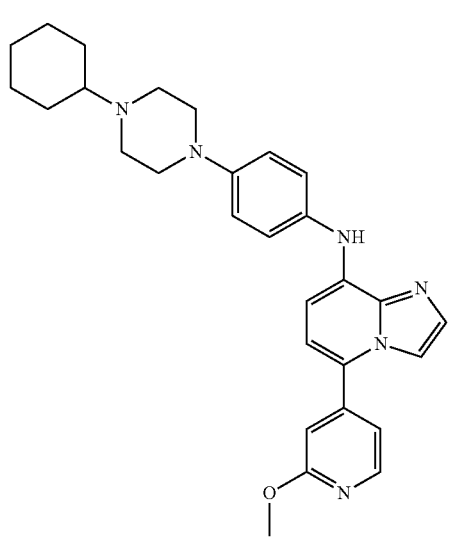
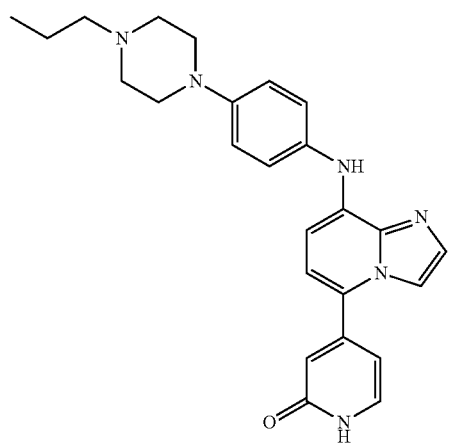

405
-continued
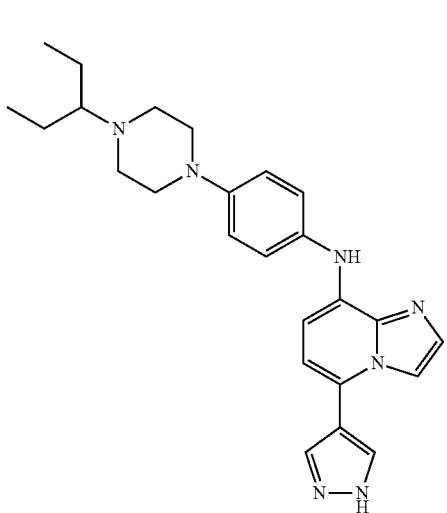
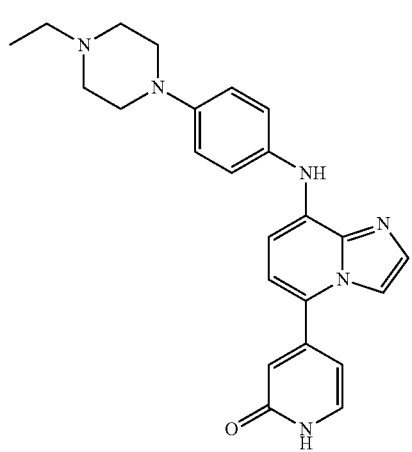
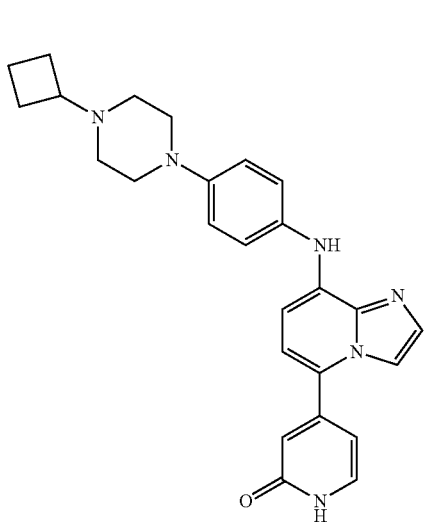
406
-continued
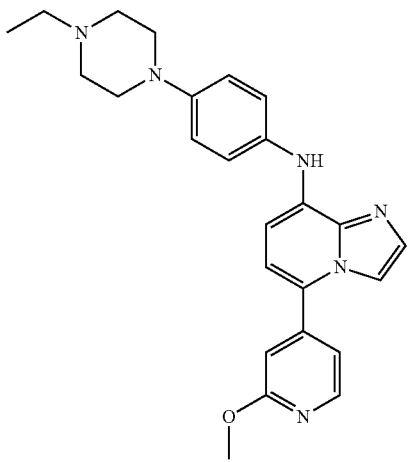
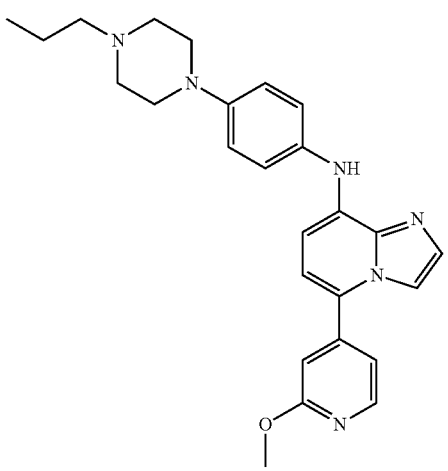
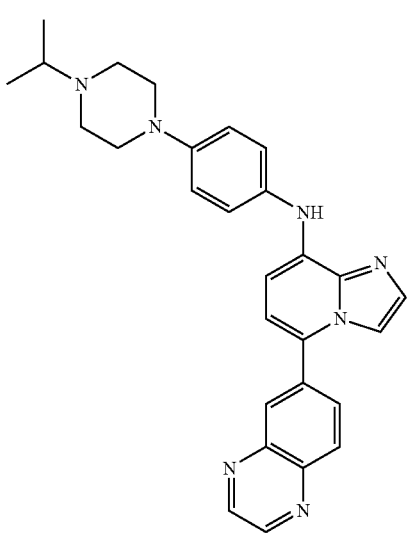

407
-continued
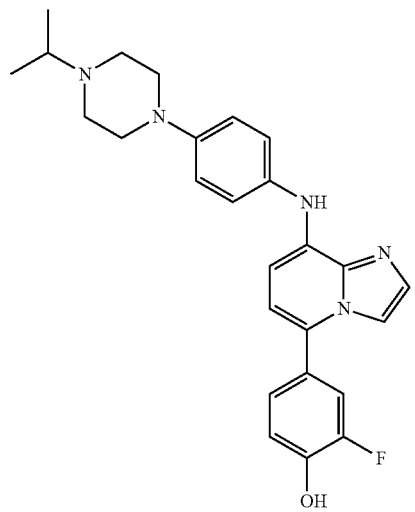
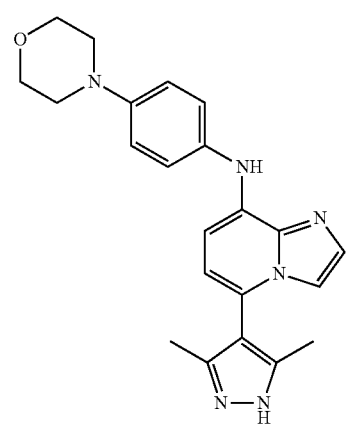
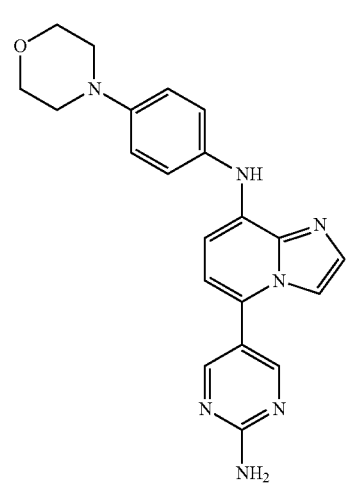
408
-continued
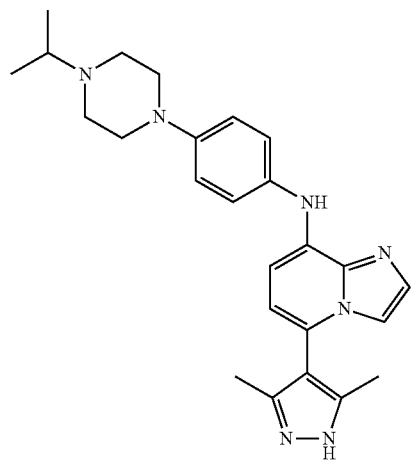
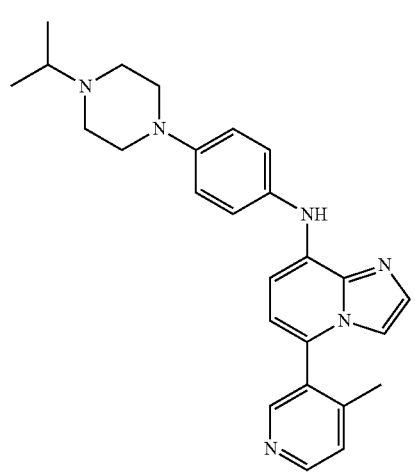
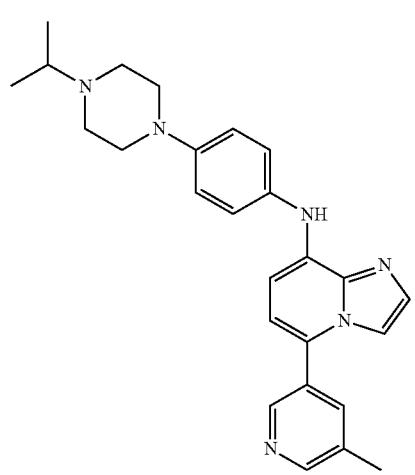

409
-continued
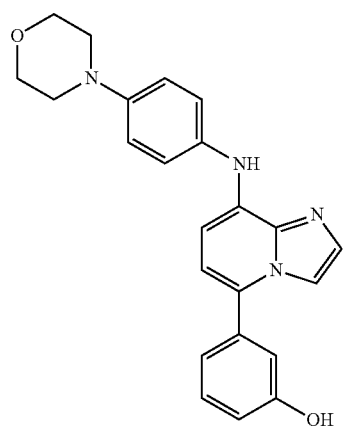
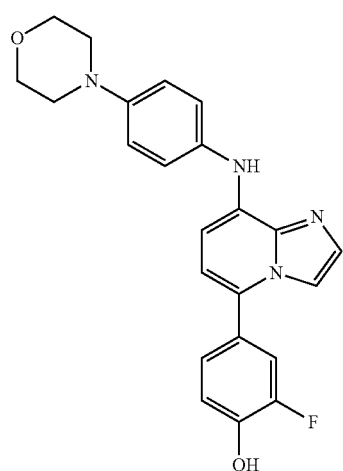
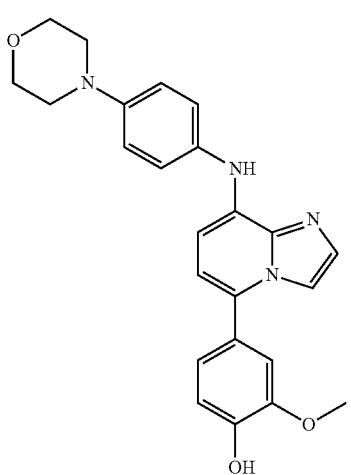
410
-continued
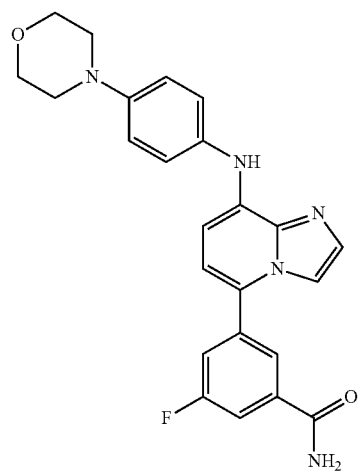
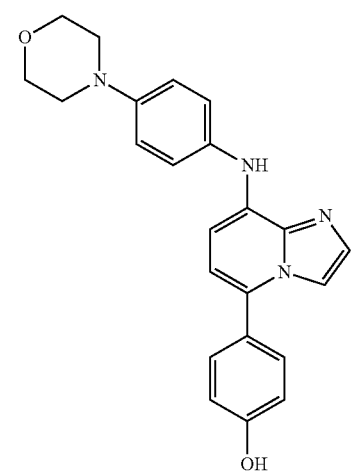
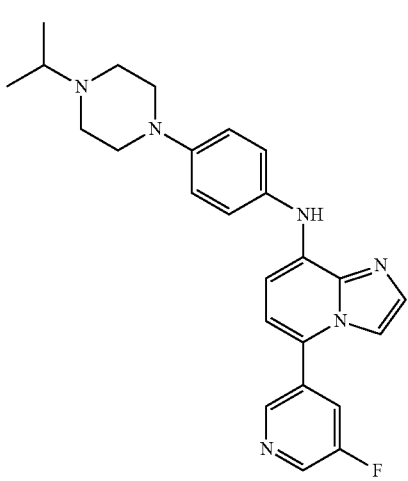

411
-continued
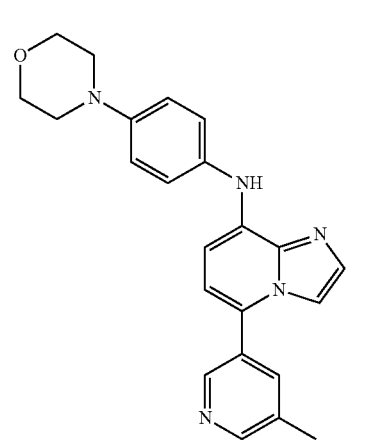
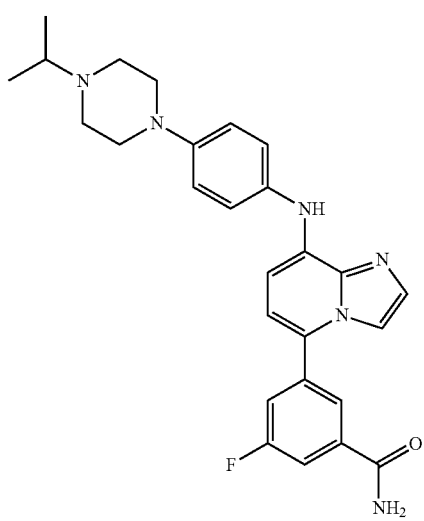
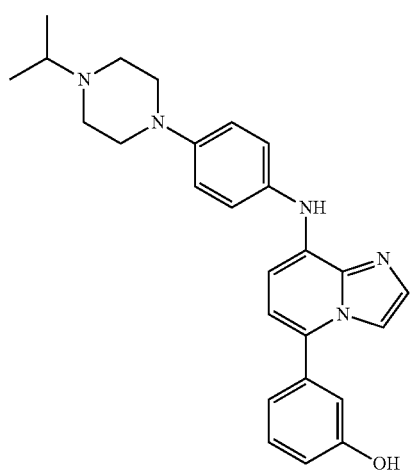
412
-continued
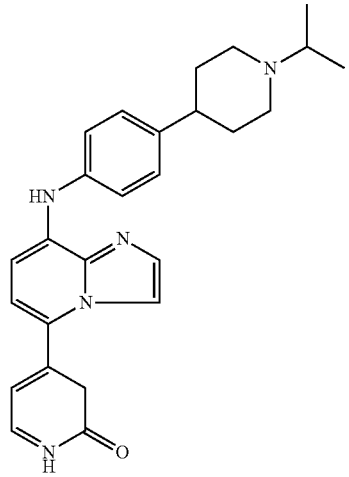
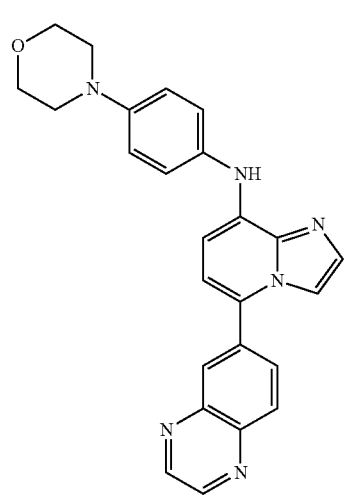
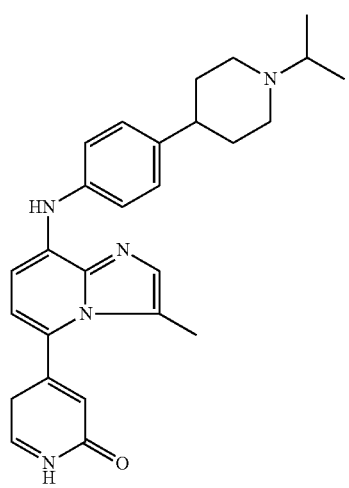

413
-continued
414
-continued
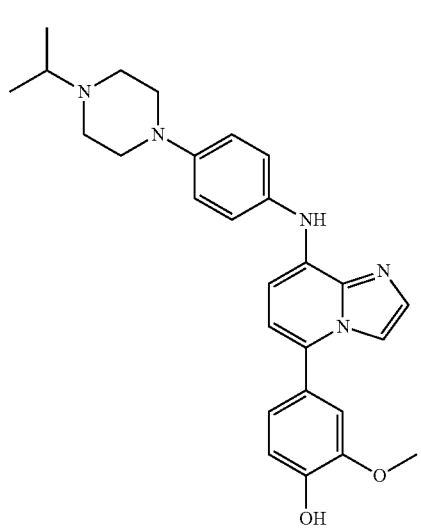
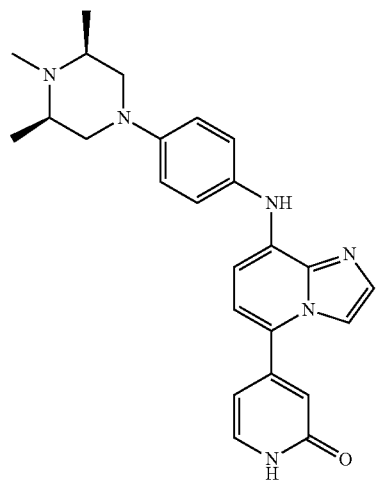
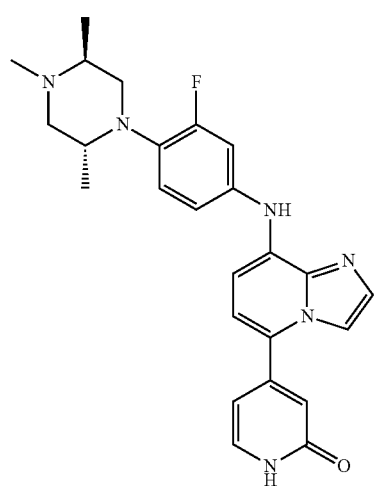
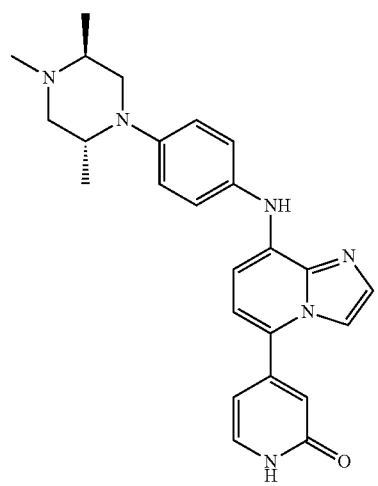
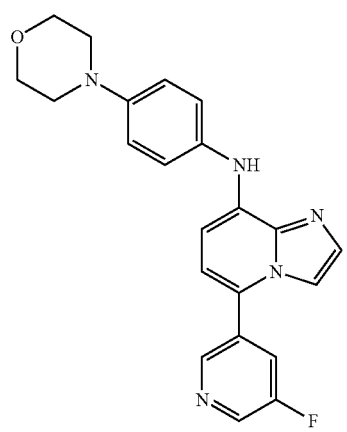
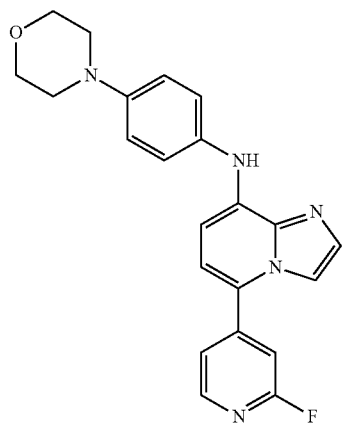

415
-continued
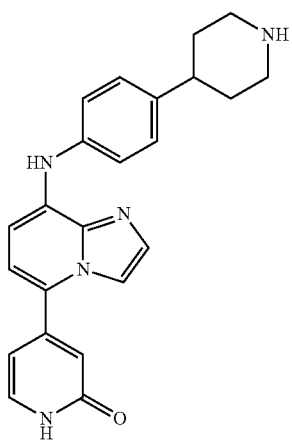
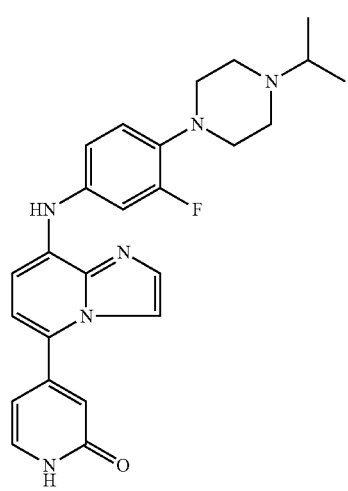
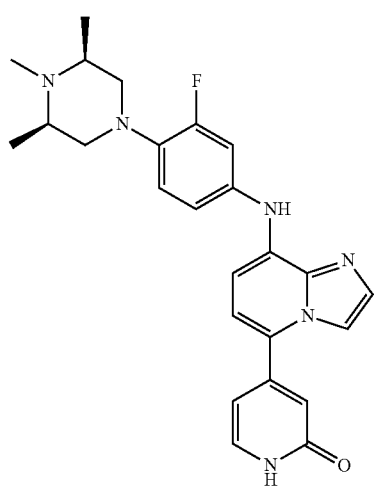
416
-continued
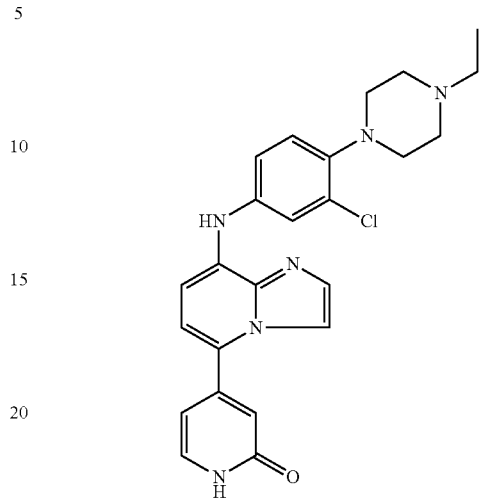
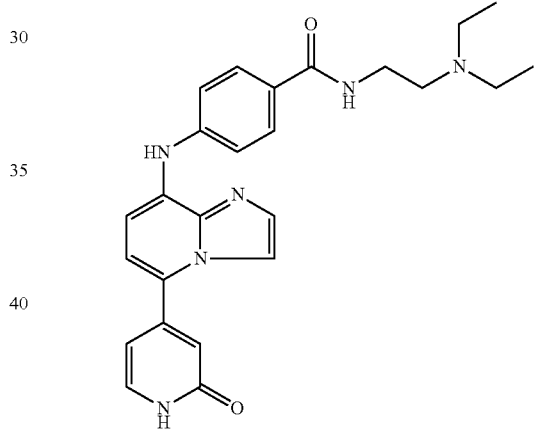
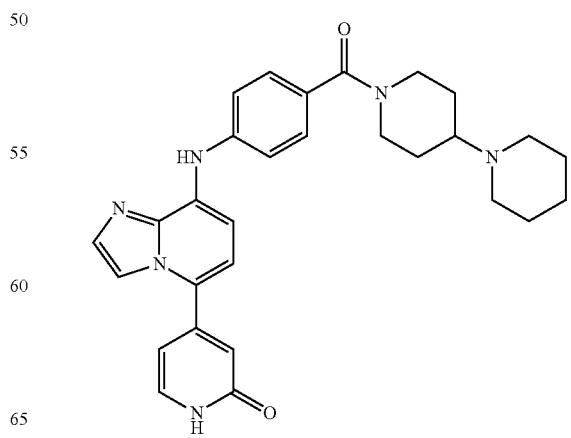

417
-continued
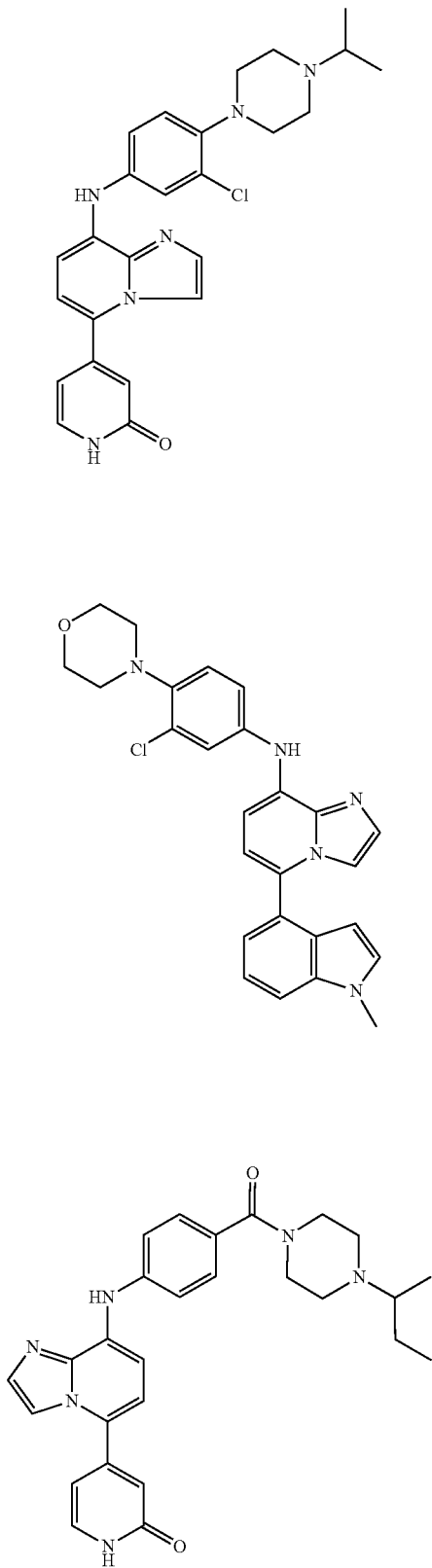
418
-continued
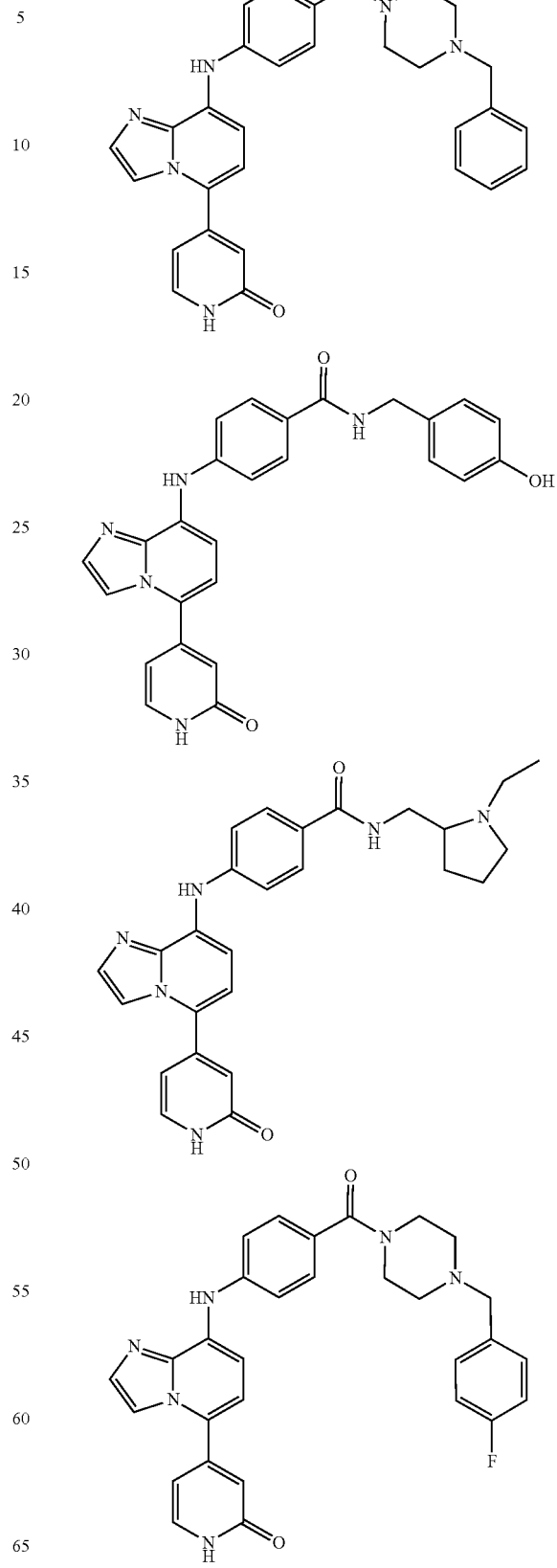

419
-continued
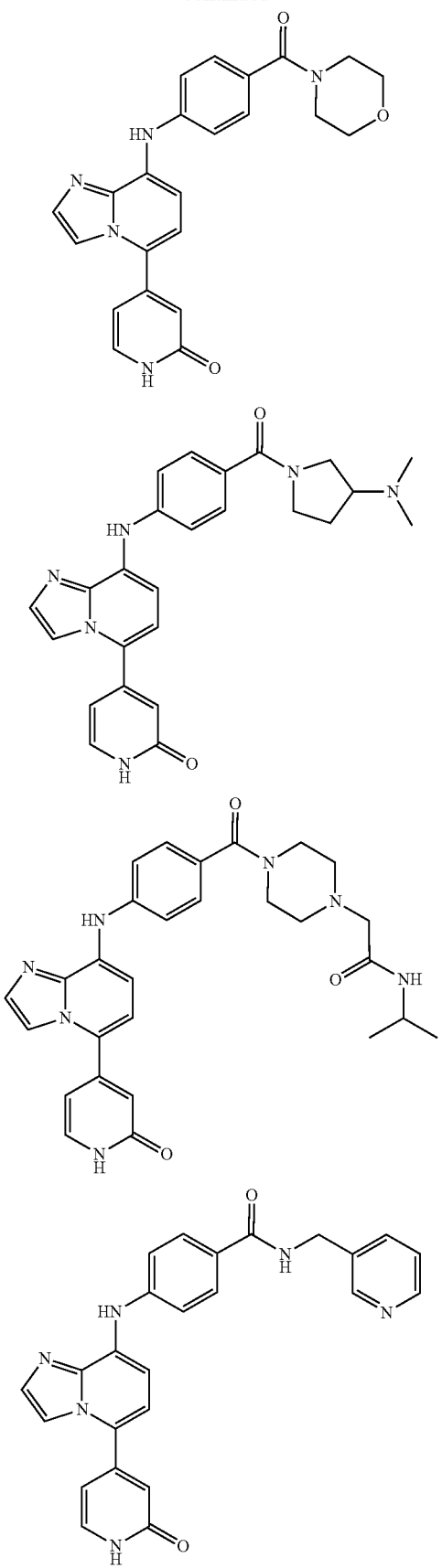
420
-continued
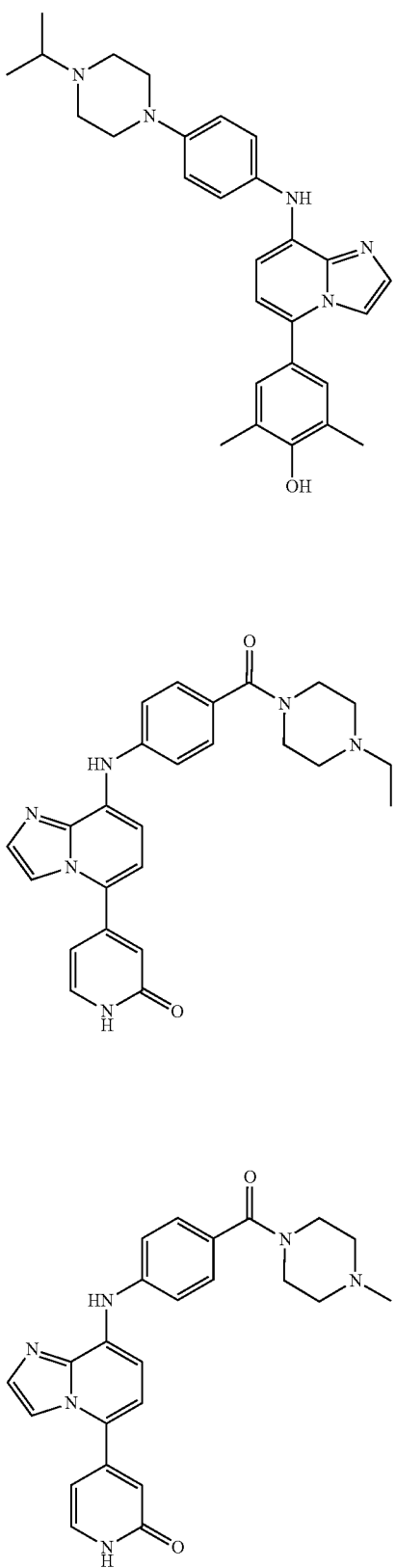

421
-continued
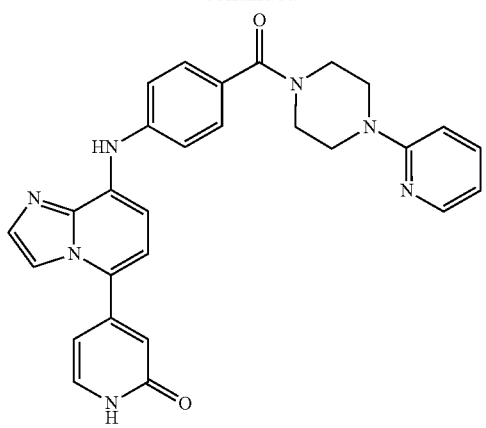
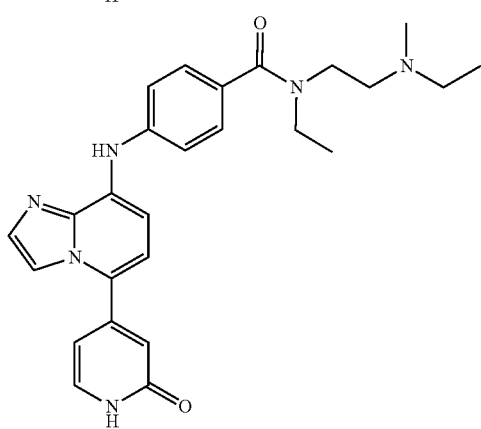
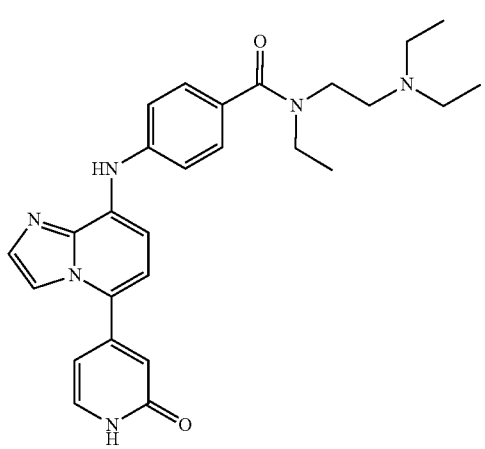
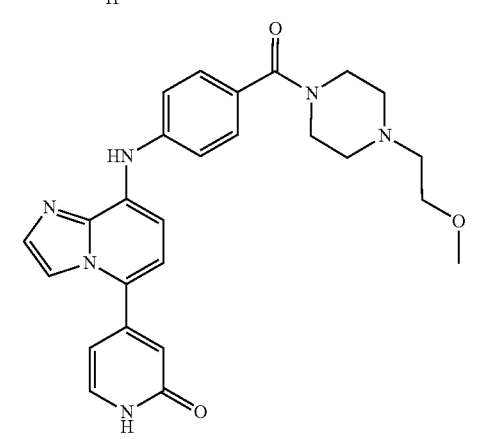
422
-continued
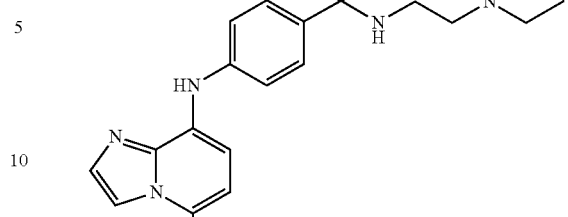
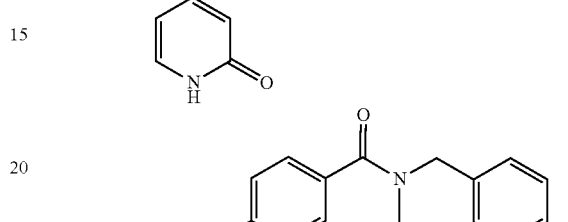
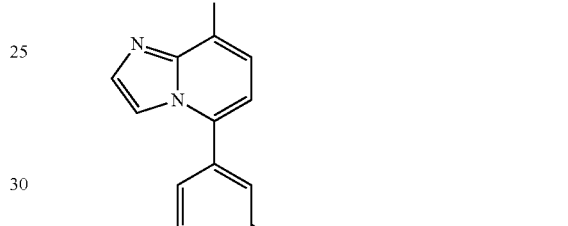
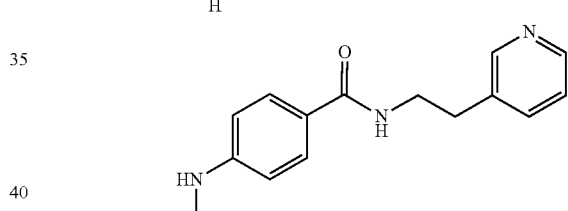
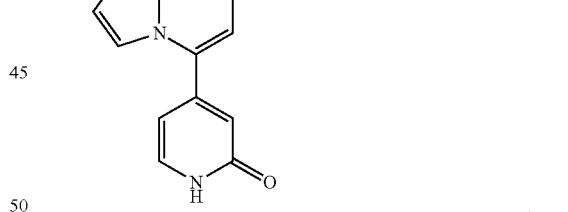
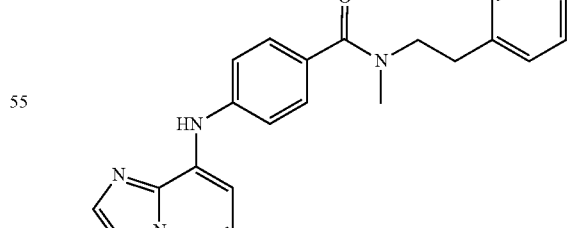

423
-continued
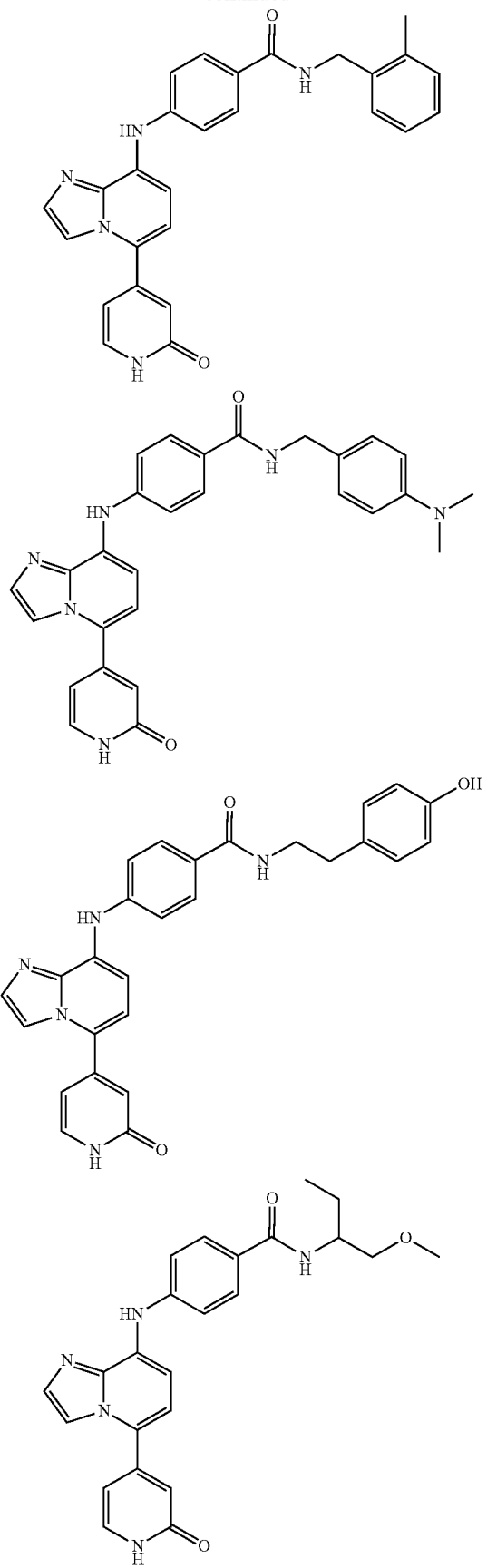
424
-continued
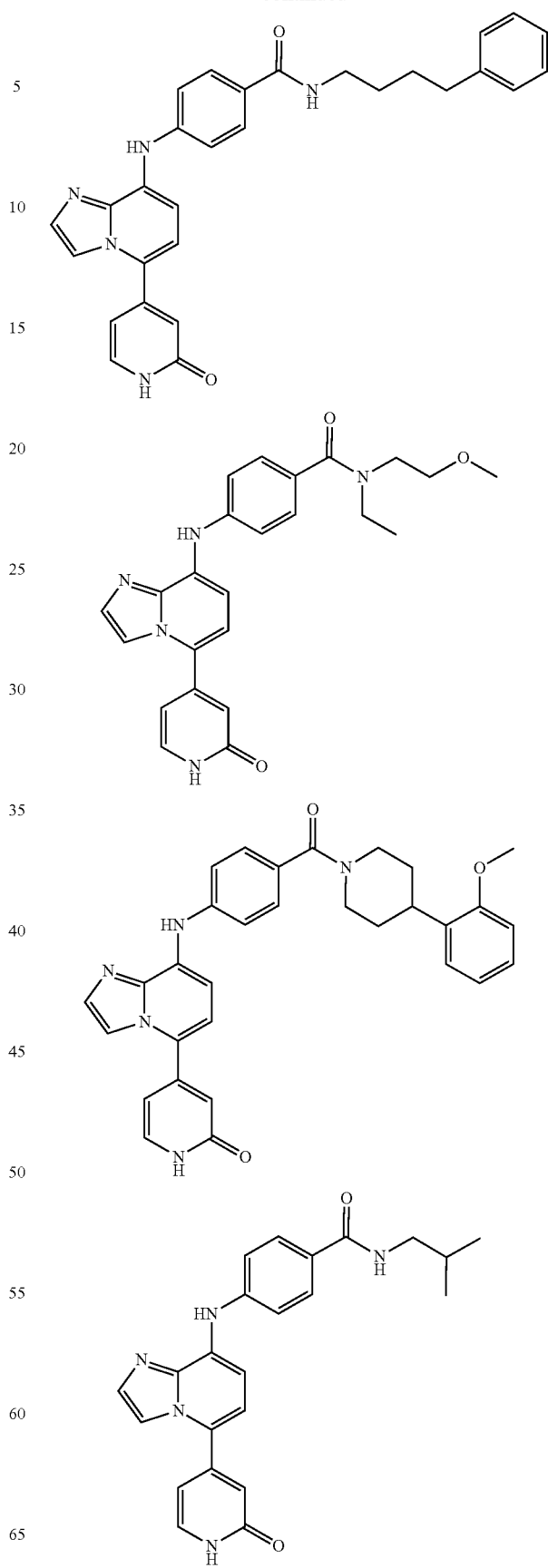

425
-continued
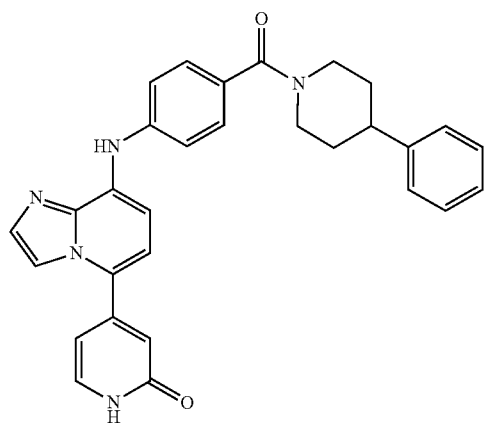
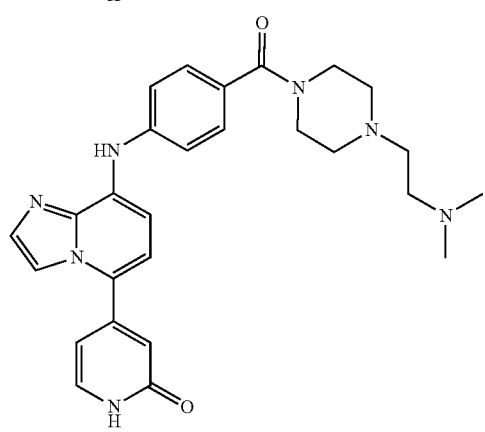
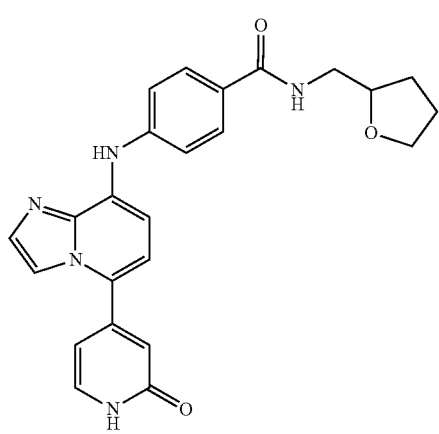
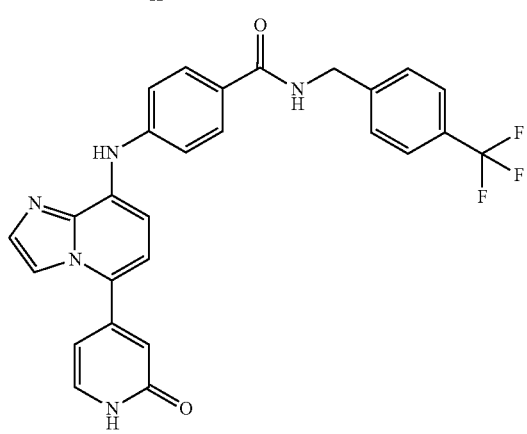
426
-continued
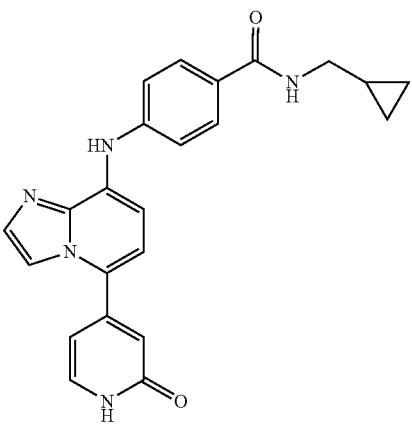
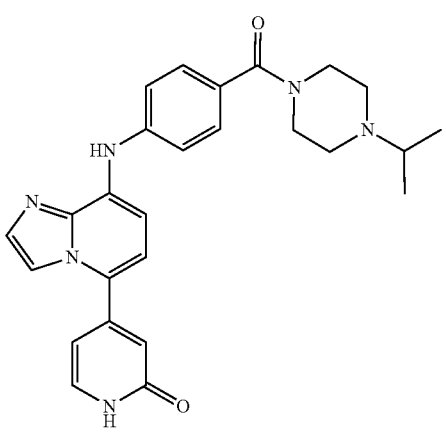
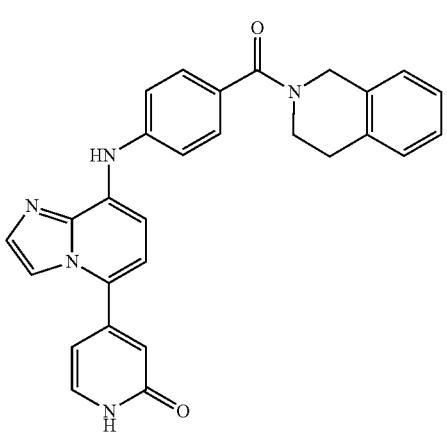
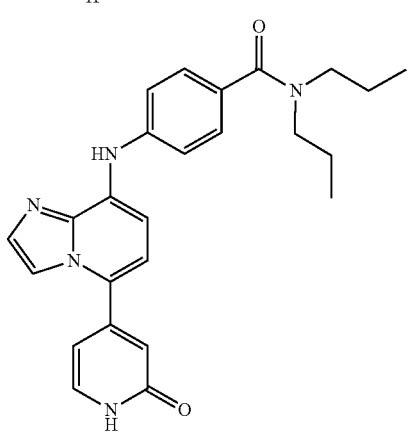

427
-continued
428
-continued
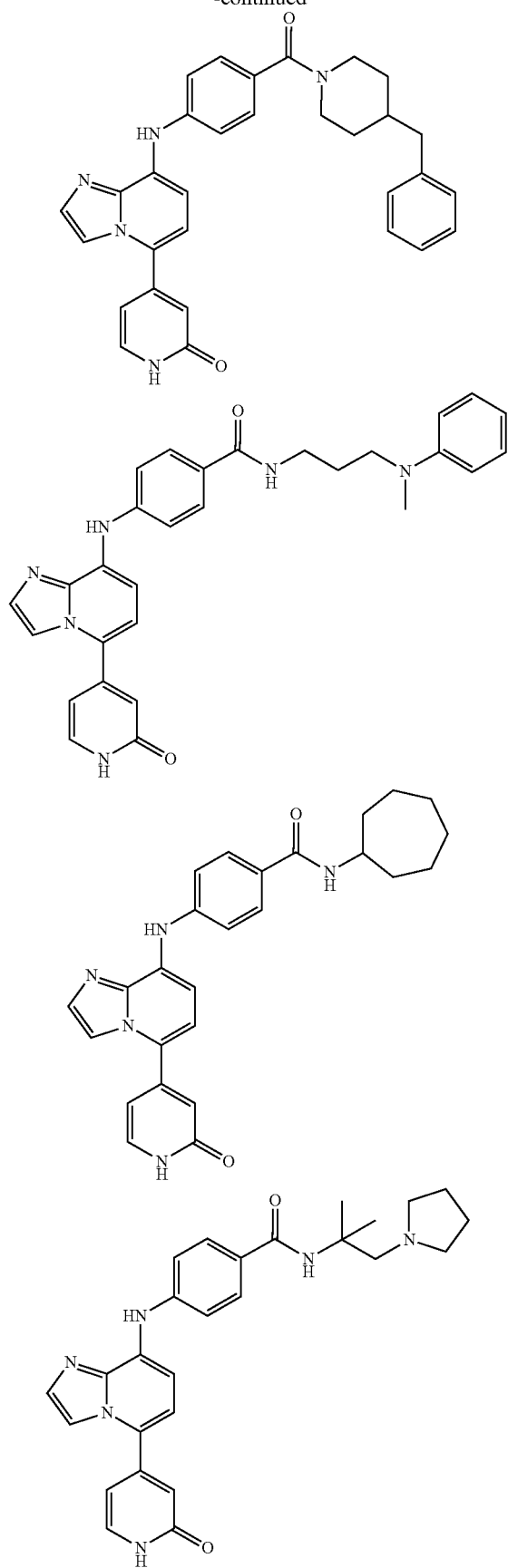
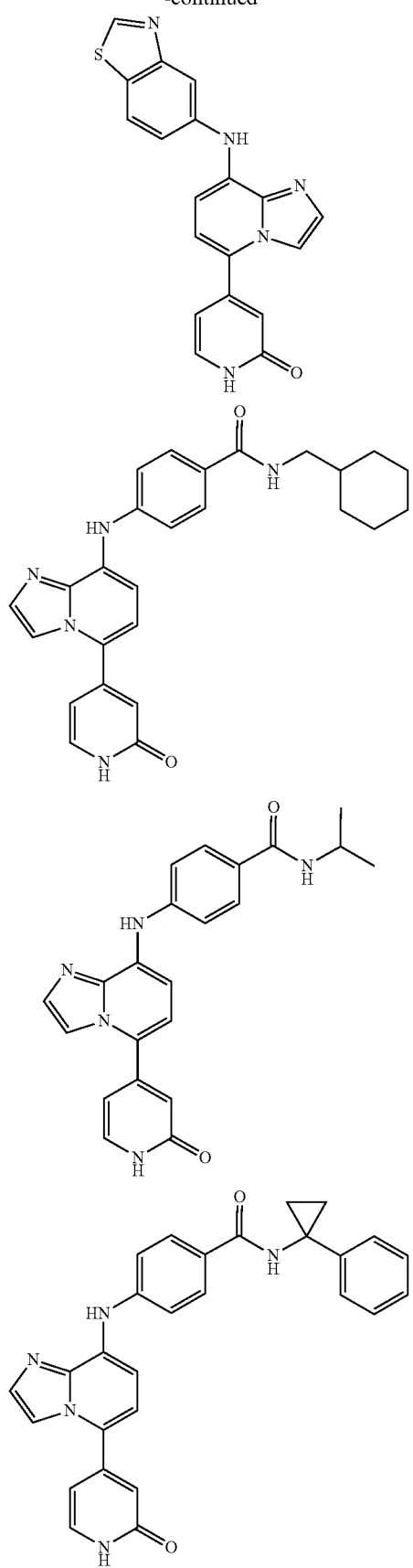

429
-continued
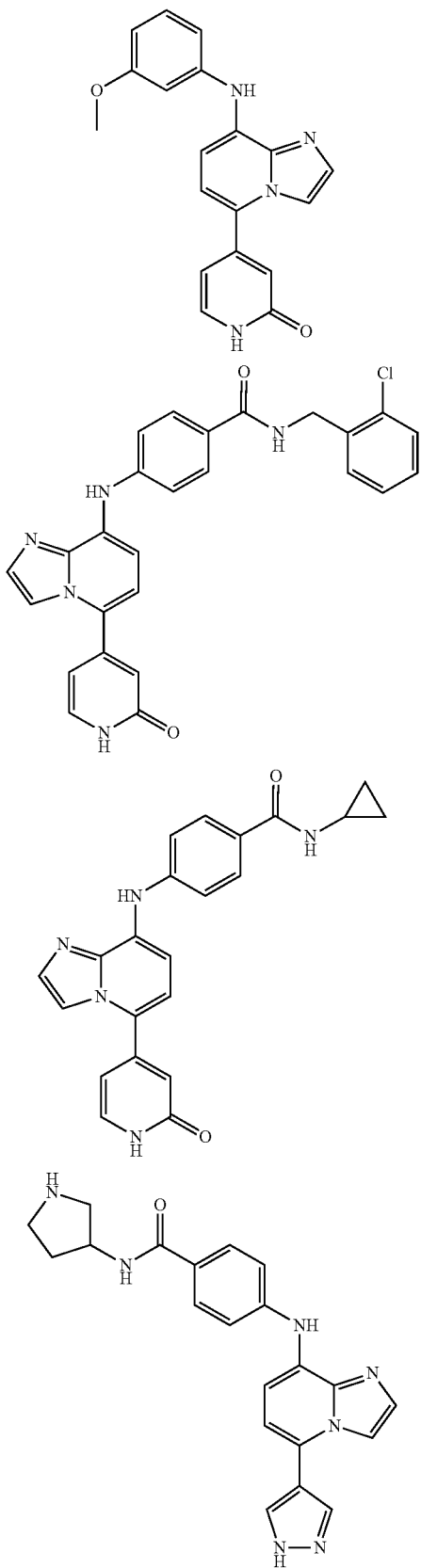
430
-continued
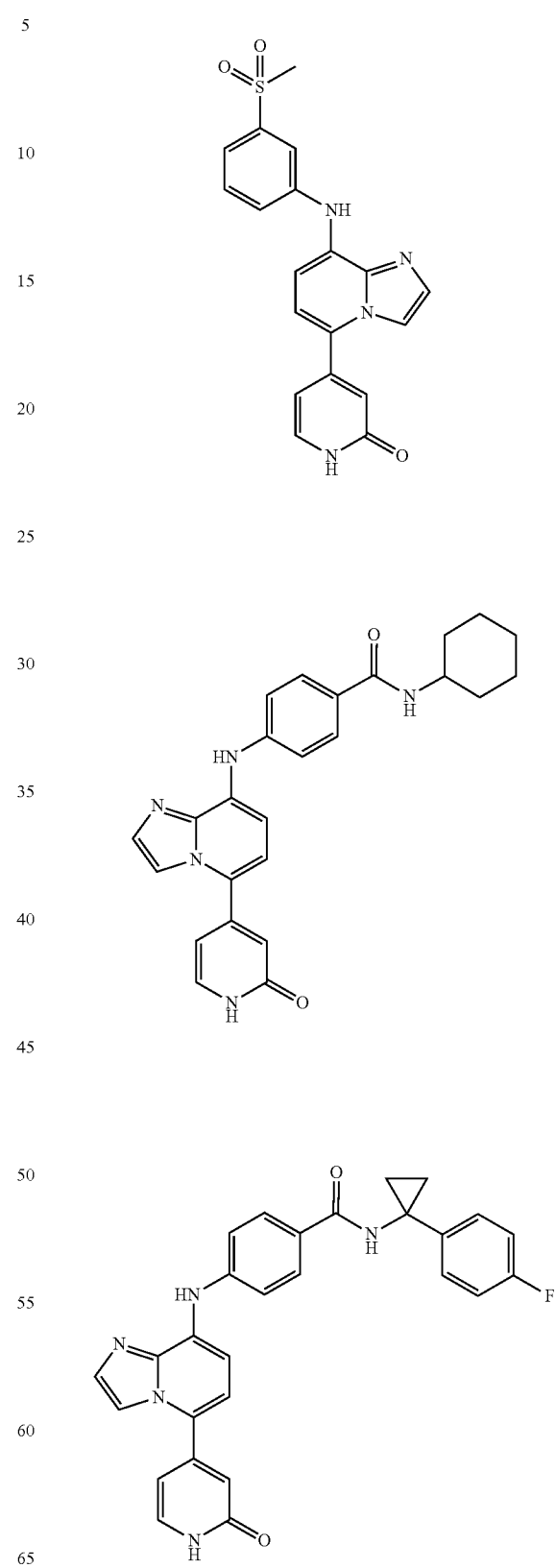

431
-continued
432
-continued
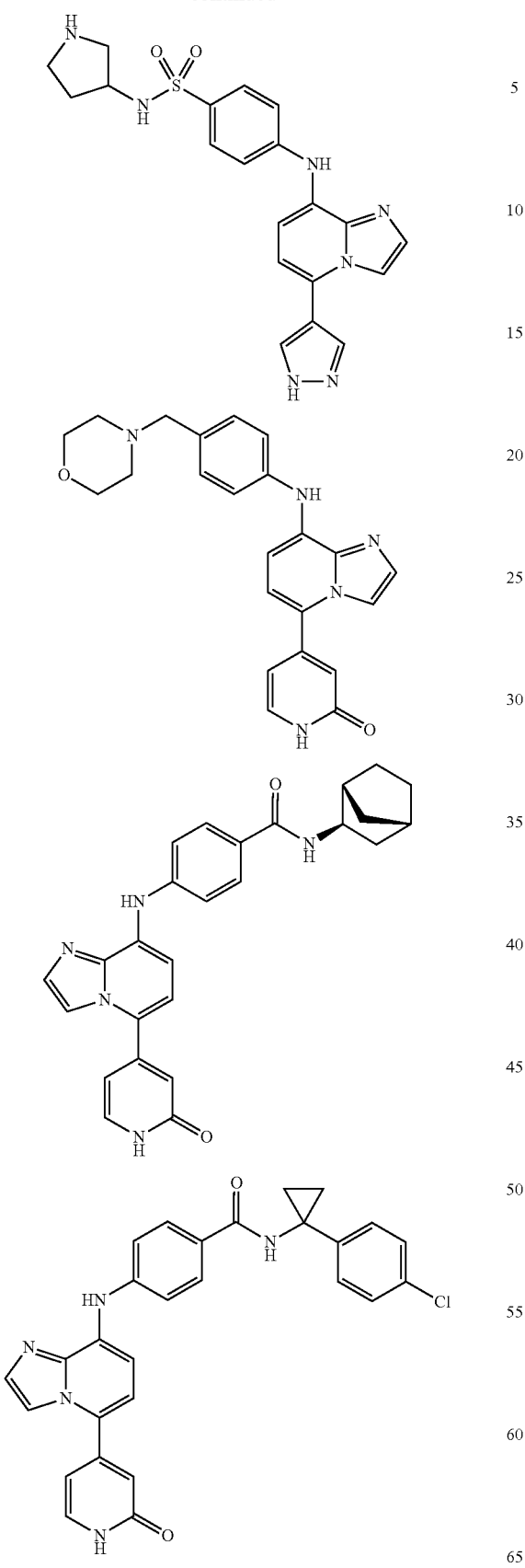
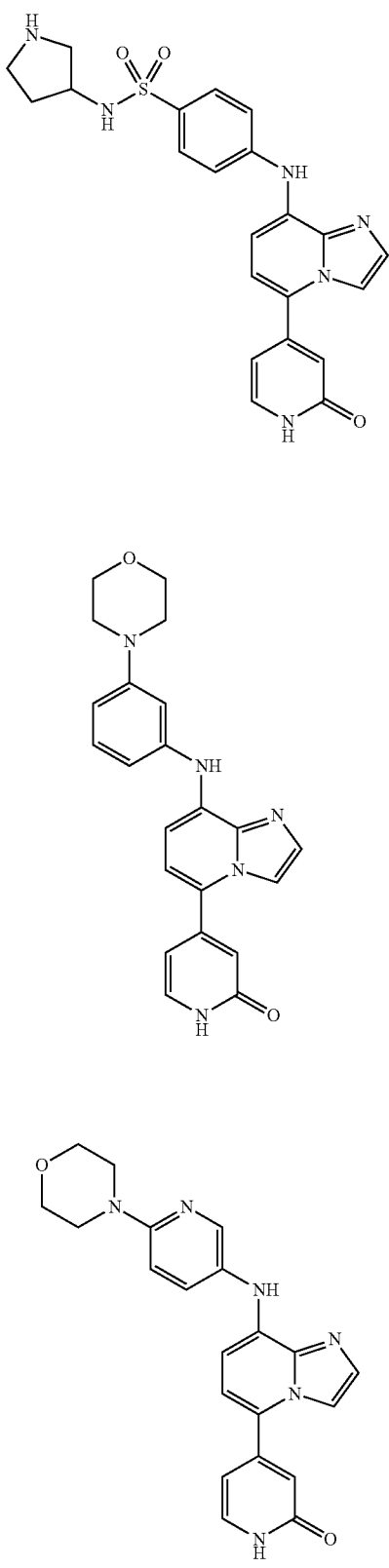

433
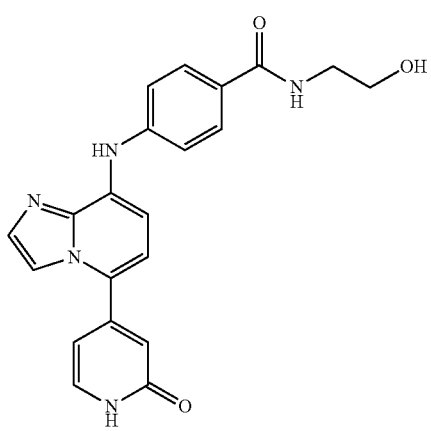
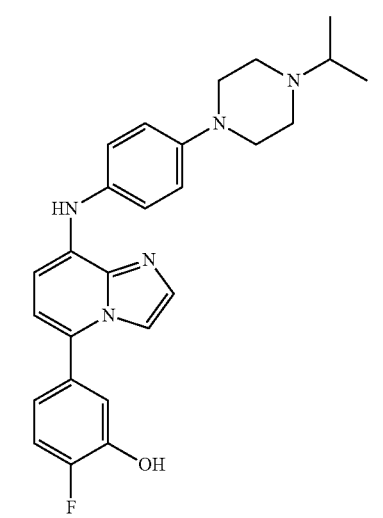
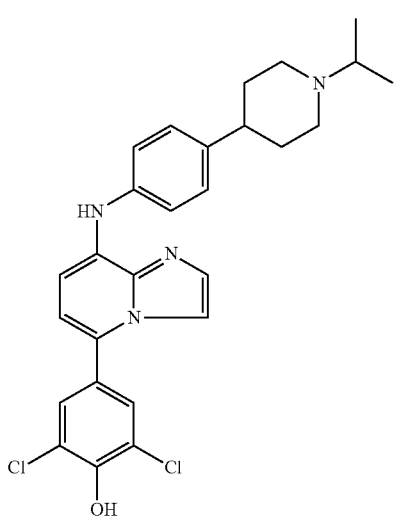
434
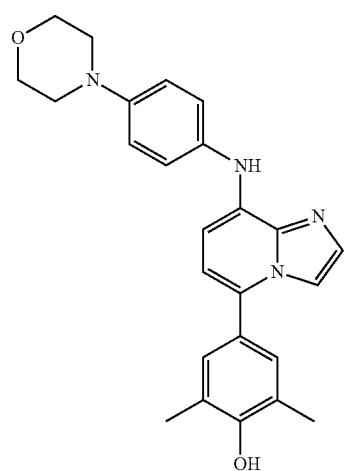
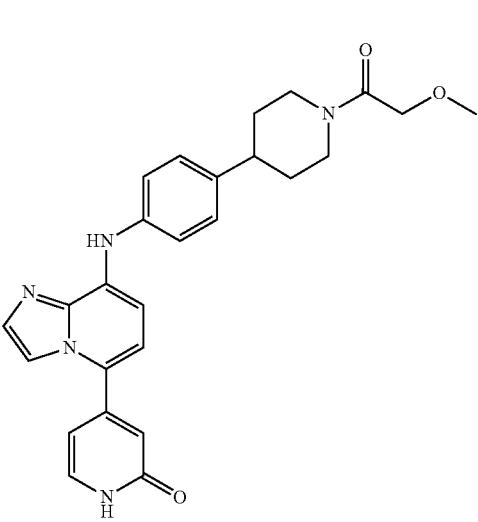

435
-continued
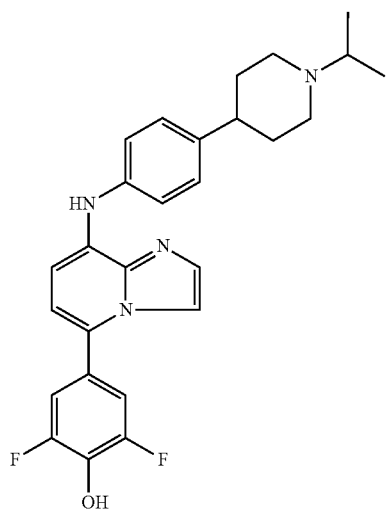
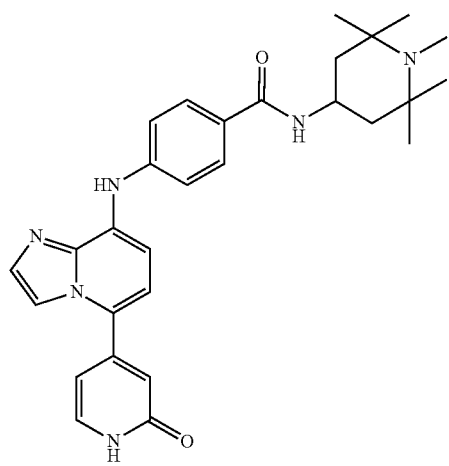
436
-continued
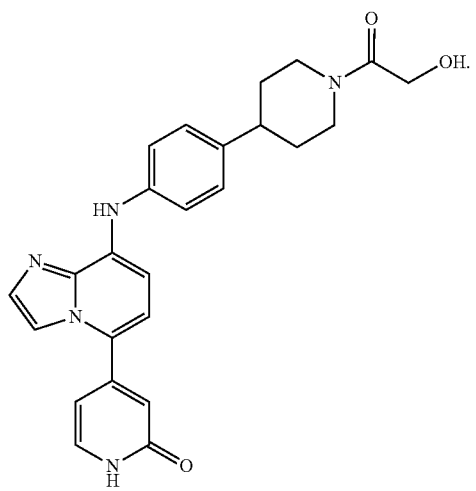
23. A compound selected from any one of:
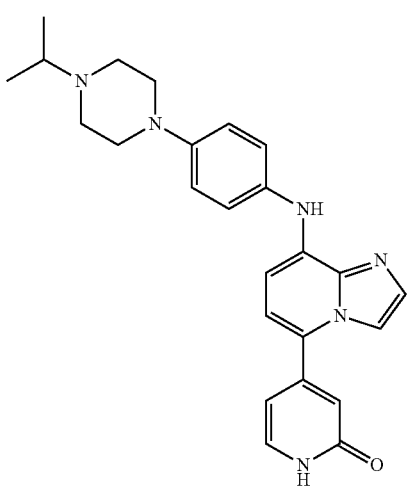
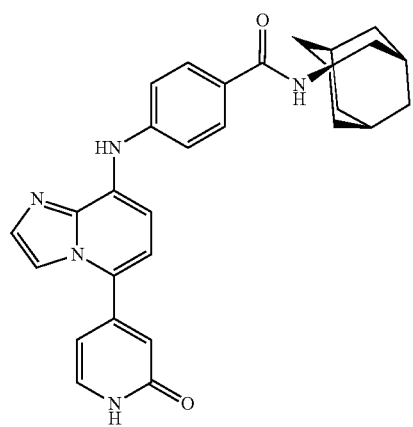
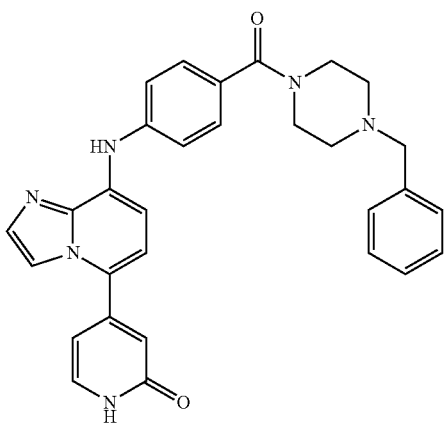

437
-continued
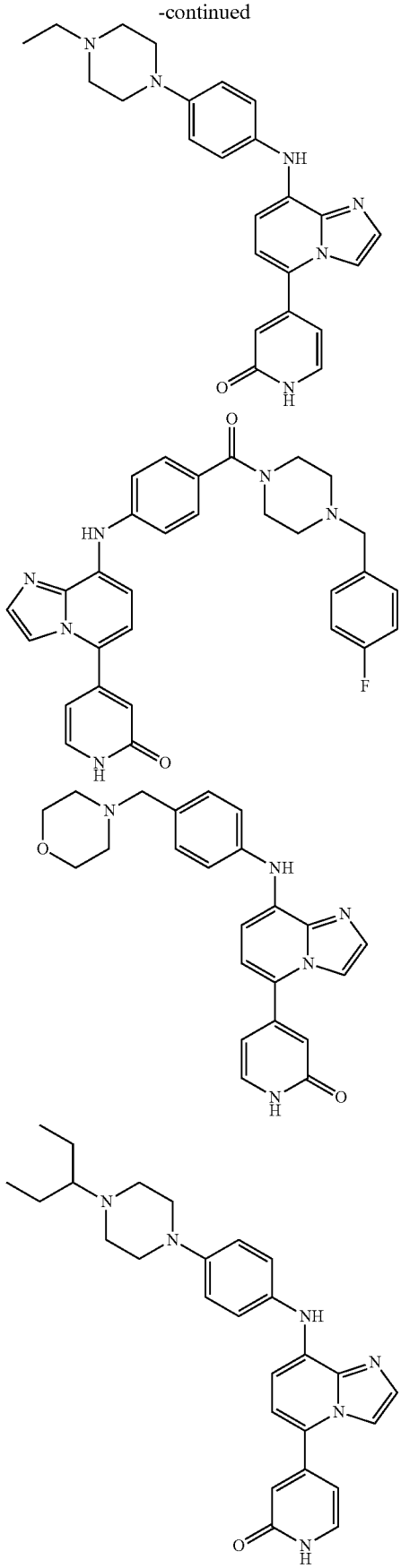
438
-continued
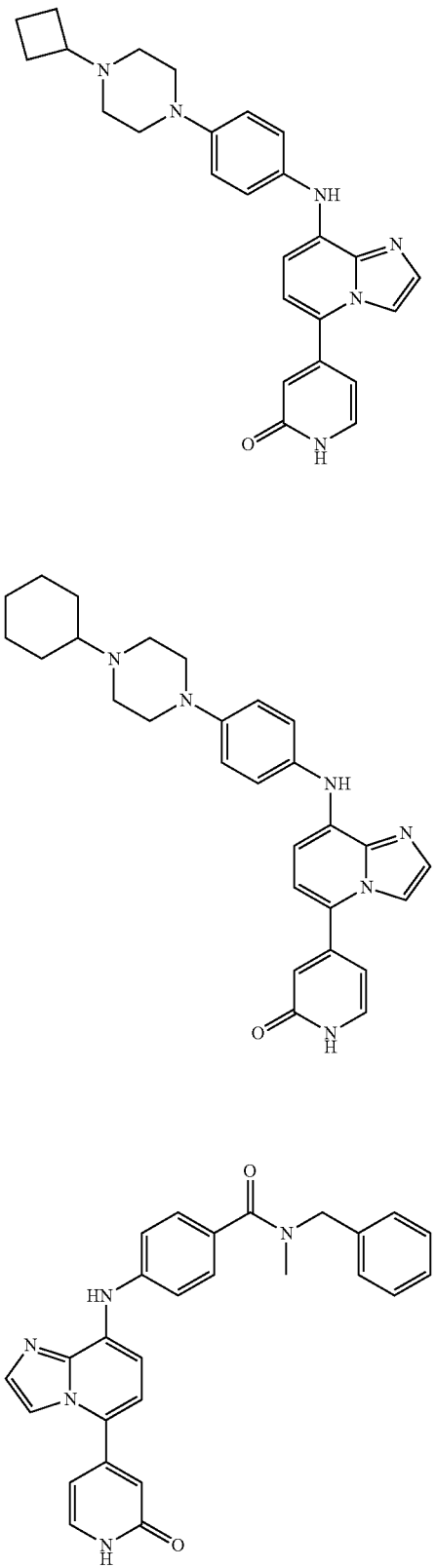

439
-continued
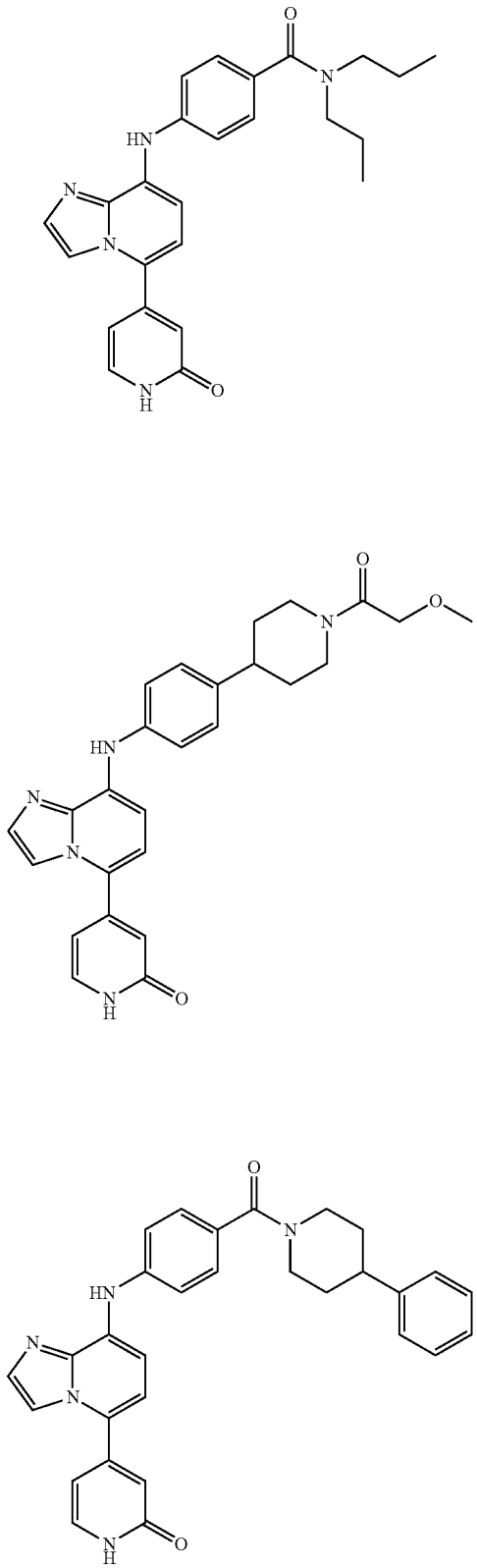
440
-continued
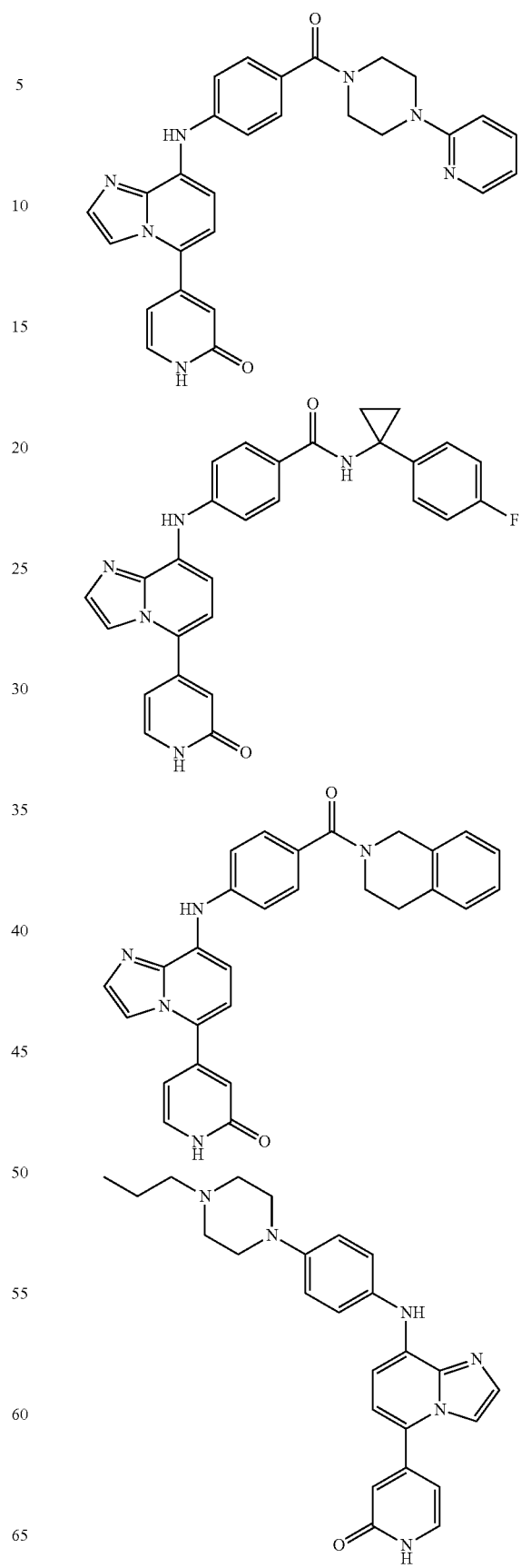

441
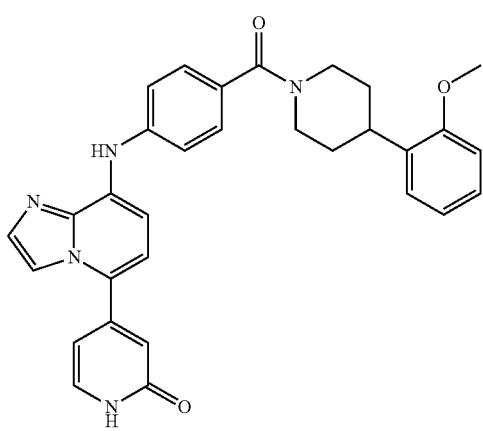
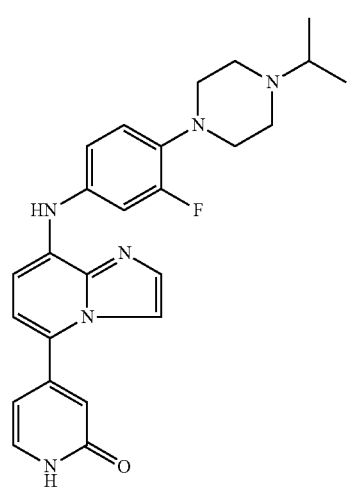
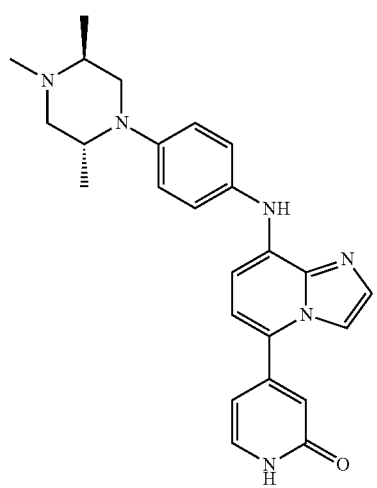
442
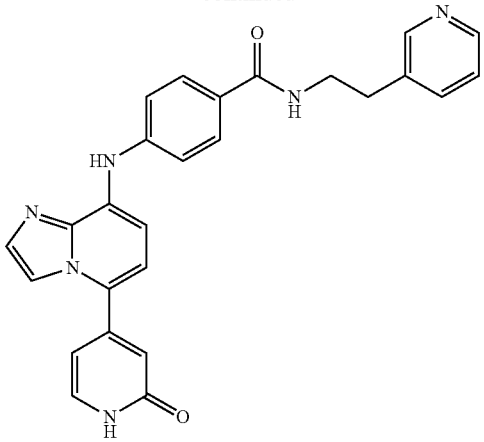
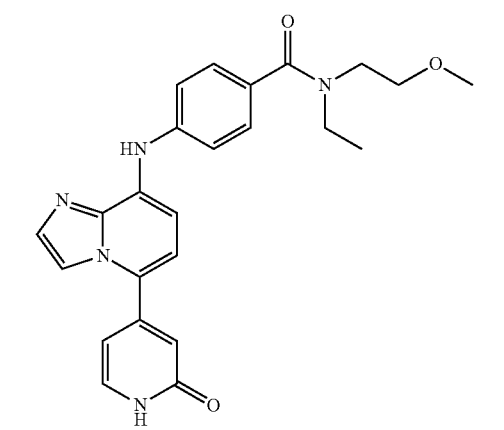
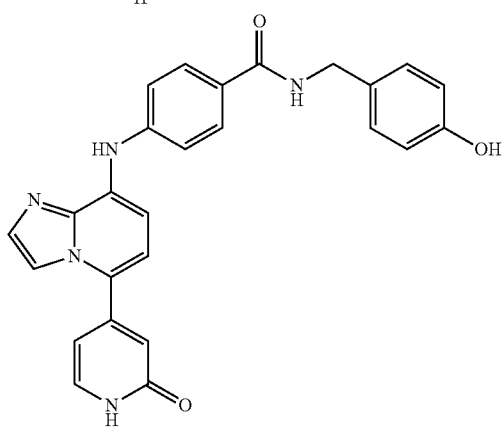
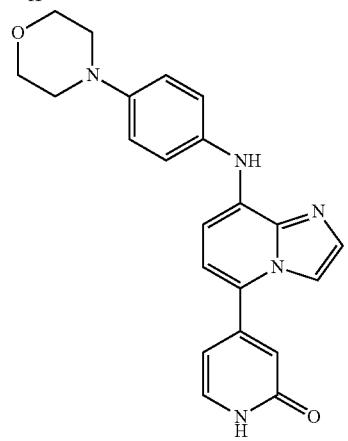

443
-continued
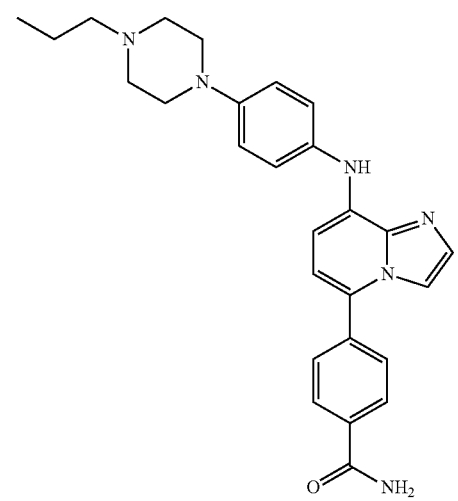
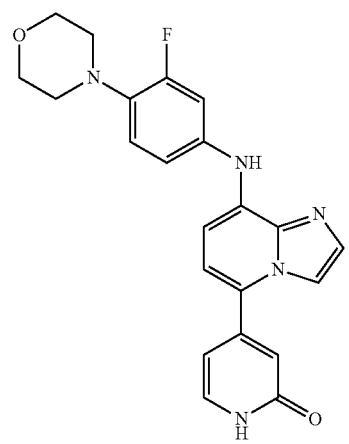
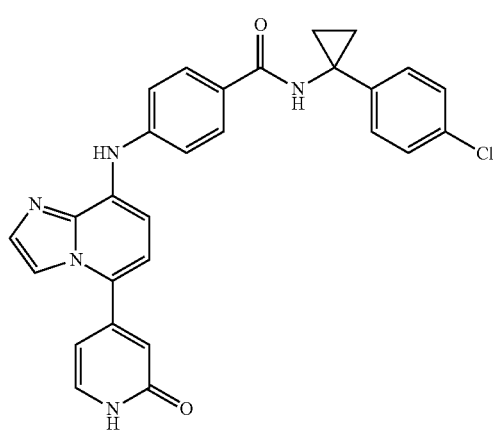
444
-continued
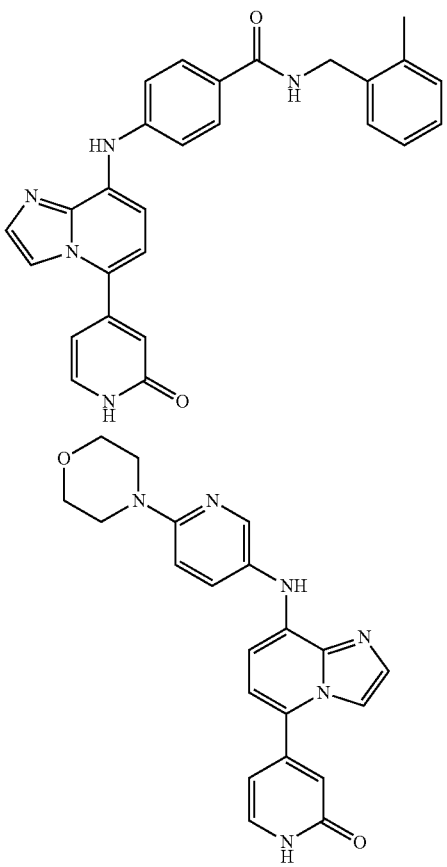
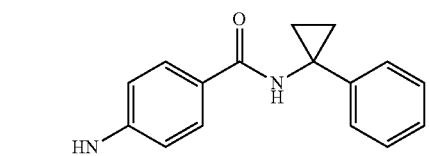
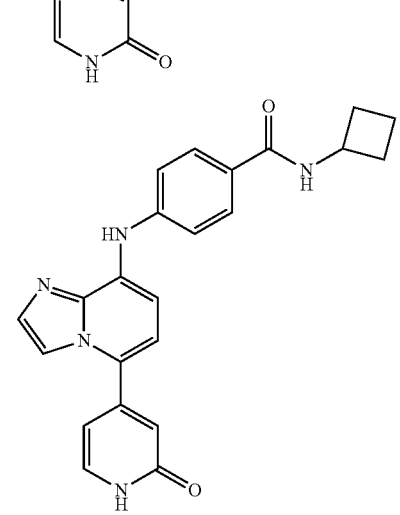

445
-continued
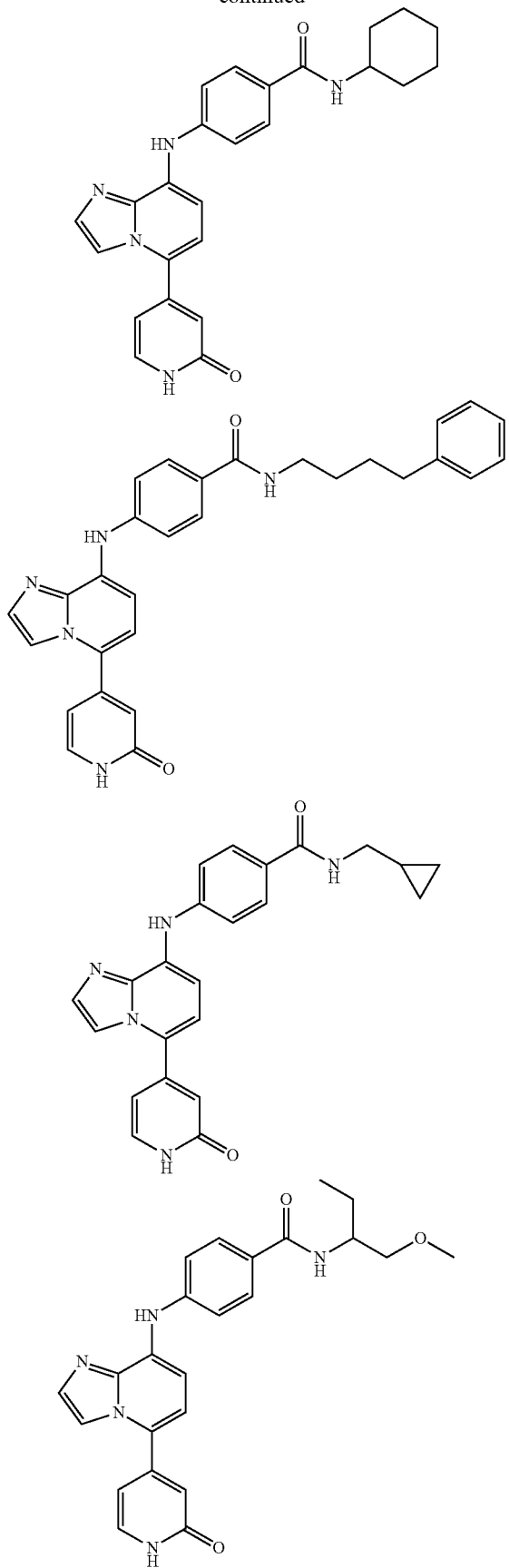
446
-continued
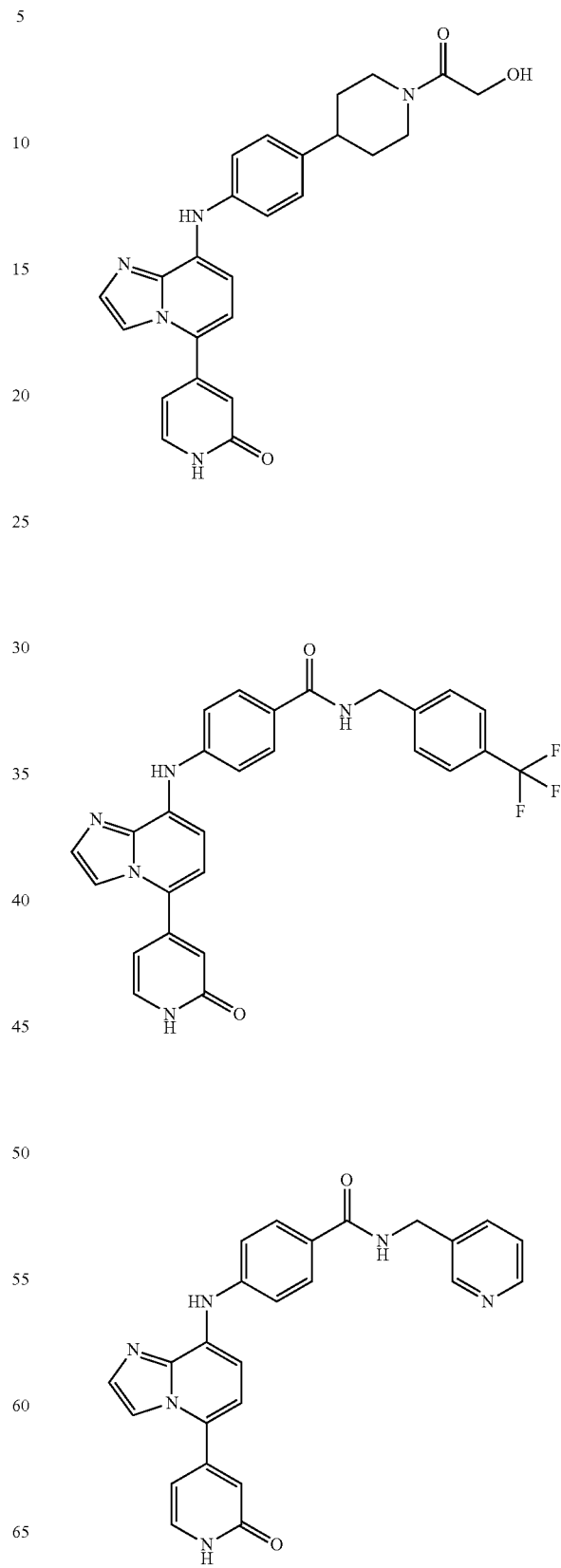

-continued

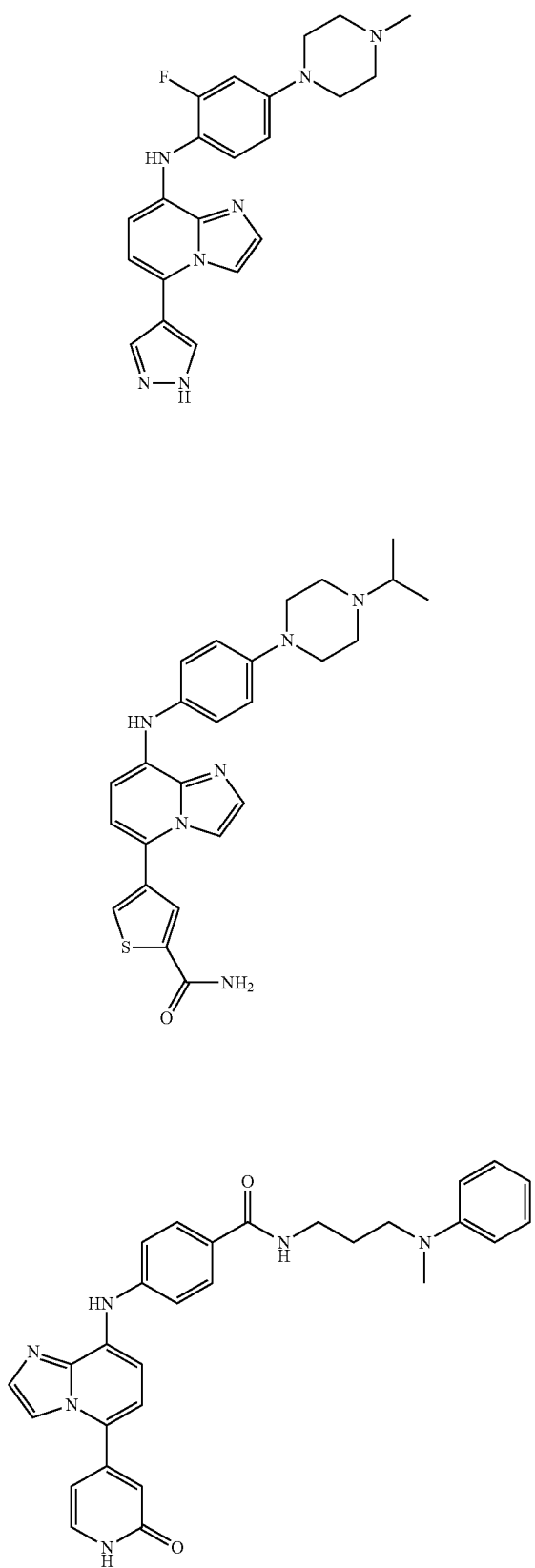

-continued

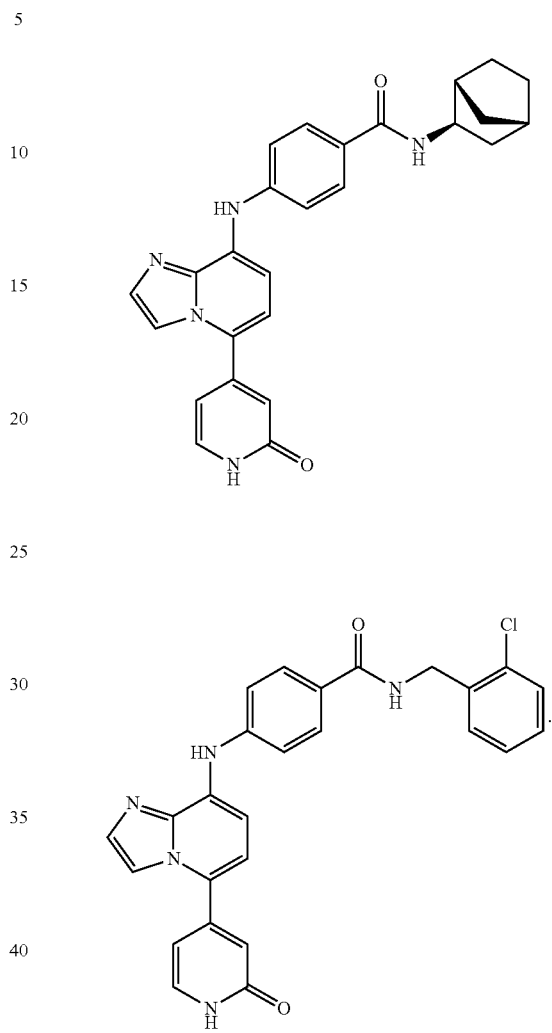

24. A pharmaceutical composition comprising an effective therapeutically effective amount of a compound according to claim 1, in admixture with a pharmaceutically acceptable carrier.

25. The compound according to claim 1, wherein each $R^{1b}$ is H.

26. The compound according to claim 1, wherein n1 is 1 or 2; and each $R^{1b}$ is independently selected from Me, Et, Pr, iso-Pr, Cl, F, CN, OMe, OEt, $CF_3$, $CF_2CF_3$ and $OCF_3$.

27. The compound according to claim 1, wherein n1 is 1 or 2; and each $R^{1b}$ is independently selected from Me, F, Cl and $CF_3$.

28. The compound according to claim 18 wherein each $R^{1d}$ is H.

29. The compound according to claim 20, wherein $R^a$ is H; and $R^b$ is Me, Et, Pr, i-Pr, t-Bu, i-Bu, i-pentyl, cyclopropyl, cyclobutyl, cyclopentyl, cyclohexyl, cyclopropylmethyl, phenyl, benzyl, or pyridylmethyl.

30. A compound according to claim 1, wherein L is —$CH_2$.

31. A compound according to formula VIIIa, VIIIb, VIIIc, VIIId, VIIIe, VIIIf, VIIIg, VIIIh, or VIIIi:

and wherein R² is selected from aryl, unsubstituted or substituted with C₁-C₆ alkyl, C₁-C₆ alkoxy, C₁-C₆ haloalkyl, hydroxy, cyano, carboxamido, or halo, and heteroaryl, unsubstituted or substituted with C₁-C₆ alkyl, C₁-C₆ alkoxy, C₁-C₆ haloalkyl, hydroxy, cyano, carboxamido, or halo; A is CH or N; and $R^{1c}$ is hydrogen, substituted or unsubstituted alkyl, substituted or unsubstituted aryl, substituted or unsubstituted aralkyl, substituted or unsubstituted heteroaryl or substituted or unsubstituted cycloalkyl.

32. A compound according to formula XXIIa, XXIIb, XXIIc, XXIId, XXIIe, or XXIIf:
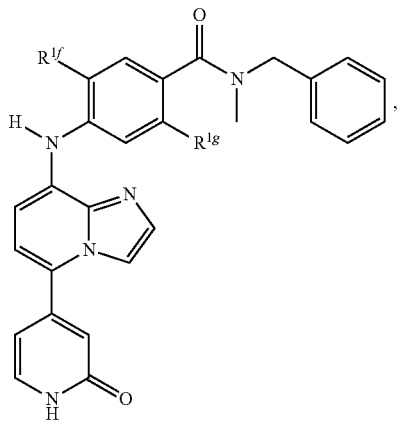
XXIIa
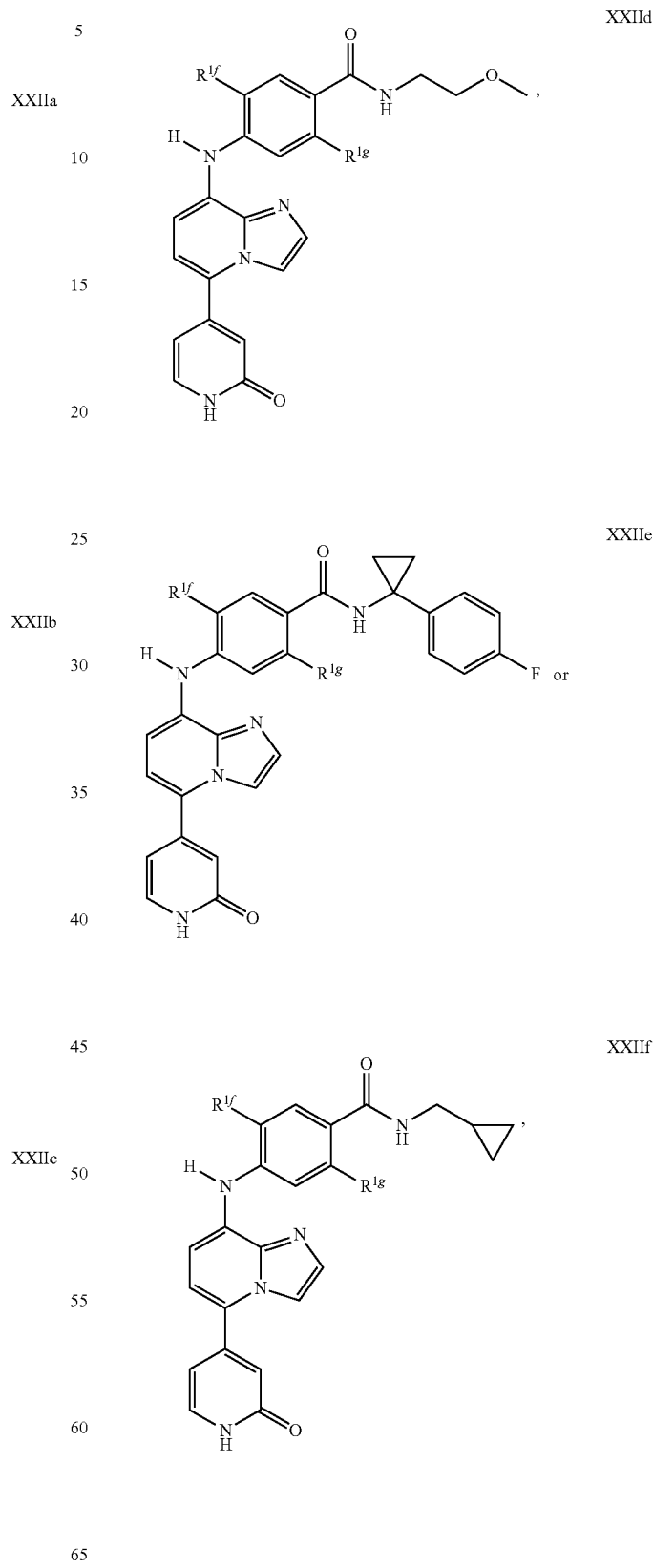
and wherein each $R^{1f}$ and $R^{1g}$ is hydrogen or F.

33. A compound according to claim 1, wherein R² is
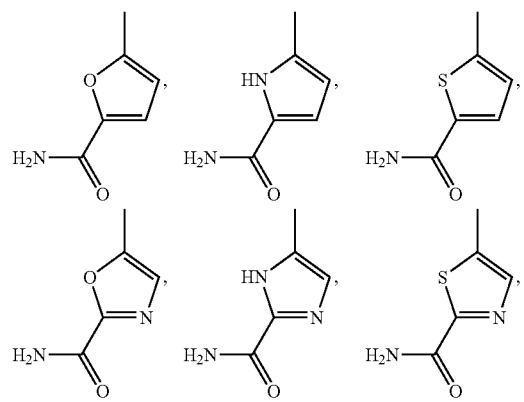
-continued
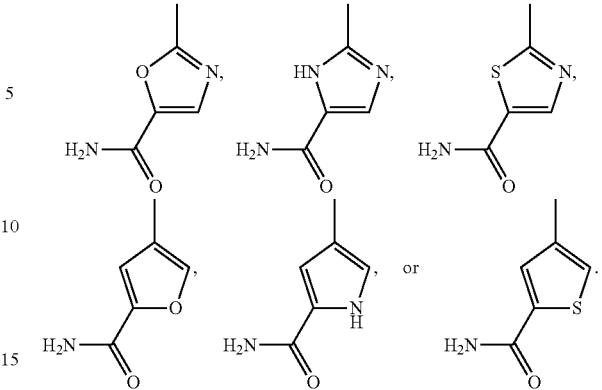
* * * * *